US011912718B2

(12) United States Patent
Yang

(10) Patent No.: US 11,912,718 B2
(45) Date of Patent: Feb. 27, 2024

(54) SOLID FORMS OF A THIENOPYRIMIDINEDIONE ACC INHIBITOR AND METHODS FOR PRODUCTION THEREOF

(71) Applicant: Gilead Apollo, LLC, Foster City, CA (US)

(72) Inventor: Xiaowei Yang, Foster City, CA (US)

(73) Assignee: Gilead Apollo, LLC, Foster City, CA (US)

(*) Notice: Subject to any disclaimer, the term of this patent is extended or adjusted under 35 U.S.C. 154(b) by 0 days.

(21) Appl. No.: 17/393,030

(22) Filed: Aug. 3, 2021

(65) Prior Publication Data

US 2022/0064181 A1 Mar. 3, 2022

Related U.S. Application Data

(60) Continuation of application No. 16/598,411, filed on Oct. 10, 2019, now Pat. No. 11,104,687, which is a division of application No. 16/217,935, filed on Dec. 12, 2018, now Pat. No. 10,487,090, which is a division of application No. 15/446,873, filed on Mar. 1, 2017, now Pat. No. 10,183,951.

(60) Provisional application No. 62/303,237, filed on Mar. 3, 2016, provisional application No. 62/302,755, filed on Mar. 2, 2016.

(51) Int. Cl.
| | |
|---|---|
| *C07D 309/12* | (2006.01) |
| *C07D 495/04* | (2006.01) |
| *C12P 41/00* | (2006.01) |
| *A61P 1/16* | (2006.01) |
| *A61P 3/00* | (2006.01) |
| *A61P 3/06* | (2006.01) |
| *A61K 31/519* | (2006.01) |

(52) U.S. Cl.
CPC .......... *C07D 495/04* (2013.01); *A61K 31/519* (2013.01); *A61P 1/16* (2018.01); *A61P 3/00* (2018.01); *A61P 3/06* (2018.01); *C07D 309/12* (2013.01); *C12P 41/001* (2013.01); *C12Y 301/01003* (2013.01); *C07B 2200/07* (2013.01); *C07B 2200/13* (2013.01)

(58) Field of Classification Search
CPC ............................ C07D 309/12; C07C 69/003
See application file for complete search history.

(56) References Cited

U.S. PATENT DOCUMENTS

| | | | |
|---|---|---|---|
| 4,670,560 A | 6/1987 | Press et al. | |
| 6,180,635 B1 | 1/2001 | Cheshire et al. | |
| 6,197,780 B1 | 3/2001 | Munter et al. | |
| 8,969,557 B2 | 3/2015 | Harriman et al. | |
| 9,346,822 B2 | 5/2016 | Cho et al. | |
| 9,453,026 B2 | 9/2016 | Harriman et al. | |
| 9,944,655 B2 | 4/2018 | Harriman et al. | |
| 9,988,399 B2 | 6/2018 | Greenwood et al. | |
| 10,472,374 B2 | 11/2019 | Bhat et al. | |
| 10,487,090 B2 | 11/2019 | Calimsiz et al. | |
| 2003/0187254 A1 | 10/2003 | Perry et al. | |
| 2003/0191142 A1 | 10/2003 | Cheshire et al. | |
| 2005/0124636 A1 | 6/2005 | Sharma et al. | |
| 2006/0039943 A1 | 2/2006 | Applebaum et al. | |
| 2007/0208040 A1 | 9/2007 | Elzein et al. | |
| 2008/0287465 A1 | 11/2008 | Tumey et al. | |
| 2010/0113473 A1 | 5/2010 | Player et al. | |
| 2011/0288114 A1 | 11/2011 | Turner | |
| 2013/0123231 A1 | 5/2013 | Harriman et al. | |
| 2016/0297834 A1 | 10/2016 | Harriman et al. | |
| 2017/0145028 A1 | 5/2017 | Ghosh et al. | |
| 2017/0166582 A1 | 6/2017 | Ghosh et al. | |
| 2017/0166583 A1 | 6/2017 | Ghosh et al. | |
| 2017/0166584 A1 | 6/2017 | Ghosh et al. | |
| 2017/0166585 A1 | 6/2017 | Bennett et al. | |
| 2017/0267690 A1 | 9/2017 | Alexander et al. | |
| 2018/0021341 A1 | 1/2018 | Harriman et al. | |
| 2019/0241582 A1 | 8/2019 | Ghosh et al. | |
| 2019/0330224 A1 | 10/2019 | Ghosh et al. | |
| 2019/0375759 A1 | 12/2019 | Ghosh et al. | |
| 2019/0381045 A1 | 12/2019 | Harriman et al. | |
| 2020/0010478 A1 | 1/2020 | Ghosh et al. | |
| 2020/0017519 A1 | 1/2020 | Ghosh et al. | |
| 2020/0102323 A1 | 4/2020 | Bhat et al. | |
| 2020/0148699 A1 | 5/2020 | Harriman et al. | |

FOREIGN PATENT DOCUMENTS

| | | |
|---|---|---|
| CN | 1106663 A | 8/1995 |
| CN | 1301162 A | 6/2001 |
| EP | 0640606 A1 | 3/1995 |
| EP | 2189458 | 5/2010 |
| EP | 02351743 A1 | 8/2011 |
| JP | 62-289583 A | 12/1987 |
| JP | 02-225485 A | 9/1990 |
| JP | 08-073467 A | 3/1996 |

(Continued)

OTHER PUBLICATIONS

Boyd et al. (Tetrahedron: Asymmetry (1993), 4(6), 1307-24).*
Abe, et al., "Reactions of 2-Amino-,2-Alkylamino-, and 2-Piperidino-1-aza-azulenes with Aryl and Chlorosulfonyl Isocyanates", Journal of Heterocyclic Chemistry, 1996, 33(4), 1323-1331.
Ashizawa, et al., Science of crystallization and polymorphic phenomenon of pharmaceutical product. Japan, Maruzen Planet Co., Ltd., Sep. 20, 2002, p. 3-16, 273-278. (In Japanese with Partial English Translation).
Bhattacharya, et al. in Brittain, ed. Polymorphism in Pharmaceutical Solids, 2009, p. 334.
Caplus record for US 2007/020840 A1 by Elzein et al. (retrieved Nov. 2013).
CAS Registry No. 1089778-56-2; STN Entry Date Dec. 25, 2008.
CAS Registry No. 1089786-92-4; STN Entry Date Dec. 25, 2008.

(Continued)

*Primary Examiner* — Susanna Moore
(74) *Attorney, Agent, or Firm* — Sheppard Mullin Richter & Hampton LLP

(57) ABSTRACT

The present invention provides solid forms of compounds useful as inhibitors of Acetyl CoA Carboxylase (ACC), compositions thereof, methods of producing the same, and methods of using the same in the treatment of ACC-mediated diseases.

1 Claim, 46 Drawing Sheets

(56) References Cited

FOREIGN PATENT DOCUMENTS

| | | |
|---|---|---|
| JP | 09-110873 A | 4/1997 |
| JP | 2002-500666 A | 1/2002 |
| JP | 2002-541258 A | 12/2002 |
| JP | 2004-518732 A | 6/2004 |
| JP | 2007-302703 A | 11/2007 |
| JP | 2009-528389 A | 8/2009 |
| WO | WO 97/007119 A1 | 2/1997 |
| WO | WO 97/040846 A1 | 11/1997 |
| WO | WO 98/54190 A1 | 12/1998 |
| WO | WO 00/61583 A1 | 10/2000 |
| WO | WO 02/064598 A1 | 8/2002 |
| WO | WO 2004/014916 A1 | 2/2004 |
| WO | WO 2006/014647 A2 | 2/2006 |
| WO | WO 2007/103776 A2 | 9/2007 |
| WO | WO 2008/143262 A1 | 11/2008 |
| WO | WO 2011/080277 A1 | 7/2011 |
| WO | WO 2012/090219 | 7/2012 |
| WO | WO 2013/071169 | 5/2013 |
| WO | WO 2014/182943 | 11/2014 |
| WO | WO 2014/182950 | 11/2014 |
| WO | WO 2015/007451 | 1/2015 |
| WO | WO 2017/075056 | 5/2017 |
| WO | WO 2017/091600 | 6/2017 |
| WO | WO 2017/091602 | 6/2017 |
| WO | WO 2018/133858 | 7/2018 |
| WO | WO 2019/066467 | 4/2019 |

OTHER PUBLICATIONS

CAS Registry No. 1089787-86-9; STN Entry Date Dec. 25, 2008.
CAS Registry No. 1089789-10-5; STN Entry Date Dec. 25, 2008.
CAS Registry No. 1089797-59-0; STN Entry Date Dec. 25, 2008.
CAS Registry No. 1089798-87-7; STN Entry Date Dec. 25, 2008.
CAS Registry No. 1089800-09-8; STN Entry Date Dec. 25, 2008.
CAS Registry No. 1089806-06-3; STN Entry Date Dec. 25, 2008.
CAS Registry No. 1089806-14-3; STN Entry Date Dec. 25, 2008.
CAS Registry No. 1089806-45-0; STN Entry Date Dec. 25, 2008.
CAS Registry No. 1089806-99-4; STN Entry Date Dec. 25, 2008.
CAS Registry No. 1089807-07-7; STN Entry Date Dec. 25, 2008.
CAS Registry No. 1089808-09-2; STN Entry Date Dec. 25, 2008.
CAS Registry No. 1089809-28-8; STN Entry Date Dec. 25, 2008.
CAS Registry No. 1089823-87-9; STN Entry Date Dec. 25, 2008.
CAS Registry No. 1089878-58-9; STN Entry Date Dec. 25, 2008.
CAS Registry No. 1089894-24-5; STN Entry Date Dec. 25, 2008.
CAS Registry No. 1089894-94-9; STN Entry Date Dec. 25, 2008.
CAS Registry No. 1089895-94-2; STN Entry Date Dec. 25, 2008.
CAS Registry No. 1089938-46-4; STN Entry Date Dec. 25, 2008.
CAS Registry No. 1089955-70-0; STN Entry Date Dec. 25, 2008.
CAS Registry No. 1089956-79-5; STN Entry Date Dec. 25, 2008.
CAS Registry No. 1089957-54-9; STN Entry Date Dec. 25, 2008.
CAS Registry No. 1089966-20-0; STN Entry Date Dec. 25, 2008.
CAS Registry No. 1089970-09-1; STN Entry Date Dec. 25, 2008.
CAS Registry No. 1089971-35-6; STN Entry Date Dec. 25, 2008.
CAS Registry No. 1089971-50-5; STN Entry Date Dec. 25, 2008.
CAS Registry No. 1089972-49-5; STN Entry Date Dec. 25, 2008.
CAS Registry No. 1089977-31-0; STN Entry Date Dec. 25, 2008.
CAS Registry No. 1089978-05-1; STN Entry Date Dec. 25, 2008.
CAS Registry No. 1089981-89-4; STN Entry Date Dec. 25, 2008.
CAS Registry No. 1089983-19-6; STN Entry Date Dec. 25, 2008.
CAS Registry No. 1089986-32-2; STN Entry Date Dec. 25, 2008.
CAS Registry No. 1089987-08-5; STN Entry Date Dec. 25, 2008.
CAS Registry No. 1089988-38-4; STN Entry Date Dec. 25, 2008.
Cho et al., "Thieno[2,3-d]pyrimidine-3-acetic acids. A new class of nonpeptide endothelin receptor antagonists," Chemical & Pharmaceutical Bulletin, vol. 46, No Month Listed 1998 (pp. 1724-1737).
Corbett, "Review of recent acetyl-CoA carboxylase inhibitor patents: mid-2007-2008," Expert Opinion on Therapeutic Patents, vol. 19, No. 7, No Month Listed 2009 (pp. 943-956).
Database CA [online] Chemical Abstracts Service, Columbus, Ohio, US; Quelet, Raymond et al: "Preparation of o-methoxystrene; transformation into o-methoxyphenylacetylene", XP002771178, Retrieved from STN database accession No. 1947:3573 Abstract, 2 pages. Downloaded Jun. 19, 2017.
Database Registry [online] RN 1089878-77-2, Dec. 25, 2008.
Database Registry [online] RN 1089896-86-5, Dec. 25, 2008.
Database Registry [online] RN 1089952-27-1, Dec. 25, 2008.
Database Registry [online] RN 1222836-90-9, May 13, 2010.
El-Barbary, et al. Synthesis of 5'-amino- and 5'-azido-2',5'-dideoxy nucleosides from thieno[2,3- d]pyrimidine-2,4(1H,3H)-dione. Monatshefte für Chemie. 1995; 126(5):593-600.
Extended European Search Report dated Dec. 10, 2019 for EP Application No. 19190936.5. (7 pages).
Extended European Search Report dated Dec. 17, 2019 for EP Application No. 19176040.4. (7 pages).
Extended European Search Report dated Feb. 26, 2015 for EP Application No. 12848361.7. (3 pages).
Extended European Search Report dated Jun. 7, 2018 for EP Application No. 16735485.1. (7 pages).
Extended European Search Report dated Mar. 20, 2018 for EP Application No. 17209455.9. (7 pages).
Fernandez et al., "Bayesian-regularized Genetic Neural Networks Applied to the Modeling on Non-Peptide Antagonists for the Human Luteinizing Hormone-releasing Hormone Receptor", Journal of Molecular Graphics and Modelling, 2006, 25(4), 410-422.
Hikime, Seiichiro. Experimental chemistry course (sequel) 2, Isolation and purification. Maruzen Co., Ltd., Jan. 25, 1967, p. 159-178, 186-187. (In Japanese with Partial English Translation).
International Search Report and Written Opinion dated Feb. 4, 2013 for PCT/US2012/064528. (14 pages).
International Search Report and Written Opinion dated Jun. 30, 2017 for PCT/US2017/020271. (22 pages).
International Search Report and Written Opinion dated Mar. 30, 2016 for PCT/US2016/012673. (8 pages).
Jourdan, et al. Synthesis of Cyclic and Acyclic Nucleoside Analogues Having a Thiophene or Dihydrothiophene Ring Fused to the d Side of an Uracyl, J. Heterocyclic Chem, 1995, 32, p. 953-957.
Malamas et al., "Quinazolineacetic Acids and Related Analogues as Aldose Reductase Inhibitors", Journal of Medicinal Chemistry, 1991, 34(4), 1492-1503.
Nakai, et al. New drug formulation science. Nanzando Co., Ltd., Apr. 25, 1984, p. 102-103, 232-233. (In Japanese with Partial English Translation).
Nishigaki, Sadao. Pharmaceutics—Fundamentals to Practical Application. Nanzando Co., Ltd., Sep. 20, 1977, p. 142-145. (In Japanese with Partial English Translation).
Okano, Teisuke. New general theory of pharmaceutical science. (Revised third edition), Apr. 10, 1987, Nankodo Co., Ltd., p. 111. (In Japanese with Partial English Translation).
Oshima, Hiroshi. Crystallization of Polymorphs and Pseudopolymorphs and Its Control, Pharm Stage, Jan. 15, 2007, vol. 6, No. 10, p. 48-53. (In Japanese with Partial English Translation).
Quelet, et al. Preparation of o-methoxystyrene; transformation into o-methoxyphenylacetylene. Compt. Rend. 1946; 223:159-160.
Rana, et al.: "Catalytic electrophilic halogenationsand haloalkoxylations by non-heme iron halides", Advanced Synthesis & Catalysis, vol. 256, No. 11-12, pp. 2453-2458, 2014.
Reeder, et al. An improved method for the palladium cross-coupling reaction of oxazol-2-ylzinc derivatives with aryl bromides. Org. Proc. Res. Dev. 2003, 7, 5, 696-699.
Registry (STN) [online], May 8, 2009, retrieval date Apr. 22, 2016, CAS registration Nos. 1144464-32-3, 1089988-38-4, 1089987-08-5, 1089986-32-2, 1089984-45-1, 1089983-19-6, 1089981-89-4, 1089978-89-1, 1089978-06-2, 1089978-06-2, 1089978-05-1, 1089977-32-1 and the like.
Renault, et al. Synthesis and Antiviral Evaluation of Furopyramidine Diones: Cyclic and Acyclic Nucleoside Analogues, Heterocycles, 1995, 41(5):937-945.
RN: 1778957-82-6, Database Registry [Online] Retrieved from STN, Jun. 12, 2015, Date of retrieval: Nov. 26, 2020.
Sasaki et al., "Discovery of a Thieno[2,3-d] pyrimidine-2,4-dione Bearing a p-Methoxyureidophenyl Moiety at the 6-Position: A Highly Potent and Orally Bioavailable Non-Peptide Antagonist for

(56) References Cited

OTHER PUBLICATIONS the Human Luteinizing Hormone-Releasing Hormone Receptor", Journal of Medicinal Chemistry, 2003, 46(1), 113-124.

Sunkara, et al. A Carbocyclic 7-Deazapurine-pyramidine hybrid nucleoside, Collect. Czech. Chem. Commune, 2006, vol. 71, No. 8, p. 1161-1168.

Takata, Noriyuki. API form screening and selection in drug discovery stage, Pharm Stage, Jan. 15, 2007, vol. 6, No. 10, p. 20-25. (In Japanese with Partial English Translation).

Talal, et al. Simtuzumab, an antifibrotic monoclonal antibody against lysyl oxidase-like 2 (LOXL2) enzyme, appears safe and well tolerated in patients with liver disease of diverse etiology. J of Hepatology. Apr. 2013; vol. 58, S1-632, poster #1319.

The Japanese Pharmacopoeia, Sixteenth Edition, 2011, pp. 64-68, 2070. (In Japanese with Partial English Translation).

Vlasov et al., "The Synthesis of Novel 3-Substituted 1-Alkyl-5-Methyl-6-(3-Aryl-1,2,4-Oxadiazole-5-Yl)Thieno[2,3-D]Pyrimidine-2,4(1H3H)-Diones and Their Antimicrobial Activity", Journal of Organic and Pharmaceutical Chemistry, 2011, 9(3):51-55, with English translation, 6 pages.

Wang, et al. Separation of citalopram intermediate from its acetate by solvent extraction. Separation and Purification Technology. Volume 68, Issue 1, Jun. 30, 2009, pp. 65-69.

Yamano, Mitsuhisa. Approach to Crystal Polymorph in Process Research of New Drug, Journal of Synthetic Organic Chemistry, Japan, Sep. 1, 2007, vol. 65, No. 9, p. 907(69)-913(75). (In Japanese with Partial English Translation).

You et al., "Section II Lead Optimization", Medicinal Chemistry, 2nd version, Chemical Industry Press, pp. 25-29, 2008.

Caira M.R., "Crystalline Polymorphism of Organic Compounds", Topics in Current Chemistry, Springer Verlag Berlin Heidelberg 1998, vol. 198, pp. 163-208.

Crouch et al., "Removal of Acyl Protecting Groups Using Solid NaOH and a Phase Transfer Catalyst", Letter Mar. 24, 2003, pp. 991-992.

Guillory J.K., Edited by Brittain, H.G., "Generation of Polymorphs, Hydrates, Solvates, and Amorphous Solids", Polymorphism in Pharmaceutical Solids, 1999, pp. 183-226.

Lugemwa et al., "Facile and Efficient Acetylation of Primary Alcohols and Phenols with Acetic Anhydride Catalyzed by Dried Sodium Bicarbonate", Catalysts 2013, pp. 954-965.

\* cited by examiner

SOLID FORMS OF A THIENOPYRIMIDINEDIONE ACC INHIBITOR AND METHODS FOR PRODUCTION THEREOF

CROSS REFERENCE TO RELATED APPLICATIONS

This application is a continuation of U.S. application Ser. No. 16/598,411, filed Oct. 10, 2019, now U.S. Pat. No. 11,104,687, which is a divisional of U.S. application Ser. No. 16/217,935, filed Dec. 12, 2018, now U.S. Pat. No. 10,487,090, which is a divisional of U.S. application Ser. No. 15/446,873, filed Mar. 1, 2017, now U.S. Pat. No. 10,183,951, which claims the benefit under 35 U.S.C. § 119(e) to U.S. Provisional Application No. 62/302,755, filed Mar. 2, 2016, and U.S. Provisional Application No. 62/303,237, filed Mar. 3, 2016, all of which are incorporated herein by reference.

BACKGROUND OF THE INVENTION

Obesity is a health crisis of epic proportions. The health burden of obesity, measured by quality-adjusted life-years lost per adult, has surpassed that of smoking to become the most serious, preventable cause of death. In the U.S., about 34% of adults have obesity, up from 31% in 1999 and about 15% in the years 1960 through 1980. Obesity increases the rate of mortality from all causes for both men and women at all ages and in all racial and ethnic groups. Obesity also leads to social stigmatization and discrimination, which decreases quality of life dramatically. The chronic diseases that result from obesity cost the U.S. economy more than $150 billion in weight-related medical bills each year. Furthermore, about half of the obese population, and 25% of the general population, have metabolic syndrome, a condition associated with abdominal obesity, hypertension, increased plasma triglycerides, decreased HDL cholesterol, and insulin resistance, which increases the risk for type-2 diabetes (T2DM), stroke and coronary heart disease (Harwood, Expert Opin. Ther. Targets 9: 267, 2005).

Diet and exercise, even when used in conjunction with the current pharmacotherapy, do not provide sustainable weight loss needed for long-term health benefit. Currently, only a few anti-obesity drugs are approved in the U.S., the fat absorption inhibitor orlistat (Xenical®), the 5-HT$_{2C}$ antagonist lorcaserin (Belviq®), and the combination therapy phentermine/topiramate (Qsymia®). Unfortunately, poor efficacy and unappealing gastrointestinal side effects limit the use of orlistat. Surgery can be effective but is limited to patients with extremely high Body Mass Indices (BMI) and the low throughput of surgery limits the impact of this modality to about 200 k patients per year. The majority of obesity drugs in clinical development are designed to reduce caloric intake through central action in the CNS (e.g., anorectics and satiety agents). However, the FDA has taken an unfavorable position against CNS-active agents, due to their modest efficacy and observed/potential side-effect profiles.

The continuing and increasing problem of obesity, and the current lack of safe and effective drugs for treating it, highlight the overwhelming need for new drugs to treat this condition and its underlying causes.

Another ongoing problem is the lack of antifungal drugs with activity against a broad range of fungal pathogens. Often, a given antifungal drug will have activity against one fungal species but lack activity against other, even closely related, species, such as *Candida albicans*, *Candida krusei*, and *Candida parapsilosis*.

SUMMARY

The compound, (R)-2-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3(4H)-yl)-2-methylpropanoic acid, designated herein as Compound 1, has the formula:

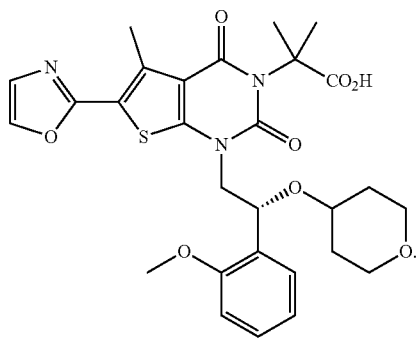

Compound 1

The present disclosure relates to various crystalline forms of Compound 1, processes for making Compound 1 and its various forms, and methods of using such forms.

Compound 1 also provides forms further described herein as "Compound 1 Form I," "Compound 1 Form II," "Compound 1 Form III," "Compound 1 Form IV," "Compound 1 Form V," "Compound 1 Form VI," "Compound 1 Form VII," "Compound 1 Form VIII," and "amorphous Compound 1."

Additional crystalline forms of Compound 1 are further described herein.

In some embodiments, crystalline forms of Compound 1 may include a salt, a co-crystal, a solvate, or a hydrate of Compound 1.

In some embodiments, crystalline forms of Compound 1 may include a salt of Compound 1. In some embodiments, Compound 1 provide forms further described herein as "Compound 1 Sodium Form I," "Compound 1 Sodium Form II," "Compound 1 Calcium Form I," "Compound 1 Magnesium Form I," "Compound 1 Diethanolamine Form I," and "Compound 1 Piperazine Form I."

Some embodiments provide for a process of preparing Compound 1, or a salt or co-crystal thereof, comprising:
(a) contacting compound G-2-a:

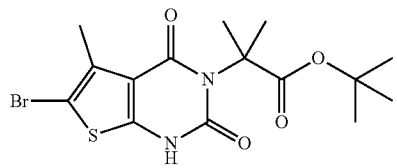

G-2-a with oxazole under conditions sufficient to form compound G-9-a:

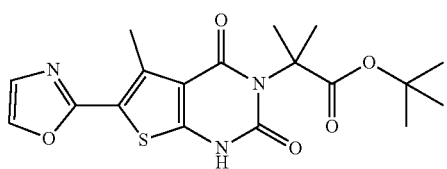
G-9-a (b) contacting compound G-9-a with compound (R)-G-1-a:

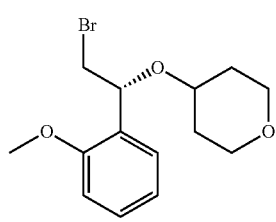
(R)-G-1-a under conditions sufficient to form a compound G-4-a:

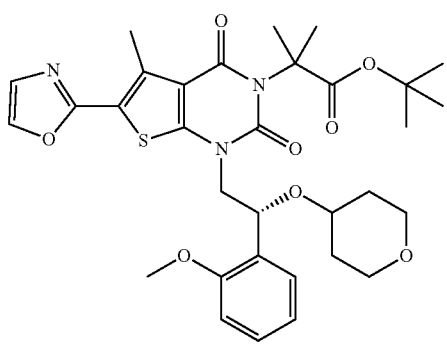
G-4-a and (c) hydrolyzing compound G-4-a under conditions sufficient to form Compound 1.

Some embodiments provide for a process of preparing Compound 1, or salt or co-crystal thereof, comprising:

(a) contacting compound (R)-G-5-a or an oxygen anion thereof:

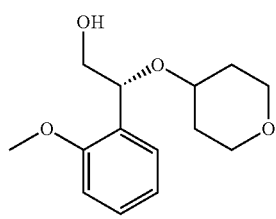
(R)-G-5-a with a sulfonylating reagent under conditions sufficient to form compound (R)-G-6-a:

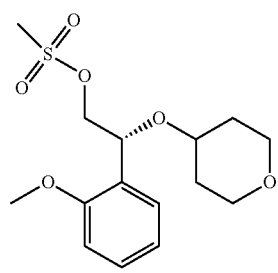
(R)-G-6-a (b) contacting compound (R)-G-6-a with a bromide salt under conditions sufficient to form compound (R)-G-1-a:

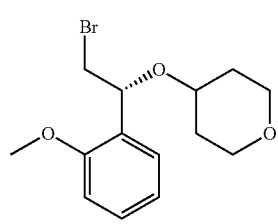
(R)-G-1-a (c) contacting compound G-2-a:

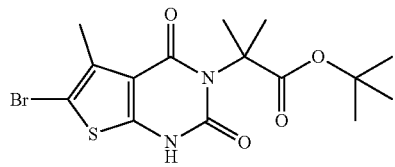
G-2-a with oxazole under conditions sufficient to form compound G-9-a:

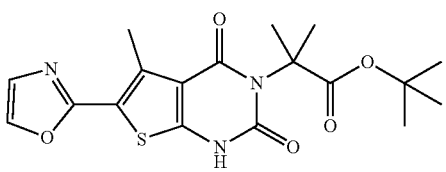
G-9-a (d) contacting compound G-9-a with compound (R)-G-1-a under conditions sufficient to form a compound G-4-a:

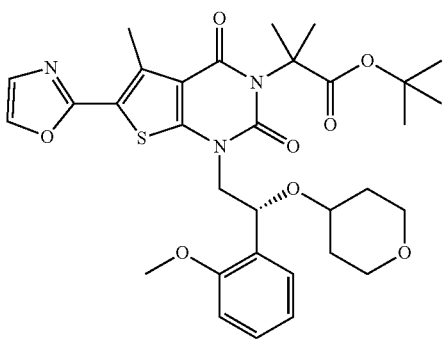
G-4-a and (e) hydrolyzing compound G-4-a under conditions sufficient to form Compound 1.

DETAILED DESCRIPTION OF CERTAIN EMBODIMENTS

1. General Description

Figure 1A:
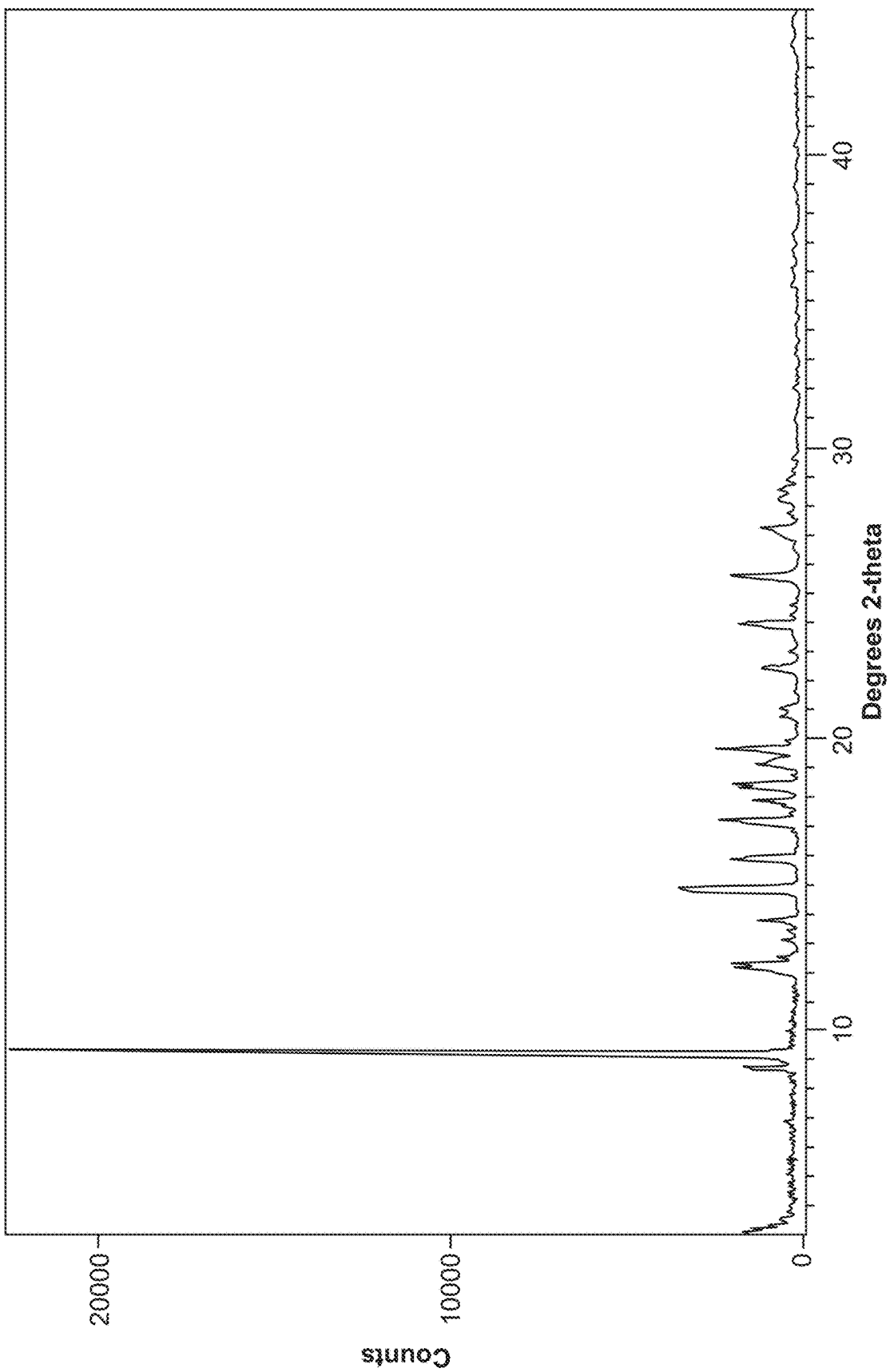
FIG. 1A depicts a X-Ray powder diffraction (XRPD) pattern of Form I of Compound 1.

United States Published Patent Application Number 2013/0123231 A1, published May 16, 2013, and incorporated herein by reference in its entirety, discloses certain thienopyrimidinedione compounds that bind to and inhibit Acetyl CoA Carboxylases 1 and 2. Such compounds include Compound 1:

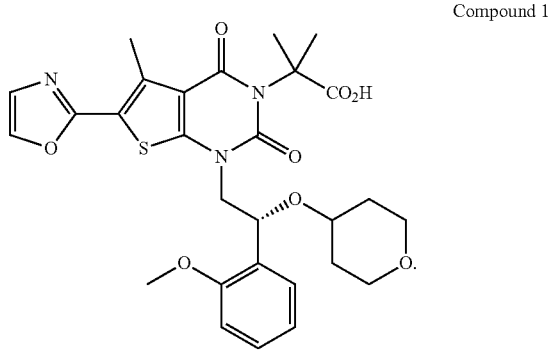 [SMILES: COc1ccccc1[C@H](Cn1c(=O)n(C(C)(C)C(=O)O)c(=O)c2c(C)c(-c3ncco3)sc21)OC1CCOCC1]

Compound 1

Compound 1, ((R)-2-(1-(2-(2-methoxyphenyl)-2-((tetrahydro-2H-pyran-4-yl)oxy)ethyl)-5-methyl-6-(oxazol-2-yl)-2,4-dioxo-1,2-dihydrothieno[2,3-d]pyrimidin-3(4H)-yl)-2-methylpropanoic acid), is designated as compound number 1-181, and the synthesis of Compound 1 is described in detail at Example 76 of U.S. Patent Publication 2013/0123231.

Compound 1 is active in a variety of assays and therapeutic models, including those demonstrating inhibition of ACC1 and/or ACC2, inhibition of fatty acid synthesis, and stimulation of fatty acid oxidation. It would be desirable to provide solid forms of Compound 1 that impart characteristics such as improved aqueous solubility, stability, and ease of formulation.

Also disclosed are novel synthetic methods for producing Compound 1 and analogs thereof, as well as novel intermediates in the synthesis of such compounds. Such methods and intermediates are amenable to large scale production, owing to high yields, favorable physicochemical properties, and reduced use of toxic reagents or solvents compared to the state of the art.

2. Solid Forms of Compound 1

In some embodiments, the present invention provides a solid form of Compound 1, or a salt, co-crystal, solvate, or hydrate thereof. In some embodiments, the solid form of Compound 1 is a salt or co-crystal. In some embodiments, the salt or co-crystal is a pharmaceutically acceptable salt or co-crystal thereof. In some embodiments, the present invention provides a solid form of Compound 1, or a pharmaceutically acceptable salt thereof. In some embodiments, the present invention provides a solid form of Compound 1, or a pharmaceutically acceptable co-crystal thereof. In some embodiments, the present invention provides a solid form of Compound 1, or a pharmaceutically acceptable salt thereof, that is substantially free of impurities. As used herein, the term "substantially free of impurities" means that the compound contains no significant amount of extraneous matter. Such extraneous matter may include residual solvents, or any other impurities that may result from the preparation of, and/or isolation of, Compound 1. In certain embodiments, at least about 95% by weight of Compound 1 is present. In still other embodiments of the invention, at least about 99% by weight of Compound 1 is present. In certain embodiments, at least about 95% by weight of Compound 1, as a salt or co-crystal thereof, is present. In still other embodiments of the invention, at least about 99% by weight of Compound 1, as a salt or co-crystal thereof is present.

According to one embodiment, Compound 1 is present in an amount of at least about 97.0, 97.5, 98.0, 98.5, 99.0, 99.5, or 99.8 weight percent where the percentages are based on the total weight of the composition. According to another embodiment, Compound 1 contains no more that about 3.0 area percent HPLC of total organic impurities and, in certain embodiments, no more that about 1.5 area percent HPLC total organic impurities relative to the total area of the HPLC chromatogram. In other embodiments, Compound 1 contains no more than about 1.0% area percent HPLC of any single impurity, and, in certain embodiments, no more than about 0.5 area percent HPLC of any single impurity, relative to the total area of the HPLC chromatogram.

In some embodiments, Compound 1 is present in an enantiomeric excess (e.e.) of about 90.0 to 99.95 percent. In some embodiments, Compound 1 is present in an enantiomeric excess (e.e.) of at least about 90.0, 91.0, 92.0, 93.0, 94.0, 95.0, 96.0, 97.0, 97.5, 98.0, 98.5, 99.0, 99.5, 99.7, 99.8, 99.9, or 99.95 percent. In some embodiments, Compound 1 is optically pure, and substantially free of its (S)-enantiomer.

In some embodiments, Compound 1 is present as a free acid. In some embodiments, Compound 1 is present as a salt. In some embodiments, Compound 1 is present as a pharmaceutically acceptable salt. In some embodiments, Compound 1 is present as a co-crystal.

In some embodiments, Compound 1 is an amorphous form of a salt or a co-crystal of Compound 1.

In some embodiments, Compound 1 is a crystalline form of a salt or a co-crystal of Compound 1. In some embodiments, the crystalline form of a salt or co-crystal of Compound I is: Compound 1 Sodium Form I, Compound 1 Sodium Form II, Compound 1 Calcium Form I, Compound 1 Magnesium Form I, Compound 1 Diethanolamine Form I, or Compound 1 Piperazine Form I.

The structure depicted for Compound 1 is also meant to include all tautomeric forms of Compound 1. Additionally structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that Compound 1 can exist in a variety of solid forms. Such forms include polymorphs, solvates, hydrates, and amorphous. All such forms are contemplated by the present invention. In certain embodiments, the present invention provides Compound 1 as a mixture of one or more solid forms selected from polymorphs, solvates, hydrates, and amorphous Compound 1.

Figure 18:
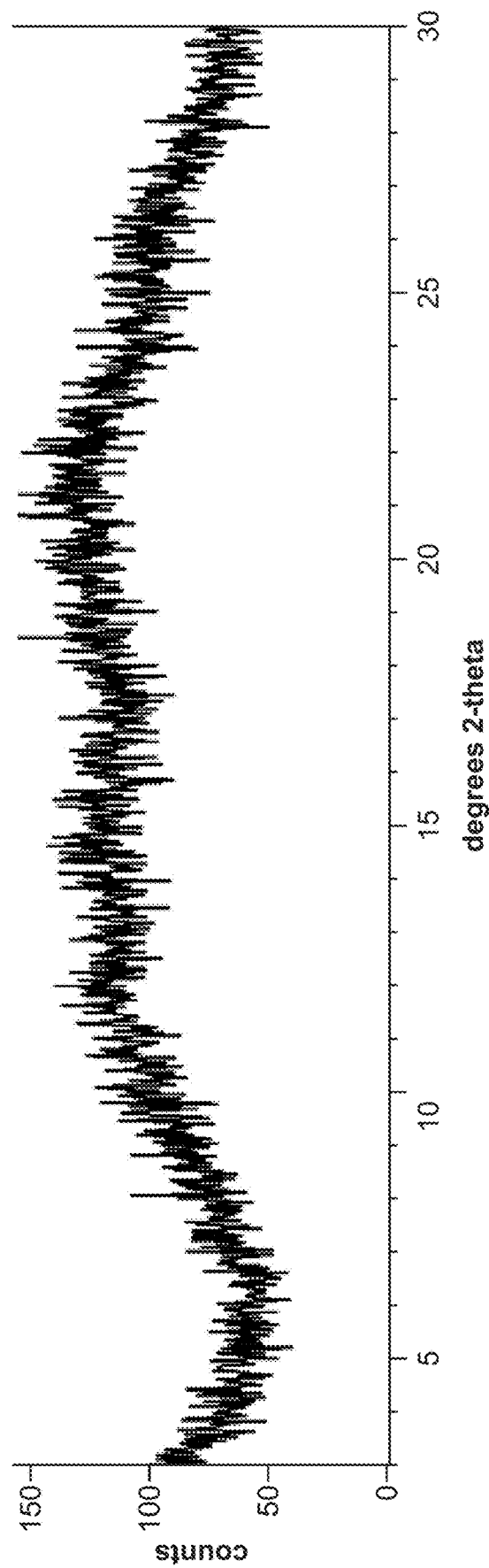
FIG. 18 depicts the X-Ray powder diffraction pattern of amorphous Compound 1.

In some embodiments, Compound 1 is an amorphous solid. FIG. 18 depicts the X-Ray powder diffraction pattern of amorphous Compound 1. In certain embodiments, the present invention provides Compound 1 as an amorphous solid substantially free of crystalline Compound 1. As used herein, the term "substantially free of crystalline Compound 1" means that the compound contains no significant amount of crystalline Compound 1. In certain embodiments, at least about 95% by weight of amorphous Compound 1 is present. In still other embodiments, of the invention, at least about 99% by weight of amorphous Compound 1 is present.

As used herein, the term "polymorph" refers to any of the different crystal structures in which a compound can crystallize. As used herein, the term "solvate" refers to a crystal form with either a stoichiometric or non-stoichiometric amount of solvent incorporated into the crystal structure. Similarly, the term "hydrate" refers specifically to a crystal form with either a stoichiometric or non-stoichiometric amount of water incorporated into the crystal structure.

In certain embodiments, Compound 1 is a crystalline solid. In some embodiments, Compound 1 is a crystalline solid substantially free of amorphous Compound 1. As used herein, the term "substantially free of amorphous Compound 1" means that the compound contains no significant amount of amorphous Compound 1. In certain embodiments, at least about 95% by weight of crystalline Compound 1 is present. In still other embodiments, of the invention, at least about 99% by weight of crystalline Compound 1 is present.

In some embodiments, Compound 1 is substantially free of any water or other solvent. In some embodiments, Compound 1 is a neat crystal form, and thus does not have any water or other solvent incorporated into its crystal structure. It has now been found that Compound 1 can exist in at least one distinct neat (i.e. anhydrous, non-solvate) crystal form. Such neat crystal forms of Compound 1 include Form I, Form VII, and Form VIII, each of which is described in detail herein.

In some embodiments, the present invention provides a solvated crystalline form of Compound 1. Such solvated crystalline forms of Compound 1 include Form II (DMF solvate), Form III (DMSO solvate), Form IV (methanol solvate), Form V (NMP solvate), and Form VI (toluene solvate).

In some embodiments, the present invention provides a crystalline form of Compound 1 selected from any of those referred to as Form I, Form II, Form III, Form IV, Form V, Form VI, Form VII, or Form VIII. Methods for preparing each of Forms I through VIII of Compound 1 are described herein.

In some embodiments, the present invention provides a polymorphic form of Compound 1 referred to as Form I.

In some embodiments, the present invention provides Form I of Compound 1, having a powder X-ray diffraction pattern substantially similar to that depicted in FIG. 1A.

As used herein, the term "about," when used in reference to a degree 2θ value refers to the stated value±0.1 degree 2θ, obtained under the sample preparation and data collection conditions described in the exemplification. In some embodiments, the term "about," when used in reference to a degree 2θ value refers to the stated value±0.2 degree 2θ. One of skill in the art will appreciate that changes in the particular XRPD acquisition parameters will affect the XRPD pattern and specific values of degrees 2θ obtained.

In some embodiments, Form I of Compound 1 is characterized in that it has one or more peaks in its powder X-ray diffraction pattern selected from those in Table 1 below.

TABLE 1

Compound 1 Form I XRPD Peaks

| Position (°2θ) | Height (cts) | Relative Intensity (%) |
| --- | --- | --- |
| 8.73 | 1552 | 6.83 |
| 9.23 | 22736 | 100 |
| 12.13 | 1828 | 8.04 |
| 12.28 | 1818 | 8.00 |
| 12.51 | 609 | 2.68 |
| 13.74 | 1245 | 5.48 |
| 14.74 | 2776 | 12.21 |
| 14.89 | 3143 | 13.82 |
| 15.83 | 1881 | 8.27 |
| 15.92 | 1400 | 6.16 |
| 17.19 | 2164 | 9.52 |
| 17.87 | 1294 | 5.69 |
| 18.32 | 1466 | 6.45 |
| 18.44 | 1556 | 6.84 |
| 19.11 | 1171 | 5.15 |
| 19.29 | 621 | 2.74 |
| 19.60 | 2289 | 10.07 |
| 19.91 | 359 | 1.58 |
| 20.74 | 561 | 2.47 |
| 21.04 | 528 | 2.32 |
| 22.49 | 919 | 4.04 |
| 23.85 | 964 | 4.24 |
| 23.96 | 1534 | 6.75 |
| 25.58 | 1762 | 7.75 |
| 27.00 | 541 | 2.38 |
| 27.29 | 957 | 4.21 |
| 28.17 | 454 | 2.00 |
| 28.58 | 512 | 2.26 |
| 28.92 | 339 | 1.49 |
| 35.54 | 242 | 1.06 |
| 38.91 | 131 | 0.58 |

In some embodiments, Form I of Compound 1 is characterized in that it has two or more peaks in its powder X-ray diffraction pattern selected from those in Table 1. In some embodiments, Form I of Compound 1 is characterized in that it has three or more peaks in its powder X-ray diffraction pattern selected from those in Table 1. In some embodiments, Form I of Compound 1 is characterized in that it has four or more peaks in its powder X-ray diffraction pattern selected from those in Table 1. In some embodiments, Form I of Compound 1 is characterized in that it has five or more peaks in its powder X-ray diffraction pattern selected from those in Table 1. In some embodiments, Form I of Compound 1 is characterized in that it has ten of the peaks in Table 1 in its X-ray diffraction pattern. In some embodiments, Form I of Compound 1 is characterized in that it has fifteen of the peaks in Table 1 in its X-ray diffraction pattern. In some embodiments, Form I of Compound 1 is characterized in that it has twenty of the peaks in Table 1 in its X-ray diffraction pattern. In some embodiments, Form I of Compound 1 is characterized in that it has all of the peaks in Table 1 in its X-ray diffraction pattern.

In some embodiments, Form I of Compound 1 is characterized in that it has one or more peaks in its powder X-ray diffraction pattern selected from those at about 12.51, about 14.89, about 17.19, about 19.11, about 19.91, about 28.58, and about 38.91 degrees 2θ. In some embodiments, Form I of Compound 1 is characterized in that it has two or more peaks in its powder X-ray diffraction pattern selected from those at about 12.51, about 14.89, about 17.19, about 19.11, about 19.91, about 28.58, and about 38.91 degrees 2θ. In some embodiments, Form I of Compound 1 is characterized in that it has three or more peaks in its powder X-ray diffraction pattern selected from those at about 12.51, about 14.89, about 17.19, about 19.11, about 19.91, about 28.58, and about 38.91 degrees 2θ. In some embodiments, Form I of Compound 1 is characterized in that it has four or more peaks in its powder X-ray diffraction pattern selected from those at about 12.51, about 14.89, about 17.19, about 19.11, about 19.91, about 28.58, and about 38.91 degrees 2θ. In some embodiments, Form I of Compound 1 is characterized in that it has five or more peaks in its powder X-ray diffraction pattern selected from those at about 12.51, about 14.89, about 17.19, about 19.11, about 19.91, about 28.58, and about 38.91 degrees 2θ. In some embodiments, Form I of Compound 1 is characterized in that it has six or more peaks in its powder X-ray diffraction pattern selected from those at about 12.51, about 14.89, about 17.19, about 19.11, about 19.91, about 28.58, and about 38.91 degrees 2θ. In some embodiments, Form I of Compound 1 is characterized in that it has all seven peaks in its powder X-ray diffraction pattern selected from those at about 12.51, about 14.89, about 17.19, about 19.11, about 19.91, about 28.58, and about 38.91 degrees 2θ.

In some embodiments, Form I of Compound 1 is characterized in that it has one or more peaks in its powder X-ray diffraction pattern selected from those at about 9.2, about 15.8, about 19.6, about 24.0, about 25.6, about 28.6, and about 8.7 degrees 2θ. In some embodiments, Form I of Compound 1 is characterized in that it has two or more peaks in its powder X-ray diffraction pattern selected from those at about 9.2, about 15.8, about 19.6, about 24.0, about 25.6, about 28.6, and about 8.7 degrees 2θ. In some embodiments, Form I of Compound 1 is characterized in that it has three or more peaks in its powder X-ray diffraction pattern selected from those at about 9.2, about 15.8, about 19.6, about 24.0, about 25.6, about 28.6, and about 8.7 degrees 2θ. In some embodiments, Form I of Compound 1 is characterized in that it has four or more peaks in its powder X-ray diffraction pattern selected from those at about 9.2, about 15.8, about 19.6, about 24.0, about 25.6, about 28.6, and about 8.7 degrees 2θ. In some embodiments, Form I of Compound 1 is characterized in that it has five or more peaks in its powder X-ray diffraction pattern selected from those at about 9.2, about 15.8, about 19.6, about 24.0, about 25.6, about 28.6, and about 8.7 degrees 2θ. In some embodiments, Form I of Compound 1 is characterized in that it has six or more peaks in its powder X-ray diffraction pattern selected from those at about 9.2, about 15.8, about 19.6, about 24.0, about 25.6, about 28.6, and about 8.7 degrees 2θ. In some embodiments, Form I of Compound 1 is characterized by an X-ray diffraction pattern comprising the following peaks: about 9.2, about 15.8, about 19.6, about 24.0, about 25.6, about 28.6, and about 8.7 degrees 2θ.

Figure 1B:
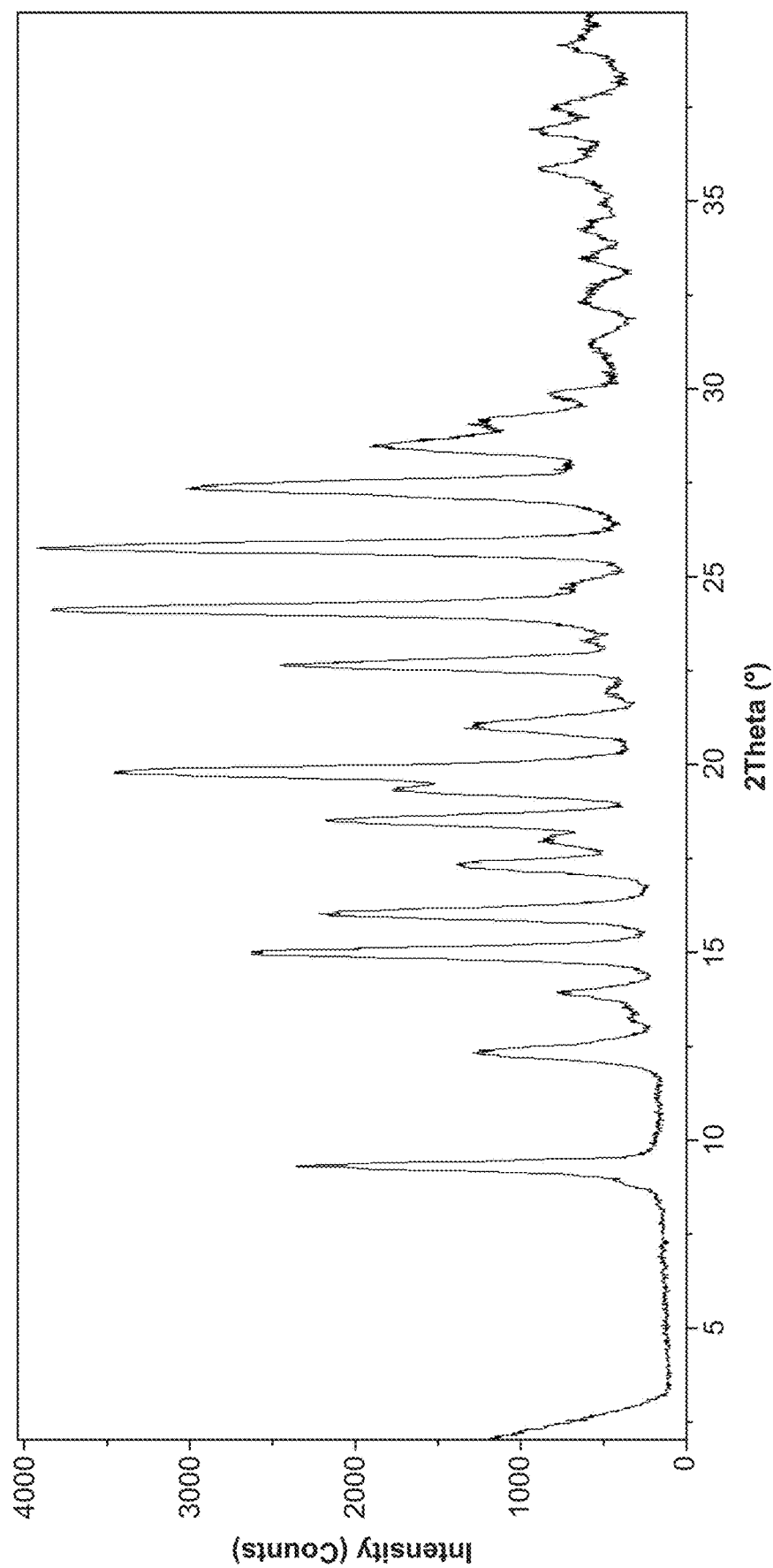
FIG. 1B depicts another X-Ray powder diffraction (XRPD) pattern of Form I of Compound 1.

In some embodiments, Form I is characterized by an X-ray powder diffractogram comprising the following peaks: 9.3, 15.0, and 19.8° 2θ±0.2° 2θ, as determined on a diffractometer using Cu-Kα radiation at a wavelength of 1.54 Å. In some embodiments, the diffractogram comprises additional peaks at 16.0, 24.0, 25.8, and 27.3° 2θ±0.2° 2θ. Compound 1 Form I is also characterized by its X-ray diffraction pattern as substantially shown in FIG. 1A. Compound 1 Form I is also characterized by its X-ray diffraction pattern as substantially shown in FIG. 1B.

Figure 2:
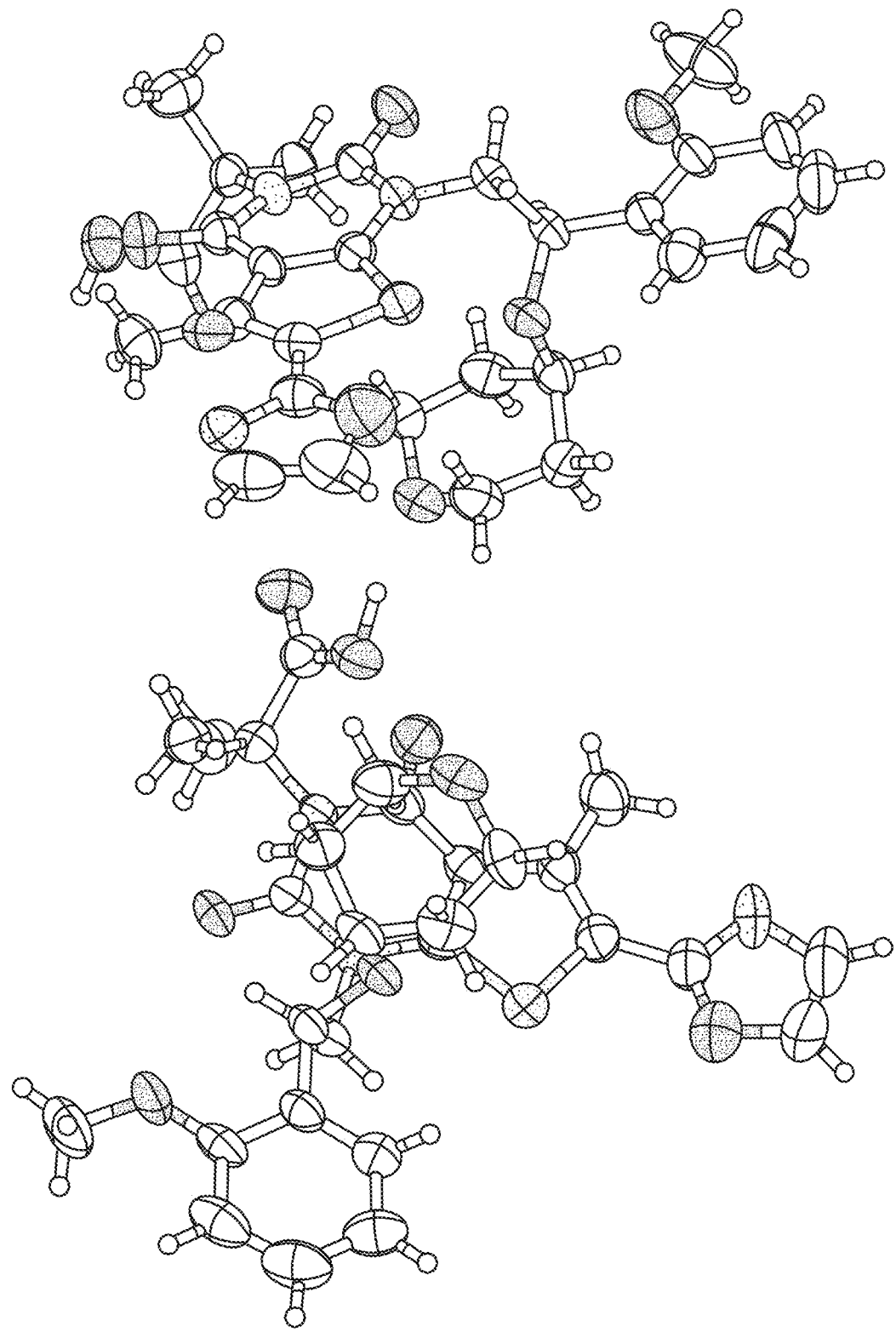
FIG. 2 depicts the ellipsoid diagram of Form I of Compound 1.

Form I of Compound 1 has been characterized via single crystal analysis and the data are summarized in Table 2 and the ellipsoid diagram is shown in FIG. 2.

TABLE 2

Crystal Data and Data Collection Parameters

| | |
|---|---|
| Empirical formula | $C_{28}H_{31}N_3O_8S$ |
| Formula weight (g mol − 1) | 569.62 |
| Temperature (K) | 293(2) |
| Wavelength (Å) | 1.54184 |
| Crystal system | orthorhombic |
| Space group | C2221 |
| Unit cell parameters | |
| a = 14.77743(18) Å | α = 90° |
| b = 14.62619(16) Å | β = 90° |
| c = 51.7778(8) Å | γ = 90° |
| Unit cell volume (Å3) | 11191.1(3) |
| Cell formula units, Z | 16 |
| Calculated density (g cm − 3) | 1.352 |
| Absorption coefficient (mm − 1) | 1.495 |
| F(000) | 4800 |
| Crystal size (mm3) | 0.19 × 0.13 × 0.06 |
| Reflections used for cell measurement | 15725 |
| θ range for cell measurement | 3.5010°-77.2150° |
| Total reflections collected | 29754 |
| Index ranges | −18 ≤ h ≤ 18; −14 ≤ k ≤ 18; −63≤l≤58 |
| θ range for data collection | θ min = 3.414°, θ max = 77.642° |
| Completeness to θ max | 98.2% |
| Completeness to θ full = 67.684° | 99.7% |
| Absorption correction | multi-scan |
| Transmission coefficient range | 0.918-1.000 |
| Refinement method | full matrix least-squares on Fsqd |
| Independent reflections | 11199 [Rint = 0.0330, Rσ = 0.0361] |
| Reflections [I > 2σ(I)] | 9830 |
| Reflections/restraints/parameters | 11199/0/737 |
| Goodness-of-fit on F2 | S = 1.05 |
| Final residuals [I > 2σ(I)] | R = 0.0446, Rw = 0.1187 |
| Final residuals [all reflections] | R = 0.0516, Rw = 0.1250 |
| Largest diff. peak and hole (e Å − 3) | 0.405, −0.297 |
| Max/mean shift/standard uncertainty | 0.001/0.000 |
| Absolute Structure Determination | Flack parameter: −0.007(8) Hooft parameter: −0.011(7) Friedel coverage: 88.7% |

Figure 3A:
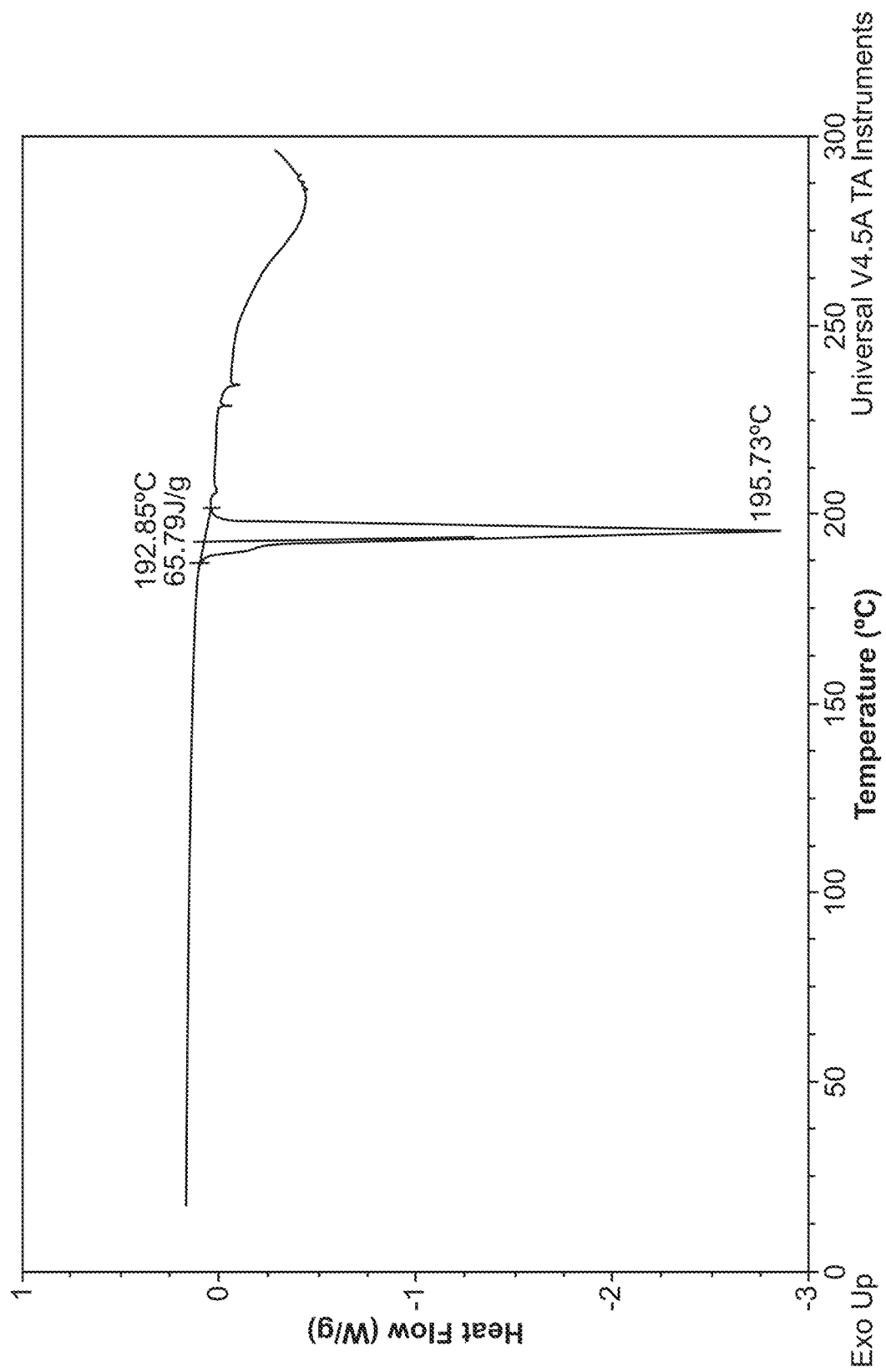
FIG. 3A depicts a differential scanning calorimeter (DSC) curve of Form I of Compound 1.
Figure 3B:
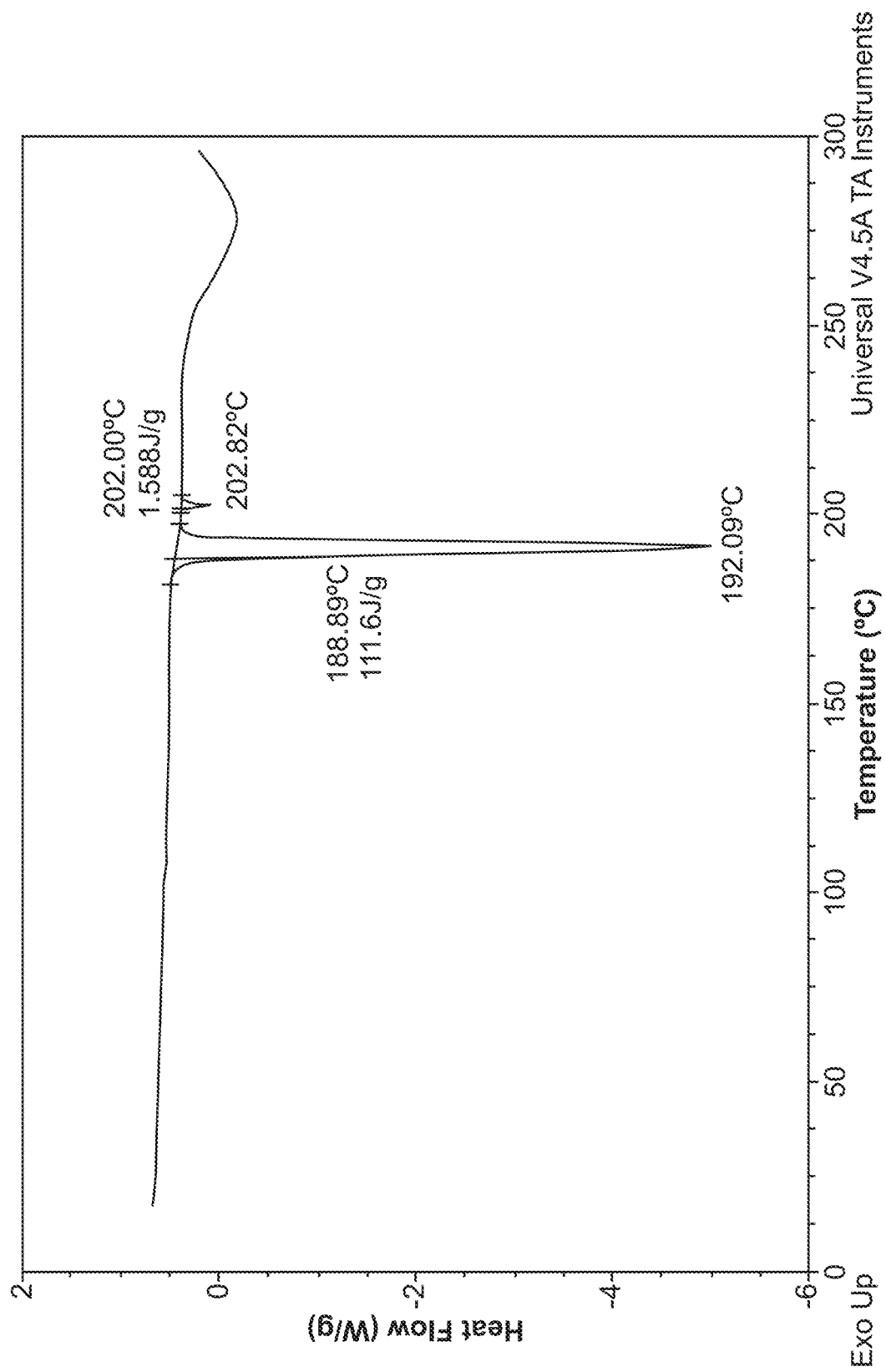
FIG. 3B depicts another differential scanning calorimeter (DSC) curve of Form I of Compound 1.

In some embodiments, Form I of Compound 1 is characterized by a differential scanning calorimetry (DSC) curve that comprises an endotherm between about 189° C. to about 193° C. Form I of Compound 1 is also characterized by its DSC curve as substantially shown in FIG. 3A. In some embodiments, Form I of Compound 1 is also characterized by its DSC curve as substantially shown in FIG. 3B.

Figure 4A:
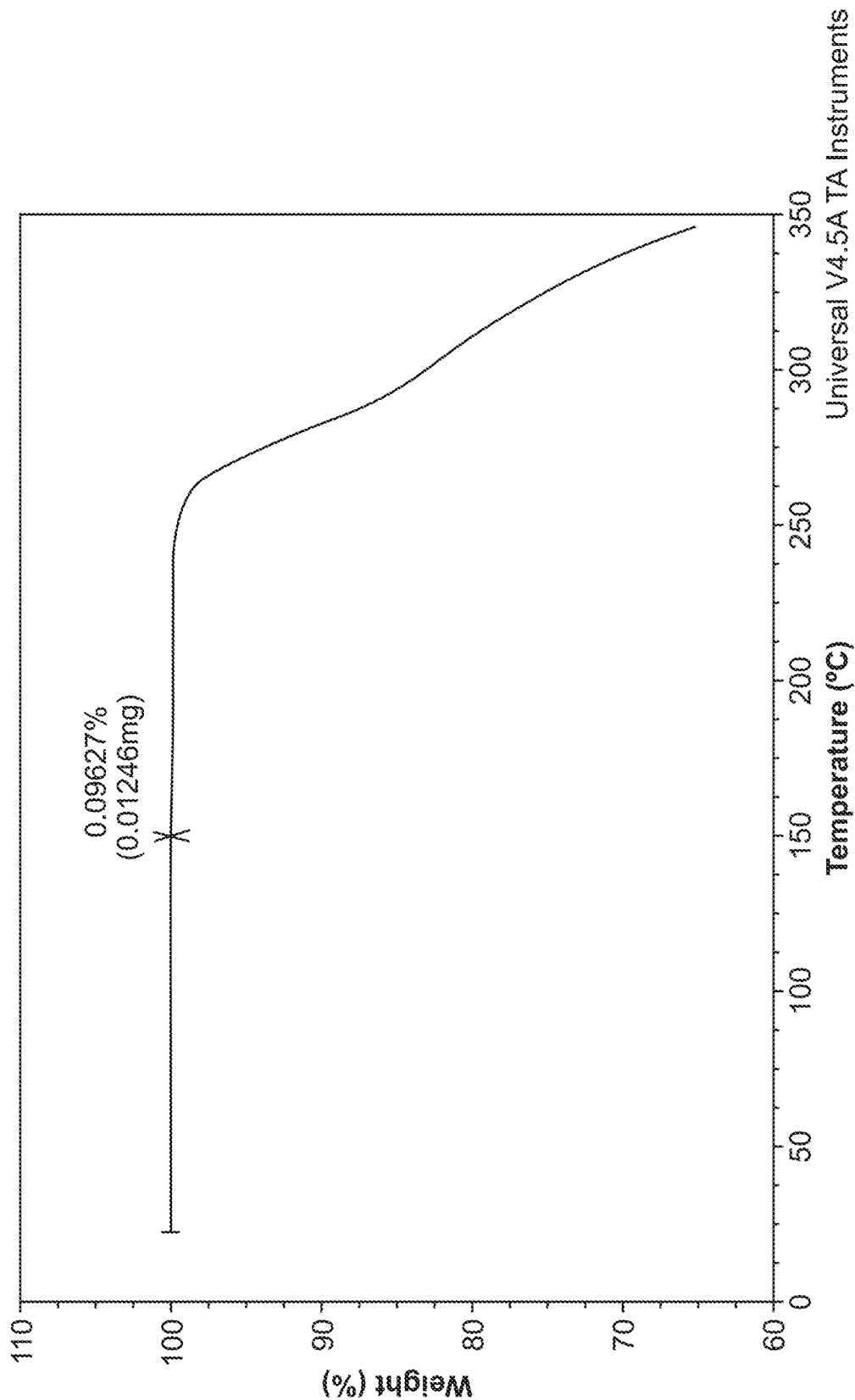
FIG. 4A depicts a thermogravimetric analysis (TGA) of Form I of Compound 1.
Figure 4B:
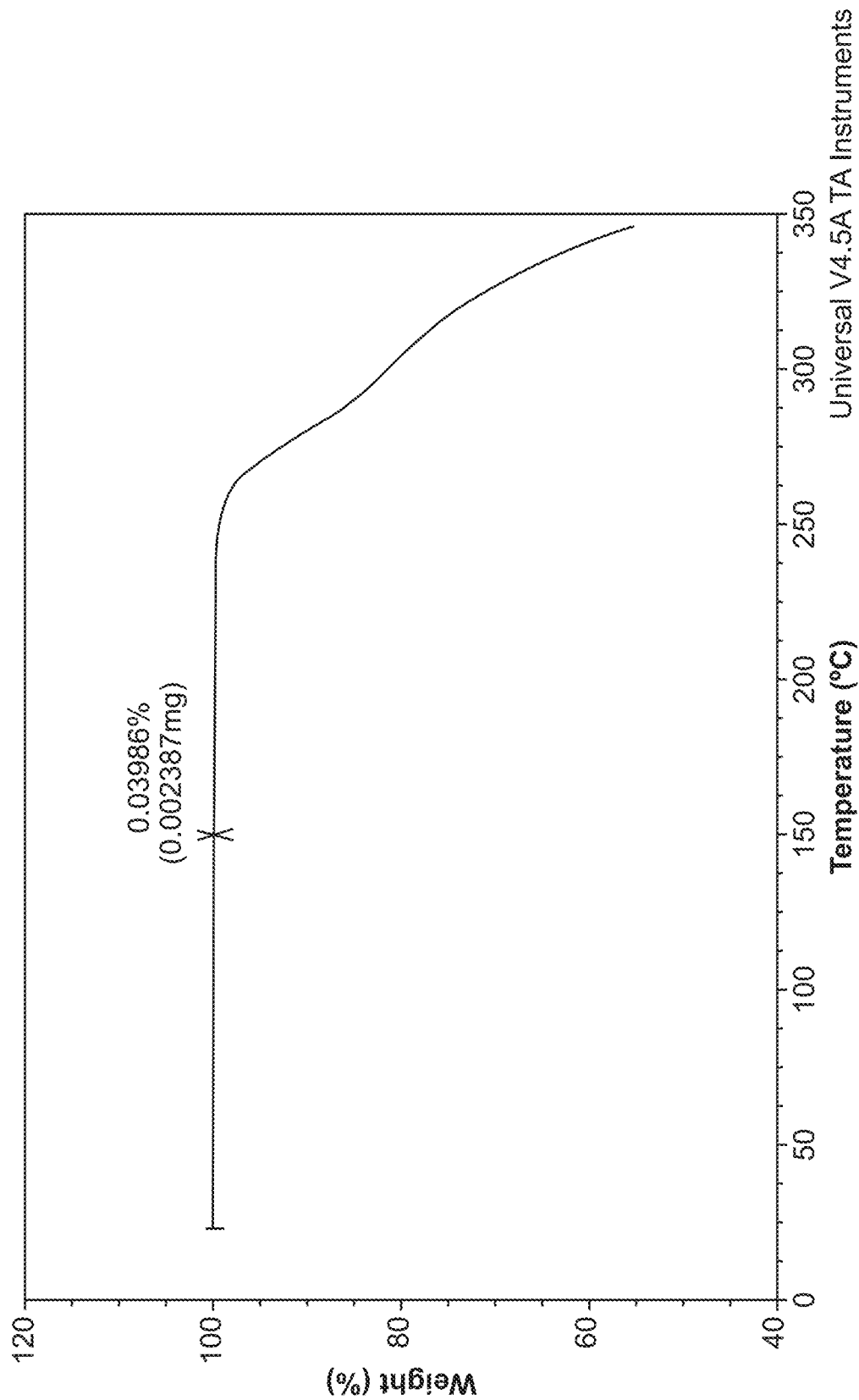
FIG. 4B depicts another thermogravimetric analysis (TGA) of Form I of Compound 1.

In some embodiments, Form I of Compound 1 is characterized by a thermogravimetric analysis (TGA) curve as substantially shown in FIG. 4A. In some embodiments, Form I of Compound 1 is characterized by a thermogravimetric analysis (TGA) curve as substantially shown in FIG. 4B.

In some embodiments, at least about 95% by weight of Form I of Compound 1 is present. In some embodiments, at least about 99% by weight of Form I of Compound 1 is present.

In some embodiments, the crystalline form is at least about 85% of Form I. In some embodiments, the crystalline form is at least about 90% of Form I. In some embodiments, the crystalline form is at least about 95% of Form I. In some embodiments, the crystalline form is at least about 99% of Form I. In some embodiments, the crystalline form is at least about 99.5% of Form I. In some embodiments, the crystalline form is at least about 99.9% of Form I. In some embodiments, the crystalline form is at least about 99.99% of Form I.

Some embodiments provide for a pharmaceutical composition comprising Compound 1 in Form I. In one embodiment, the pharmaceutical composition comprises Compound 1 wherein at least about 85% of Compound 1 is in Form I. In one embodiment, the pharmaceutical composition comprises Compound 1 wherein at least about 90% of Compound 1 is in Form I. In one embodiment, the pharmaceutical composition comprises Compound 1 wherein at least about 95% of Compound 1 is in Form I. In one embodiment, the pharmaceutical composition comprises Compound 1 wherein at least about 99% of Compound 1 is in Form I. In one embodiment, the pharmaceutical composition comprises Compound 1 wherein at least about 99.5% of Compound 1 is in Form I. In one embodiment, the pharmaceutical composition comprises Compound 1 wherein at least about 99.9% of Compound 1 is in Form I. In one embodiment, the pharmaceutical composition comprises Compound 1 wherein at least about 99.99% of Compound 1 is in Form I.

Figure 5:
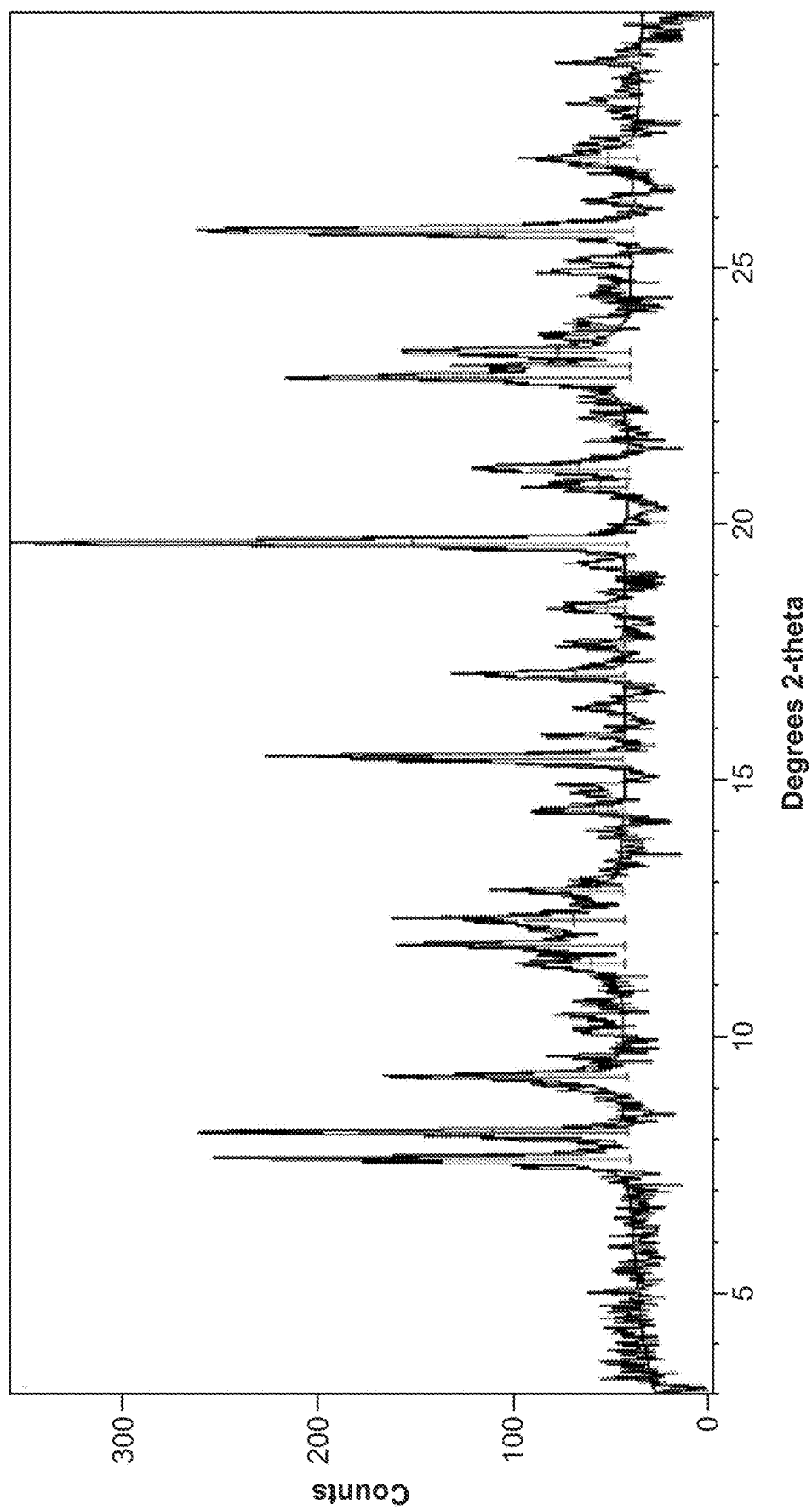
FIG. 5 depicts the X-Ray powder diffraction pattern of Form II of Compound 1.

In some embodiments, the present invention provides a solvated crystalline form of Compound 1 referred to as Form II. In some embodiments, the present invention provides Form II of Compound 1, having a powder X-ray diffraction pattern substantially similar to that depicted in FIG. 5. In some embodiments, Form II of Compound 1 is characterized in that it has one or more peaks in its powder X-ray diffraction pattern selected from those in Table 3 below.

TABLE 3

Compound 1 Form II XRPD Peaks

| Position (°2θ) | Height (cts) | Relative Intensity (%) |
|---|---|---|
| 7.56 | 124.9 | 57.7 |
| 8.09 | 137.8 | 63.7 |
| 9.18 | 77.0 | 35.6 |
| 11.34 | 34.6 | 16.0 |
| 11.74 | 75.6 | 35.0 |
| 12.21 | 51.9 | 24.0 |
| 12.80 | 35.1 | 16.2 |
| 14.37 | 31.6 | 14.6 |
| 15.38 | 96.4 | 44.6 |
| 15.80 | 28.8 | 13.3 |
| 17.01 | 50.8 | 23.5 |
| 17.56 | 30.2 | 14.0 |
| 18.30 | 20.3 | 9.4 |
| 19.56 | 216.3 | 100.0 |
| 20.67 | 28.6 | 13.2 |

TABLE 3-continued

Compound 1 Form II XRPD Peaks

| Position (°2θ) | Height (cts) | Relative Intensity (%) |
|---|---|---|
| 21.00 | 50.3 | 23.2 |
| 22.77 | 128.2 | 59.3 |
| 23.00 | 44.7 | 20.7 |
| 23.29 | 73.6 | 34.0 |
| 25.62 | 159.8 | 73.9 |
| 26.23 | 14.2 | 6.6 |
| 27.05 | 30.4 | 14.0 |
| 28.92 | 31.5 | 14.6 |

In some embodiments, Form II of Compound 1 is characterized in that it has two or more peaks in its powder X-ray diffraction pattern selected from those in Table 3. In some embodiments, Form II of Compound 1 is characterized in that it has three or more peaks in its powder X-ray diffraction pattern selected from those in Table 3. In some embodiments, Form II of Compound 1 is characterized in that it has four or more peaks in its powder X-ray diffraction pattern selected from those in Table 3. In some embodiments, Form II of Compound 1 is characterized in that it has five or more peaks in its powder X-ray diffraction pattern selected from those in Table 3. In some embodiments, Form II of Compound 1 is characterized in that it has all of the peaks in Table 3 in its X-ray diffraction pattern.

In some embodiments, Form II of Compound 1 is characterized in that it has one or more peaks in its powder X-ray diffraction pattern selected from those at about 7.56, about 8.09, about 11.34, about 11.74, about 14.37, about 15.38, about 17.56, and about 23.00 degrees 2θ. In some embodiments, Form II of Compound 1 is characterized in that it has two or more peaks in its powder X-ray diffraction pattern selected from those at about 7.56, about 8.09, about 11.34, about 11.74, about 14.37, about 15.38, about 17.56, and about 23.00 degrees 2θ. In some embodiments, Form II of Compound 1 is characterized in that it has three or more peaks in its powder X-ray diffraction pattern selected from those at about 7.56, about 8.09, about 11.34, about 11.74, about 14.37, about 15.38, about 17.56, and about 23.00 degrees 2θ. In some embodiments, Form II of Compound 1 is characterized in that it has four or more peaks in its powder X-ray diffraction pattern selected from those at about 7.56, about 8.09, about 11.34, about 11.74, about 14.37, about 15.38, about 17.56, and about 23.00 degrees 2θ. In some embodiments, Form II of Compound 1 is characterized in that it has five or more peaks in its powder X-ray diffraction pattern selected from those at about 7.56, about 8.09, about 11.34, about 11.74, about 14.37, about 15.38, about 17.56, and about 23.00 degrees 2θ. In some embodiments, Form II of Compound 1 is characterized in that it has six or more peaks in its powder X-ray diffraction pattern selected from those at about 7.56, about 8.09, about 11.34, about 11.74, about 14.37, about 15.38, about 17.56, and about 23.00 degrees 2θ. In some embodiments, Form II of Compound 1 is characterized in that it has seven or more peaks in its powder X-ray diffraction pattern selected from those at about 7.56, about 8.09, about 11.34, about 11.74, about 14.37, about 15.38, about 17.56, and about 23.00 degrees 2θ. In some embodiments, Form II of Compound 1 is characterized in that it has all eight peaks in its powder X-ray diffraction pattern selected from those at about 7.56, about 8.09, about 11.34, about 11.74, about 14.37, about 15.38, about 17.56, and about 23.00 degrees 2θ.

In some embodiments, Form II of Compound 1 is characterized in that it has one or more peaks in its powder X-ray diffraction pattern selected from those at about 12.2, about 12.8, about 17.0, about 19.6, about 21.0, and about 22.8 degrees 2θ.

Figure 6:
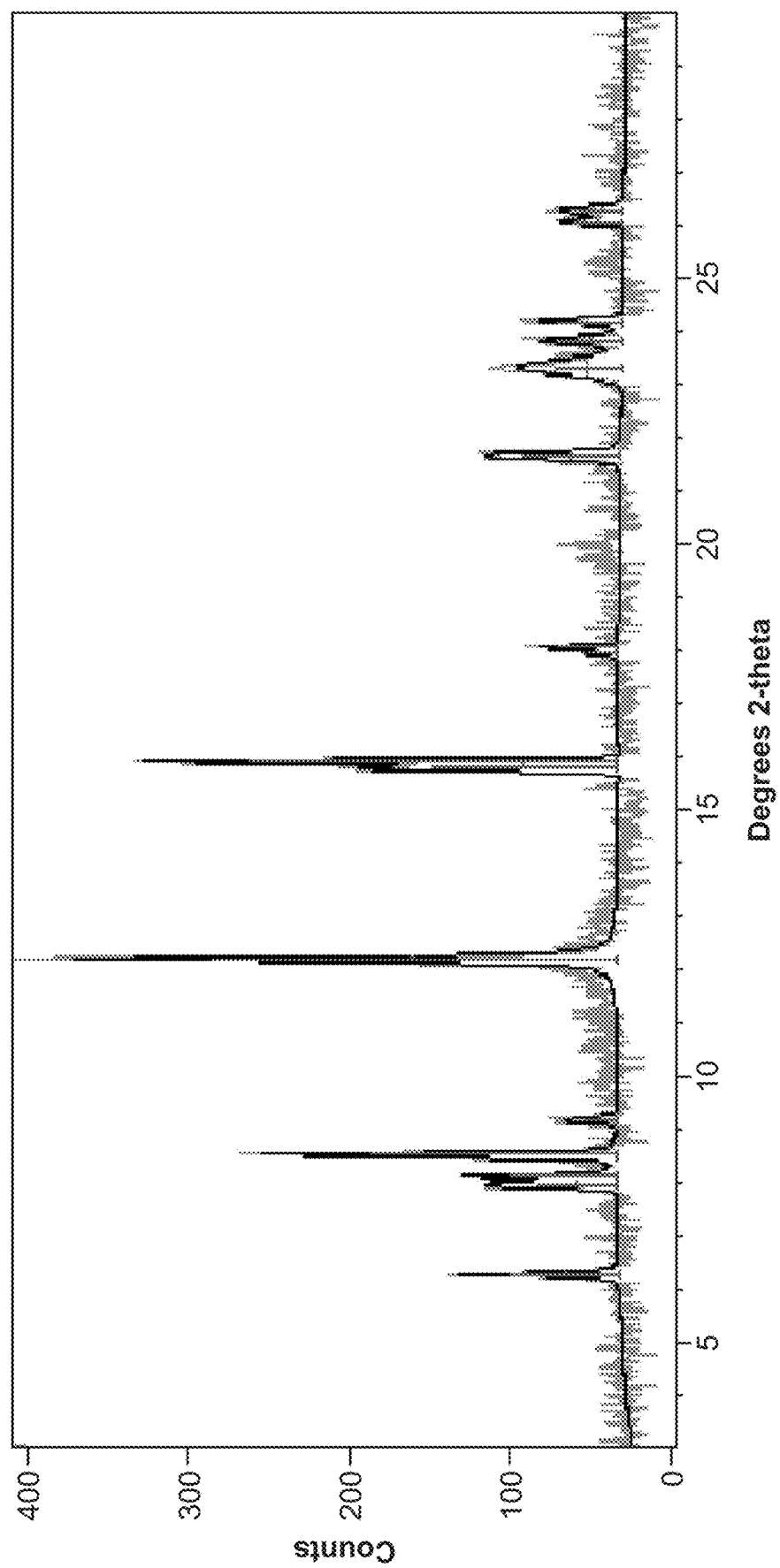
FIG. 6 depicts the X-Ray powder diffraction pattern of Form III of Compound 1.

In some embodiments, the present invention provides a solvated crystalline form of Compound 1 referred to as Form III. In some embodiments, the present invention provides Form III of Compound 1, having a powder X-ray diffraction pattern substantially similar to that depicted in FIG. 6. In some embodiments, Form III of Compound 1 is characterized in that it has one or more peaks in its powder X-ray diffraction pattern selected from those in Table 4 below.

TABLE 4

Compound 1 Form III XRPD Peaks

| Position (°2θ) | Height (cts) | Relative Intensity (%) |
|---|---|---|
| 6.27 | 38.8 | 27.5 |
| 7.95 | 51.2 | 20.5 |
| 8.10 | 67.3 | 26.9 |
| 8.50 | 153.5 | 61.4 |
| 9.16 | 21.4 | 8.6 |
| 12.18 | 250.2 | 100.0 |
| 15.76 | 114.7 | 45.8 |
| 15.88 | 227.1 | 90.8 |
| 17.89 | 18.7 | 7.5 |
| 18.02 | 38.7 | 15.5 |
| 21.61 | 61.2 | 24.5 |
| 23.27 | 42.9 | 17.1 |
| 23.78 | 39.1 | 15.6 |
| 24.14 | 41.3 | 16.5 |
| 26.00 | 33.3 | 13.3 |
| 26.21 | 28.0 | 11.2 |

In some embodiments, Form III of Compound 1 is characterized in that it has two or more peaks in its powder X-ray diffraction pattern selected from those in Table 4. In some embodiments, Form III of Compound 1 is characterized in that it has three or more peaks in its powder X-ray diffraction pattern selected from those in Table 4. In some embodiments, Form III of Compound 1 is characterized in that it has four or more peaks in its powder X-ray diffraction pattern selected from those in Table 4. In some embodiments, Form III of Compound 1 is characterized in that it has five or more peaks in its powder X-ray diffraction pattern selected from those in Table 4. In some embodiments, Form III of Compound 1 is characterized in that it has all of the peaks in in Table 4 in its X-ray diffraction pattern.

In some embodiments, Form III of Compound 1 is characterized in that it has one or more peaks in its powder X-ray diffraction pattern selected from those at about 6.27, about 18.02, about 21.61, and about 24.14 degrees 2θ. In some embodiments, Form III of Compound 1 is characterized in that it has two or more peaks in its powder X-ray diffraction pattern selected from those at about 6.27, about 18.02, about 21.61, and about 24.14 degrees 2θ. In some embodiments, Form III of Compound 1 is characterized in that it has three or more peaks in its powder X-ray diffraction pattern selected from those at about 6.27, about 18.02, about 21.61, and about 24.14 degrees 2θ. In some embodiments, Form III of Compound 1 is characterized in that it has all four peaks in its powder X-ray diffraction pattern selected from those at about 6.27, about 18.02, about 21.61, and about 24.14 degrees 2θ.

In some embodiments, Form III of Compound 1 is characterized in that it has one or more peaks in its powder X-ray diffraction pattern selected from those at about 6.3, about 8.5, about 12.2, about 15.9, and about 21.6 degrees 2θ.

Figure 7A:
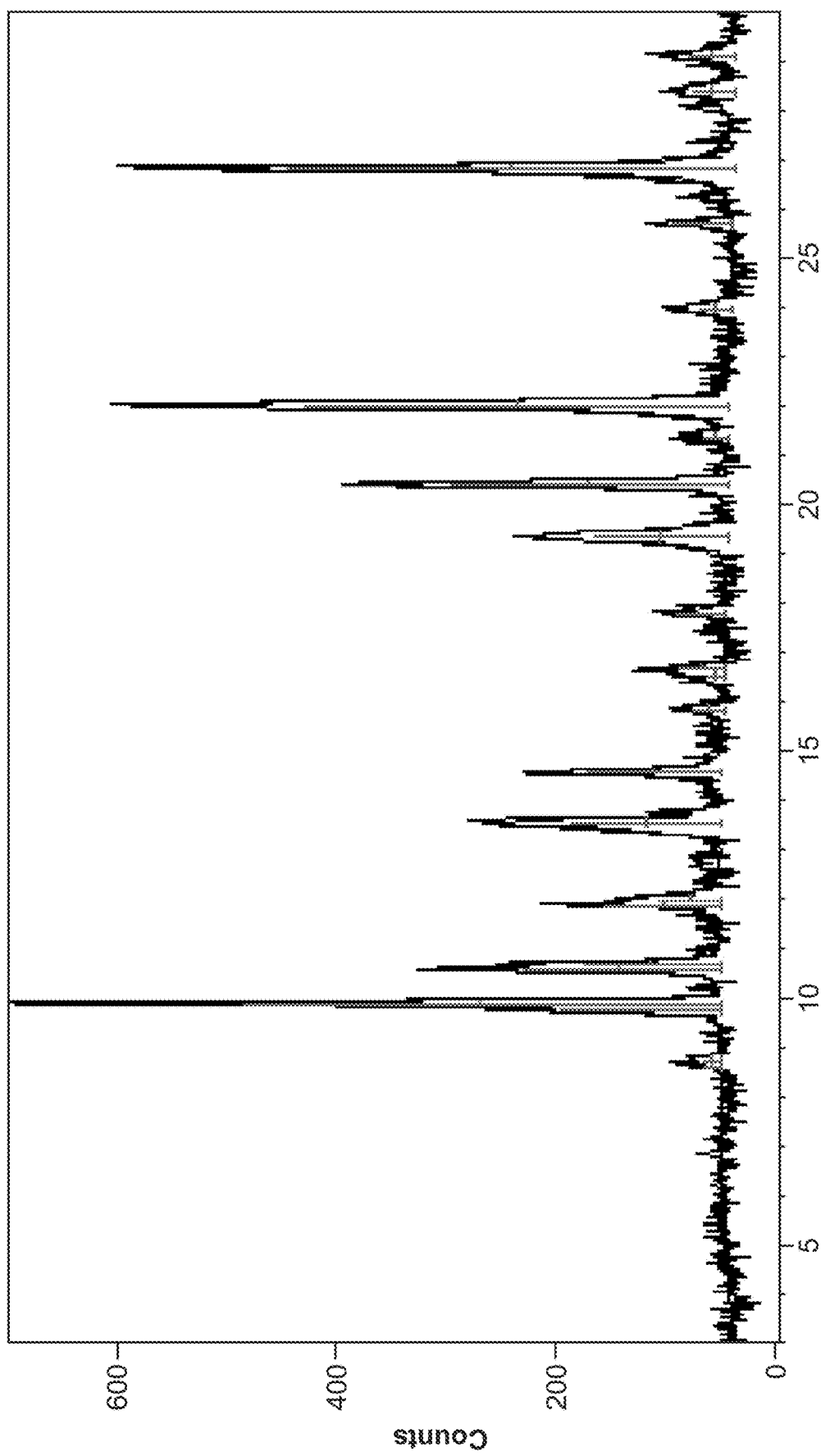
FIG. 7A depicts a X-Ray powder diffraction pattern of Form IV of Compound 1.
Figure 7B:
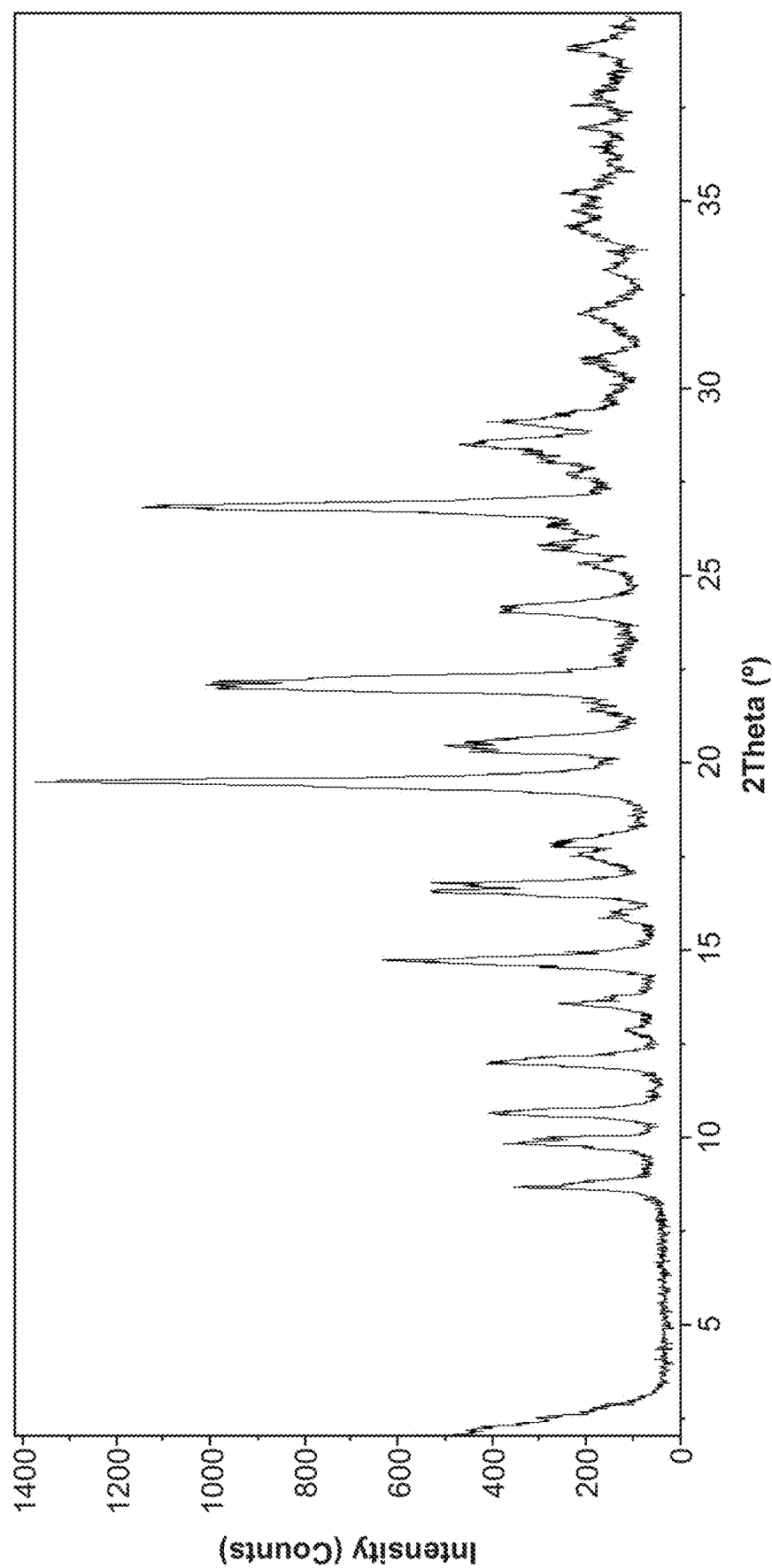
FIG. 7B depicts another X-Ray powder diffraction pattern of Form IV of Compound 1.

In some embodiments, the present invention provides a solvated crystalline form of Compound 1 referred to as Form IV. In some embodiments, the present invention provides Form IV of Compound 1, having a powder X-ray diffraction pattern substantially similar to that depicted in FIG. 7A. In some embodiments, the present invention provides Form IV of Compound 1, having a powder X-ray diffraction pattern substantially similar to that depicted in FIG. 7B. In some embodiments, Form IV of Compound 1 is characterized in that it has one or more peaks in its powder X-ray diffraction pattern selected from those listed in Table 5 below.

TABLE 5

Compound 1 Form IV XRPD Peaks

| Position (°2θ) | Height (cts) | Relative Intensity (%) |
| --- | --- | --- |
| 8.60 | 18.2 | 4.2 |
| 8.73 | 19.6 | 4.5 |
| 9.73 | 147.8 | 34.0 |
| 9.88 | 435.1 | 100 |
| 10.56 | 183.9 | 42.3 |
| 10.70 | 127.6 | 29.3 |
| 11.86 | 107.8 | 24.8 |
| 11.97 | 58.2 | 13.4 |
| 13.50 | 139.5 | 32.1 |
| 14.54 | 126.5 | 29.1 |
| 15.80 | 29.7 | 6.8 |
| 16.46 | 19.2 | 4.4 |
| 16.62 | 41.5 | 9.5 |
| 17.74 | 46.1 | 10.6 |
| 19.30 | 120.7 | 27.7 |
| 20.36 | 253.3 | 58.2 |
| 21.30 | 24.6 | 5.7 |
| 21.94 | 385.6 | 88.6 |
| 23.90 | 30.7 | 7.1 |
| 25.61 | 55.5 | 12.8 |
| 26.72 | 405.3 | 93.2 |
| 28.28 | 41.3 | 9.5 |
| 29.02 | 43.2 | 9.9 |

In some embodiments, Form IV of Compound 1 is characterized in that it has two or more peaks in its powder X-ray diffraction pattern selected from those in Table 5. In some embodiments, Form IV of Compound 1 is characterized in that it has three or more peaks in its powder X-ray diffraction pattern selected from those in Table 5. In some embodiments, Form IV of Compound 1 is characterized in that it has four or more peaks in its powder X-ray diffraction pattern selected from those in Table 5. In some embodiments, Form IV of Compound 1 is characterized in that it has five or more peaks in its powder X-ray diffraction pattern selected from those in Table 5. In some embodiments, Form IV of Compound 1 is characterized in that it has all of the peaks in Table 5 in its X-ray diffraction pattern.

In some embodiments, Form IV of Compound 1 is characterized in that it has one or more peaks in its powder X-ray diffraction pattern selected from those at about 9.73, about 9.88, about 10.56, about 10.70, about 11.86, about 11.97, about 14.54, about 16.62, about 21.30, about 21.94, and about 26.72 degrees 2θ. In some embodiments, Form IV of Compound 1 is characterized in that it has two or more peaks in its powder X-ray diffraction pattern selected from those at about 9.73, about 9.88, about 10.56, about 10.70, about 11.86, about 11.97, about 14.54, about 16.62, about 21.30, about 21.94, and about 26.72 degrees 2θ. In some embodiments, Form IV of Compound 1 is characterized in that it has three or more peaks in its powder X-ray diffraction pattern selected from those at about 9.73, about 9.88, about 10.56, about 10.70, about 11.86, about 11.97, about 14.54, about 16.62, about 21.30, about 21.94, and about 26.72 degrees 2θ. In some embodiments, Form IV of Compound 1 is characterized in that it has four or more peaks in its powder X-ray diffraction pattern selected from those at about 9.73, about 9.88, about 10.56, about 10.70, about 11.86, about 11.97, about 14.54, about 16.62, about 21.30, about 21.94, and about 26.72 degrees 2θ. In some embodiments, Form IV of Compound 1 is characterized in that it has five or more peaks in its powder X-ray diffraction pattern selected from those at about 9.73, about 9.88, about 10.56, about 10.70, about 11.86, about 11.97, about 14.54, about 16.62, about 21.30, about 21.94, and about 26.72 degrees 2θ. In some embodiments, Form IV of Compound 1 is characterized in that it has six or more peaks in its powder X-ray diffraction pattern selected from those at about 9.73, about 9.88, about 10.56, about 10.70, about 11.86, about 11.97, about 14.54, about 16.62, about 21.30, about 21.94, and about 26.72 degrees 2θ. In some embodiments, Form IV of Compound 1 is characterized in that it has seven or more peaks in its powder X-ray diffraction pattern selected from those at about 9.73, about 9.88, about 10.56, about 10.70, about 11.86, about 11.97, about 14.54, about 16.62, about 21.30, about 21.94, and about 26.72 degrees 2θ. In some embodiments, Form IV of Compound 1 is characterized in that it has nine or more peaks in its powder X-ray diffraction pattern selected from those at about 9.73, about 9.88, about 10.56, about 10.70, about 11.86, about 11.97, about 14.54, about 16.62, about 21.30, about 21.94, and about 26.72 degrees 2θ. In some embodiments, Form IV of Compound 1 is characterized in that it has ten or more peaks in its powder X-ray diffraction pattern selected from those at about 9.73, about 9.88, about 10.56, about 10.70, about 11.86, about 11.97, about 14.54, about 16.62, about 21.30, about 21.94, and about 26.72 degrees 2θ. In some embodiments, Form IV of Compound 1 is characterized in that it has all eleven peaks in its powder X-ray diffraction pattern selected from those at about 9.73, about 9.88, about 10.56, about 10.70, about 11.86, about 11.97, about 14.54, about 16.62, about 21.30, about 21.94, and about 26.72 degrees 2θ.

In some embodiments, Form IV of Compound 1 is characterized in that it has one or more peaks in its powder X-ray diffraction pattern selected from those at about 9.9, about 10.6, about 11.9, about 14.5, about 16.6, about 21.9, and about 26.7 degrees 2θ.

In some embodiments, Form IV of Compound 1 is characterized by an X-ray powder diffractogram comprising the following peaks: 9.9, 10.7, 19.5, 22.0, and 26.8° 2θ±0.2° 2θ, as determined on a diffractometer using Cu-Kα radiation at a wavelength of 1.54 Å. The diffractogram comprises additional peaks at 8.7, 12.0, and 14.7° 2θ±0.2° 2θ. Compound 1 Form IV is also characterized by its X-ray diffraction pattern as substantially shown in FIG. 7A. Compound 1 Form IV is also characterized by its X-ray diffraction pattern as substantially shown in FIG. 7B.

Figure 8:
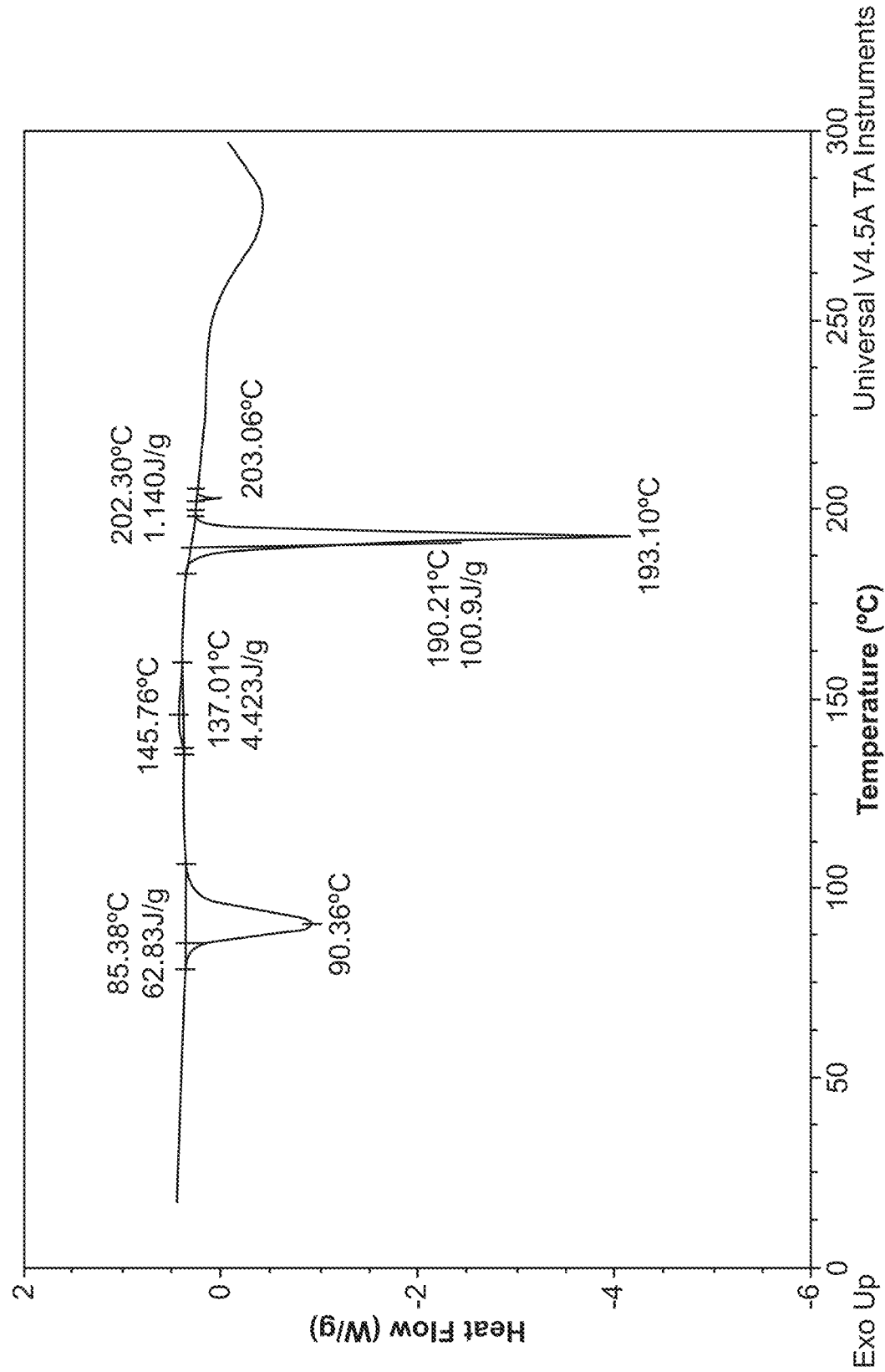
FIG. 8 depicts the differential scanning calorimeter (DSC) curve of Form IV of Compound 1.

In some embodiments, Form IV of Compound 1 is characterized by a differential scanning calorimetry (DSC) curve that comprises an endotherms at 85 and 190 and 202° C. and exotherm at 146° C. Form IV of Compound 1 is also characterized by its DSC curve as substantially shown in FIG. 8.

Figure 9:
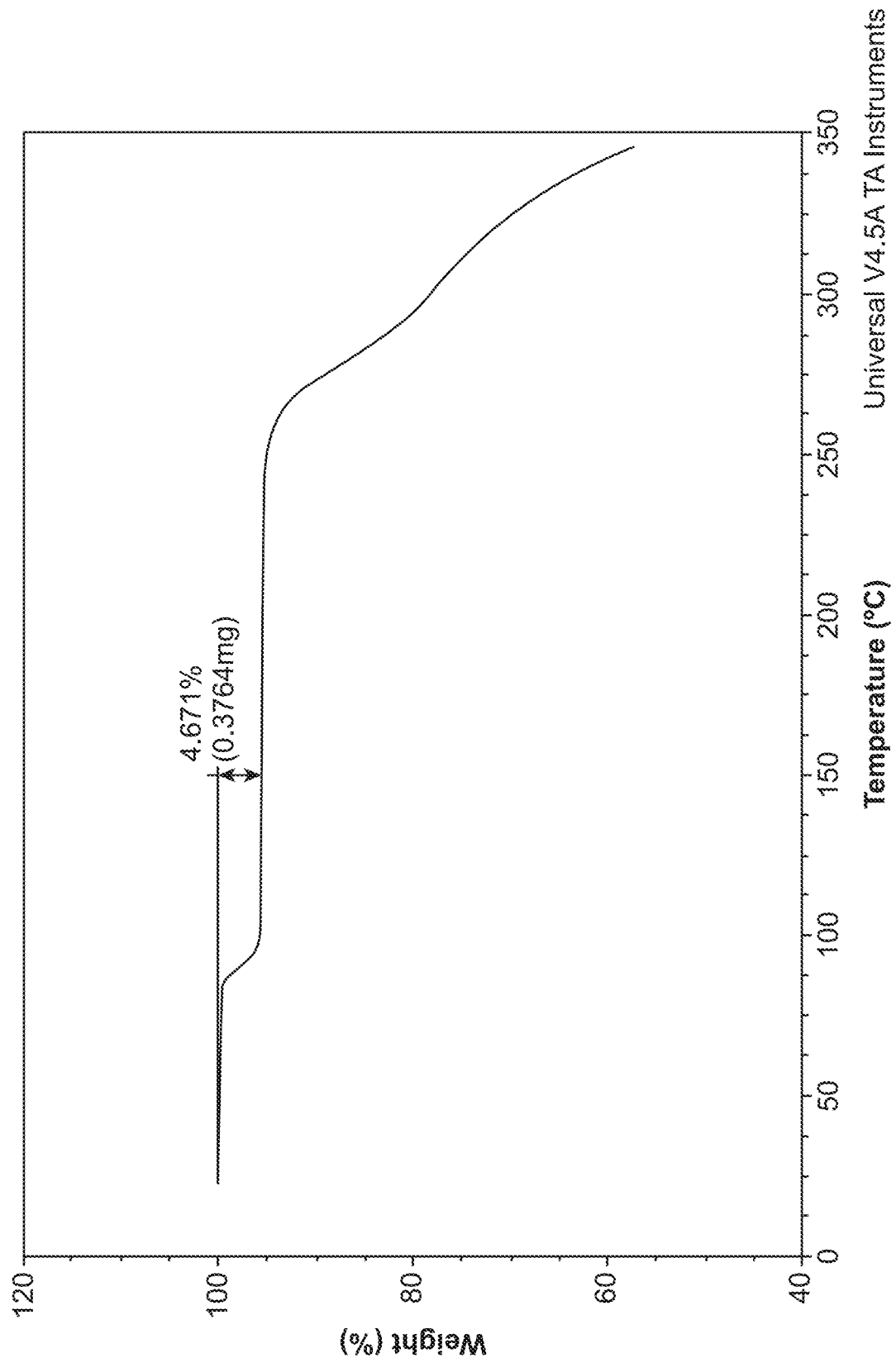
FIG. 9 depicts the thermogravimetric analysis (TGA) of Form IV of Compound 1.

In some embodiments, Form IV of Compound 1 is characterized by a thermogravimetric analysis (TGA) curve as substantially shown in FIG. 9.

Figure 10:
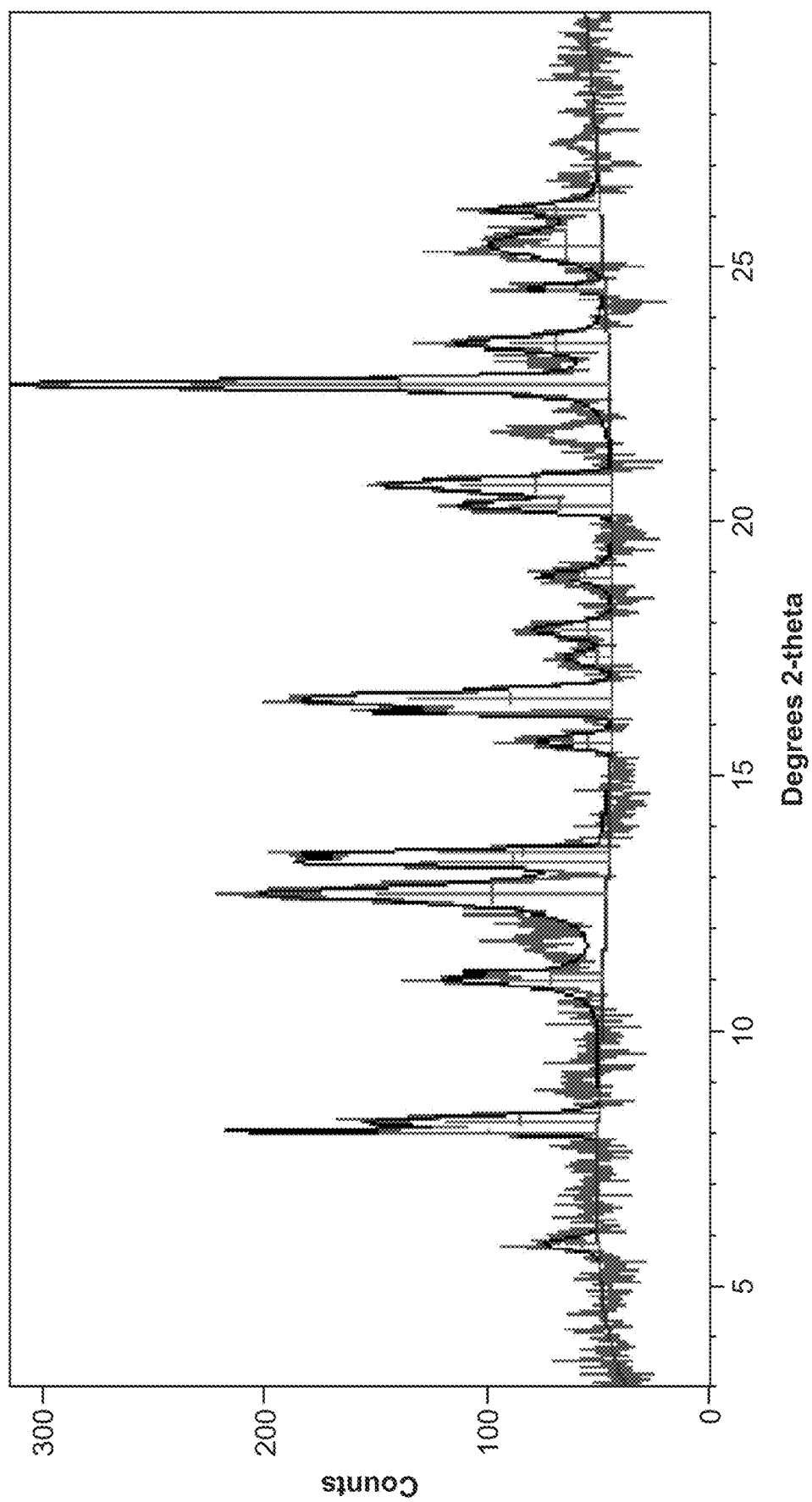
FIG. 10 depicts the X-Ray powder diffraction pattern of Form V of Compound 1.

In some embodiments, the present invention provides a solvated crystalline form of Compound 1 referred to as Form V. In some embodiments, the present invention provides Form V of Compound 1, having a powder X-ray diffraction pattern substantially similar to that depicted in FIG. 10. In some embodiments, Form V of Compound 1 is characterized in that it has one or more peaks in its powder X-ray diffraction pattern selected from those in Table 6 below.

TABLE 6

Compound 1 Form V XRPD Peaks

| Position (°2θ) | Height (cts) | Relative Intensity (%) |
|---|---|---|
| 5.85 | 16.3 | 9 |
| 8.03 | 98.6 | 52 |
| 8.23 | 70.0 | 37 |
| 11.02 | 47.7 | 25 |
| 11.15 | 24.2 | 13 |
| 12.69 | 104.3 | 55 |
| 13.34 | 85.9 | 45 |
| 13.50 | 77.2 | 41 |
| 15.68 | 22.3 | 12 |
| 16.23 | 75.1 | 40 |
| 16.28 | 37.2 | 20 |
| 16.51 | 92.8 | 49 |
| 17.32 | 14.6 | 8 |
| 17.87 | 24.0 | 13 |
| 18.93 | 26.0 | 14 |
| 20.29 | 47.2 | 25 |
| 20.69 | 69.6 | 37 |
| 22.66 | 189.4 | 100 |
| 23.47 | 45.9 | 24 |
| 24.56 | 27.3 | 14 |
| 25.40 | 33.4 | 18 |
| 26.08 | 40.3 | 21 |

In some embodiments, Form V of Compound 1 is characterized in that it has two or more peaks in its powder X-ray diffraction pattern selected from those in Table 6. In some embodiments, Form V of Compound 1 is characterized in that it has three or more peaks in its powder X-ray diffraction pattern selected from those in Table 6. In some embodiments, Form V of Compound 1 is characterized in that it has four or more peaks in its powder X-ray diffraction pattern selected from those in Table 6. In some embodiments, Form V of Compound 1 is characterized in that it has five or more peaks in its powder X-ray diffraction pattern selected from those in Table 6. In some embodiments, Form V of Compound 1 is characterized in that it has all of the peaks in Table 6 in its X-ray diffraction pattern.

In some embodiments, Form V of Compound 1 is characterized in that it has one or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has two or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has three or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has four or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has five or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has six or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has seven or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has eight or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has nine or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has ten or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has eleven or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has twelve or more peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ. In some embodiments, Form V of Compound 1 is characterized in that it has all thirteen peaks in its powder X-ray diffraction pattern selected from those at about 5.85, about 8.23, about 11.02, about 11.15, about 12.69, about 13.34, about 16.23, about 16.28, about 17.32, about 18.93, about 23.47, about 24.56, and about 25.40 degrees 2θ.

In some embodiments, Form V of Compound 1 is characterized in that it has one or more peaks in its powder X-ray diffraction pattern selected from those at about 8.0, about 11.0, about 12.7, about 13.3, about 16.3, about 17.9, about 20.3, about 22.6, about 23.5, and about 24.6 degrees 2θ.

Figure 11A:
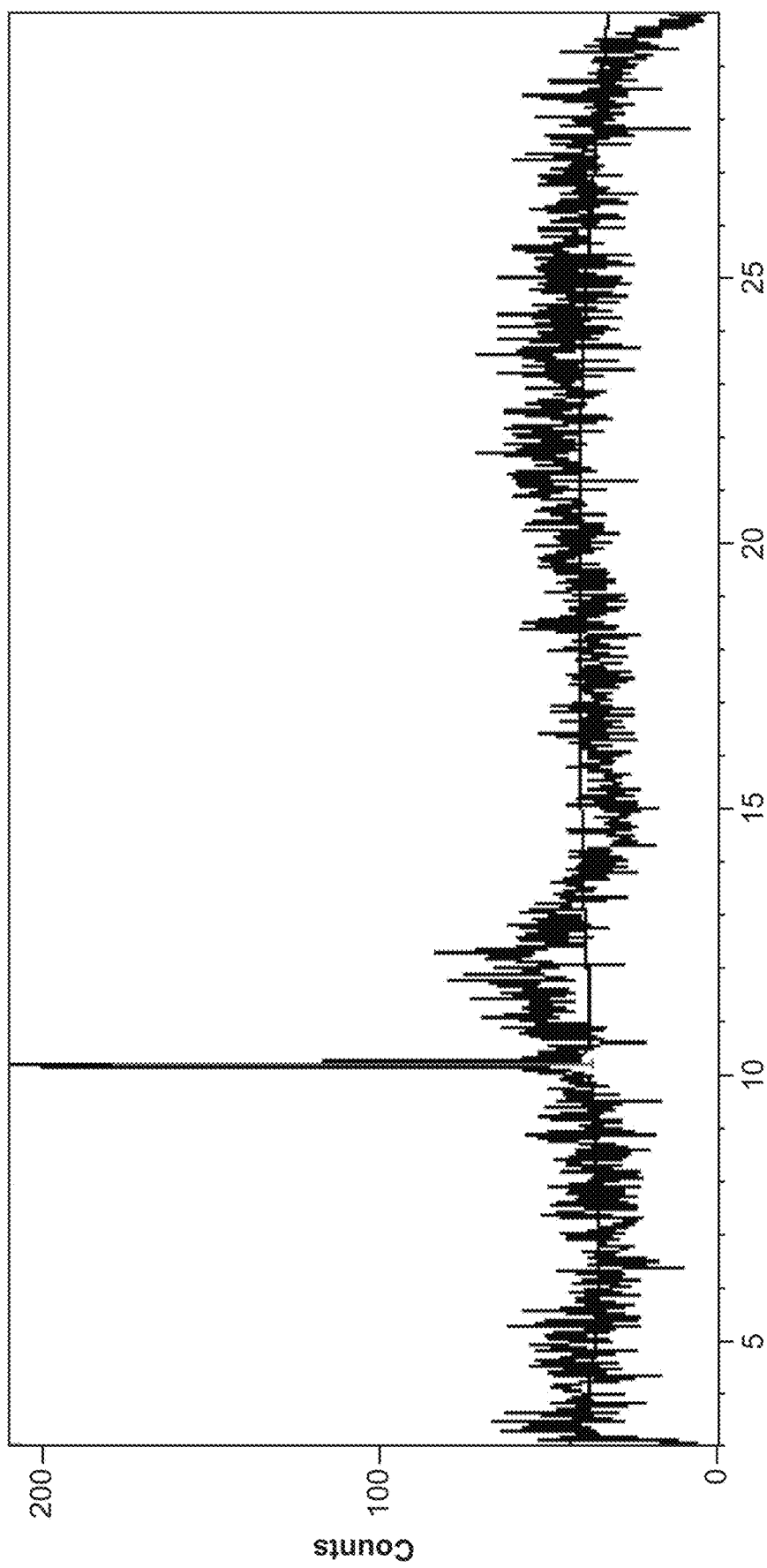
FIG. 11A depicts a X-Ray powder diffraction pattern of Form VI of Compound 1.
Figure 11B:
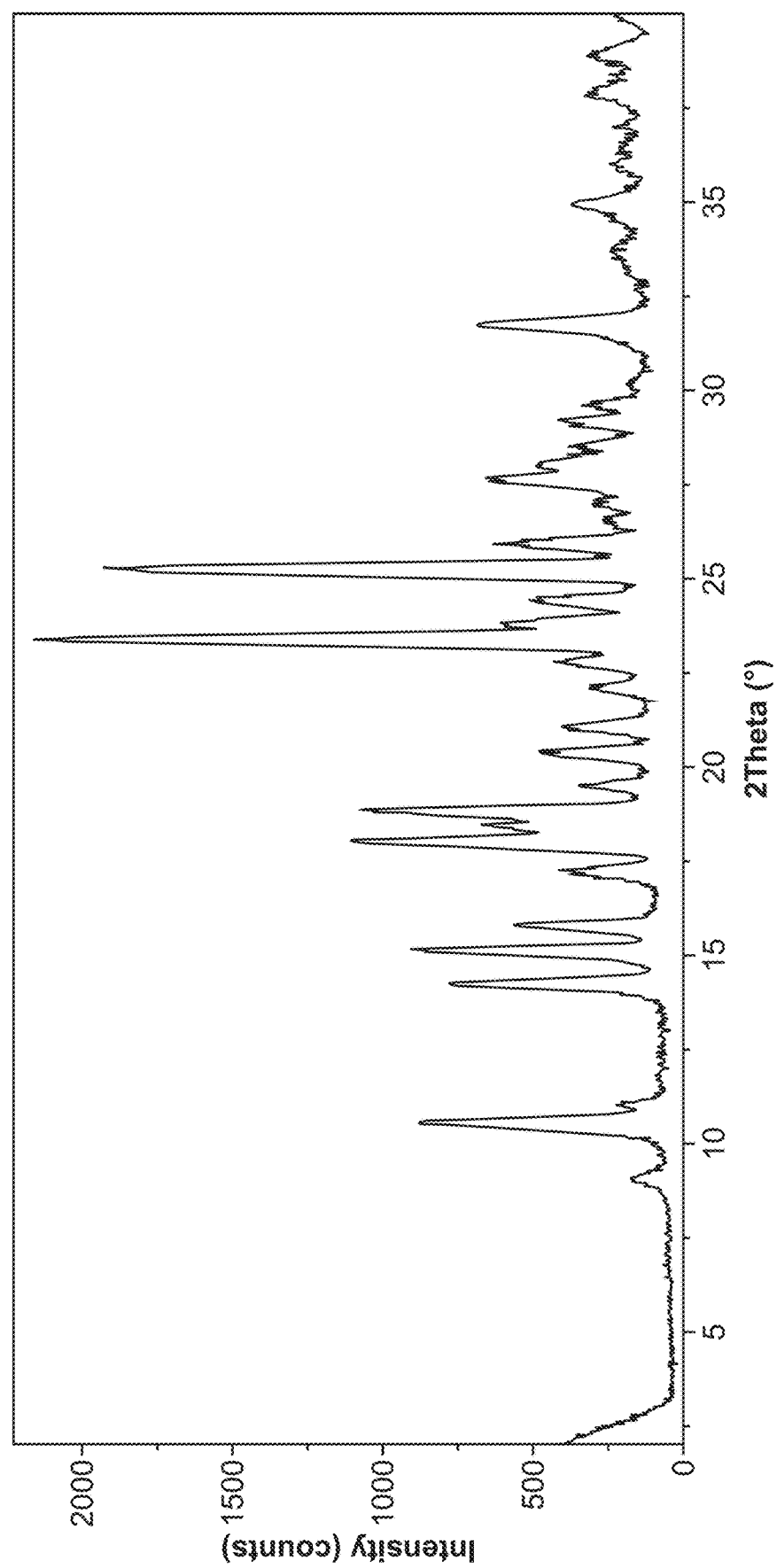
FIG. 11B depicts another X-Ray powder diffraction pattern of Form VI of Compound 1.

In some embodiments, the present invention provides a solvated crystalline form of Compound 1 referred to as Form VI. In some embodiments, the present invention provides Form VI of Compound 1, having a powder X-ray diffraction pattern substantially similar to that depicted in FIG. 11A. In some embodiments, the present invention provides Form VI of Compound 1, having a powder X-ray diffraction pattern substantially similar to that depicted in FIG. 11B. In some embodiments, Form VI of Compound 1 is characterized in that it has a peaks in its powder X-ray diffraction pattern selected from those in Table 7 below.

TABLE 7

Compound 1 Form VI XRPD Peaks

| Position (°2θ) | Height (cts) | Relative Intensity (%) |
|---|---|---|
| 10.19 | 142.1 | 100 |

In some embodiments, Form VI of Compound 1 is characterized in that it has a peak at about 10.19 degrees 2θ in its powder X-ray diffraction pattern.

In some embodiments, Form VI is characterized by an X-ray powder diffractogram comprising the following peaks: 18.0, 23.4, and 25.3° 2θ±0.2° 2θ, as determined on a diffractometer using Cu-Kα radiation at a wavelength of 1.54 Å. The diffractogram comprises additional peaks at 10.5, 14.2, 15.1, and 18.8° 2θ±0.2° 2θ. Compound 1 Form VI is also characterized by its X-ray diffraction pattern as substantially shown in FIG. 11A. Compound 1 Form VI is also characterized by its X-ray diffraction pattern as substantially shown in FIG. 11B.

Figure 12:
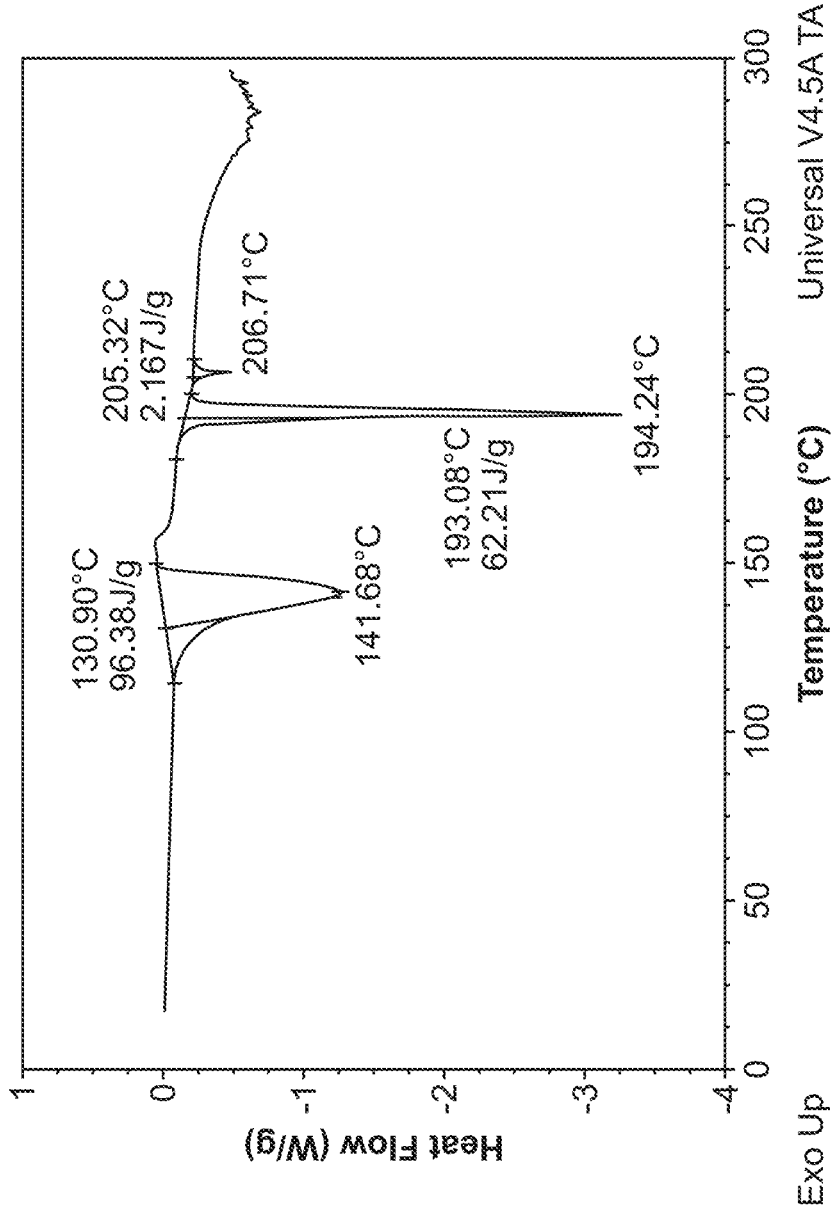
FIG. 12 depicts the differential scanning calorimeter (DSC) curve of Form VI of Compound 1.

In some embodiments, Form VI of Compound 1 is characterized by a differential scanning calorimetry (DSC) curve that comprises an endotherms at 131° C., 193° C., and 205° C. Form VI of Compound 1 is also characterized by its DSC curve as substantially shown in FIG. 12.

Figure 13:
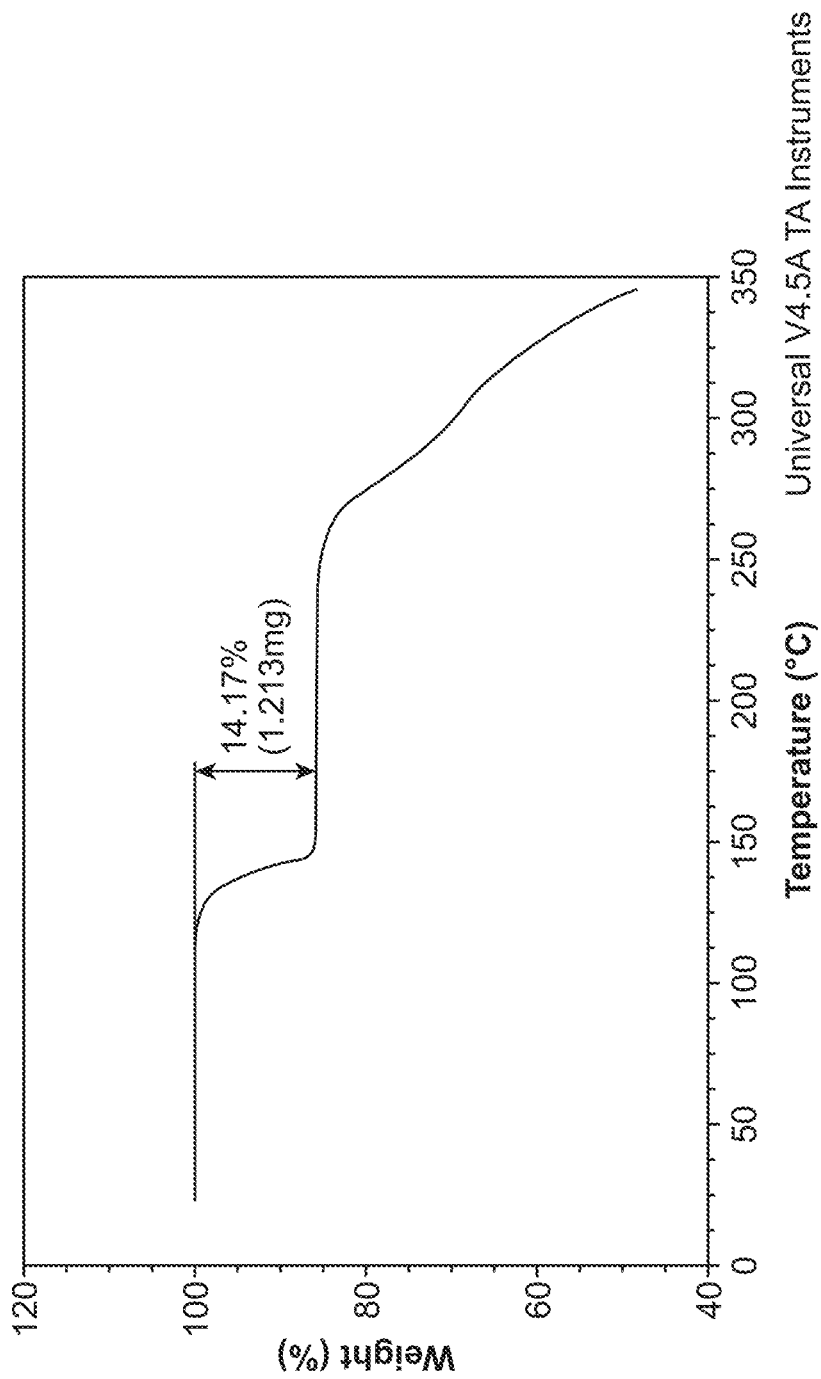
FIG. 13 depicts the thermogravimetric analysis (TGA) of Form VI of Compound 1.

In some embodiments, Form VI of Compound 1 is characterized by a thermogravimetric analysis (TGA) curve as substantially shown in FIG. 13.

Figure 14:
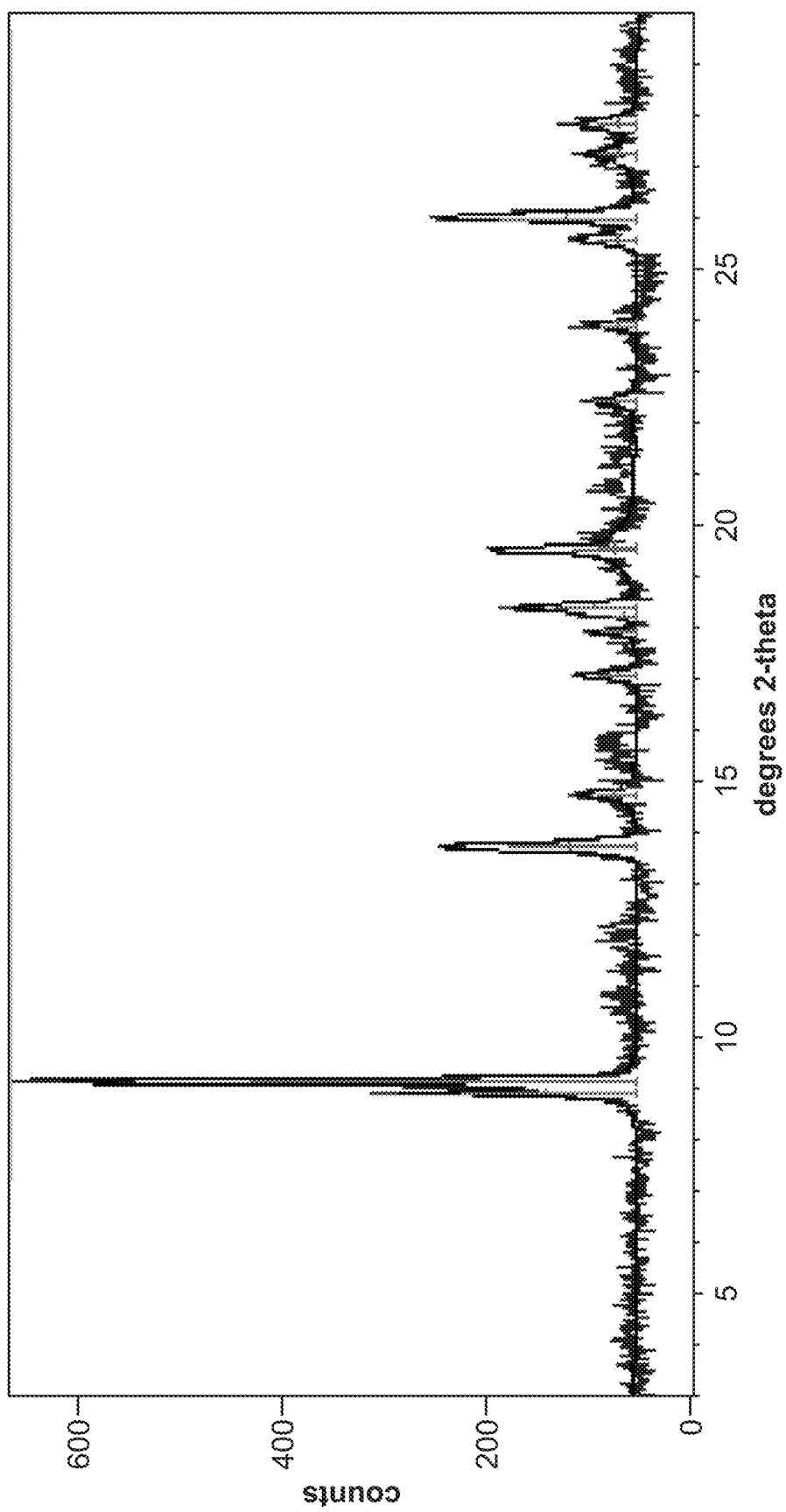
FIG. 14 depicts the X-Ray powder diffraction pattern of Form VII of Compound 1.

In some embodiments, the present invention provides a polymorphic form of Compound 1 referred to as Form VII. In some embodiments, the present invention provides Form VII of Compound 1, having a powder X-ray diffraction pattern substantially similar to that depicted in FIG. 14. In some embodiments, Form VII of Compound 1 is characterized in that it has one or more peaks in its powder X-ray diffraction pattern selected from those in Table 8 below.

TABLE 8

Compound 1 Form VII XRPD Peaks

| Position (°2θ) | Height (cts) | Relative Intensity (%) |
|---|---|---|
| 8.94 | 175.4 | 46 |
| 9.16 | 381.3 | 100 |
| 13.73 | 126.6 | 33.19 |
| 14.74 | 38.9 | 10.19 |
| 17.05 | 37.7 | 9.9 |
| 17.90 | 35.0 | 9.17 |
| 18.22 | 24.2 | 6.35 |
| 18.38 | 82.5 | 21.64 |
| 19.47 | 64.5 | 16.92 |
| 19.51 | 39.6 | 10.37 |
| 22.37 | 43.3 | 11.36 |
| 23.85 | 35.8 | 9.39 |
| 23.94 | 24.2 | 6.36 |
| 25.53 | 37.8 | 9.9 |
| 25.96 | 137.4 | 36.03 |
| 27.17 | 38.5 | 10.1 |
| 27.76 | 38.5 | 10.1 |

In some embodiments, Form VII of Compound 1 is characterized in that it has two or more peaks in its powder X-ray diffraction pattern selected from those in Table 8. In some embodiments, Form VII of Compound 1 is characterized in that it has three or more peaks in its powder X-ray diffraction pattern selected from those in Table 8. In some embodiments, Form VII of Compound 1 is characterized in that it has four or more peaks in its powder X-ray diffraction pattern selected from those in Table 8. In some embodiments, Form VII of Compound 1 is characterized in that it has five or more peaks in its powder X-ray diffraction pattern selected from those in Table 8. In some embodiments, Form VII of Compound 1 is characterized in that it has all of the peaks in Table 8 in its X-ray diffraction pattern.

In some embodiments, Form VII of Compound 1 is characterized in that it has one or more peaks in its powder X-ray diffraction pattern selected from those at about 8.94, about 17.90, and about 27.76 degrees 2θ; in addition to having one or more peaks selected from about 9.16, about 13.73, about 14.74, about 17.05, about 18.22, about 18.38, about 19.47, about 19.51, about 22.37, about 23.85, about 23.94, about 25.53, about 25.96, and about 27.17 degrees 2θ. In some embodiments, Form VII of Compound 1 is characterized in that it has two or more peaks in its powder X-ray diffraction pattern selected from those at about 8.94, about 17.90, and about 27.76 degrees 2θ; in addition to having one or more peaks selected from about 9.16, about 13.73, about 14.74, about 17.05, about 18.22, about 18.38, about 19.47, about 19.51, about 22.37, about 23.85, about 23.94, about 25.53, about 25.96, and about 27.17 degrees 2θ. In some embodiments, Form VII of Compound 1 is characterized in that it has one or more peaks in its powder X-ray diffraction pattern selected from those at about 8.94, about 17.90, and about 27.76 degrees 2θ; in addition to having a peak at about 25.96 degrees 2θ. In some embodiments, Form VII of Compound 1 is characterized in that it has one or more peaks in its powder X-ray diffraction pattern selected from those at about 8.94, about 27.76 degrees 2θ; in addition to having a peak at about 25.96 degrees 2θ. In some embodiments, Form VII of Compound 1 is characterized in that it has all three peaks in its powder X-ray diffraction pattern selected from those at about 8.94, about 27.76, and about 25.96 degrees 2θ.

In some embodiments, Form VII of Compound 1 is characterized in that it has one or more peaks in its powder X-ray diffraction pattern selected from those at about 9.2, about 13.7, about 14.7, about 17.1, about 18.4, about 19.5, about 22.4, about 23.9, about 25.5, and about 26.0 degrees 2θ.

Figure 15A:
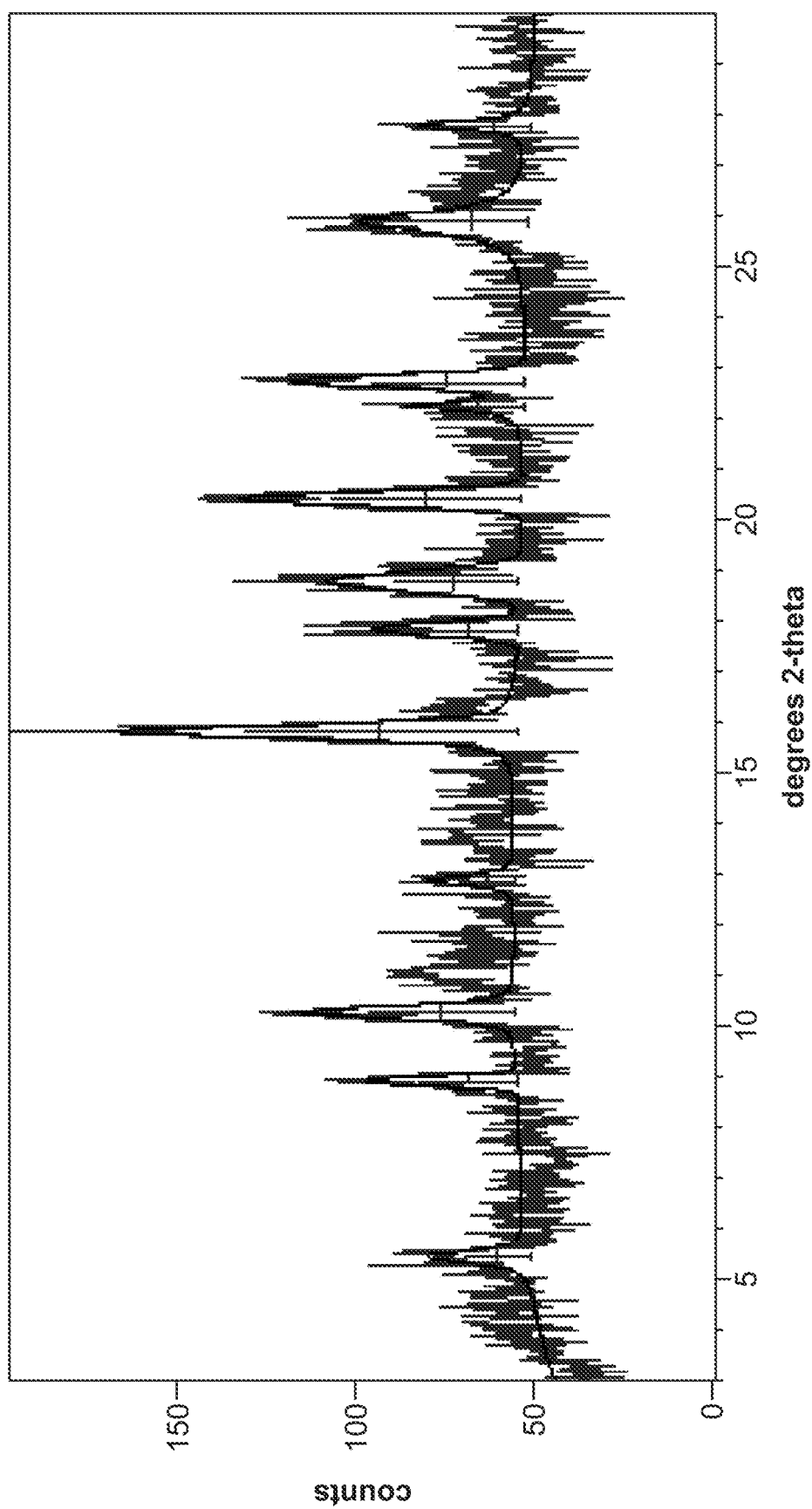
FIG. 15A depicts a X-Ray powder diffraction pattern of Form VIII of Compound 1.
Figure 15B:
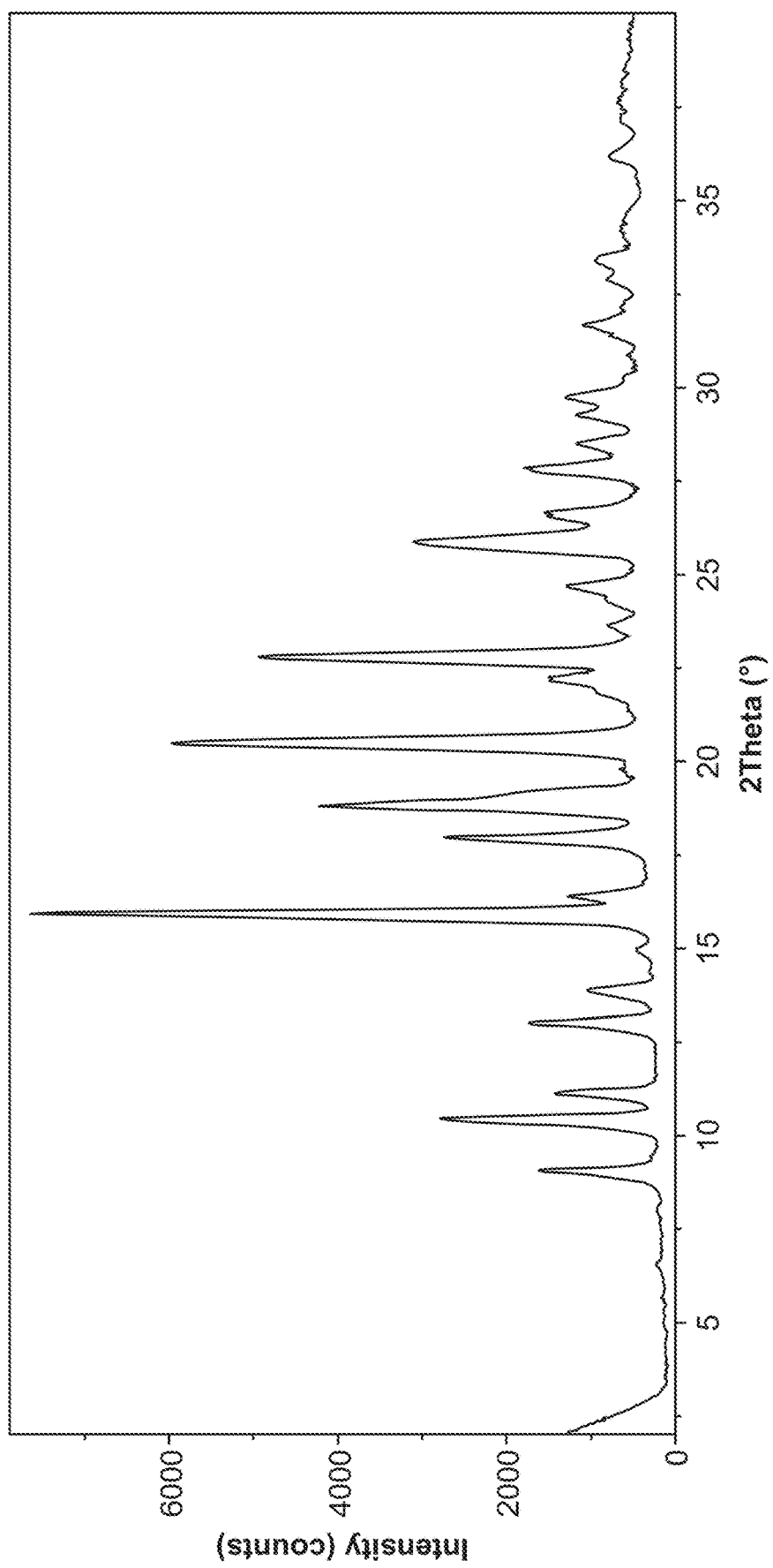
FIG. 15B depicts another X-Ray powder diffraction pattern of Form VIII of Compound 1.

In some embodiments, the present invention provides a polymorphic form of Compound 1 referred to as Form VIII. In some embodiments, the present invention provides Form VIII of Compound 1, having a powder X-ray diffraction pattern substantially similar to that depicted in FIG. 15A. In some embodiments, the present invention provides Form VIII of Compound 1, having a powder X-ray diffraction pattern substantially similar to that depicted in FIG. 15B. In some embodiments, Form VIII of Compound 1 is characterized in that it has one or more peaks in its powder X-ray diffraction pattern selected from those in Table 9 below.

TABLE 9

Compound 1 Form VIII XRPD Peaks

| Position (°2θ) | Height (cts) | Relative Intensity (%) |
|---|---|---|
| 5.50 | 18.8 | 24.4 |
| 8.95 | 28.2 | 36.6 |

TABLE 9-continued

Compound 1 Form VIII XRPD Peaks

| Position (°2θ) | Height (cts) | Relative Intensity (%) |
|---|---|---|
| 10.31 | 42.4 | 54.9 |
| 12.90 | 16.6 | 21.5 |
| 15.82 | 77.2 | 100.0 |
| 17.84 | 27.3 | 35.4 |
| 18.77 | 36.3 | 47.0 |
| 20.40 | 54.0 | 70.0 |
| 22.23 | 25.3 | 32.8 |
| 22.71 | 43.4 | 56.2 |
| 25.83 | 32.6 | 42.2 |
| 27.73 | 22.5 | 29.2 |

In some embodiments, Form VIII of Compound 1 is characterized in that it has two or more peaks in its powder X-ray diffraction pattern selected from those in Table 9. In some embodiments, Form VIII of Compound 1 is characterized in that it has three or more peaks in its powder X-ray diffraction pattern selected from those in Table 9. In some embodiments, Form VIII of Compound 1 is characterized in that it has four or more peaks in its powder X-ray diffraction pattern selected from those in Table 9. In some embodiments, Form VIII of Compound 1 is characterized in that it has five or more peaks in its powder X-ray diffraction pattern selected from those in Table 9. In some embodiments, Form VIII of Compound 1 is characterized in that it has all of the peaks in Table 9 in its X-ray diffraction pattern.

In some embodiments, Form VIII of Compound 1 is characterized in that it has one or more peaks in its powder X-ray diffraction pattern selected from those at about 5.50, about 10.31, about 18.77, about 22.23, and about 25.83 degrees 2θ. In some embodiments, Form VIII of Compound 1 is characterized in that it has two or more peaks in its powder X-ray diffraction pattern selected from those at about 5.50, about 10.31, about 18.77, about 22.23, and about 25.83 degrees 2θ. In some embodiments, Form VIII of Compound 1 is characterized in that it has three or more peaks in its powder X-ray diffraction pattern selected from those at about 5.50, about 10.31, about 18.77, about 22.23, and about 25.83 degrees 2θ. In some embodiments, Form VIII of Compound 1 is characterized in that it has four or more peaks in its powder X-ray diffraction pattern selected from those at about 5.50, about 10.31, about 18.77, about 22.23, and about 25.83 degrees 2θ. In some embodiments, Form VIII of Compound 1 is characterized in that it has all five peaks in its powder X-ray diffraction pattern selected from those at about 5.50, about 10.31, about 18.77, about 22.23, and about 25.83 degrees 2θ.

In some embodiments, Form VIII of Compound 1 is characterized in that it has one or more peaks in its powder X-ray diffraction pattern selected from those at about 5.5, about 10.3, about 15.8, about 18.8, about 20.4, about 22.7, and about 25.8 degrees 2θ.

In some embodiments, Form VIII is characterized by an X-ray powder diffractogram comprising the following peaks: 16.0, 20.5, and 22.8° 2θ±0.2° 2θ, as determined on a diffractometer using Cu-Kα radiation at a wavelength of 1.54 Å. The diffractogram comprises additional peaks at 9.1, 10.5, 18.8, and 25.8° 2θ±0.2° 2θ. Compound 1 Form VIII is also characterized by its X-ray diffraction pattern as substantially shown in FIG. 15A. Compound 1 Form VIII is also characterized by its X-ray diffraction pattern as substantially shown in FIG. 15B.

In some embodiments, Form VIII of Compound 1 is characterized by a differential scanning calorimetry (DSC) curve that comprises an endotherm at 205° C. Form VIII of Compound 1 is also characterized by its DSC curve as substantially shown in FIG. 16.

Figure 17:
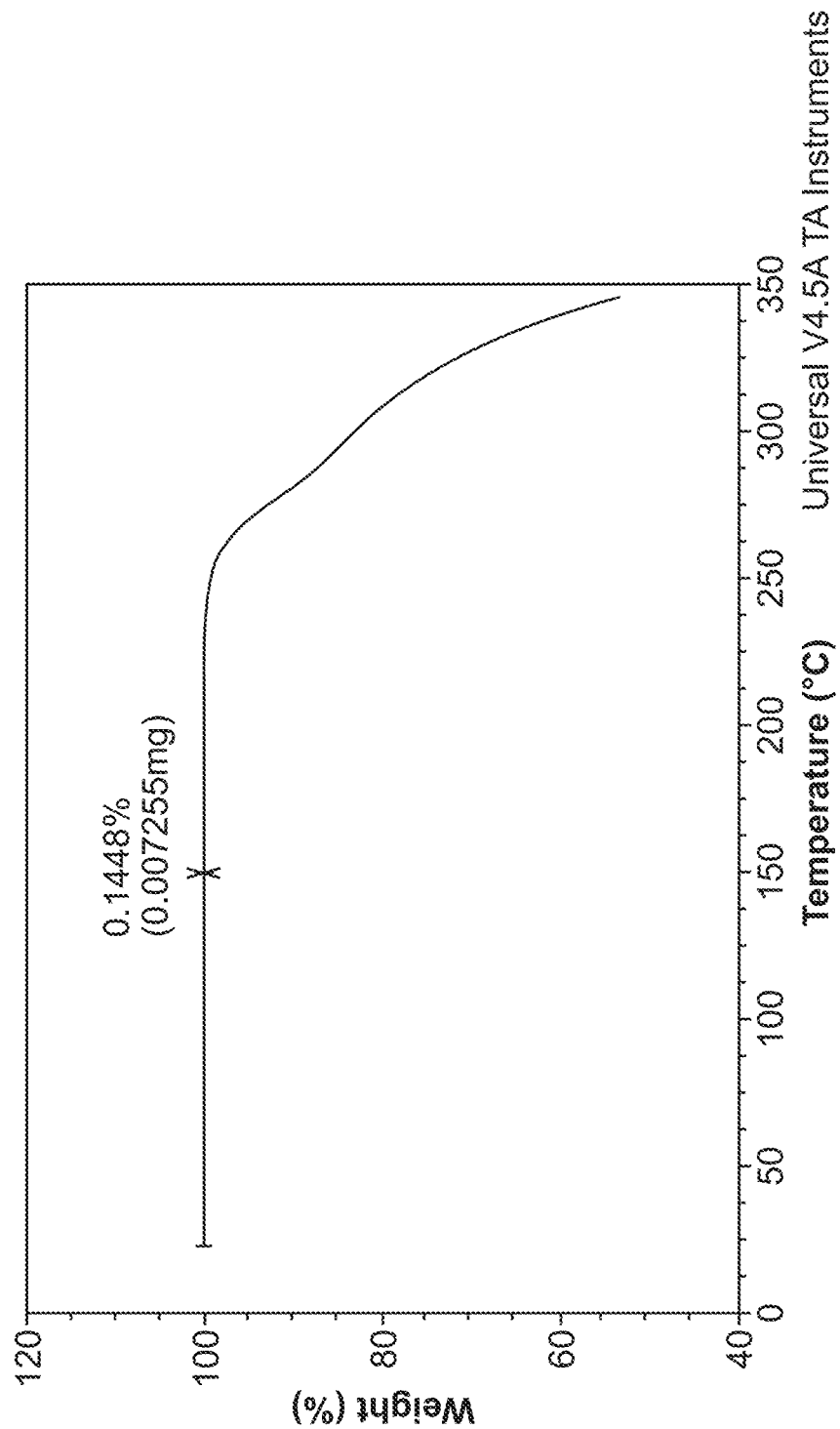
FIG. 17 depicts the thermogravimetric analysis (TGA) of Form VIII of Compound 1.

In some embodiments, Form VIII of Compound 1 is characterized by a thermogravimetric analysis (TGA) curve as substantially shown in FIG. 17.

Some embodiments herein provide for a crystalline form of a sodium salt or co-crystal of Compound 1, which is referred to as Compound 1 Sodium Form I. In some embodiments, Compound 1 Sodium Form I is characterized by an X-ray powder diffractogram comprising the following peaks: 7.5, 8.2, 20.4, and 20.9° 2θ±0.2° 2θ, as determined on a diffractometer using Cu-Kα radiation at a wavelength of 1.54 Å. The diffractogram comprises additional peaks at 14.8, 17.5, 24.0, and 27.7° 2θ±0.2° 2θ. Compound 1 Sodium Form I is also characterized by its full X-ray diffraction pattern as substantially shown in FIG. 19.

In some embodiments, Compound 1 Sodium Form I is characterized by a differential scanning calorimetry (DSC) curve that comprises an endotherm at about 37° C. and an endotherm at about 283° C. Compound 1 Sodium Form I also is characterized by its DSC curve as substantially shown in FIG. 20.

Figure 21:
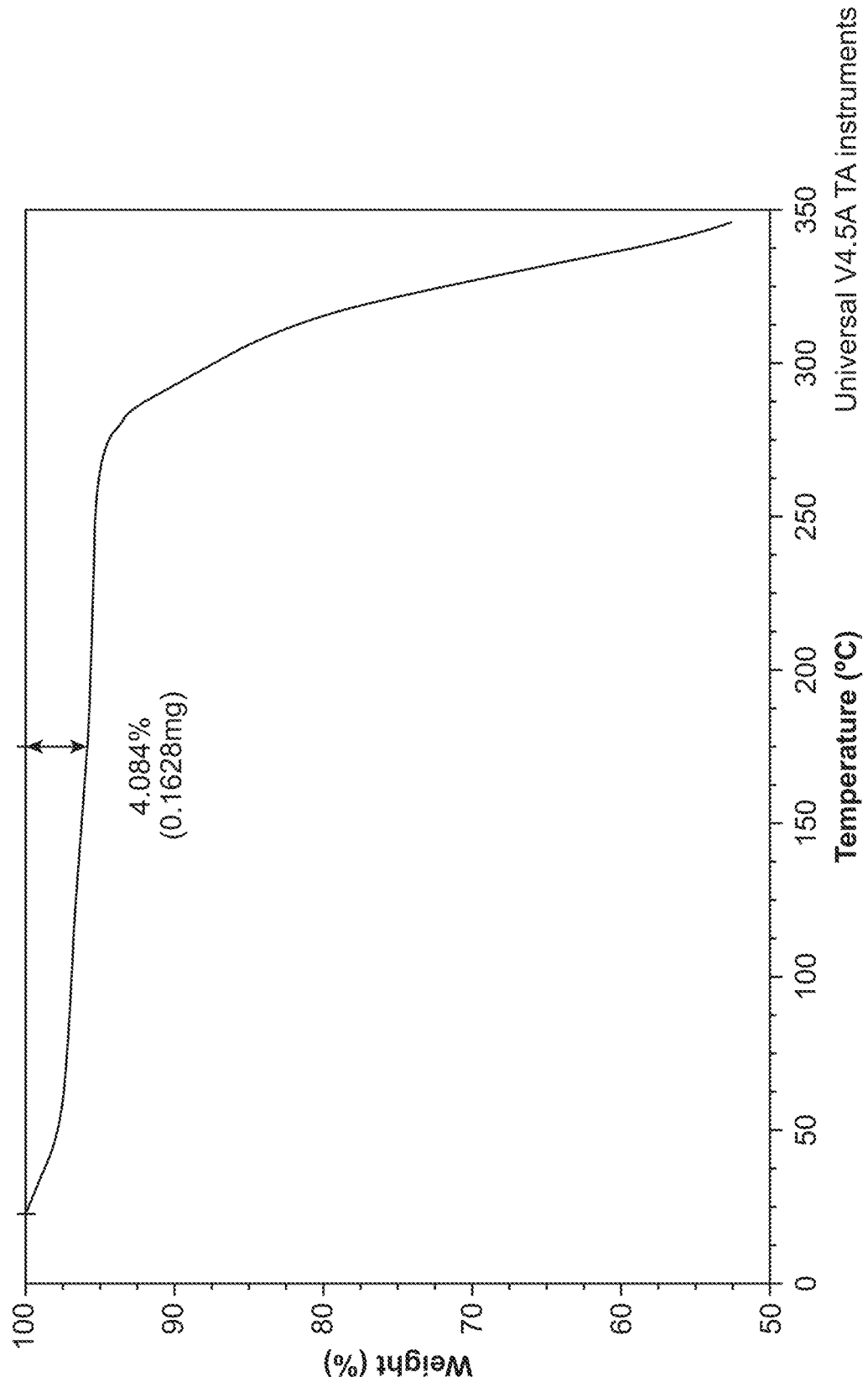
FIG. 21 depicts the thermogravimetric analysis (TGA) of Compound 1 Sodium Form I.

In some embodiments, Compound 1 Sodium Form I is characterized by a thermogravimetric analysis (TGA) curve as substantially shown in FIG. 21.

Some embodiments herein provide for a crystalline form of a sodium salt or co-crystal of Compound 1, which is referred to as Compound 1 Sodium Form II. In some embodiments, Compound 1 Sodium Form II is characterized by an X-ray powder diffractogram comprising the following peaks: 4.8, 6.7, 15.6, and 24.2° 2θ±0.2° 2θ, as determined on a diffractometer using Cu-Kα radiation at a wavelength of 1.54 Å. The diffractogram comprises additional peaks at 17.9, 29.2, 32.5, and 38.0° 2θ±0.2° 2θ. Compound 1 Sodium Form II is also characterized by its full X-ray diffraction pattern as substantially shown in FIG. 22.

In some embodiments, Compound 1 Sodium Form II is characterized by a differential scanning calorimetry (DSC) curve that comprises an endotherm at about 19° C., an endotherm at about 78° C., and an endotherm at about 136° C. Compound 1 Sodium Form II also is characterized by its DSC curve as substantially shown in FIG. 23.

Figure 24:
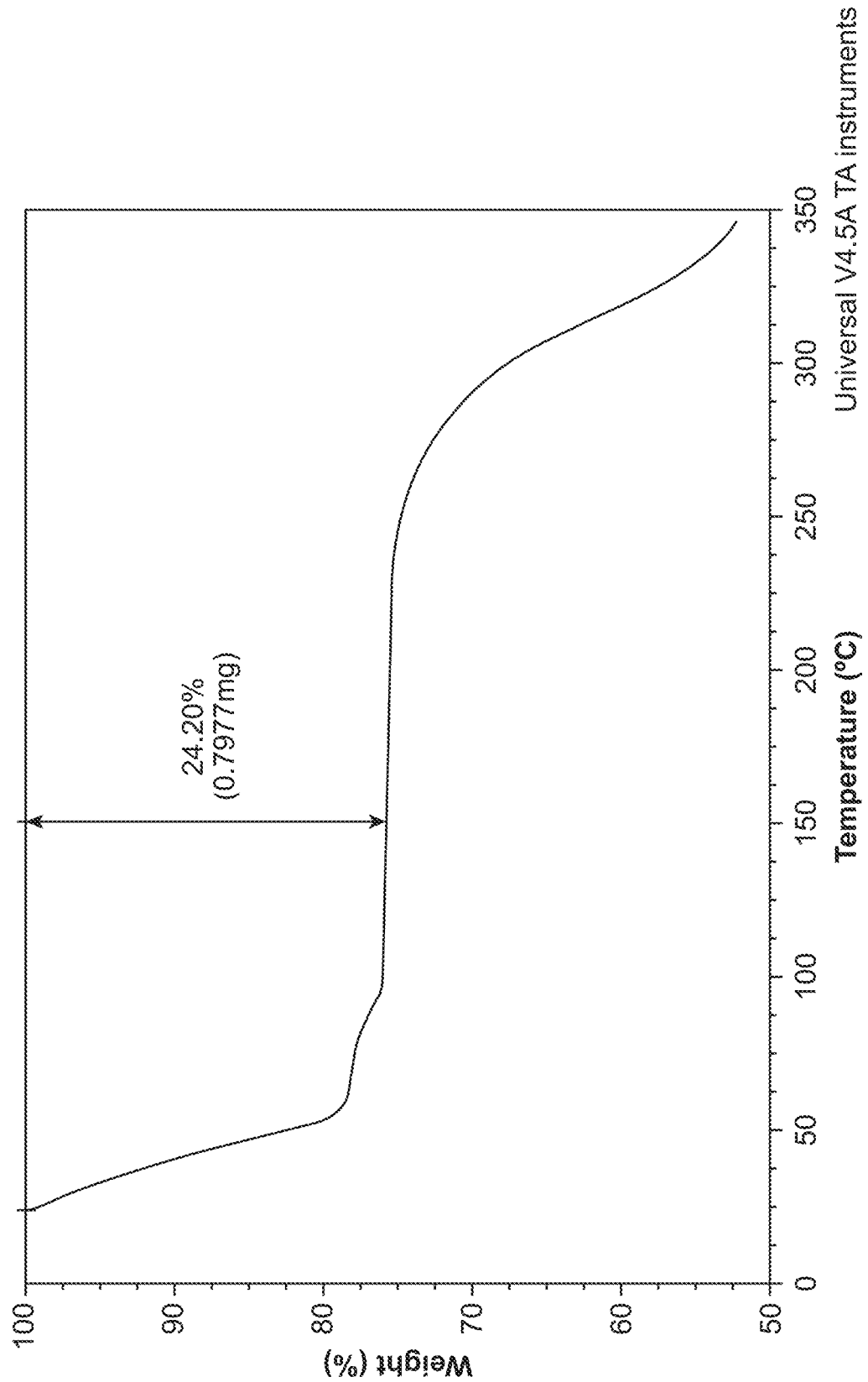
FIG. 24 depicts the thermogravimetric analysis (TGA) of Compound 1 Sodium Form II.

In some embodiments, Compound 1 Sodium Form II is characterized by a thermogravimetric analysis (TGA) curve as substantially shown in FIG. 24.

Some embodiments herein provide for a crystalline form of a calcium salt or co-crystal of Compound 1, which is referred to as Compound 1 Calcium Form I. In some embodiments, Compound 1 Calcium Form I is characterized by an X-ray powder diffractogram comprising the following peaks: 10.1, 14.3, and 20.4° 2θ±0.2° 2θ, as determined on a diffractometer using Cu-Kα radiation at a wavelength of 1.54 Å. The diffractogram comprises additional peaks at 3.6, 7.8, 21.6, 27.3, 28.9° 2θ±0.2° 2θ. Compound 1 Calcium Form I is also characterized by its full X-ray diffraction pattern as substantially shown in FIG. 25.

In some embodiments, Compound 1 Calcium Form I is characterized by a differential scanning calorimetry (DSC) curve that comprises an endotherm at about 17° C., an endotherm at about 72° C., an endotherm at about 180° C., and an endotherm at about 202° C. Compound 1 Calcium Form I also is characterized by its DSC curve as substantially shown in FIG. 26.

Figure 27:
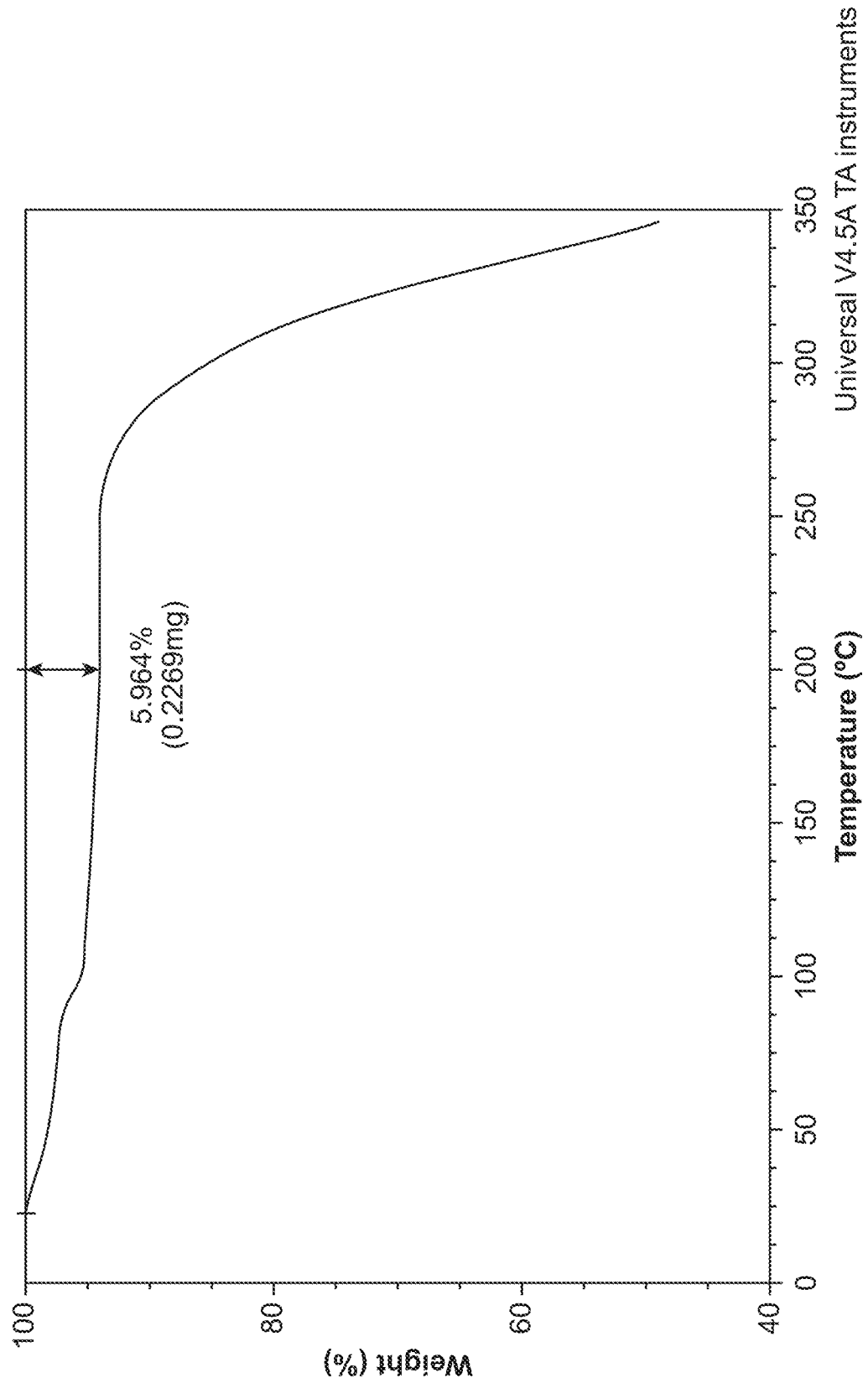
FIG. 27 depicts the thermogravimetric analysis (TGA) of Compound 1 Calcium Form I.

In some embodiments, Compound 1 Calcium Form I is characterized by a thermogravimetric analysis (TGA) curve as substantially shown in FIG. 27.

Some embodiments herein provide for a crystalline form of a magnesium salt or co-crystal of Compound 1, which is referred to as Compound 1 Magnesium Form I. In some embodiments, Compound 1 Magnesium Form I is characterized by an X-ray powder diffractogram comprising the following peaks: 8.2, 16.9, 19.1, and 21.2° 2θ±0.2° 2θ, as determined on a diffractometer using Cu-Kα radiation at a wavelength of 1.54 Å. The diffractogram comprises additional peaks at 15.8, 24.1, 26.1, and 27.1° 2θ±0.2° 2θ. Compound 1 Magnesium Form I is also characterized by its full X-ray diffraction pattern as substantially shown in FIG. 28.

In some embodiments, Compound 1 Magnesium Form I is characterized by a differential scanning calorimetry (DSC) curve that comprises an endotherm at about 53° C. Compound 1 Magnesium Form I also is characterized by its DSC curve as substantially shown in FIG. 29.

Figure 30:
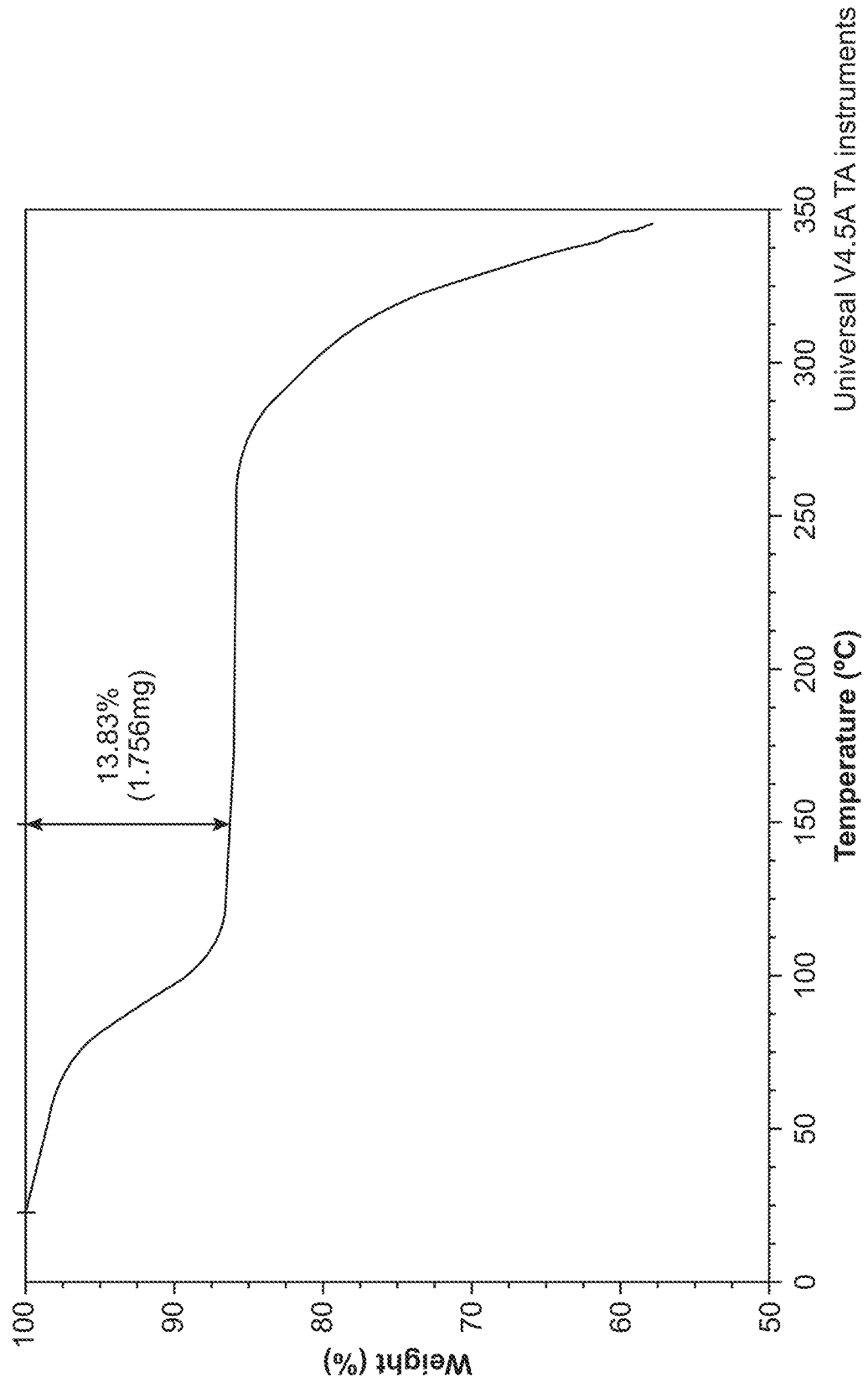
FIG. 30 depicts the thermogravimetric analysis (TGA) of Compound 1 Magnesium Form I.

In some embodiments, Compound 1 Magnesium Form I is characterized by a thermogravimetric analysis (TGA) curve as substantially shown in FIG. 30.

Some embodiments herein provide for a crystalline form of a diethanolamine salt or co-crystal of Compound 1, which is referred to as Compound 1 Diethanolamine Form I. In some embodiments, Compound 1 Diethanolamine Form I is characterized by an X-ray powder diffractogram comprising the following peaks: 5.1, 8.0, 17.0, 25.1° 2θ±0.2° 2θ, as determined on a diffractometer using Cu-Kα radiation at a wavelength of 1.54 Å. The diffractogram comprises additional peaks at 13.4, 16.4, 20.4, and 22.6° 2θ±0.2° 2θ. Compound 1 Diethanolamine Form I is also characterized by its full X-ray diffraction pattern as substantially shown in FIG. 31.

In some embodiments, Compound 1 Diethanolamine Form I is characterized by a differential scanning calorimetry (DSC) curve that comprises an endotherm at about 118° C. Compound 1 Diethanolamine Form I also is characterized by its DSC curve as substantially shown in FIG. 32.

Figure 33:
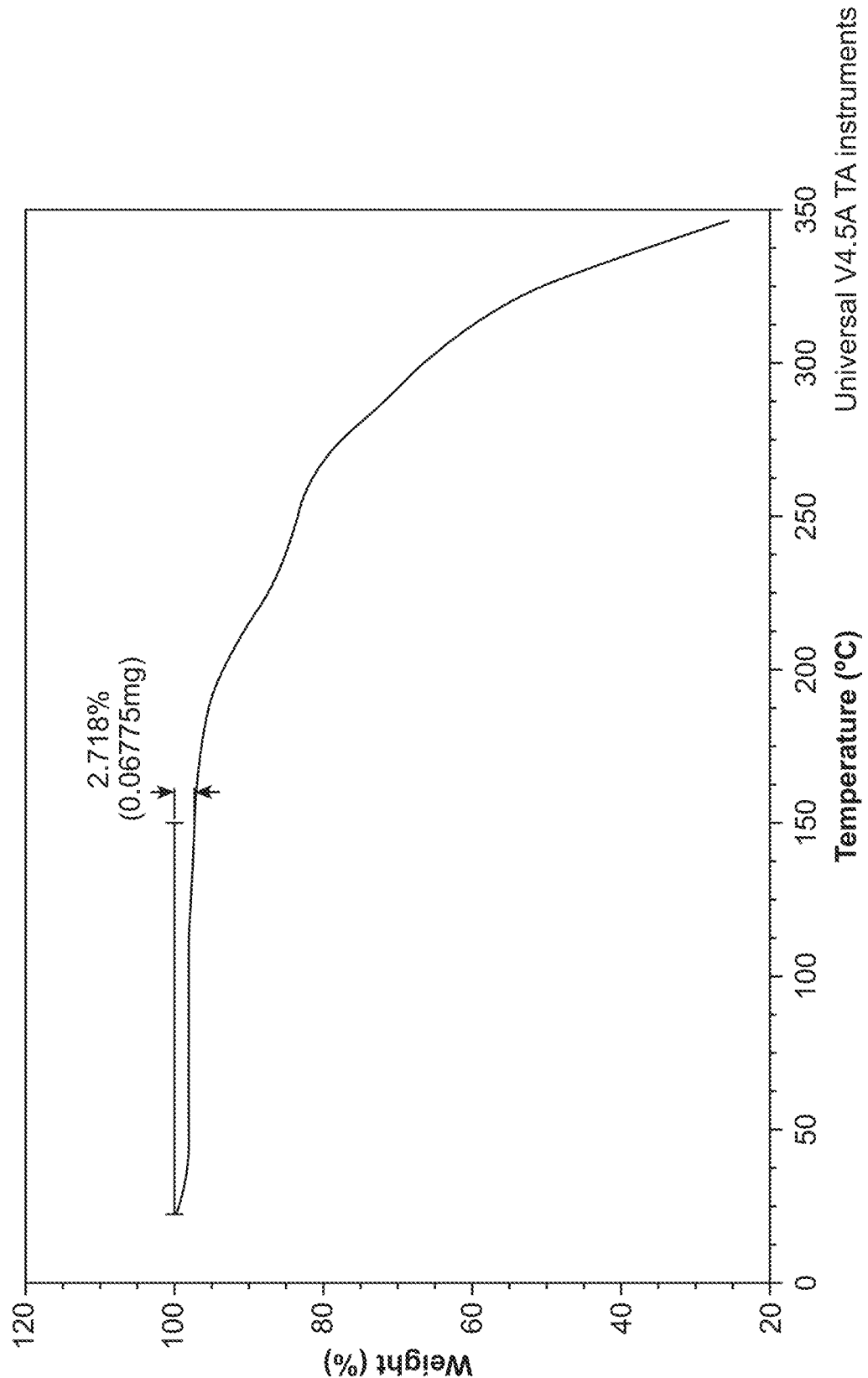
FIG. 33 depicts the thermogravimetric analysis (TGA) of Compound 1 Diethanolamine Form I.

In some embodiments, Compound 1 Diethanolamine Form I is characterized by a thermogravimetric analysis (TGA) curve as substantially shown in FIG. 33.

Some embodiments herein provide for a crystalline form of a piperazine salt or co-crystal of Compound 1, which is referred to as Compound 1 Piperazine Form I. In some embodiments, Compound 1 Piperazine Form I is characterized by an X-ray powder diffractogram comprising the following peaks: 5.6, 8.0, 10.5, and 15.9° 2θ±0.2° 2θ, as determined on a diffractometer using Cu-Kα radiation at a wavelength of 1.54 Å. The diffractogram comprises additional peaks at 13.3, 17.9, 22.1, and 24.3° 2θ±0.2° 2θ. Compound 1 Piperazine Form I is also characterized by its full X-ray diffraction pattern as substantially shown in FIG. 34.

In some embodiments, Compound 1 Piperazine Form I is characterized by a differential scanning calorimetry (DSC) curve that comprises an endotherm at about 27° C. and an endotherm at about 139° C. Compound 1 Piperazine Form I also is characterized by its DSC curve as substantially shown in FIG. 35.

Figure 36:
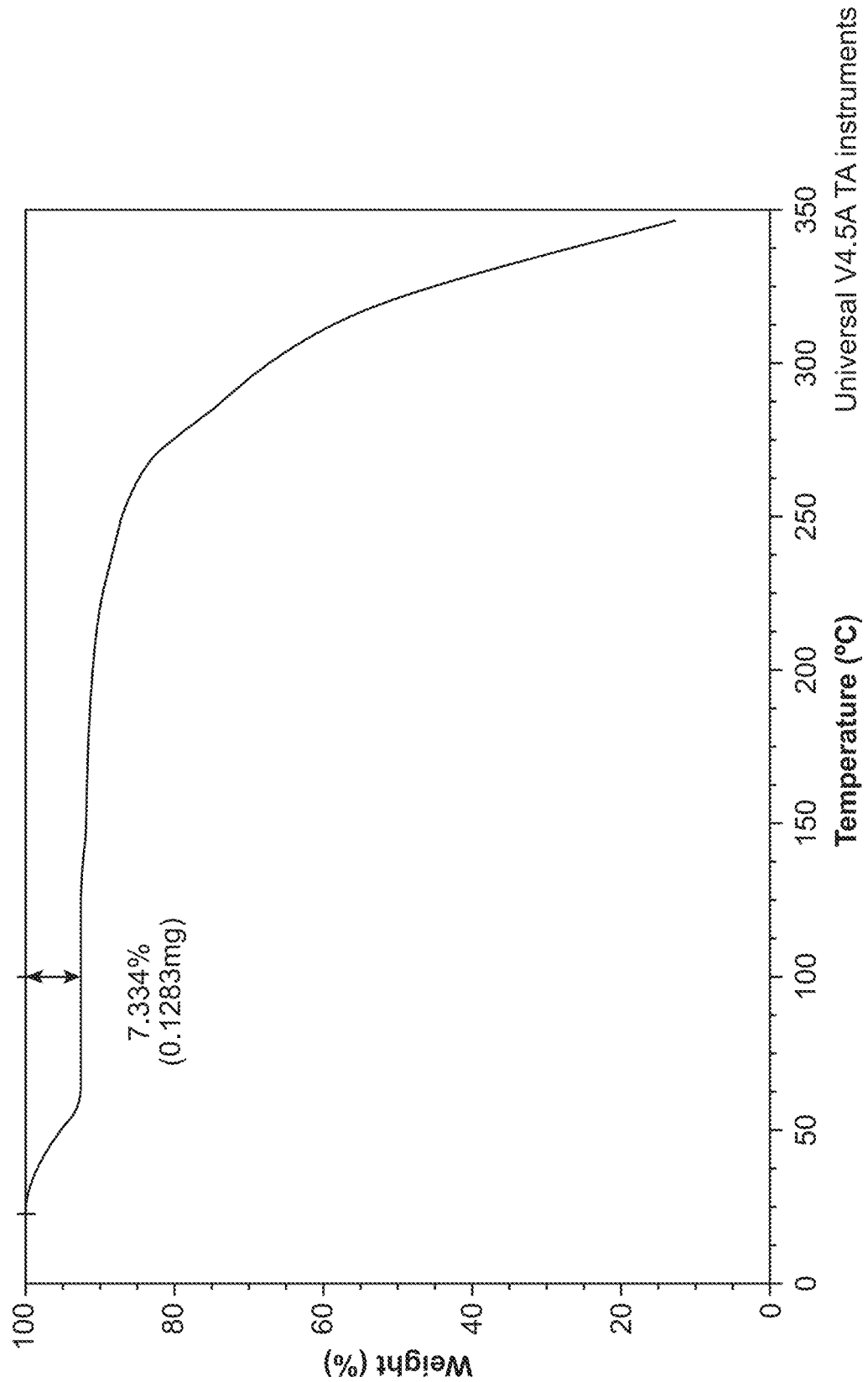
FIG. 36 depicts the thermogravimetric analysis (TGA) of Compound 1 Piperazine Form I.

In some embodiments, Compound 1 Piperazine Form I is characterized by a thermogravimetric analysis (TGA) curve as substantially shown in FIG. 36.

3. Compounds and Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry" Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

"Alkoxy" refers to the group "alkyl-O—". Examples of alkoxy groups include methoxy, ethoxy, n-propoxy, iso-propoxy, n-butoxy, tert-butoxy, sec-butoxy, n-pentoxy, n-hexoxy, and 1,2-dimethylbutoxy.

The term "halogen" means F, Cl, Br, or I.

The term "ring" means a cycloalkyl group or heterocyclic ring as defined herein.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring."

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The term "aralkyl" refers to aryl-alkylene, wherein aryl and alkylene are as defined herein.

The term "aralkoxy" refers to aryl-alkoxy, wherein aryl and alkoxy are as defined herein.

The term "aryloxyalkyl" refers to aryl-O-alkylene, wherein aryl and alkylene are as defined herein.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7 to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}$ $CH(OR°2$; —$(CH_2)_{0-4}$ $SR°$; —$(CH_2)_{0-4}Ph$, which may be substituted with R°; —(CH$_2$)$_{0-4}$O(CH$_2$)$_{0-1}$Ph which may be substituted with R°; —CH═CHPh, which may be substituted with R°; —(CH$_2$)$_{0-4}$O(CH$_2$)$_{0-1}$-pyridyl which may be substituted with R°; —NO$_2$; —CN; —N$_3$)—(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$ SR°—; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$ SSR°; —(CH$_2$)$_{0-4}$ S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono—or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$, —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$ NH$_2$, —(CH$_2$)$_{0-2}$ NHR$^\bullet$, —(CH$_2$)$_{0-2}$ NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$; wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S.

Suitable divalent substituents on a saturated carbon atom of an "optionally substituted" group include the following: ═O, ═S, ═NNR*$_2$, ═NNHC(O)R*, ═NNHC(O)OR*, ═NNHS(O)$_2$R*, ═NR*, ═NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_{1-4}$ aliphatic, —CH$_2$Ph, —O(CH$_2$)$_{0-1}$ Ph, or a 5-6-membered saturated, partially unsaturated, or aryl ring having 0-4 heteroatoms independently selected from nitrogen, oxygen, or sulfur.

The term "co-crystal" refers to a molecular complex of an ionized or non-ionized Compound 1 (or any other compound disclosed herein) and one or more non-ionized co-crystal formers (such as a pharmaceutically acceptable salt) connected through non-covalent interactions.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, as does the Handbook of Pharmaceutical Salts: Properties, Selection, and Use, 2$^{nd}$ Revised Edition, P. Heinrich Stahl and Camille G. Wermuth, Eds. Wiley, April, 2011, each of which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include metal ions (including aluminum, zinc, alkali metals, alkaline earth metals), ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, those derived from nontoxic ammonium, quaternary ammonium, and primary, secondary or tertiary amine cations, including but not limited to those derived from natural or non-naturally-occurring amino acids. Representative amine or ammonium-based salts include but are not limited to those derived from arginine, betaine, hydrabamine, choline, diethylamine, lysine, benzathine, 2-(diethylamino)-ethanol, ethanolamine, 1-(2-hydroxyethyl)-pyrrolidine, diethanolamine, ammonia, deanol, N-methyl-glucamine, tromethamine, triethanolamine, 4-(2-hydroxyethyl)-morpholine, 1H-imidazole, ethylenediamine, piperazine, procaine, and benethamine.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

The term "reaction conditions" is intended to refer to the physical and/or environmental conditions under which a chemical reaction proceeds. The term "under conditions sufficient to" or "under reaction conditions sufficient to" is intended to refer to the reaction conditions under which the desired chemical reaction can proceed. Examples of reaction conditions include, but are not limited to, one or more of following: reaction temperature, solvent, pH, pressure, reaction time, mole ratio of reactants, the presence of a base or acid, or catalyst, radiation, concentration, etc. Reaction conditions may be named after the particular chemical reaction in which the conditions are employed, such as, coupling conditions, hydrogenation conditions, acylation conditions, reduction conditions, etc. Reaction conditions for most reactions are generally known to those skilled in the art or can be readily obtained from the literature. Exemplary reaction conditions sufficient for performing the chemical transformations provided herein can be found throughout, and in particular, the examples below. It is also contemplated that the reaction conditions can include reagents in addition to those listed in the specific reaction.

4. General Methods for Providing the Present Compounds

The present processes may be performed using methods disclosed herein and routine modifications thereof which will be apparent given the disclosure herein and methods well known in the art. Conventional and well-known synthetic methods may be used in addition to the teachings herein. The synthesis of typical compounds described herein, e.g. compounds having structures described by Compound 1, or other formulas or compounds disclosed herein (i.e. I, G-1, G-1-a, G-2, G-2-a, G-2-b, G-3, G-3-b, G-4, G-4-a, G-4-b, G-5, G-5-a, G-6, G-6-a, G-7, G-7-a, G-8, G-8-a, G-8-b, G-9, G-9-a, G-10, G-11, G-12, G-13, G-13-a, etc.) may be accomplished as described in the following examples. If available, reagents may be purchased commercially, e.g. from Sigma Aldrich or other chemical suppliers.

Typical embodiments of compounds in accordance with the present disclosure may be synthesized using the general reaction schemes described below. It will be apparent given the description herein that the general schemes may be altered by substitution of the starting materials with other materials having similar structures to result in products that are correspondingly different. Descriptions of syntheses follow to provide numerous examples of how the starting materials may vary to provide corresponding products. Given a desired product for which the substituent groups are defined, the necessary starting materials generally may be determined by inspection. Starting materials are typically obtained from commercial sources or synthesized using published methods. For synthesizing compounds which are embodiments of the present disclosure, inspection of the structure of the compound to be synthesized will provide the identity of each substituent group. The identity of the final product will generally render apparent the identity of the necessary starting materials by a simple process of inspection, given the examples herein.

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given, other process and purification conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), 2-methyltetrahydrofuran ("MeTHF"), dimethylformamide ("DMF"), chloroform, methylene chloride (or dichloromethane), diethyl ether, methanol, 2-propanol, pyridine and the like). Unless specified to the contrary, the solvents used in the reactions of the present disclosure are inert organic solvents, and the reactions are carried out under an inert gas, preferably nitrogen.

In each of the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium, and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A single stereoisomer, e.g., an enantiomer, substantially free of its stereoisomer may be obtained by resolution of the racemic mixture using a method such as formation of diastereomers using optically active resolving agents (Stereochemistry of Carbon Compounds, (1962) by E. L. Eliel, McGraw Hill; Lochmuller, C. H., (1975) *J. Chromatogr.*, 113, 3) 283-302). Racemic mixtures of chiral compounds of the disclosure can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched substrate. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. (1982) *J. Org. Chem.* 47:4165), of the racemic mixture, and analyzing the NMR spectrum for the presence of the two atropisomeric diastereomers. Stable diastereomers of atropisomeric compounds can be separated and isolated by normal- and reverse-phase chromatography following methods for separation of atropisomeric naphthyl-isoquinolines (Hoye, T., WO 96/15111). By method (3), a racemic mixture of two enantiomers can be separated by chromatography using a chiral stationary phase (Chiral Liquid Chromatography (1989) W. J. Lough, Ed. Chapman and Hall, New York; Okamoto, (1990) *J. of Chromatogr.* 513:375-378). Enriched or purified enantiomers can be distinguished by methods used to distinguish other chiral molecules with asymmetric carbon atoms, such as optical rotation and circular dichroism.

In some embodiments, compounds of the present invention of formula I (including, but not limited to Compound 1) can be generally prepared according to the method described in 2013/0123231 A1, the entirety of which is incorporated herein by reference.

In some embodiments, the present invention provides synthetic methods and synthetic intermediates for the production of compounds of formula I:

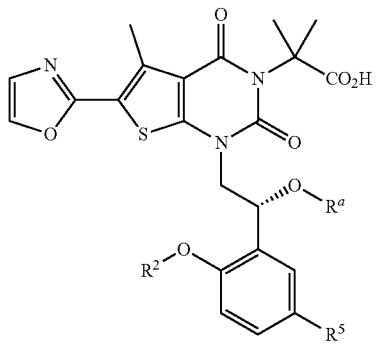

or a pharmaceutically acceptable salt or agriculturally acceptable salt thereof, wherein:

R$^a$ is an optionally substituted group selected from a 3-7 membered ring having 0-2 heteroatoms selected from nitrogen, oxygen, and sulfur, and a C$_{1-6}$ aliphatic;

R$^2$ is hydrogen, or optionally substituted C$_{1-6}$ aliphatic; and

R$^5$ is hydrogen or halogen.

As defined generally above, R$^a$ is an optionally substituted group selected from 3-7 membered ring and a C$_{1-6}$ aliphatic. In some embodiments, R$^a$ is an optionally substituted 3-7 membered ring. In some embodiments, R$^a$ is an optionally substituted 6-membered monocyclic ring. In some embodiments, R$^a$ is an optionally substituted 6-membered monocyclic heterocyclic ring. In some embodiments, R$^a$ is tetrahydropyranyl. In some embodiments, R$^a$ is tetrahydropyran-4-yl. In some embodiments, R$^a$ is an optionally substituted C$_{1-6}$ aliphatic group. In some embodiments, R$^a$ is an optionally substituted C$_{1-6}$ alkyl group.

As defined generally above, R$^2$ is hydrogen, or optionally substituted C$_{1-6}$ aliphatic. In some embodiments, R$^2$ is hydrogen. In some embodiments, R$^2$ is optionally substituted C$_{1-6}$ aliphatic. In some embodiments, R$^2$ is optionally substituted C$_{1-6}$ alkyl. In some embodiments, R$^2$ is C$_{1-6}$ alkyl. In some embodiments, R$^2$ is methyl.

As defined generally above R$^5$ is hydrogen or halogen. In some embodiments, R$^5$ is hydrogen. In some embodiments, R$^5$ is halogen. In some embodiments, R$^5$ is fluoro.

In some embodiments, compounds of formula I are prepared according the method depicted in Scheme 1, wherein each of R$^a$, R$^e$, R$^2$, R$^5$ are as defined in classes and subclasses herein, both singly and in combination.

Scheme 1. Synthesis of Compounds of Formula I.

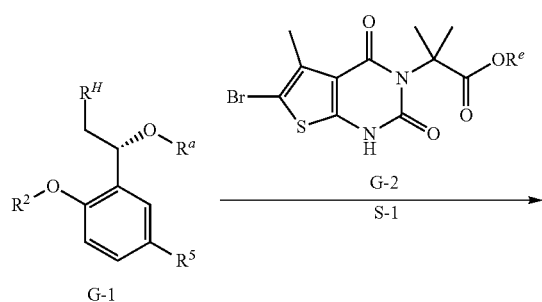

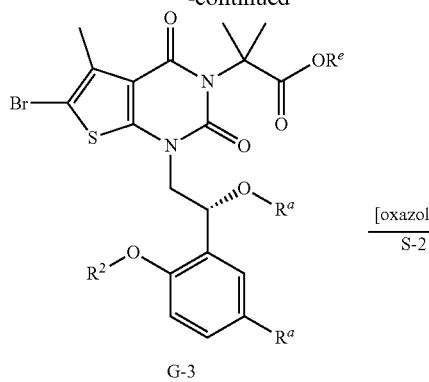

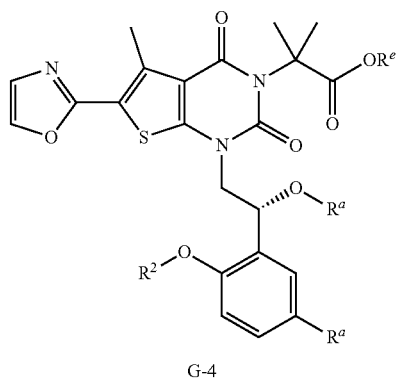

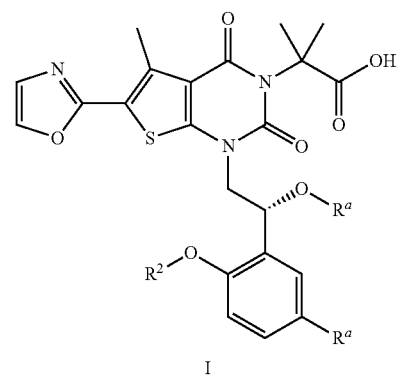

As used herein, R$^H$ is a leaving group. In some embodiments, R$^H$ is a halogen or sulfonate. In some embodiments, R$^H$ is a halogen. In some embodiments, R$^H$ is chloro. In some embodiments, R$^H$ is bromo. In some embodiments, R$^H$ is iodo. In some embodiments, R$^H$ is a sulfonate. In some embodiments, R$^H$ is a mesylate, a triflate, a benzenesulfonate, a tosylate, a brosylate, or a nosylate.

As used herein, R$^e$ is a carboxyl protecting group. In some embodiments, R$^e$ is —Si(R$^P$)$_3$ or optionally substituted C$_{1-6}$ aliphatic; wherein each R$^P$ is independently C$_{1-6}$ aliphatic or phenyl. In some embodiments, R$^e$ is —Si(R$^P$)$_3$. In some embodiments, R$^e$ is optionally substituted C$_{1-6}$ aliphatic. In some embodiments, R$^e$ is optionally substituted C$_{1-6}$ alkyl. In some embodiments, R$^e$ is t-butyl. In some embodiments, R$^e$ is benzyl. In some embodiments, R$^e$ is benzhydryl. In some embodiments, R$^e$ is trityl.

In some embodiments, step S-1 comprises the alkylation of intermediate G-2 by intermediate G-1, thereby forming intermediate G-3. One of ordinary skill will appreciate that a variety of leaving groups R$^H$ are suitable to effect the alkylation of G-2. In some embodiments, the alkylation is mediated by a base. In some embodiments, the base is an alkoxide base. In some embodiments, the base is an alkali metal alkoxide. In some embodiments, the base is potassium t-butoxide. In some embodiments, the base is sodium t-butoxide. In some embodiments, the base is potassium t-amyloxide. In some embodiments, the base is a carbonate base. In some embodiments, the carbonate base is an alkali metal carbonate. In some embodiments, the alkali metal carbonate is potassium carbonate or cesium carbonate. In some embodiments, the alkali metal carbonate is potassium carbonate, potassium bicarbonate, cesium carbonate, or cesium bicarbonate. In some embodiments, the alkali metal carbonate is potassium carbonate. In some embodiments, the alkali metal carbonate is potassium carbonate or potassium bicarbonate. In some embodiments, the alkali metal carbonate is cesium carbonate. In some embodiments, the alkali metal carbonate is cesium carbonate or cesium bicarbonate. In some embodiments, step S-1 proceeds in a polar solvent. In some embodiments, the polar solvent is a polar aprotic solvent. In some embodiments, the polar aprotic solvent is N-methylpyrrolidone (NMP). In some embodiments, the polar aprotic solvent is dimethylformamide (DMF). In some embodiments, the polar aprotic solvent is dimethylacetamide (DMA). In some embodiments, crystalline intermediate G-3 is purified by crystallization.

In some embodiments, step S-2 comprises the coupling of intermediate G-3 with an oxazole synthon (oxazole), thereby forming intermediate G-4. In some embodiments, the coupling is a metal-catalyzed coupling. In some embodiments, the metal-catalyzed coupling is a Negishi coupling. One of skill in the art will appreciate that a Negishi coupling is a transition metal-catalyzed cross-coupling of an organic halide or sulfonate compound with an organozinc compound. In some embodiments, the oxazole synthon is an oxazole zincate. In some embodiments, the oxazole zincate is formed by metal exchange between 2-lithio-oxazole and a zinc salt. In some embodiments the zinc salt is $ZnCl_2$. In some embodiments, the 2-lithio-oxazole is formed by treating oxazole with n-butyllithium. In some embodiments, the 2-lithio-oxazole is formed at a temperature below −40° C. In some embodiments, the 2-lithio-oxazole is formed at a temperature below about −40° C. In some embodiments, the 2-lithio-oxazole is formed at a temperature below −60° C. In some embodiments, the 2-lithio-oxazole is formed at a temperature below about −60° C. In some embodiments, the metal catalyst is a palladium catalyst. In some embodiments, the palladium catalyst is $Pd(PPh_3)_4$. In some embodiments, crystalline intermediate G-4 is purified by crystallization.

In some embodiments, the oxazole is treated with a metalating agent selected from isopropyl magnesium chloride, isopropyl magnesium bromide, TMPZnCl—LiCl, TMPMgCl—LiCl, and isopropyl magnesium chloride/lithium chloride (wherein TMP refers to 2,2,6,6-tetramethylpiperidine). In some embodiments, the metalating agent is isopropyl magnesium chloride. In some embodiments, the oxazole is treated with isopropyl magnesium chloride (2 M in THF). In some embodiments, the oxazole is treated with a metalating agent at about −20° C. to about −10° C. In some embodiments, the oxazole is treated with a metalating agent at about −15° C. In some embodiments, the solvent is tetrahydrofuran, 2-methyltetrahydrofuran, or a mixture thereof. In some embodiments, the solvent is tetrahydrofuran and 2-methyltetrahydrofuran. In some embodiments, the reaction further comprises adding $ZnCl_2$ to form an oxazole zincate. In some embodiments, the reaction further comprises adding $ZnCl_2$ as a solution in 2-methyltetrahydrofuran. In some embodiments, the catalyst used in the Negishi coupling is a palladium catalyst selected from $Pd(PPh_3)_4$, tBuXPhos Pd precatalyst, XPhos Pd precatalyst, RuPhos Pd precatalyst, and Pd-PEPPSI-IPent (dichloro[1,3-bis(2,6-di-3-pentylphenyl)imidazol-2-ylidene](3-chloropyridyl)palladium(II)). Such precatalysts are described in, for example, Bruneau et al., ACS Catal., 2015, 5(2), pp. 1386-1396. In some embodiments, the catalyst is $Pd(PPh_3)_4$. In some embodiments, the reaction mixture is heated to greater than about 50° C. after addition of $ZnCl_2$. In some embodiments, the reaction mixture is heated to about 65° C.

In some embodiments, step S-3 comprises the deprotection of ester intermediate G-4 to provide a compound of formula I. In some embodiments, where $R^e$ is benzyl or benzhydryl, the deprotection is a catalytic hydrogenation using a hydrogen source. In some embodiments, the catalyst is a palladium catalyst. In some embodiments, the palladium catalyst is palladium on carbon. In some embodiments, the hydrogen source is $H_2$. In some embodiments, residual hydrogen catalyst is removed by means of a palladium scavenger. In some embodiments, the palladium scavenger is a thiol. In some embodiments, the thiol is SiliaMetS thiol. In some embodiments, the deprotection is a hydrolysis reaction. In some embodiments, the hydrolysis is an acidic hydrolysis. In some embodiments, the acid is a strong, protic acid. In some embodiments, the acid is sulfuric acid. In some embodiments, the acid is sulfuric acid, tetrafluoroboric acid, methanesulfonic acid, nitric acid, or hydrochloric acid. In some embodiments, the reaction occurs in a co-solvent, wherein the co-solvent is an alcohol. In some embodiments, the co-solvent is 2-propanol, t-butanol, t-amyl alcohol, or ethanol. In some embodiments, the co-solvent is 2-propanol, t-butanol, t-amyl alcohol, ethanol, or acetonitrile.

In some embodiments, the temperature of the hydrolysis reaction is maintained between 5 and 10° C. In some embodiments, the temperature of the hydrolysis reaction is between about 0 and about 20° C. In some embodiments, the temperature of the hydrolysis reaction is between about 2 and about 8° C. In some embodiments, the temperature of the hydrolysis reaction is maintained between about 2 and about 10° C. In some embodiments, the product is purified by crystallization. In some embodiments, the product is crystallized from an alcohol solution. In some embodiments, the alcohol solution is a mixture of ethanol and water. In some embodiments, the product is crystallized from a mixture of acetonitrile and water.

In some embodiments, intermediates of formula G-1 are prepared according to the method depicted in Scheme 2, wherein each of $R^a$, $R^H$, $R^2$, $R^5$ are as defined in classes and subclasses herein, both singly and in combination.

Scheme 2. Synthesis of Intermediates of Formula G-1

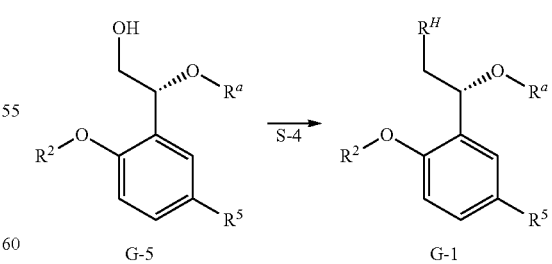

In some embodiments, step S-4 comprises the conversion of the hydroxyl group of intermediate G-5 to a leaving group, $R^H$. In some embodiments, intermediate G-5 is an alcohol or an oxygen anion thereof. In some embodiments, where $R^H$ is a sulfonate group, G-5 is treated with a sulfonylating reagent. In some embodiments, the sulfonate group is a mesylate, a triflate, a benzenesulfonate, a tosylate, a brosylate, or a nosylate. In some embodiments, the sulfonylating reagent is a sulfonyl halide. In some embodiments the sulfonylating reagent is a sulfonyl chloride. In some embodiments the sulfonyl chloride is methanesulfonyl chloride.

In some embodiments, where $R^H$ is a halogen, the hydroxyl group is converted directly to a halogen by means of a halogenating reagent. In some embodiments, the halogenating reagent is a brominating reagent.

In some embodiments, where $R^H$ is a halogen, the hydroxyl group is first converted to a first leaving group, and then that first leaving group is further converted to the halogen. In some embodiments, the first leaving group is a sulfonate. In some embodiments, the sulfonate is a mesylate, a triflate, a benzenesulfonate, a tosylate, a brosylate, or a nosylate. In some embodiments, the sulfonate is a methanesulfonate. In some embodiments, the methanesulfonylate is formed by treatment of G-5 with methanesulfonyl chloride. In some embodiments, the sulfonate is formed in the presence of a base. In some embodiments, the base is an amine base. In some embodiments, the amine base is triethylamine, diisopropylethylamine (Hunig's base), 1,8-diazabicyclo[5.4.0]undec-7-ene, pyridine, or dimethylaminopyridine (DMAP). In some embodiments, the amine base is trimethylamine. In some embodiments, the amine base is triethylamine. In some embodiments, the solvent is 2-methyltetrahydrofuran, tetrahydrofuran, or dichloromethane. In some embodiments, the solvent is 2-methyltetrahydrofuran. In some embodiments, the reaction further comprises a promoter. In some embodiments, the promoter is NaI or tetrabutylammonium iodide. In some embodiments, the reaction takes place at about 20° C. to about 30° C. In some embodiments, the reaction takes place at about 22° C.

In some embodiments, the first leaving group is further converted to a halogen by displacement with halide. In some embodiments, the halide is bromide. In some embodiments, the source of halide is a metal halide. In some embodiments, the source of bromide is a metal bromide. In some embodiments, the metal bromide is an alkali metal bromide. In some embodiments, the alkali metal bromide is LiBr. In some embodiments, the alkali metal bromide is NaBr. In some embodiments, the alkali metal bromide is KBr. In some embodiments, this displacement further comprises a promoter. In some embodiments, the promoter is a phase transfer catalyst. The promoter can include, but is not limited to tetramethylammonium bromide or tetrabutylammonium bromide. In some embodiments, the displacement takes place in a polar solvent. In some embodiments, the polar solvent is a polar aprotic solvent. In some embodiments, the polar aprotic solvent is N-methylpyrrolidone (NMP). In some embodiments, the polar aprotic solvent is dimethylformamide (DMF). In some embodiments, the polar aprotic solvent is dimethylacetamide (DMAc). In some embodiments, the polar aprotic solvent is ethyl acetate (EtOAc). In some embodiments, the reaction takes place at about 50° C. to about 60° C. In some embodiments, the reaction takes place at about 55° C. In some embodiments, leaving group formation step S-4 and alkylation step S-1 are performed together without the isolation of intermediate G-1.

In some embodiments, intermediates of formula G-5 are prepared according to the method depicted in Scheme 3, wherein each of $R^a$, $R^2$, $R^5$ are as defined in classes and subclasses herein, both singly and in combination.

Scheme 3. Synthesis of Intermediates of Formula G-5

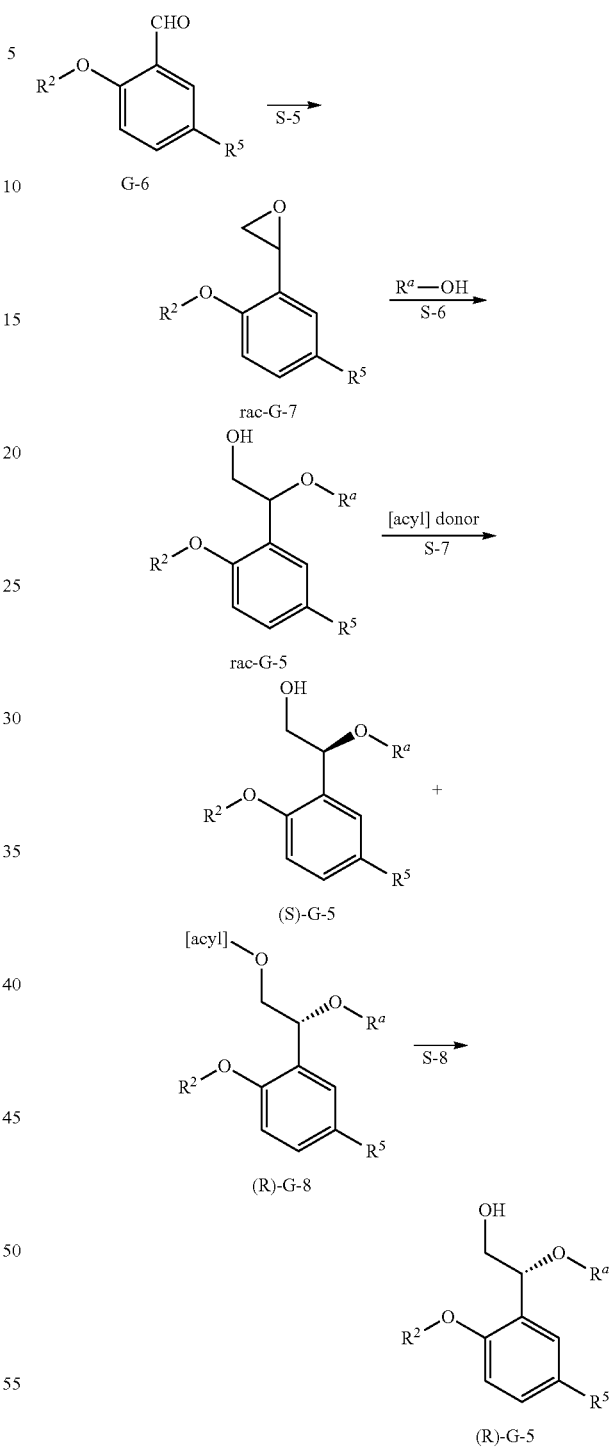

In some embodiments, step S-5 comprises the epoxidation of aldehyde G-6, thereby forming the epoxide of formula rac-G-7. In some embodiments, the epoxidation is a Corey-Chaykovsky epoxidation. One of skill in the art will appreciate that a Corey-Chaykovsky epoxidation is the use of a sulfur ylide to convert a carbonyl compound to its corresponding epoxide. In some embodiments, the sulfur ylide is formed from a trimethylsulfonium or trimethylsulfoxonium salt. In some embodiments, the sulfur ylide is formed from trimethylsulfoxonium iodide. In some embodiments, the sulfur ylide is formed from trimethylsulfoxonium mesylate.

In some embodiments, step S-6 comprises epoxide opening of intermediate rac-G-7 by an alcohol of formula $R^a$—OH, wherein $R^a$ is as defined in classes and subclasses herein, thereby forming intermediate rac-G-5. In some embodiments, the epoxide opening is acid catalyzed. In some embodiments, the acid is a Lewis acid. In some embodiments, the Lewis acid is a metal halide or metal sulfonate. In some embodiments, the Lewis acid is an iron salt. In some embodiments, the Lewis acid is $FeCl_3$. In some embodiments, step S-6 is conducted without additional solvent. In some embodiments, the Lewis acid is $BF_3$-$Et_2O$. In some embodiments, the solvent of step S-6 is toluene. In some embodiments, the acid is $HBF_4$-$OEt_2$, $HBF_4$-water, or camphorsulfonic acid. In some embodiments, the solvent of step S-6 is dichloromethane.

In some embodiments, step S-7 comprises the selective acylation of the (R)-isomer of intermediate G-5, with an [acyl] donor, thereby producing intermediate (R)-G-8 and residual (S)-G-5. In some embodiments, the [acyl] donor is of the formula $R^xC(O)OR^y$, wherein $R^x$ is optionally substituted $C_{1-4}$ aliphatic; and $R^y$ is optionally substituted $C_{1-4}$ aliphatic or optionally substituted $C_{1-4}$ acyl. In some embodiments, the [acyl] donor provides a $C_4$-acyl group. In some embodiments, the [acyl] donor is an optionally substituted 4-7 membered lactone or an optionally substituted 4-7 membered cyclic anhydride. In some embodiments, the [acyl] donor is an optionally substituted 4-7 membered cyclic anhydride. In some embodiments, the [acyl] donor is vinyl acetate, and [acyl] is acetyl. In some embodiments, the [acyl] donor is vinyl butyrate, and [acyl] is butyryl. In some embodiments, the [acyl] donor is succinic anhydride, and [acyl] is succinyl.

In some embodiments, the acylation is a kinetic resolution. In some embodiments the kinetic resolution is accomplished by a lipase enzyme. In some embodiments, the lipase enzyme is *Candida antarctica* lipase B (CAL-B). In some embodiments, the lipase enzyme is Novozyme 435. In some embodiments, the acylation reaction is conducted in THF solvent. In some embodiments, the acylation reaction is conducted in toluene solvent. In some embodiments, the acylation reaction is conducted in a mixture of THF and toluene. In some embodiments, when [acyl] is succinyl, unreacted intermediate G-5 is separated from (R)-G-8 by forming the succinate anion under aqueous basic conditions and extracting the unreacted neutral alcohol species into an organic solvent.

In some embodiments, step S-8 comprises the hydrolysis of enantiomerically enriched intermediate (R)-G-8, thereby forming (R)-G-5. In some embodiments, the hydrolysis is an aqueous hydrolysis. In some embodiments, the aqueous hydrolysis is an alkaline hydrolysis. In some embodiments, the aqueous hydrolysis is mediated by hydroxide. In some embodiments, the aqueous hydrolysis is mediated by sodium hydroxide. In some embodiments, steps S-7 and S-8 are performed without the isolation of intermediate (R)-G-8.

In some embodiments, the (R)-G-8 produced has an enantiomeric excess of greater than 70%, 80%, 90%, 95%, 97%, 98%, 99%, or 99.5%.

In some embodiments, compounds of formula G-4 are prepared according to the method depicted in Scheme 4, wherein each of $R^a$, $R^e$, $R^H$, $R^2$, $R^5$ are as defined in classes and subclasses herein, both singly and in combination.

Scheme 4. Alternate Synthesis of Intermediates of Formula G-4

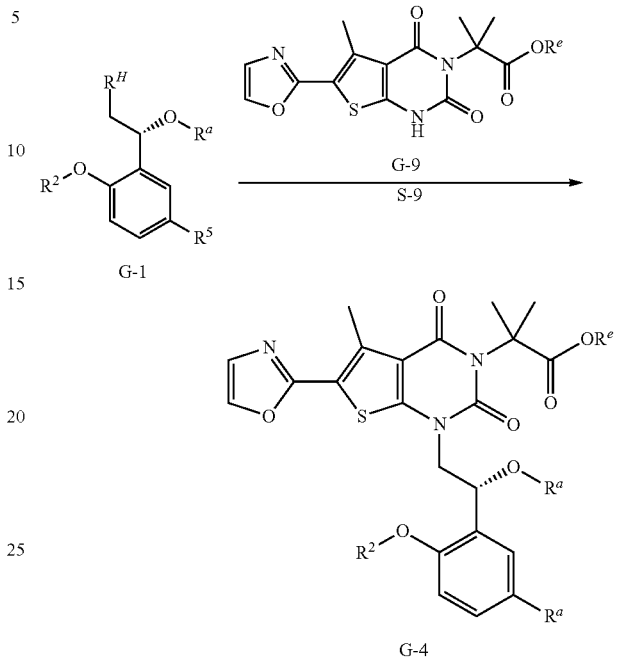

In some embodiments, step S-9 comprises the alkylation of intermediate G-9 by alkyl halide G-1, thereby forming intermediate G-4. In some embodiments, the alkylation is mediated by a base. In some embodiments, the base is an alkoxide base. In some embodiments, the base is an alkali metal alkoxide. In some embodiments, the base is potassium t-butoxide. In some embodiments, the base is sodium t-butoxide. In some embodiments, the base is potassium t-amyloxide. In some embodiments, the base is a carbonate base. In some embodiments, the carbonate base is an alkali metal carbonate. In some embodiments, the alkali metal carbonate is sodium carbonate, sodium bicarbonate, potassium carbonate, potassium bicarbonate, cesium carbonate, cesium bicarbonate, potassium phosphate tribasic, or potassium phosphate dibasic. In some embodiments, the alkali metal carbonate is potassium carbonate or cesium carbonate. In some embodiments, the alkali metal carbonate is potassium carbonate. In some embodiments, the alkali metal carbonate is potassium bicarbonate. In some embodiments, the alkali metal carbonate is cesium bicarbonate. In some embodiments, step S-9 proceeds in a polar solvent. In some embodiments, the polar solvent is a polar aprotic solvent. In some embodiments, the polar aprotic solvent is N-methylpyrrolidone (NMP). In some embodiments, the polar aprotic solvent is dimethylformamide (DMF). In some embodiments, the polar aprotic solvent is dimethylacetamide (DMA). In some embodiments, the reaction takes place at a temperature of about 90° C. to about 100° C. In some embodiments, the reaction takes place at a temperature of about 100° C. to about 140° C. In some embodiments, the reaction takes place at a temperature of about 115° C.

In some embodiments, compounds of formula G-2 and G-9 are prepared according to the method depicted in Scheme 5, wherein $R^e$ is as defined in classes and subclasses herein.

Scheme 5. Synthesis of Intermediates of Formulas G-2 and G-9

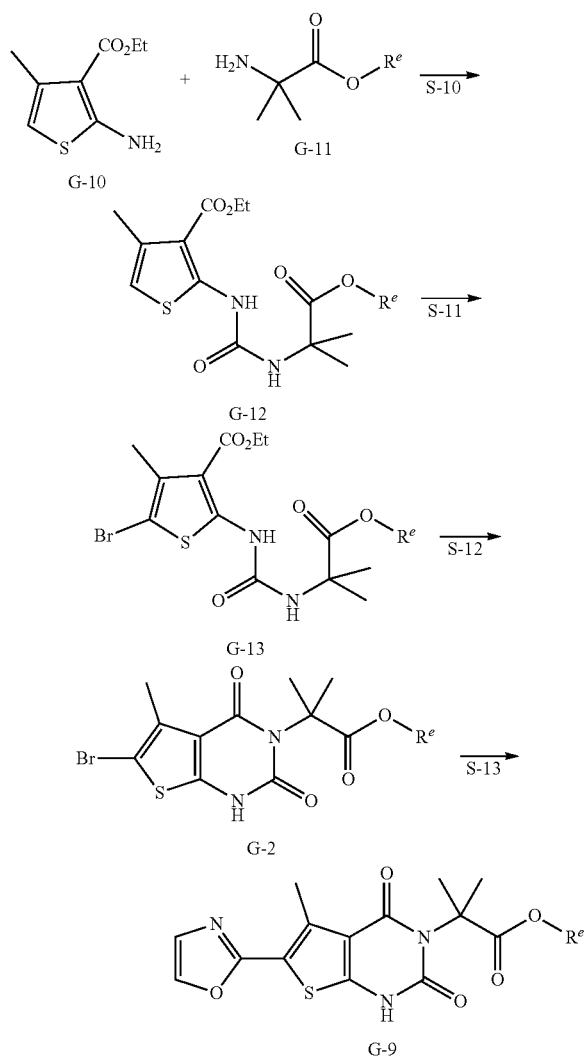

In some embodiments, step S-10 comprises a urea formation between intermediates G-10 (or a salt thereof), and G-11 (or a salt thereof), thereby forming the intermediate of formula G-12. In some embodiments, the urea formation proceed using a carbonyl source. In some embodiments, the carbonyl source is carbonyldiimidazole (CDI). In some embodiments, the carbonyl source is triphosgene. In some embodiments, the intermediate of formula G-11 is used as its hydrochloride salt. In some embodiments, an additional base is used. In some embodiments, the base is an amine base. In some embodiments, the amine base is triethylamine.

In some embodiments, step S-11 comprises the bromination of an intermediate of formula G-12, thereby forming an intermediate of formula G-13. In some embodiments, the brominating reagent is N-bromosuccinimide. In some embodiments, the bromination is conducted in a polar aprotic solvent. In some embodiments, the polar aprotic solvent is dimethylformamide (DMF).

In some embodiments, step S-12 comprises the intramolecular cyclization of an intermediate of formula G-13, thereby forming an intermediate of formula G-2. In some embodiments, the intramolecular cyclization is effected by a strong base. In some embodiments, the strong base is an alkali metal alkoxide. In some embodiments, the alkali metal alkoxide is potassium t-butoxide. In some embodiments, the intramolecular cyclization is conducted in an ether solvent. In some embodiments, the ether solvent is 1,4-dioxane.

In some embodiments, step S-13 comprises the coupling of intermediate G-2 with an oxazole synthon (oxazole or oxazole metallate), thereby forming intermediate G-9. In some embodiments, the coupling is a metal-catalyzed coupling. In some embodiments, the metal-catalyzed coupling is a Negishi coupling. One of skill in the art will appreciate that a Negishi coupling is a transition metal-catalyzed cross-coupling of an organic halide or sulfonate compound with an organozinc compound. In some embodiments, the oxazole synthon is an oxazole zincate. In some embodiments, the oxazole zincate is formed by metal exchange between 2-lithio-oxazole and a zinc salt. In some embodiments the zinc salt is $ZnCl_2$. In some embodiments, the 2-lithio-oxazole is formed by treating oxazole with n-butyllithium. In some embodiments, the 2-lithio-oxazole is formed at a temperature below −40° C. In some embodiments, the 2-lithio-oxazole is formed at a temperature below −60° C. In some embodiments, the transition metal catalyst is a palladium catalyst. In some embodiments, the palladium catalyst is $Pd(PPh_3)_4$. In some embodiments, crystalline intermediate G-4 is purified by crystallization.

In some embodiments, the oxazole is treated with a metalating agent selected from isopropyl magnesium chloride, isopropyl magnesium bromide, TMPZnCl—LiCl, TMPMgCl—LiCl, and isopropyl magnesium chloride/lithium chloride (wherein TMP refers to 2,2,6,6-tetramethylpiperidine). In some embodiments, the metalating agent is isopropyl magnesium chloride. In some embodiments, the oxazole is treated with isopropyl magnesium chloride (2 M in THF). In some embodiments, the oxazole is treated with a metalating agent at about −20° C. to about −10° C. In some embodiments, the oxazole is treated with a metalating agent at about −15° C. In some embodiments, the solvent is tetrahydrofuran, 2-methyltetrahydrofuran, or a mixture thereof. In some embodiments, the solvent is tetrahydrofuran and 2-methyltetrahydrofuran. In some embodiments, the reaction further comprises adding $ZnCl_2$ to form an oxazole zincate. In some embodiments, the reaction further comprises adding $ZnCl_2$ as a solution in 2-methyltetrahydrofuran. In some embodiments, the catalyst used in the Negishi coupling is a palladium catalyst selected from $Pd(PPh_3)_4$, tBuXPhos Pd precatalyst, XPhos Pd precatalyst, RuPhos Pd precatalyst, and Pd-PEPPSI-IPent (dichloro[1,3-bis(2,6-di-3-pentylphenyl)imidazol-2-ylidene](3-chloropyridyl)palladium(II)). Such precatalysts are described in, for example, Bruneau et al., ACS Catal., 2015, 5(2), pp. 1386-1396. In some embodiments, the catalyst is $Pd(PPh_3)_4$. In some embodiments, the reaction mixture is heated to greater than about 50° C. after addition of $ZnCl_2$. In some embodiments, the reaction mixture is heated to about 65° C.

Scheme 6. Synthesis of Intermediate G-13-a

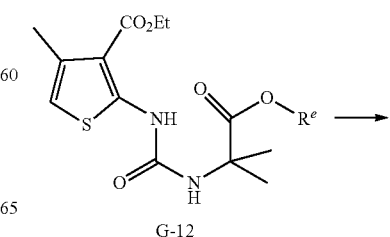

-continued

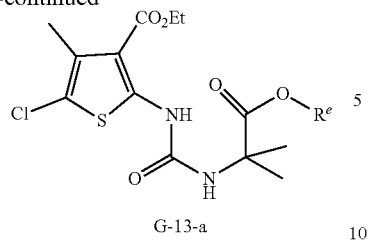

G-13-a

In some embodiments, step S-11 comprises the chlorination of an intermediate of formula G-12, thereby forming an intermediate of formula G-13-a. In some embodiments, the chlorinating reagent is N-chlorosuccinimide. In some embodiments, G-13-a can be used in step S-12 in place of G-13 as described above to form the chloro analog of G-2, which can be used in step S-13 in place of G-2.

Some embodiments provide for a process for preparing Compound 1:

Compound 1

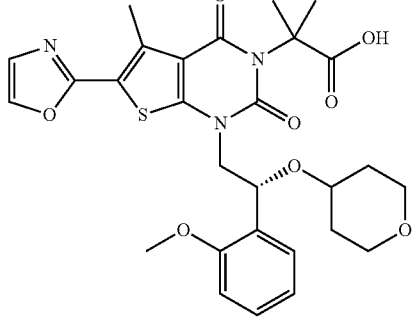

comprising contacting compound G-4-a:

G-4-a

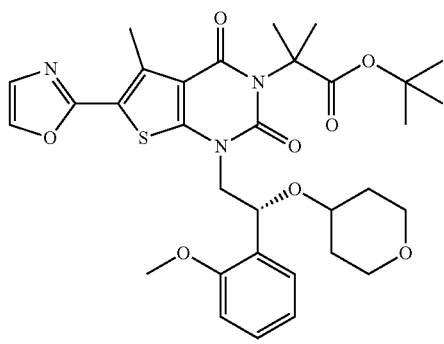

with acid.

Some embodiments provide for a process for preparing compound G-4-a:

G-4-a

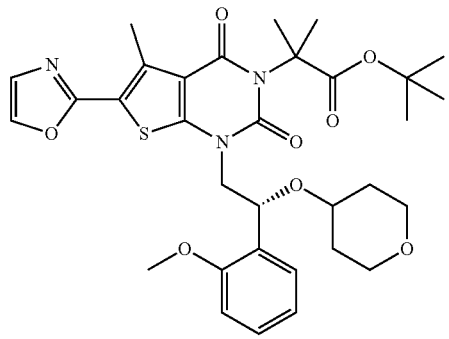

comprising contacting compound G-9-a:

G-9-a

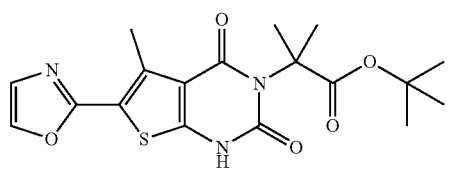

with a compound of the formula H-1:

H-1

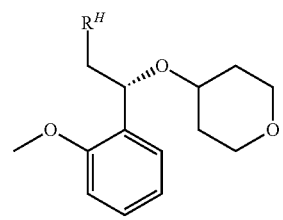

wherein $R^H$ is halogen.

In some embodiments, $R^H$ is bromo.

Some embodiments provide for a process for preparing Compound 1:

Compound 1

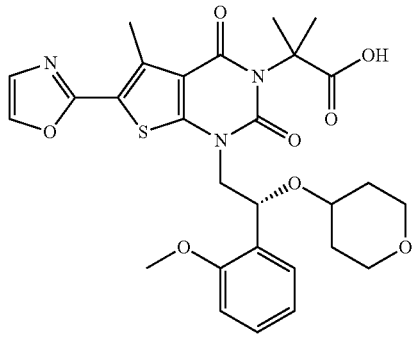

comprising contacting a compound of the formula G-4-b:

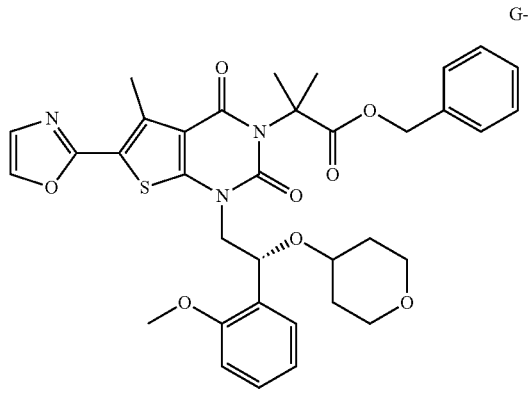

G-4-b with a hydrogen source and a palladium catalyst.

Some embodiments provide for a process for preparing an enantiomerically enriched compound of formula (R)-G-5:

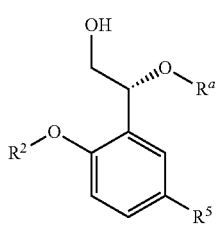

(R)-G-5 wherein $R^a$ is an optionally substituted group selected from a 3-7 membered ring having 0-2 heteroatoms selected from nitrogen, oxygen, and sulfur, and $C_{1-6}$ aliphatic;

$R^2$ is hydrogen, or optionally substituted $C_{1-6}$ aliphatic; and $R^5$ is hydrogen or halogen;

comprising the steps of:

a) contacting a racemic compound of formula rac-G-5:

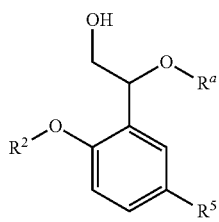

rac-G-5 with a lipase enzyme and an [acyl] donor, thereby forming a compound of formula (R)-G-8:

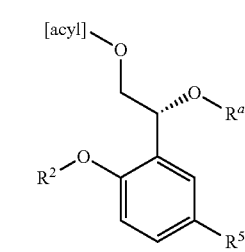

(R)-G-8 wherein [acyl] is a $C_1$-$C_7$ acyl group; and b) removing the [acyl] group;

thereby preparing the enantiomerically enriched compound of formula (R)-G-5.

In some embodiments, the compound of formula (R)-G-5 is:

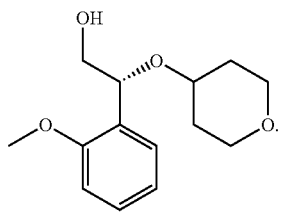

(R)-G-5

In some embodiments, the [acyl] donor is an optionally substituted 4-7 membered lactone or 4-7 membered optionally substituted cyclic anhydride; or a compound of the formula $R^xC(O)OR^y$, wherein $R^x$ is optionally substituted $C_{1-4}$ aliphatic; and $R^y$ is optionally substituted $C_{1-4}$ aliphatic or optionally substituted $C_{1-4}$ acyl.

In some embodiments, the [acyl] is a $C_4$ acyl group.

In some embodiments, the lipase enzyme is *Candida antarctica* lipase B.

Some embodiments provide for a process of preparing a compound G-9-a:

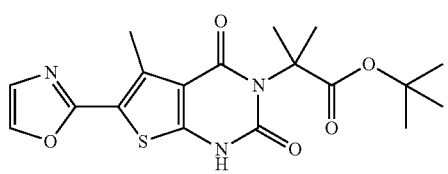

G-9-a contacting compound G-2-a:

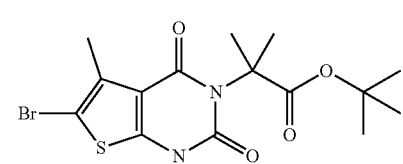

G-2-a with oxazole under conditions sufficient to form compound G-9-a.

In some embodiments, the reaction conditions comprise a solvent, wherein the solvent is tetrahydrofuran, 2-methyltetrahydrofuran, or a mixture thereof. In some embodiments, the solvent is tetrahydrofuran and 2-methyltetrahydrofuran.

In some embodiments, the reaction conditions comprise a metalating agent. In some embodiments, the metalating agent selected from isopropyl magnesium chloride, isopropyl magnesium bromide, TMPZnCl—LiCl, TMPMgCl—LiCl, and isopropyl magnesium chloride/lithium chloride (wherein TMP refers to 2,2,6,6-tetramethylpiperidine). In some embodiments, the metalating agent is isopropyl magnesium chloride. In some embodiments, the reaction conditions comprise contacting the oxazole and metalating agent at about −20° C. to −10° C. or about −15° C.

In some embodiments, the reaction conditions comprise adding $ZnCl_2$. In some embodiments, the catalyst is a palladium catalyst selected from $Pd(PPh_3)_4$, tBuXPhos Pd precatalyst, XPhos Pd precatalyst, RuPhos Pd precatalyst, and Pd-PEPPSI-IPent (dichloro[1,3-bis(2,6-di-3-pentylphenyl)imidazol-2-ylidene](3-chloropyridyl)palladium(II)). In some embodiments, the catalyst is $Pd(PPh_3)_4$. In some embodiments, the reaction mixture is heated to greater than about 50° C. after addition of $ZnCl_2$. In some embodiments, the reaction mixture is heated to about 60° C. to about 70° C. after addition of $ZnCl_2$.

Some embodiments provide for a process of preparing a compound (R)-G-1-a:

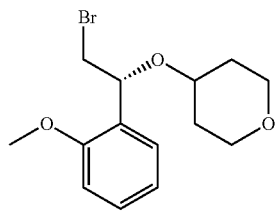

(R)-G-1-a comprising:
(a) contacting compound (R)-G-5-a or an oxygen anion thereof:

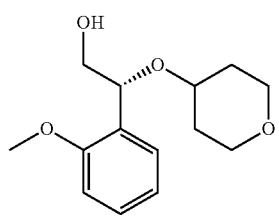

(R)-G-5-a with a sulfonylating reagent under conditions sufficient to form compound (R)-G-6-a:

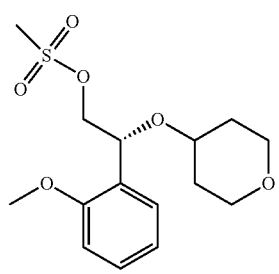

(R)-G-6-a (b) contacting compound (R)-G-6-a with a bromide salt under conditions sufficient to form compound (R)-G-1-a.

In some embodiments, the sulfonylating reagent is methanesulfonyl chloride.

In some embodiments, the reaction conditions of step (a) comprise a base. In some embodiments, the base is triethylamine, diisopropylethylamine (Hunig's base), 1,8-diazabicyclo[5.4.0]undec-7-ene, pyridine, or dimethylaminopyridine (DMAP). In some embodiments, the base is triethylamine. In some embodiments, the reaction conditions of step (a) comprise a solvent selected from 2-methyltetrahydrofuran, tetrahydrofuran, and dichloromethane. In some embodiments, the solvent is 2-methyltetrahydrofuran. In some embodiments, the reaction conditions of step (a) comprise a promoter. In some embodiments, the promoter is NaI or tetrabutylammonium iodide. In some embodiments, the reaction conditions of step (a) comprise a temperature of about 20° C. to about 30° C. In some embodiments, the reaction conditions of step (a) comprise a temperature of about 22° C.

In some embodiments, the bromide salt is LiBr, NaBr, or KBr. In some embodiments, the bromide salt is LiBr. In some embodiments, the bromide salt is an ammonium salt. In some embodiments, the bromide salt is tetrabutylammonium bromide.

In some embodiments, the reaction conditions of step (b) comprise a solvent selected from N-methylpyrrolidone (NMP), dimethylformamide (DMF), and dimethylacetamide (DMAc). In some embodiments, the solvent is NMP. In some embodiments, the reaction conditions of step (b) comprise a temperature of about 50° C. to about 60° C. In some embodiments, the reaction conditions of step (b) comprise a temperature of about 55° C.

Some embodiments provide for a process of preparing Compound 1:

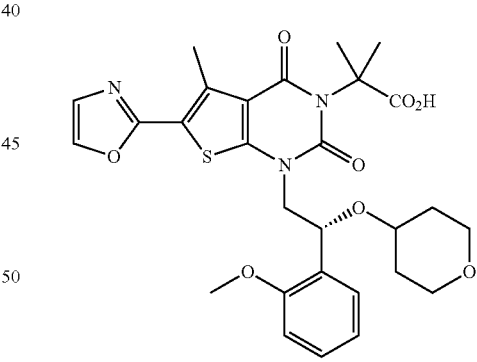

Compound 1 or salt or co-crystal thereof, comprising:
(a) contacting compound G-2-a:

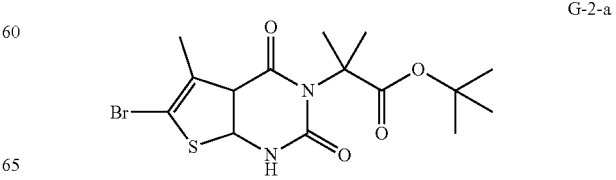

G-2-a with oxazole under conditions sufficient to form compound G-9-a:

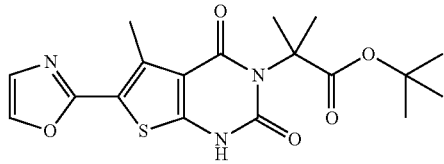

G-9-a (b) contacting compound G-9-a with compound (R)-G-1-a:

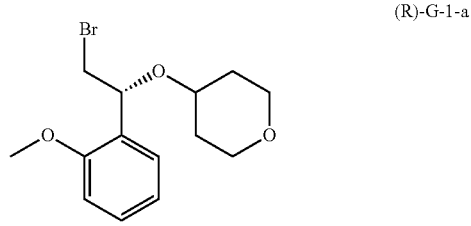 [SMILES: COc1ccccc1[C@H](CBr)OC1CCOCC1]

(R)-G-1-a under conditions sufficient to form a compound G-4-a:

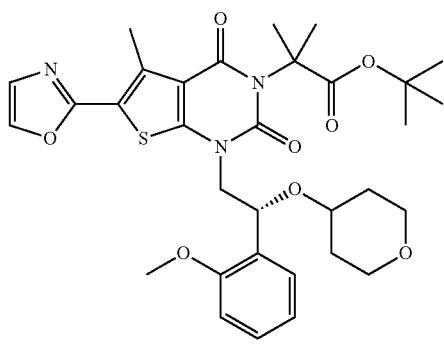

G-4-a and (c) hydrolyzing compound G-4-a under conditions sufficient to form Compound 1.

In some embodiments, the reaction conditions of step (a) comprise a solvent, wherein the solvent is tetrahydrofuran, 2-methyltetrahydrofuran, or a mixture thereof. In some embodiments, the solvent is tetrahydrofuran and 2-methyltetrahydrofuran.

In some embodiments, the reaction conditions of step (a) comprise a metalating agent. In some embodiments, the metalating agent selected from isopropyl magnesium chloride, isopropyl magnesium bromide, TMPZnCl—LiCl, TMPMgCl—LiCl, and isopropyl magnesium chloride/lithium chloride (wherein TMP refers to 2,2,6,6-tetramethylpiperidine). In some embodiments, the metalating agent is isopropyl magnesium chloride. In some embodiments, the reaction conditions of step (a) comprise contacting the oxazole and metalating agent at about −20° C. to −10° C. or about −15° C.

In some embodiments, the reaction conditions of step (a) comprise adding $ZnCl_2$. In some embodiments, the catalyst is a palladium catalyst selected from $Pd(PPh_3)_4$, tBuXPhos Pd precatalyst, XPhos Pd precatalyst, RuPhos Pd precatalyst, and Pd-PEPPSI-IPent. In some embodiments, the catalyst is $Pd(PPh_3)_4$. In some embodiments, the reaction mixture is heated to greater than about 50° C. after addition of $ZnCl_2$. In some embodiments, the reaction mixture is heated to about 60° C. to about 70° C. after addition of $ZnCl_2$.

In some embodiments, the reaction conditions of step (b) comprise a base. In some embodiments, the base is sodium carbonate, sodium bicarbonate, potassium carbonate, potassium bicarbonate, cesium carbonate, cesium bicarbonate, potassium phosphate tribasic, or potassium phosphate dibasic. In some embodiments, the base is sodium carbonate, sodium bicarbonate, potassium carbonate, potassium bicarbonate, cesium carbonate, or cesium bicarbonate. In some embodiments, the base is potassium carbonate. In some embodiments, the base is potassium carbonate or potassium bicarbonate.

In some embodiments, the reaction conditions of step (b) comprise a solvent selected from N-methylpyrrolidone (NMP), dimethylformamide (DMF), and dimethylacetamide (DMA). In some embodiments, the solvent is NMP.

In some embodiments, the reaction conditions of step (b) comprise a temperature of about 100° C. to about 140° C. In some embodiments, the reaction conditions of step (b) comprise a temperature of about 115° C.

In some embodiments, the reaction conditions of step (c) comprise an acid. In some embodiments, the acid is sulfuric acid, tetrafluoroboric acid, methanesulfonic acid, nitric acid, or hydrochloric acid. In some embodiments, the acid is sulfuric acid. In some embodiments, the acid is hydrochloric acid.

In some embodiments, the reaction conditions of step (c) comprise a co-solvent. In some embodiments, the co-solvent is an alcohol. In some embodiments, the co-solvent is 2-propanol, t-butanol, t-amyl alcohol, ethanol, or acetonitrile.

In some embodiments, the reaction conditions of step (c) comprise a temperature of about 5 and 10° C. In some embodiments, the reaction conditions of step (c) comprise a temperature between about 0 and about 20° C. In some embodiments, the reaction conditions of step (c) comprise between about 2 and about 8° C.

Some embodiments provide for a process of preparing Compound 1:

Compound 1

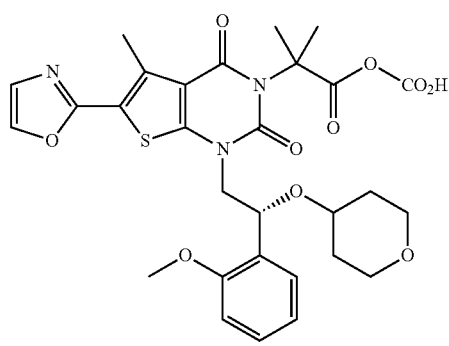

or a salt or co-crystal thereof, comprising:

(a) contacting compound (R)-G-6-a:

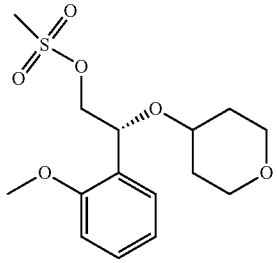
(R)-G-6-a with a bromide salt under conditions sufficient to form compound (R)-G-1-a:

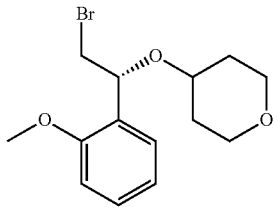
(R)-G-1-a (b) contacting compound G-2-a:

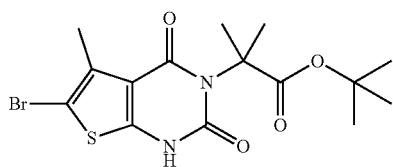
G-2-a with oxazole under conditions sufficient to form compound G-9-a:

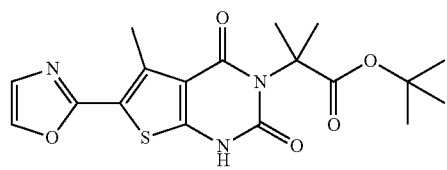
G-9-a (c) contacting compound G-9-a with compound (R)-G-1-a under conditions sufficient to form a compound G-4-a:

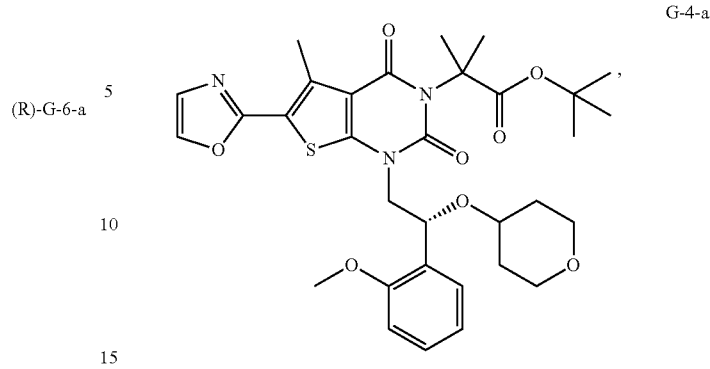
G-4-a and (d) hydrolyzing compound G-4-a under conditions sufficient to form Compound 1.

In some embodiments, the bromide salt is LiBr, NaBr, or KBr. In some embodiments, the bromide salt is LiBr. In some embodiments, the bromide salt is an ammonium salt. In some embodiments, the bromide salt is tetrabutylammonium bromide.

In some embodiments, the reaction conditions of step (a) comprise a solvent selected from N-methylpyrrolidone (NMP), dimethylformamide (DMF), and dimethylacetamide (DMAc). In some embodiments, the solvent is NMP. In some embodiments, the reaction conditions of step (a) comprise a temperature of about 50° C. to about 60° C. In some embodiments, the reaction conditions of step (a) comprise a temperature of about 55° C.

In some embodiments, the bromide salt is LiBr, NaBr, or KBr. In some embodiments, the bromide salt is LiBr. In some embodiments, the bromide salt is an ammonium salt. In some embodiments, the bromide salt is tetrabutylammonium bromide.

In some embodiments, the reaction conditions of step (b) comprise a solvent, wherein the solvent is tetrahydrofuran, 2-methyltetrahydrofuran, or a mixture thereof. In some embodiments, the solvent is tetrahydrofuran and 2-methyltetrahydrofuran.

In some embodiments, the reaction conditions of step (b) comprise a metalating agent. In some embodiments, the metalating agent selected from isopropyl magnesium chloride, isopropyl magnesium bromide, TMPZnCl—LiCl, TMPMgCl—LiCl, and isopropyl magnesium chloride/lithium chloride (wherein TMP refers to 2,2,6,6-tetramethylpiperidine). In some embodiments, the metalating agent is isopropyl magnesium chloride. In some embodiments, the reaction conditions of step (b) comprise contacting the oxazole and metalating agent at about −20° C. to −10° C. or about −15° C.

In some embodiments, the reaction conditions of step (b) comprise adding $ZnCl_2$. In some embodiments, the catalyst is a palladium catalyst selected from $Pd(PPh_3)_4$, tBuXPhos Pd precatalyst, XPhos Pd precatalyst, RuPhos Pd precatalyst, and Pd-PEPPSI-IPent. In some embodiments, the catalyst is $Pd(PPh_3)_4$. In some embodiments, the reaction mixture is heated to greater than about 50° C. after addition of $ZnCl_2$. In some embodiments, the reaction mixture is heated to about 60° C. to about 70° C. after addition of $ZnCl_2$.

In some embodiments, the reaction conditions of step (c) comprise a base. In some embodiments, the base is sodium carbonate, sodium bicarbonate, potassium carbonate, potassium bicarbonate, cesium carbonate, cesium bicarbonate, potassium phosphate tribasic, or potassium phosphate dibasic. In some embodiments, the base is sodium carbonate, sodium bicarbonate, potassium carbonate, potassium bicarbonate, cesium carbonate, cesium bicarbonate, potassium phosphate tribasic, or potassium phosphate dibasic. In some embodiments, the base is sodium carbonate, sodium bicarbonate, potassium carbonate, potassium bicarbonate, cesium carbonate, or cesium bicarbonate. In some embodiments, the base is potassium carbonate. In some embodiments, the base is potassium carbonate or potassium bicarbonate.

In some embodiments, the reaction conditions of step (c) comprise a solvent selected from N-methylpyrrolidone (NMP), dimethylformamide (DMF), and dimethylacetamide (DMA). In some embodiments, the solvent is NMP.

In some embodiments, the reaction conditions of step (c) comprise a temperature of about 90° C. to about 100° C. In some embodiments, the reaction conditions of step (c) comprise a temperature of about 100° C. to about 140° C. In some embodiments, the reaction conditions of step (c) comprise a temperature of about 115° C.

In some embodiments, the reaction conditions of step (d) comprise an acid. In some embodiments, the acid is sulfuric acid, tetrafluoroboric acid, methanesulfonic acid, nitric acid, or hydrochloric acid. In some embodiments, the acid is sulfuric acid. In some embodiments, the acid is hydrochloric acid.

In some embodiments, the reaction conditions of step (d) comprise a co-solvent. In some embodiments, the co-solvent is an alcohol. In some embodiments, the co-solvent is 2-propanol, t-butanol, t-amyl alcohol, ethanol, or acetonitrile.

In some embodiments, the reaction conditions of step (d) comprise a temperature of about 5 and 10° C. In some embodiments, the reaction conditions of step (d) comprise a temperature between about 0 and about 20° C. In some embodiments, the reaction conditions of step (e) comprise between about 2 and about 8° C.

Some embodiments provide for a process of preparing Compound 1:

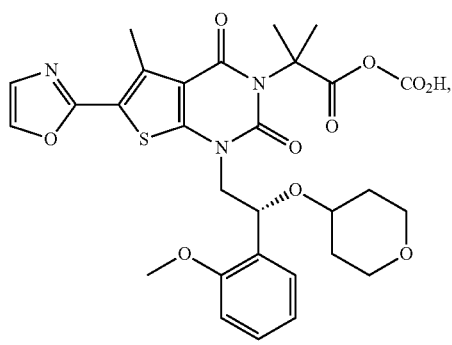

Compound 1 or salt or co-crystal thereof, comprising:
(a) contacting compound (R)-G-5-a or an oxygen anion thereof:

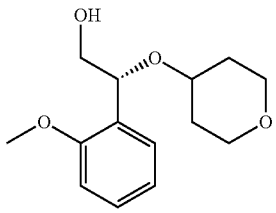

(R)-G-5-a with a sulfonylating reagent under conditions sufficient to form compound (R)-G-6-a:

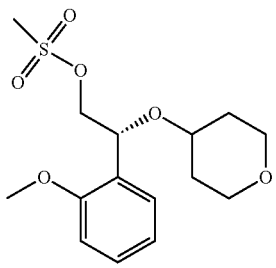

(R)-G-6-a (b) contacting compound (R)-G-6-a with a bromide salt under conditions sufficient to form compound (R)-G-1-a:

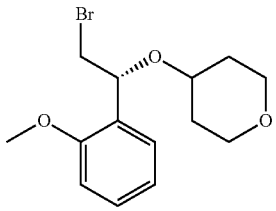

(R)-G-1-a (c) contacting compound G-2-a:

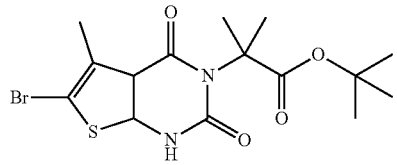

G-2-a with oxazole under conditions sufficient to form compound G-9-a:

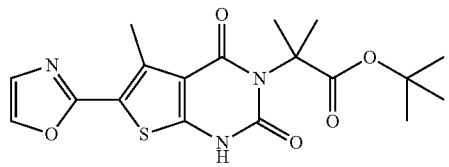

G-9-a (d) contacting compound G-9-a with compound (R)-G-1-a under conditions sufficient to form a compound G-4-a:

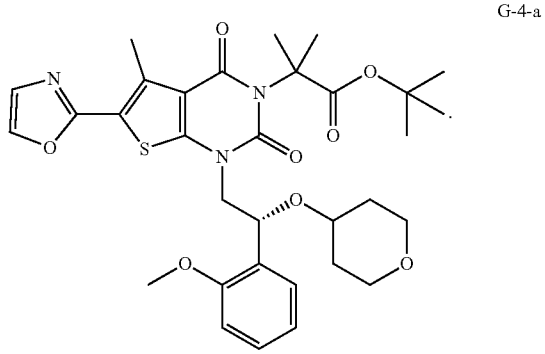 [SMILES: COc1ccccc1[C@H](Cn1c(=O)n(C(C)(C)C(=O)OC(C)(C)C)c(=O)c2c(C)c(-c3ncco3)sc21)OC1CCOCC1]

and (e) hydrolyzing compound G-4-a under conditions sufficient to form Compound 1.

In some embodiments, the sulfonylating reagent is methanesulfonyl chloride.

In some embodiments, the reaction conditions of step (a) comprise a base. In some embodiments, the base is triethylamine, diisopropylethylamine (Hunig's base), 1,8-diazabicyclo[5.4.0]undec-7-ene, pyridine, or dimethylaminopyridine (DMAP). In some embodiments, the base is triethylamine. In some embodiments, the reaction conditions of step (a) comprise a solvent selected from 2-methyltetrahydrofuran, tetrahydrofuran, and dichloromethane. In some embodiments, the solvent is 2-methyltetrahydrofuran. In some embodiments, the reaction conditions of step (a) comprise a promoter. In some embodiments, the promoter is NaI or tetrabutylammonium iodide. In some embodiments, the reaction conditions of step (a) comprise a temperature of about 20° C. to about 30° C. In some embodiments, the reaction conditions of step (a) comprise a temperature of about 22° C.

In some embodiments, the bromide salt is LiBr, NaBr, or KBr. In some embodiments, the bromide salt is LiBr. In some embodiments, the bromide salt is an ammonium salt. In some embodiments, the bromide salt is tetrabutylammonium bromide.

In some embodiments, the reaction conditions of step (b) comprise a solvent selected from N-methylpyrrolidone (NMP), dimethylformamide (DMF), and dimethylacetamide (DMAc). In some embodiments, the solvent is NMP. In some embodiments, the reaction conditions of step (b) comprise a temperature of about 50° C. to about 60° C. In some embodiments, the reaction conditions of step (b) comprise a temperature of about 55° C.

In some embodiments, the reaction conditions of step (c) comprise a solvent, wherein the solvent is tetrahydrofuran, 2-methyltetrahydrofuran, or a mixture thereof. In some embodiments, the solvent is tetrahydrofuran and 2-methyltetrahydrofuran.

In some embodiments, the reaction conditions of step (c) comprise a metalating agent. In some embodiments, the metalating agent selected from isopropyl magnesium chloride, isopropyl magnesium bromide, TMPZnCl—LiCl, TMPMgCl—LiCl, and isopropyl magnesium chloride/lithium chloride (wherein TMP refers to 2,2,6,6-tetramethylpiperidine). In some embodiments, the metalating agent is isopropyl magnesium chloride. In some embodiments, the reaction conditions of step (c) comprise contacting the oxazole and metalating agent at about −20° C. to −10° C. or about −15° C.

In some embodiments, the reaction conditions of step (c) comprise adding $ZnCl_2$. In some embodiments, the catalyst is a palladium catalyst selected from $Pd(PPh_3)_4$, tBuXPhos Pd precatalyst, XPhos Pd precatalyst, RuPhos Pd precatalyst, and Pd-PEPPSI-IPent. In some embodiments, the catalyst is $Pd(PPh_3)_4$. In some embodiments, the reaction mixture is heated to greater than about 50° C. after addition of $ZnCl_2$. In some embodiments, the reaction mixture is heated to about 60° C. to about 70° C. after addition of $ZnCl_2$.

In some embodiments, the reaction conditions of step (d) comprise a base. In some embodiments, the base is sodium carbonate, sodium bicarbonate, potassium carbonate, potassium bicarbonate, cesium carbonate, cesium bicarbonate, potassium phosphate tribasic, or potassium phosphate dibasic. In some embodiments, the base is sodium carbonate, sodium bicarbonate, potassium carbonate, potassium bicarbonate, cesium carbonate, cesium bicarbonate, potassium phosphate tribasic, or potassium phosphate dibasic. In some embodiments, the base is sodium carbonate, sodium bicarbonate, potassium carbonate, potassium bicarbonate, cesium carbonate, or cesium bicarbonate. In some embodiments, the base is potassium carbonate. In some embodiments, the base is potassium carbonate or potassium bicarbonate.

In some embodiments, the reaction conditions of step (d) comprise a solvent selected from N-methylpyrrolidone (NMP), dimethylformamide (DMF), and dimethylacetamide (DMA). In some embodiments, the solvent is NMP.

In some embodiments, the reaction conditions of step (d) comprise a temperature of about 90° C. to about 100° C. In some embodiments, the reaction conditions of step (d) comprise a temperature of about 100° C. to about 140° C. In some embodiments, the reaction conditions of step (d) comprise a temperature of about 115° C.

In some embodiments, the reaction conditions of step (e) comprise an acid. In some embodiments, the acid is sulfuric acid, tetrafluoroboric acid, methanesulfonic acid, nitric acid, or hydrochloric acid. In some embodiments, the acid is sulfuric acid. In some embodiments, the acid is hydrochloric acid.

In some embodiments, the reaction conditions of step (e) comprise a co-solvent. In some embodiments, the co-solvent is an alcohol. In some embodiments, the co-solvent is 2-propanol, t-butanol, t-amyl alcohol, ethanol, or acetonitrile.

In some embodiments, the reaction conditions of step (e) comprise a temperature of about 5 and 10° C. In some embodiments, the reaction conditions of step (e) comprise a temperature between about 0 and about 20° C. In some embodiments, the reaction conditions of step (e) comprise between about 2 and about 8° C.

5. Intermediate Compounds

Some embodiments provide herein intermediates useful for the synthesis of Compound 1 or methods of making such intermediates.

Some embodiments provide for a compound of formula, G-4-a:

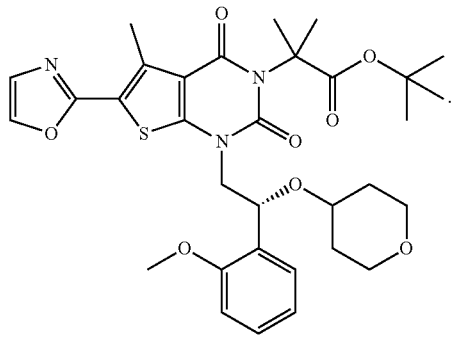

G-4-a

Some embodiments provide for a compound of formula, G-4-b:

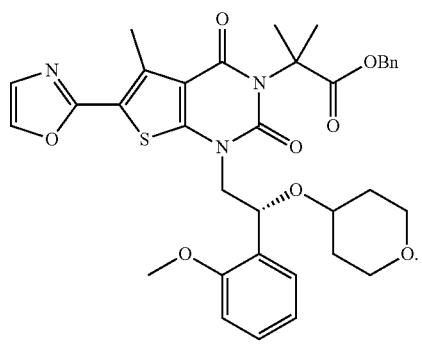

G-4-b

Some embodiments provide for a compound of formula, (R)-G-8:

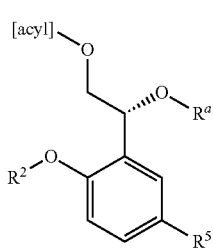

(R)-G-8 wherein:
- [acyl] is $R^xC(O)—$, wherein $R^x$ is optionally substituted $C_{1-4}$ aliphatic;
- $R^a$ is an optionally substituted group selected from a 3-7 membered ring having 0-2 heteroatoms selected from nitrogen, oxygen, and sulfur, and a $C_{1-6}$ aliphatic;
- $R^2$ is hydrogen, or optionally substituted $C_{1-6}$ aliphatic; and
- $R^5$ is hydrogen or halogen.

In some embodiments, $R^x$ is optionally substituted $C_{3-4}$ aliphatic.

Some embodiments provide for a compound of formula (R)-I-1:

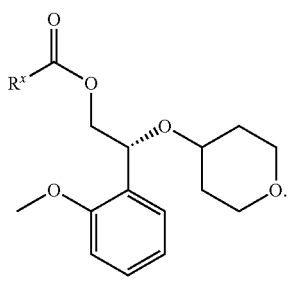

(R)-I-1 wherein $R^x$ is optionally substituted $C_{1-4}$ aliphatic.

Some embodiments provide for a compound of formula (R)-I-2:

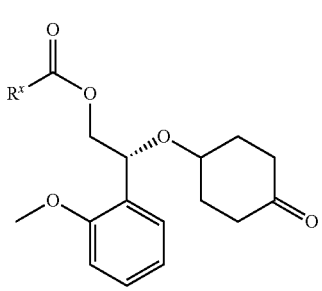

(R)-I-2 wherein $R^x$ is optionally substituted $C_{1-4}$ aliphatic.

Some embodiments provide for a compound of formula (R)-G-1:

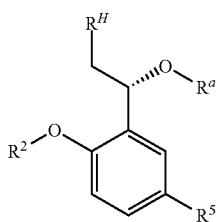

(R)-G-1 wherein:
- $R^H$ is a leaving group;
- $R^a$ is an optionally substituted group selected from a 3-7 membered ring having 0-2 heteroatoms selected from nitrogen, oxygen, and sulfur, and a $C_{1-6}$ aliphatic;
- $R^2$ is hydrogen, or optionally substituted $C_{1-6}$ aliphatic; and
- $R^5$ is hydrogen or halogen.

Some embodiments provide for a compound of formula H-1:

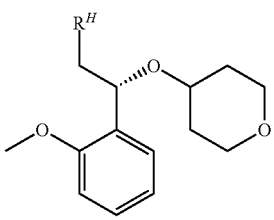

wherein R$^H$ is a leaving group.

Some embodiments provide for a compound of formula H-2:

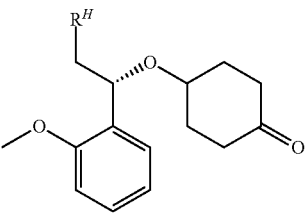

wherein R$^H$ is a leaving group.

In some embodiments, R$^H$ is halogen or sulfonate. In some embodiments, R$^H$ is bromo. In some embodiments, R$^H$ is mesylate. In some embodiments, [acyl] is succinyl. In some embodiments, the [acyl] donor is succinic anhydride.

Some embodiments provide for a compound of formula:

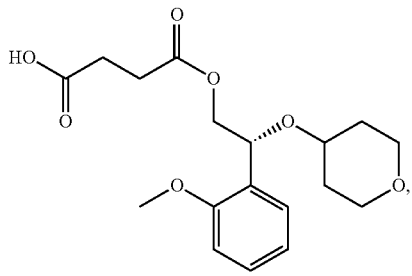 [SMILES: COc1ccccc1[C@H](COC(=O)CCC(=O)O)OC1CCOCC1]

or a salt thereof.

Some embodiments provide for a compound of formula:

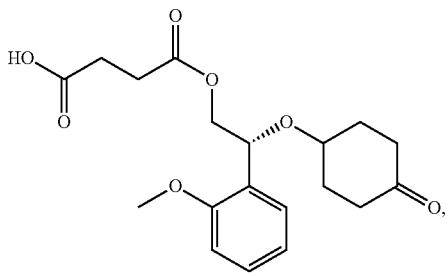 [SMILES: COc1ccccc1[C@H](COC(=O)CCC(=O)O)OC1CCC(=O)CC1]

or a salt thereof.

6. Uses, Formulation and Administration and Pharmaceutically Acceptable Compositions According to another embodiment, the invention provides a composition comprising a compound of this invention or a pharmaceutically acceptable salt, ester, or salt of ester thereof and a pharmaceutically acceptable carrier, adjuvant, or vehicle. Some embodiments provide for a composition comprising a compound as described herein, or a pharmaceutically acceptable salt or co-crystal thereof, and a pharmaceutically acceptable carrier, adjuvant, or vehicle.

Some embodiments provide for a composition comprising a crystalline form of Compound 1 as described herein. The amount of compound in compositions of this invention is such that is effective to measurably inhibit ACC, in a biological sample or in a patient. In certain embodiments, the amount of compound in compositions of this invention is such that is effective to measurably inhibit ACC, in a biological sample or in a patient. In certain embodiments, a composition of this invention is formulated for administration to a patient in need of such composition. In some embodiments, a composition of this invention is formulated for oral administration to a patient.

The term "compound" as used herein, means an ACC inhibitor of Formula I (including but not limited to Compound 1), or a solid form thereof. In some embodiments, the term "compound" as used herein, means an ACC inhibitor of Formula I (including but not limited to Compound 1), or a salt or solid form thereof. In some embodiments, a compound is Compound 1 or a pharmaceutically acceptable salt thereof. In some embodiments, a compound is the free acid of Compound 1. In some embodiments, a compound is a solid form of Compound 1. In some embodiments, a compound is a crystalline form of Compound 1. In some embodiments, a compound is Form I, Form II, Form III, Form IV, Form V, Form VI, Form VII, or Form VIII of Compound 1. In some embodiments, a compound is a polymorph of the free acid of Compound 1. In some embodiments, a compound is Form I, Form VII, or Form VIII of Compound 1. In some embodiments, a compound is a pseudopolymorph of the free acid of Compound 1. In some embodiments, a compound is Form I of Compound 1. In some embodiments, a compound is Form II of Compound 1. In some embodiments, a compound is Form III of Compound 1. In some embodiments, a compound is Form IV of Compound 1. In some embodiments, a compound is Form V of Compound 1. In some embodiments, a compound is Form VI of Compound 1. In some embodiments, a compound is Form VII of Compound 1. In some embodiments, a compound is Form VIII of Compound 1. In some embodiments, a compound is a solvate of Compound 1. In some embodiments, a compound is amorphous Compound 1. In some embodiments, a compound is a salt or co-crystal of Compound 1. In some embodiments, a compound is Compound 1 Sodium Form I. In some embodiments, a compound is Compound 1 Sodium Form II. In some embodiments, a compound is Compound 1 Calcium Form I. In some embodiments, a compound is Compound 1 Magnesium Form I. In some embodiments, a compound is Compound 1 Diethanolamine Form I. In some embodiments, a compound is Compound 1 Piperazine Form I.

The term "patient," as used herein, means an animal, preferably a mammal, and most preferably a human.

The term "pharmaceutically acceptable carrier, adjuvant, or diluent" refers to a non-toxic carrier, adjuvant, or vehicle that does not destroy the pharmacological activity of the compound with which it is formulated. Pharmaceutically acceptable carriers, adjuvants or diluents that may be used in the compositions of this invention include, but are not limited to, antiadherents, binders, coatings, colorants, disintegrants, flavors, glidants, lubricants, preservatives, sorbents, and vehicles. Examples of carriers, adjuvants, and diluents include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of ACC. In some embodiments, the inhibitorily active metabolite or residue thereof is selected from the following:

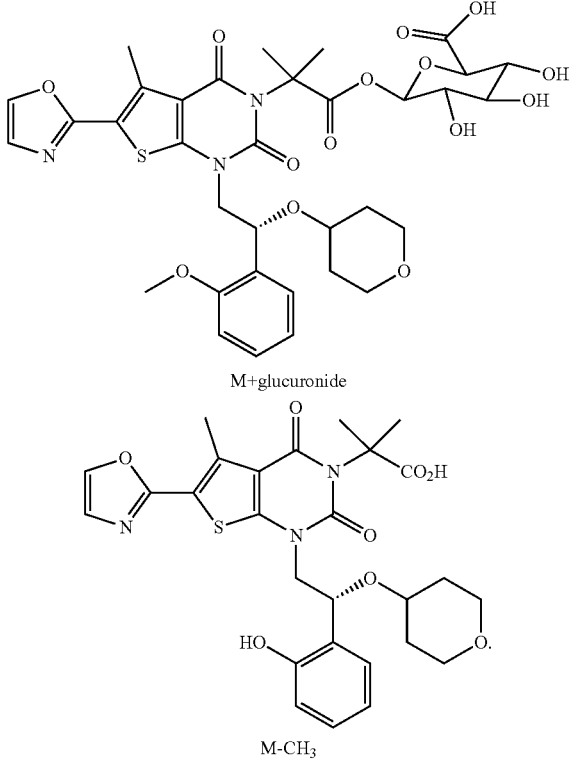

M+glucuronide

M-CH$_3$

In some embodiments, the present invention provides a metabolite of Compound 1, wherein the metabolite is the M+glucuronide conjugate. The M+glucuronide conjugate has an IC$_{50}$ at ACC1 of 5 nM. In some embodiments, the present invention provides a metabolite of Compound 1, wherein the metabolite is a M-CH$_3$ demethylated metabolite.

The M-CH$_3$ metabolite of Compound 1 has an IC$_{50}$ at ACC1 of 22 nM. In some embodiments, a provided metabolite of Compound 1 is isolated.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, a pharmaceutically acceptable composition comprising a form of Compound 1 as described herein is administered as a capsule. In some embodiments, a pharmaceutically acceptable composition comprising a form of Compound 1 as described herein is administered as a tablet.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

In some embodiments, a crystalline form of Compound 1 is administered at a dose of about 2 milligrams to about 500 milligrams per day, about 2 milligrams to about 400 milligrams per day, about 2 milligrams to about 300 milligrams per day, about 2 milligrams to about 200 milligrams per day, or about 2 milligrams to about 100 milligrams per day. In some embodiments, a crystalline form of Compound 1 is administered at a dose of about 5 milligrams per day, about 6 milligrams per day, about 7 milligrams per day, about 8 milligrams per day, about 9 milligrams per day, about 10 milligrams per day, about 11 milligrams per day, about 12 milligrams per day, about 13 milligrams per day, about 14 milligrams per day, about 15 milligrams per day, 16 milligrams per day, 17 milligrams per day, 18 milligrams per day, 19 milligrams per day, 20 milligrams per day, 21 milligrams per day, 22 milligrams per day, 23 milligrams per day, 24 milligrams per day, or 25 milligrams per day.

In some embodiments, a crystalline form of Compound 1 is administered at a dose of greater than about 5 milligrams per day, greater than about 10 milligrams per day, greater than about 15 milligrams per day, greater than about 20 milligrams per day, greater than about 25 milligrams per day, greater than about 30 milligrams per day, greater than about 35 milligrams per day, greater than about 40 milligrams per day, greater than about 45 milligrams per day, or greater than about 50 milligrams per day. In some embodiments, a crystalline form of Compound 1 is administered at a dose of less than about 300 milligrams per day, less than about 275 milligrams per day, less than about 250 milligrams per day, less than about 225 milligrams per day, less than about 200 milligrams per day, less than about 175 milligrams per day, less than about 150 milligrams per day, less than about 125 milligrams per day, less than about 100 milligrams per day.

In some embodiments, a crystalline form of Compound 1 is administered at a dose of about 5 milligrams once daily, about 20 milligrams once daily, about 30 milligrams once daily, about 50 milligrams once daily, about 80 milligrams once daily, about 100 milligrams once daily, about 150 milligrams once daily, about 200 milligrams once daily, about 500 milligrams once daily, about 800 milligrams once daily, or about 1000 milligrams once daily.

In some embodiments, a crystalline form of Compound 1 is administered at a dose of about 10 milligrams twice daily, about 25 milligrams twice daily, about 50 milligrams twice daily, or about 100 milligrams twice daily.

Pharmaceutical Uses

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "therapeutically effective amount" refers to an amount of the compound as described herein that is sufficient to effect treatment as defined above, when administered to a patient (particularly a human) in need of such treatment in one or more doses. The therapeutically effective amount will vary, depending upon the patient, the disease being treated, the weight and/or age of the patient, the severity of the disease, or the manner of administration as determined by a qualified prescriber or care giver.

Acetyl-CoA carboxylase (ACC) catalyzes the ATP-dependent carboxylation of acetyl-CoA to form malonyl-CoA. This reaction, which proceeds in two half-reactions, a biotin carboxylase (BC) reaction and a carboxyltransferase (CT) reaction, is the first committed step in fatty acid (FA) biosynthesis and is the rate-limiting reaction for the pathway. In addition to its role as a substrate in FA biosynthesis, malonyl-CoA, the product of the ACC-catalyzed reaction, also plays an important regulatory role in controlling mitochondrial FA uptake through allosteric inhibition of carnitine palmitoyltransferase I (CPT-I), the enzyme catalyzing the first committed step in mitochondrial FA oxidation. Malonyl-CoA, therefore, is a key metabolic signal for the control of FA production and utilization in response to dietary changes and altered nutritional requirements in animals, for example during exercise, and therefore plays a key role in controlling the switch between carbohydrate and fat utilization in liver and skeletal muscle (Harwood, 2005).

In mammals, ACC exists as two tissue-specific isozymes, ACC1 which is present in lipogenic tissues (liver, adipose) and ACC2, which is present in oxidative tissues (liver, heart, skeletal muscle). ACC1 and ACC2 are encoded by separate genes, display distinct cellular distributions, and share 75% overall amino acid sequence identity, except for an extension at the N-terminus of ACC2 that direct ACC2 to the mitochondrial membrane. ACC1, which lacks this targeting sequence, is localized to the cytoplasm. In the heart and skeletal muscle, which have a limited capacity to synthesize fatty acids, the malonyl-CoA formed by ACC2 functions to regulate FA oxidation. In the liver, the malonyl-CoA formed in the cytoplasm through the actions of ACC1 is utilized for FA synthesis and elongation leading to triglyceride formation and VLDL production, whereas the malonyl-CoA formed at the mitochondrial surface by ACC2 acts to regulate FA oxidation (Tong and Harwood, *J. Cellular Biochem.* 99: 1476, 2006). This compartmentalization of malonyl-CoA results from a combination of synthesis proximity (Abu-Elheiga et al., PNAS (USA) 102: 12011, 2005) and the rapid action of malonyl-CoA decarboxylase (Cheng et al., *J. Med. Chem.* 49:1517, 2006).

Simultaneous inhibition of the enzymatic activities of ACC1 and ACC2 offers the ability to inhibit de novo FA production in lipogenic tissues (e.g. liver & adipose) while at the same time stimulating FA oxidation in oxidative tissues (e.g. liver & skeletal muscle) and therefore offers an attractive modality for favorably affecting, in a concerted manner, a multitude of cardiovascular risk factors associated with obesity, diabetes, insulin resistance, and the metabolic syndrome.

Several lines of evidence strongly support the concept of direct inhibition of ACC activity as an important therapeutic target for treating obesity, diabetes, insulin resistance, and the metabolic syndrome.

Abu-Elheiga et al. (*Proc. Natl. Acad. Sci. USA* 100: 10207-10212, 2003) demonstrated that ACC2 knock-out mice exhibit reduced skeletal and cardiac muscle malonyl-CoA, increased muscle FA oxidation, reduced hepatic fat, reduced total body fat, elevated skeletal muscle uncoupling protein-3 (UCP3) which is indicative of increased energy expenditure, reduced body weight, reduced plasma free FAs, reduced plasma glucose, and reduced tissue glycogen, and are protected from diet-induced diabetes and obesity.

Savage et al. (*J. Clin. Invest.* 116: 817, 2006), using ACC1 and ACC2 antisense oligonucleotides, demonstrated stimulation of FA oxidation in isolated rat hepatocytes and in rats fed high-fat diets, and lowering of hepatic triglycerides, improvements in insulin sensitivity, reductions in hepatic glucose production, and increases in UCP1 mRNA in high fat-fed rats. These effects were greater when both ACC1 and ACC2 expression were suppressed than when either ACC1 or ACC2 expression alone was suppressed.

Harwood et al. (*J. Biol. Chem.* 278: 37099, 2003) demonstrated that the isozyme-nonselective ACC inhibitor, CP-640186, which equally inhibits ACC1 and ACC2 ($IC_{50}$~60 nM) isolated from rat, mouse, monkey and human without inhibiting either pyruvate carboxylase or propionyl-CoA carboxylase, reduced FA synthesis, triglyceride synthesis and secretion in Hep-G2 cells without affecting cholesterol synthesis, and reduced apoB secretion without affecting apoA1 secretion. CP-640186 also stimulated FA oxidation in C2C12 cells and in rat muscle slices and increased CPT-I activity in Hep-G2 cells. In experimental animals, CP-640186 acutely reduced malonyl-CoA concentration in both lipogenic and oxidative tissues in both the fed and fasted state, reduced liver and adipose tissue FA synthesis, and increased whole body FA oxidation. In sucrose-fed rats treated with CP-640186 for three weeks, CP-640186 time- and dose-dependently reduced liver, muscle and adipose triglycerides, reduced body weight due to selective fat reduction without reducing lean body mass, reduced leptin levels, reduced the hyperinsulinemia produced by the high sucrose diet without changing plasma glucose levels, and improved insulin sensitivity.

Saha et al. (*Diabetes* 55:A288, 2006) demonstrated stimulation of insulin sensitivity in insulin-resistant rat muscle tissue by CP-640186 within 30 min of compound administration, and studies by Furler et al. (*Diabetes* 55:A333, 2006) used dual tracer analysis to show that acute (46 min) treatment of rats with CP-640186 stimulated FA clearance without decreasing glucose clearance.

ACC is the rate-limiting enzyme in fatty acid synthesis and its product, malonyl CoA, serves as an important regulator of fatty acid oxidation. Hence, ACC inhibitors both reduce de novo lipid synthesis and promote the oxidation of existing fat. This dual effect on lipid metabolism raises the possibility that ACC inhibitors will be substantially more effective in reducing excess fat than other mechanisms. Furthermore, ACC inhibitors will impact insulin sensitivity, plasma and tissue triglycerides, and fasting plasma glucose as a consequence of whole-body and tissue-specific fat mass reduction without the need for poly-pharmacy.

For the treatment of obesity and other metabolic disorders, ACC inhibitors need only access the liver and muscle in the peripheral compartment. For oncological indications, tumor penetration is also required. However, avoiding the CNS will address many of side effects associated with the late-stage obesity programs targeting CNS receptors. ACC inhibitors are also expected to have superior safety profiles to existing metabolic disease agents. For example, it is unlikely that an ACC inhibitor will precipitate life-threatening hypoglycemia as is often seen with insulin mimetics, insulin secretagogues, and insulin degradation inhibitors. Also, since ACC inhibitors will reduce whole-body fat mass, they will be superior to the glitazones that increase whole-body fat mass as part of their mechanism of action.

A peripherally acting agent that causes significant weight loss and improves other metabolic endpoints fits well within the U.S. FDA's requirements for approval of a new obesity agent. However, if an approval for obesity continues to be challenging in 5-7 years, ACC inhibitors could be approved for familial combined hyperlipidemia and non-alcoholic steatohepatitis (NASH). There are currently no marketed ACC inhibitors, so an isozyme-nonselective ACC inhibitor would represent first-in-class therapy for treating obesity and metabolic syndrome, in addition to other disorders mediated by ACC enzymes.

The activity of a provided compound as an inhibitor of ACC or treatment for obesity or metabolic syndrome, may be assayed in vitro or in vivo. An in vivo assessment of the efficacy of the compounds of the invention may be made using an animal model of obesity or metabolic syndrome, e.g., a rodent or primate model. Cell-based assays may be performed using, e.g., a cell line isolated from a tissue that expresses ACC. Additionally, biochemical or mechanism-based assays, e.g., transcription assays using a purified protein, Northern blot, RT-PCR, etc., may be performed. In vitro assays include assays that determine cell morphology, protein expression, and/or the cytotoxicity, enzyme inhibitory activity, and/or the subsequent functional consequences of treatment of cells with compounds of the invention. Alternate in vitro assays quantitate the ability of the inhibitor to bind to protein or nucleic acid molecules within the cell. Inhibitor binding may be measured by radiolabeling the inhibitor prior to binding, isolating the inhibitor/target molecule complex and determining the amount of radiolabel bound. Alternatively, inhibitor binding may be determined by running a competition experiment where new inhibitors are incubated with purified proteins or nucleic acids bound to known radioligands. Detailed conditions for assaying a compound utilized in this invention as an inhibitor of ACC are set forth in the Examples below. The aforementioned assays are exemplary and not intended to limit the scope of the invention. The skilled practitioner can appreciate that modifications can be made to conventional assays to develop equivalent assays that obtain the same result.

A provided compound or composition thereof may be administered using any amount and any route of administration effective for treating or lessening the severity of a metabolic disorder or condition, cancer, a bacterial infection, a fungal infection, a parasitic infection (e.g. malaria), an autoimmune disorder, a neurodegenerative or neurological disorder, schizophrenia, a bone-related disorder, liver disease, or a cardiac disorder.

In some embodiments, a provided compound or composition thereof may be administered using any amount and any route of administration effective for treating or lessening the severity of a disease associated with ACC (Tong et al. "Acetyl-coenzyme A carboxylase: crucial metabolic enzyme and attractive target for drug discovery" Cell and Molecular Life Sciences (2005) 62, 1784-1803).

In some embodiments, a provided compound or composition thereof may be administered using any amount and any route of administration effective for treating or lessening the severity of a metabolic disorder, disease, or condition. In some embodiments, the metabolic disorder is obesity, metabolic syndrome, diabetes or diabetes-related disorders including Type 1 diabetes (insulin-dependent diabetes mellitus, IDDM) and Type 2 diabetes (non-insulin-dependent diabetes mellitus, NIDDM), impaired glucose tolerance, insulin resistance, hyperglycemia, diabetic complications, including, but not limited to atherosclerosis, coronary heart disease, stroke, peripheral vascular disease, nephropathy, hypertension, neuropathy and nephropathy; obesity comorbidities including but not limited to metabolic syndrome, dyslipidemia, hypertension, insulin resistance, diabetes (including Type 1 and Type 2 diabetes), coronary artery disease, and heart failure. In some embodiments, the metabolic disorder, disease or condition is non-alcoholic fatty liver disease or hepatic insulin resistance. In some embodiments, the metabolic disorder is non-alcoholic steatohepatitis.

Combination Therapy

In some embodiments, the present invention provides a method of treating a metabolic disorder, disease, or condition described herein, comprising administering a compound of the invention in conjunction with one or more pharmaceutical agents. Suitable pharmaceutical agents that may be used in combination with the compounds of the present invention include anti-obesity agents (including appetite suppressants), anti-diabetic agents, anti-hyperglycemic agents, lipid lowering agents, and anti-hypertensive agents.

Suitable lipid lowering agents that can be used in conjunction with a provided compound or composition thereof include but are not limited to, bile acid sequestrants, HMG-CoA reductase inhibitors, HMG-CoA synthase inhibitors, cholesterol absorption inhibitors, acyl coenzyme A-cholesterol acyl transferase (ACAT) inhibitors, CETP inhibitors, squalene synthetase inhibitors, PPAR-alpha agonists, FXR receptor modulators, LXR receptor modulators, lipoprotein synthesis inhibitors, renin-angiotensin system inhibitors, PPAR-delta partial agonists, bile acid reabsorption inhibitors, PPAR-gamma agonists, triglyceride synthesis inhibitors, microsomal triglyceride transport inhibitors, transcription modulators, squalene epoxidase inhibitors, low density lipoprotein receptor inducers, platelet aggregation inhibitors, 5-LO or FLAP inhibitors, niacin, and niacin-bound chromium.

Suitable anti-hypertensive agents that can be used in conjunction with a provided compound or composition thereof include but are not limited to diuretics, beta-adrenergic blockers, calcium channel blockers, angiotensin converting enzyme (ACE) inhibitors, neutral endopeptidase inhibitors, endothelin antagonists, vasodilators, angiotensin II receptor antagonists, alpha/beta adrenergic blockers, alpha 1 blockers, alpha 2 agonists, aldosterone inhibitors, mineralocorticoid receptor inhibitors, renin inhibitors, and angiopoietin 2 binding agents.

Suitable anti-diabetic agents that can be used in conjunction with a provided compound or composition thereof include but are not limited to other acetyl-CoA carboxylase (ACC) inhibitors, DGAT-1 inhibitors, AZD7687, LCQ908, DGAT-2 inhibitors, monoacylglycerol O-acyltransferase inhibitors, PDE-10 inhibitors, AMPK activators, sulfonylureas (e.g. acetohexamide, chlorpropamide, diabinese, glibenclamide, glipizide, glyburide, blimipiride, gliclazide, glipentide, gliquidone, glisolamide, tolazamide, tolbutamide), meglitinides, alpha-amylase inhibitors (e.g. tendamistat, treastatin, AL-3688), alpha-glucoside hydrolase inhibitors (e.g. acarbose), alpha-glucosidase inhibitors (e.g. adiposine, camiglibose, emiglitate, miglitol, voglibose, pradimicin-Q, sarbostatin), PPAR-gamma agonists (e.g. balaglitazone, ciglitazone, darglitazone, englitazone, isaglitazone, pioglitazone, rosiglitazone, troglitazone), PPAR-alpha/gamma agonists (e.g. CLX-0940, GW-1536, GW-1929, GW-2433, KRP-297, L-796449, LR-90, MK-0767, SB-219994), biguanides (e.g. metformin, buformin), GLP-1 modulators (exendin-3, exendin-4), liraglutide, albiglutide, exenatide (Byetta), taspoglutide, lixisenatide, dulaglutide, semaglutide, N,N-9924, TTP-054, PTP-1B inhibitors (trodusquemine, hyrtiosal extract), SIRT-1 inhibitors (e.g. resveratrol, GSK2245840, GSK184072), DPP-IV inhibitors (e.g. sitagliptin, vildagliptin, alogliptin, dutogliptin, linagliptin, saxagliptin), insulin secretagogues, fatty acid oxidation inhibitors, A2 antagonists, JNK inhibitors, glucokinase activators (e.g. TTP-399, TTP-355, TTP-547, AZD1656, ARRY403, MK-0599, TAK-329, AZD5658, GKM-001), insulin, insulin mimetics, glycogen phosphorylase inhibitors (e.g. GSK1362885), VPAC2 receptor agonists, SGLT2 inhibitors (dapagliflozin, canagliflozin, BI-10733, tofogliflozin, ASP-1941, THR1474, TS-071, ISIS388626, LX4211), glucagon receptor modulators, GPR119 modulators (e.g. MBX-2982, GSK1292263, APD597, PSN821), FGF21 derivatives, TGR5 (GPBAR1) receptor agonists (e.g. INT777), GPR40 agonists (e.g. TAK-875), GPR120 agonists, nicotinic acid receptor (HM74A) activators, SGLT1 inhibitors (e.g. GSK1614235), carnitine palmitoyl transferase enzyme inhibitors, fructose 1,6-diphosphatase inhibitors, aldose reductase inhibitors, mineralocorticoid receptor inhibitors, TORC2 inhibitors, CCR2 inhibitors, CCR5 inhibitors, PKC (e.g. PKC-alpha, PKC-beta, PKC-gamma) inhibitors, fatty acid synthetase inhibitors, serine palmitoyl transferase inhibitors, GPR81 modulators, GPR39 modulators, GPR43 modulators, GPR41 modulators, GPR105 modulators, Kv1.3 inhibitors, retinol binding protein 4 inhibitors, glucocorticoid receptor modulators, somatostatin receptor (e.g. SSTR1, SSTR2, SSTR3, SSTR5) inhibitors, PDHK2 inhibitors, PDHK4 inhibitors, MAP4K4 inhibitors, IL1-beta modulators, and RXR-alpha modulators.

Suitable anti-obesity agents include but are not limited to, 11-beta-hydroxysteroid dehydrogenase 1 inhibitors, stearoyl-CoA desaturase (SCD-1) inhibitors, MCR-4 agonists, CCK-A agonists, monoamine reuptake inhibitors (e.g. sibutramine), sympathomimetic agents, beta-3-adrenergic receptor agonists, dopamine receptor agonists (e.g. bromocriptine), melanocyte-stimulating hormone and analogs thereof, 5-$HT_{2C}$ agonists (e.g. lorcaserin/Belviq), melanin concentrating hormone antagonists, leptin, leptin analogs, leptin agonists, galanin antagonists, lipase inhibitors (e.g. tetrahydrolipstatin/Orlistat), anorectic agents (e.g. bombesin agonists), NPY antagonists (e.g. velneperit), $PYY_{3-36}$ (and analogs thereof), BRS3 modulators, opioid receptor mixed antagonists, thyromimetic agents, dehydroepiandrosterone, glucocorticoid agonists or antagonists, orexin antagonists, GLP-1 agonists, ciliary neurotrophic factors (e.g. Axokine), human agouti-related protein (AGRP) inhibitors, H3 antagonists or inverse agonists, neuromedin U agonists, MTP/ApoB inhibitors (e.g. gut-selective MTP inhibitors such as dirlotapide, JTT130, Usistapide, SLX4090), MetAp2 inhibitors (e.g. ZGN-433), agents with mixed modulatory activity at two or more of glucagon, GIP, and GLP1 receptors (e.g. MAR-701, ZP2929), norepinephrine reuptake inhibitors, opioid antagonists (e.g. naltrexone), CB1 receptor antagonists or inverse agonists, ghrelin agonists or antagonists, oxyntomodulin and analogs thereof, monoamine uptake inhibitors (e.g. tesofensine), and combination agents (e.g. buprorion plus zonisamide (Empatic), pramlintide plus metreleptin, buprorion plus naltrexone (Contrave), phentermine plus topiramate (Qsymia).

In some embodiments, the anti-obesity agents used in combination with a provided compound or composition thereof are selected from gut-selective MTP inhibitors (e.g. dirlotapide, mitratapide, implitapide, R56918), CCK-A agonists, 5-$HT_{2C}$ agonists (e.g. lorcaserin/Belviq), MCR4 agonists, lipase inhibitors (e.g. Cetilistat), $PYY_{3-36}$ (including analogs and PEGylated analogs thereof), opioid antagonists (e.g. naltrexone), oleoyl estrone, obinepitide, pramlintide, tesofensine, leptin, bromocriptine, orlistat, AOD-9604, and sibutramine.

In some embodiments, a provided compound or composition, according to the method of the present invention, may be administered using any amount and any route of administration effective for treating or lessening the severity of a LKB1 or Kras associated disease. In some embodiments, the LKB1 or Kras associated disease is selected from hepatocellular carcinoma, LKB1 mutant cancers, LKB1 loss of heterozygosity (LOH) driven cancers, Kras mutant cancers, Peutz-Jeghers syndrome (PJS), Cowden's disease (CD), and tubeous sclerosis (TS) (Makowski et al. "Role of LKB1 in Lung Cancer Development" British Journal of Cancer (2008) 99, 683-688). In some embodiments, the LKB1 or Kras associated disease is a Kras positive/LKB1 deficient lung tumor.

In some embodiments, a provided compound or composition, according to the method of the present invention, may be administered using any amount and any route of administration effective for treating or lessening the severity of a cancer, or inhibiting the growth of or inducing apoptosis in cancer cells (Wang et al. "Acetyl-CoA Carboxylase-alpha Inhibitor TOFA Induces Human Cancer Cell Apoptosis" Biochem Biophys Res Commun. (2009) 385(3), 302-306; Chajes et al. "Acetyl-CoA Carboxylase alpha Is Essential to Breast Cancer Cell Survival" Cancer Res. (2006) 66, 5287-5294; Beckers et al. "Chemical Inhibition of Acetyl-CoA Carboxylase Induces Growth Arrest and Cytotoxicity Selectivity in Cancer Cells" Cancer Res. (2007) 8180-8187; Brusselmans et al. "RNA Interference-Mediated Silencing of the Acetyl-CoA-Carboxylase-alpha Gene Induces Growth Inhibition and Apoptosis of Prostate Cancer Cells" Cancer Res. (2005) 65, 6719-6725; Brunet et al. "BRCA1 and Acetyl-CoA Carboxylase: The Metabolic Syndrom of Breast Cancer" Molecular Carcinogenesis (2008) 47, 157-163; Cairns et al. "Regulation of Cancer Cell Metabolism" (2011) 11, 85-95; Chiaradonna et al. "From Cancer Metabolism to New Biomarkers and Drug Targets" Biotechnology Advances (2012) 30, 30-51).

In some embodiments, a provided compound or composition, according to the method of the present invention, may be administered using any amount and any route of administration effective for treating or lessening the severity of a melanoma. In some embodiments, the melanoma is one bearing an activated MAPK pathway (Petti et al. "AMPK activators inhibit the proliferation of human melanomas bearing the activated MAPK pathway" Melanoma Research (2012) 22, 341-350).

A provided compound finds special utility in triple negative breast cancer, as the tumor suppressor protein BRCA1 binds and stabilizes the inactive form of ACC, thus regulating de novo lipid synthesis. Deletion or mutation of this tumor suppressor protein results in the loss of the binding and stabilization of the inactive form of ACC, resulting in increased capacity for ACC-driven de novo lipogenesis, resulting in cancer cell proliferation. See Brunet et al. "BRCA1 and acetyl-CoA carboxylase: the metabolic syndrome of breast cancer" Mol. Carcinog. (2008) 47(2), 157-163.

In some embodiments, a provided compound or composition, according to the method of the present invention, may be administered using any amount and any route of administration effective for treating or lessening the severity of a liposarcoma. Liposarcomas have been shown to depend on de novo long-chain fatty acid synthesis for growth, and inhibition of ACC by soraphen A inhibited lipogenesis as well as tumor cell growth (Olsen et al. "Fatty acid synthesis is a therapeutic target in human liposarcoma" International J. of Oncology (2010) 36, 1309-1314).

In some embodiments, a provided compound or composition, according to the method of the present invention, may be administered using any amount and any route of administration effective for treating or lessening the severity of a liver disease. In some embodiments, the liver disease is selected from alcoholic fatty liver disease (AFLD), familial combined hyperlipidemia, hepatitis (including hepatitis A, hepatitis B, and hepatitis C), hepatocellular carcinoma, non-alcoholic fatty liver disease (NAFLD), non-alcoholic steatohepatitis (NASH), liver cancer, liver fibrosis, liver inflammation, cholangiocarcinoma, angiosarcoma, hemangiosarcoma, and progressive familial intrahepatic cholestasis. In some embodiments, the liver disease is non-alcoholic steatoheptatitis. In some embodiments, the liver disease is hepatocellular carcinoma.

Some embodiments provided herein provide for methods of treating non-alcoholic steatohepatitis (NASH) comprising administering a therapeutically effective amount of a crystalline form of Compound 1 as described herein or a composition as described herein.

Some embodiments provided herein provide for the use of a crystalline form of Compound 1 as described herein or a composition as described herein in the treatment of treating non-alcoholic steatohepatitis (NASH).

Some embodiments provided herein provide for methods of treating non-alcoholic steatohepatitis (NASH) comprising administering a therapeutically effective amount of Form I of Compound 1 or a composition comprising Form I of Compound 1.

Some embodiments provided herein provide for the use of Form I of Compound 1 or a composition comprising Form I of Compound 1 in the treatment of treating non-alcoholic steatohepatitis (NASH).

Some embodiments provided herein provide for methods of treating hepatocellular carcinoma (HCC) comprising administering a therapeutically effective amount of a crystalline form of Compound 1 as described herein or a composition as described herein. Some embodiments provided herein provide for the use of a crystalline form of Compound 1 as described herein or a composition as described herein in the treatment of HCC. In some embodiments, a crystalline form of Compound 1 is administered as an adjuvant therapy. In some embodiments, the crystalline form of Compound 1 or composition described herein are administered after curative surgery, local ablation, or liver transplantation.

Some embodiments provided herein provide for methods of treating hepatocellular carcinoma (HCC) comprising administering a therapeutically effective amount of Form I of Compound 1 or a composition comprising Form I of Compound 1.

In some embodiments, a method of treating hepatocellular carcinoma (HCC) comprises administering a therapeutically effective amount of a crystalline form of Compound 1 as described herein or a composition as described herein in combination with surgical resection, liver transplantation, radiofrequency ablation, percutaneous ethanol injection, transarterial embolization, radiation, or chemotherapy. In some embodiments, a method of treating hepatocellular carcinoma (HCC) comprises administering a therapeutically effective amount of Form I of Compound 1 or a composition comprising Form I of Compound 1 in combination with surgical resection, liver transplantion, radiofrequency ablation, percutaneous ethanol injection, transarterial embolization, radiation, or chemotherapy.

In some embodiments, a provided compound or composition, according the method of the present invention, may be administered in combination with sorafenib for the treatment of hepatocellular carcinoma.

In some embodiments, a provided compound or composition, according to the method of the present invention, may be administered using any amount and any route of administration effective for treating or lessening the severity of a bacterial infection or inhibiting the growth of bacteria. In some embodiments, the bacterial infection is acne vulgaris.

In some embodiments, a provided compound or composition, according to the method of the present invention, may be administered using any amount and any route of administration effective for treating or lessening the severity of a fungal infection or inhibiting the growth of fungal cells (Shen et al. "A Mechanism for the Potent Inhibition of Eukaryotic Acetyl-Coenzyme A Carboxylase by Soraphen A, a Macrocyclic Polyketide Natural Product" Molecular Cell (2004) 16, 881-891).

In some embodiments, a provided compound inhibits one or more species of fungi at an MIC of 2 µg/mL or less. In some embodiments, a compound of the present invention inhibits at least one of *C. albicans, C. krusei,* and *C. parapsilosis* at a concentration of 2 µg/mL or less. In some embodiments, a compound of the present invention inhibits at least one of *C. albicans, C. krusei,* and *C. parapsilosis* at a concentration of 1 µg/mL or less. In some embodiments, a compound of the present invention inhibits at least two of *C. albicans, C. krusei,* and *C. parapsilosis* at a concentration of 2 µg/mL or less. In some embodiments, a compound of the present invention inhibits at least two of *C. albicans, C. krusei,* and *C. parapsilosis* at a concentration of 1 µg/mL or less. In some embodiments, a compound of the present invention inhibits each of *C. albicans, C. krusei,* and *C. parapsilosis* at a concentration of 2 µg/mL or less. In some embodiments, a compound of the present invention inhibits each of *C. albicans, C. krusei,* and *C. parapsilosis* at a concentration of 1 µg/mL In some embodiments, a provided compound inhibits at least one of *Botrtyis cinerea, Collectotrichum graminicola, Diplodia maydis, Fusarium moniliforme, Fusarium virguliforme, Phytophthora capsici, Rhizoctonia solani,* and *Septoria* at a concentration of 2 µg/mL or less. In some embodiments, a provided compound inhibits at least one of *Botrtyis cinerea, Collectotrichum graminicola, Diplodia maydis, Fusarium moniliforme, Fusarium virguliforme, Phytophthora capsici, Rhizoctonia solani,* and *Septoria* at a concentration of 1 µg/mL or less. In some embodiments, a compound of the present invention inhibits at least two of *Botrtyis cinerea, Collectotrichum graminicola, Diplodia maydis, Fusarium moniliforme, Fusarium virguliforme, Phytophthora capsici, Rhizoctonia solani,* and *Septoria* at a concentration of 2 µg/mL or less. In some embodiments, a compound of the present invention inhibits at least two of *Botrtyis cinerea, Collectotrichum graminicola, Diplodia maydis, Fusarium moniliforme, Fusarium virguliforme, Phytophthora capsici, Rhizoctonia solani,* and *Septoria* at a concentration of 1 µg/mL or less. In some embodiments, a compound of the present invention inhibits at least three of *Botrtyis cinerea, Collectotrichum graminicola, Diplodia maydis, Fusarium moniliforme, Fusarium virguliforme, Phytophthora capsici, Rhizoctonia solani,* and *Septoria* at a concentration of 2 µg/mL or less. In some embodiments, a compound of the present invention inhibits at least three of *Botrtyis cinerea, Collectotrichum graminicola, Diplodia maydis, Fusarium moniliforme, Fusarium virguliforme, Phytophthora capsici, Rhizoctonia solani,* and *Septoria* at a concentration of 1 µg/mL or less.

In some embodiments, a provided compound or composition, according to the method of the present invention, may be administered using any amount and any route of administration effective for treating or lessening the severity of a bacterial infection (Tong, L. et al. J. Cell. Biochem. (2006) 99, 1476-1488).

In some embodiments, a provided compound or composition, according to the method of the present invention, may be administered using any amount and any route of administration effective for treating or lessening the severity of a viral infection (Munger et al. Nat. Biotechnol. (2008) 26, 1179-1186). In some embodiments, the viral infection is Hepatitis C. In some embodiments, the viral infection is Hepatitis B. In some embodiments, the viral infection is Hepatitis A.

In some embodiments, a provided compound or composition, according to the method of the present invention, may be administered using any amount and any route of administration effective for treating or lessening the severity of a neurological disease (Henderson et al. Neurotherapeutics (2008) 5, 470-480; Costantini et al. Neurosci. (2008) 9 Suppl. 2:S16; Baranano et al. Curr. Treat. Opin. Neurol. (2008) 10, 410-419).

In some embodiments, a provided compound or composition, according to the method of the present invention, may be administered using any amount and any route of administration effective for treating or lessening the severity of a parasitic infection or inhibiting the growth of parasites (e.g. malaria and toxoplasma: Gornicki et al. "Apicoplast fatty acid biosynthesis as a target for medical intervention in apicomplexan parasites" International Journal of Parasitology (2003) 33, 885-896; Zuther et al. "Growth of *Toxoplasma gondii* is inhibited by aryloxyphenoxypropionate herbicides targeting acetyl-CoA carboxylase" PNAS (1999) 96 (23) 13387-13392).

In some embodiments, a provided compound or composition, according to the method of the present invention, may be administered using any amount and any route of administration effective for treating or lessening the severity of a cardiac disorder. In some embodiments, the cardiac disorder is cardiac hypertrophy. In some embodiments the cardiac disorder is treated or its severity lessened by the cardioprotective mechanism resulting from increased fatty acid oxidation via ACC inhibition (Kolwicz et al. "Cardiac-specific deletion of acetyl CoA carboxylase 2 (ACC2) prevents metabolic remodeling during pressure-overload hypertrophy" Circ. Res. (2012); DOI: 10.1161/CIRCRESAHA.112.268128).

In certain embodiments, a provided compound or composition, according to the method of the present invention, may be used as herbicides. In some embodiments, the present invention provides a method to inhibit the growth or viability of plants comprising treating plants with compounds of the present invention. In some embodiments of the present invention, a provided compound or composition can be used to inhibit the growth or viability of plants by inhibiting ACC. In some embodiments, the method of the present invention comprises using a provided compound or composition to inhibit fatty acid production in or increase fatty acid oxidation in plants.

The exact amount required will vary from subject to subject, depending on the species, age, and general condition of the subject, the severity of the infection, the particular agent, its mode of administration, and the like. A provided compound or composition of the invention is preferably formulated in dosage unit form for ease of administration and uniformity of dosage. The expression "dosage unit form" as used herein refers to a physically discrete unit of agent appropriate for the patient to be treated. It will be understood, however, that the total daily usage of a provided compound or composition of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

A pharmaceutically acceptable composition of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, a provided compound of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a provided compound, it is often desirable to slow the absorption of a compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending a compound in an oil vehicle. Injectable depot forms are made by forming microencapsule matrices of a compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

A provided compound can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting ACC in a biological sample comprising the step of contacting said biological sample with a provided compound, or a composition comprising said compound.

In certain embodiments, the invention relates to a method of modulating fatty acid levels in a biological sample comprising the step of contacting said biological sample with a provided compound, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of enzymes in a biological sample is useful for a variety of purposes that are known to one of skill in the art. Examples of such purposes include, but are not limited to biological assays, gene expression studies, and biological target identification.

Another embodiment of the present invention relates to a method of inhibiting ACC in a patient comprising the step of administering to said patient a provided compound, or a composition comprising said compound.

According to another embodiment, the invention relates to a method of inhibiting fatty acid production, stimulating fatty acid oxidation, or both, in a patient comprising the step of administering to said patient a provided compound, or a composition comprising said compound. According to certain embodiments, the invention relates to a method of inhibiting fatty acid production, stimulating fatty acid oxidation, or both in a patient, leading to decreasing obesity or alleviating symptoms of metabolic syndrome, comprising the step of administering to said patient a provided compound, or a composition comprising said compound. In other embodiments, the present invention provides a method for treating a disorder mediated by ACC, in a patient in need thereof, comprising the step of administering to said patient a provided compound or pharmaceutically acceptable composition thereof. Such disorders are described in detail herein.

In some embodiments, a provided compound or composition thereof may be used in a method of treating obesity or another metabolic disorder. In certain embodiments, a provided compound or composition thereof may be used to treat obesity or other metabolic disorder in a mammal. In certain embodiments the mammal is a human patient. In certain embodiments, a provided compound or composition thereof may be used to treat obesity or other metabolic disorder in a human patient.

In some embodiments, the present invention provides a method of treating obesity or another metabolic disorder, comprising administering a provided compound or composition thereof to a patient with obesity or another metabolic disorder. In certain embodiments, the method of treating obesity or another metabolic disorder comprises administering a provided compound or composition thereof to a mammal. In certain embodiments, the mammal is a human. In some embodiments, the metabolic disorder is dyslipidemia or hyperlipidemia. In some embodiments, the obesity is a symptom of Prader-Willi syndrome, Bardet-Biedl syndrome, Cohen syndrome or MOMO syndrome. In some embodiments, the obesity is a side effect of the administration of another medication, including but not limited to insulin, sulfonylureas, thiazolidinediones, antipsychotics, antidepressants, steroids, anticonvulsants (including phenytoin and valproate), pizotifen, or hormonal contraceptives.

In certain embodiments, the present invention provides a method of treating cancer or another proliferative disorder, comprising administering a provided compound or composition thereof to a patient with cancer or another proliferative disorder. In certain embodiments, the method of treating cancer or another proliferative disorder comprises administering a provided compound or composition thereof to a mammal. In certain embodiments, the mammal is a human.

As used herein, the terms "inhibition of cancer" and "inhibition of cancer cell proliferation" refer to the inhibition, or decrease in the rate, of the growth, division, maturation or viability of cancer cells, and/or causing the death of cancer cells, individually or in aggregate with other cancer cells, by cytotoxicity, nutrient depletion, or the induction of apoptosis.

Examples of tissues containing cancerous cells whose proliferation is inhibited by the a provided compound or composition thereof described herein and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the cancer treated by a provided compound or composition thereof is a melanoma, liposarcoma, lung cancer, breast cancer, prostate cancer, leukemia, kidney cancer, esophageal cancer, brain cancer, lymphoma or colon cancer. In certain embodiments, the cancer is a primary effusion lymphoma (PEL). In certain preferred embodiments, the cancer to be treated by a provided compound or composition thereof is one bearing an activated MAPK pathway. In some embodiments, the cancer bearing an activated MAPK pathway is a melanoma. In certain preferred embodiments, the cancer treated by a provided compound or composition thereof is one associated with BRCA1 mutation. In an especially preferred embodiment, the cancer treated by a provided compound or composition thereof is a triple negative breast cancer.

In certain embodiments, the diseases which can be treated by a provided compound or composition thereof are neurological disorders. In some embodiments, the neurological disorder is Alzheimer's Disease, Parkinson's Disease, epilepsy, ischemia, Age Associated Memory Impairment, Mild Cognitive Impairment, Friedreich's Ataxia, GLUT1-deficient epilepsy, Leprechaunism, Rabson-Mendenhall Syndrome, Coronary Arterial Bypass Graft dementia, anaesthesia-induced memory loss, amyotrophic lateral sclerosis, glioma or Huntington's Disease.

In certain embodiments, the disease which can be treated by a provided compound or composition thereof is an infectious disease. In some embodiments, the infectious disease is a viral infection. In some embodiments the viral infection is cytomegalovirus infection or influenza infection. In some embodiments, the infectious disease is a fungal infection. In some embodiments, the infectious disease is a bacterial infection.

Depending upon the particular condition, or disease, to be treated, additional therapeutic agents, which are normally administered to treat that condition, may be administered in combination with a provided compound or composition thereof. As used herein, additional therapeutic agents that are normally administered to treat a particular disease, or condition, are known as "appropriate for the disease, or condition, being treated."

In certain embodiments, a provided compound or composition thereof is administered in combination with one or more additional antifungal (antimycotic) agents for the treatment of a fungal infection. In some embodiments, the one or more additional antifungal (antimycotic) agents are selected from polyene antifungals (including but not limited to amphotericin B (as amphotericin B deoxycholate, amphotericin B lipid complex, or liposomal amphotericin B), candicidin, filipin, hamycin, natamycin, nystatin, and rimocidin), azole antifungals (including but not limited to abafungin, albaconazole, bifonazole, butoconazole, clotrimazole, econazole, efinaconazole, epoxiconazole, fenticonazole, fluconazole, isavuconazole, isoconazole, itraconazole, ketoconazole, luliconazole, miconazole, omoconazole, oxiconazole, posaconazole, propiconazole, ravuconazole, sertaconazole, sulconazole, terconazole, tioconazole, and voriconazole), allylamines (including but not limited to amorolfin, butenafine, naftifine, and terbinafine), echinocandins (including but not limited to anidulafungin, caspofungin, and micafungin), benzoic acid, ciclopirox, flucytosine, griseofulvin, haloprogin, tolnaftate, undecylenic acid, and crystal violet.

In certain embodiments, a provided compound or composition thereof is administered in combination with another inhibitor of ACC or antiobesity agent. In some embodiments, a provided compound or composition thereof is administered in combination with one or more other therapeutic agents. Such therapeutic agents include, but are not limited to agents such as orlistat (Xenical), CNS stimulants, Qsymia, or Belviq.

In certain embodiments, a provided compound or a composition thereof is administered in combination with another anti-cancer, cytotoxin, or chemotherapeutic agent, to a patient in need thereof.

In certain embodiments, the anti-cancer or chemotherapeutic agents used in combination with a provided compound or composition thereof include, but are not limited to, metformin, phenformin, buformin, imatinib, nilotinib, gefitinib, sunitinib, carfilzomib, salinosporamide A, retinoic acid, cisplatin, carboplatin, oxaliplatin, mechlorethamine, cyclophosphamide, chlorambucil, ifosfamide, azathioprine, mercaptopurine, doxifluridine, fluorouracil, gemcitabine, methotrexate, tioguanine, vincristine, vinblastine, vinorelbine, vindesine, podophyllotoxin, etoposide, teniposide, tafluposide, paclitaxel, docetaxel, irinotecan, topotecan, amsacrine, actinomycin, doxorubicin, daunorubicin, valrubicin, idarubicin, epirubicin, plicamycin, mitomycin, mitoxantrone, melphalan, busulfan, capecitabine, pemetrexed, epothilones, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, Accutane®, Actinomycin-D, Adriamycin®, Adrucil®, Afinitor®, Agrylin®, Ala-Cort®, Aldesleukin, Alemtuzumab, ALIMTA, Alitretinoin, Alkaban-AQ®, Alkeran®, All-transretinoic Acid, Alpha Interferon, Altretamine, Amethopterin, Amifostine, Aminoglutethimide, Anagrelide, Anandron®, Anastrozole, Arabinosylcytosine, Ara-C, Aranesp®, Aredia®, Arimidex®, Aromasin®, Arranon®, Arsenic Trioxide, Arzerra™, Asparaginase, ATRA, Avastin®, Azacitidine, BCG, BCNU, Bendamustine, Bevacizumab, Bexarotene, BEXXAR®, Bicalutamide, BiCNU, Blenoxane®, Bleomycin, Bortezomib, Busulfan, Busulfex®, C225, Calcium Leucovorin, Campath®, Camptosar®, Camptothecin-11, Capecitabine, Carac™, Carboplatin, Carmustine, Carmustine Wafer, Casodex®, CC-5013, CCI-779, CCNU, CDDP, CeeNU, Cerubidine®, Cetuximab, Chlorambucil, Citrovorum Factor, Cladribine, Cortisone, Cosmegen®, CPT-11, Cytadren®, Cytosar-U®, Cytoxan®, Dacarbazine, Dacogen, Dactinomycin, Darbepoetin Alfa, Dasatinib, Daunomycin, Daunorubicin Hydrochloride, Daunorubicin Liposomal, DaunoXome®, Decadron, Decitabine, Delta-Cortef®, Deltasone®, Denileukin, Diftitox, DepoCyt™, Dexamethasone, Dexamethasone Acetate, Dexamethasone Sodium Phosphate, Dexasone, Dexrazoxane, DHAD, DIC, Diodex, Docetaxel, Doxil®, Doxorubicin, Doxorubicin Liposomal, Droxia™, DTIC, DTIC-Dome®, Duralone®, Efudex®, Eligard™, Ellence™, Eloxatin™, Elspar®, Emcyt®, Epirubicin, Epoetin Alfa, Erbitux, Erlotinib, Erwinia L-asparaginase, Estramustine, Ethyol, Etopophos®, Etoposide, Etoposide Phosphate, Eulexin®, Everolimus, Evista®, Exemestane, Fareston®, Faslodex®, Femara®, Filgrastim, Floxuridine, Fludara®, Fludarabine, Fluoroplex®, Fluorouracil, Fluorouracil (cream), Fluoxymesterone, Flutamide, Folinic Acid, FUDR®, Fulvestrant, G-CSF, Gefitinib, Gemcitabine, Gemtuzumab, ozogamicin, Gemzar Gleevec™, Gliadel® Wafer, GM-CSF, Goserelin, Granulocyte—Colony Stimulating Factor, Granulocyte Macrophage Colony Stimulating Factor, Halotestin®, Herceptin®, Hexadrol, Hexalen®, Hexamethylmelamine, HMM, Hycamtin®, Hydrea®, Hydrocort Acetate®, Hydrocortisone, Hydrocortisone Sodium Phosphate, Hydrocortisone Sodium Succinate, Hydrocortone Phosphate, Hydroxyurea, Ibritumomab, Ibritumomab, Tiuxetan, Idamycin®, Idarubicin Ifex®, IFN-alpha, Ifosfamide, IL-11, IL-2, Imatinib mesylate, Imidazole Carboxamide, Interferon alfa, Interferon Alfa-2b (PEG Conjugate), Interleukin-2, Interleukin-11, Intron A® (interferon alfa-2b), Iressa®, Irinotecan, Isotretinoin, Ixabepilone, Ixempra™, Kidrolase®, Lanacort®, Lapatinib, L-asparaginase, LCR, Lenalidomide, Letrozole, Leucovorin, Leukeran, Leukine™, Leuprolide, Leurocristine, Leustatin™, Liposomal Ara-C, Liquid Pred®, Lomustine, L-PAM, L-Sarcolysin, Lupron®, Lupron Depot®, Matulane®, Maxidex, Mechlorethamine, Mechlorethamine Hydrochloride, Medralone®, Medrol®, Megace®, Megestrol, Megestrol Acetate, Melphalan, Mercaptopurine, Mesna, Mesnex™, Methotrexate, Methotrexate Sodium, Methylprednisolone, Meticorten®, Mitomycin, Mitomycin-C, Mitoxantrone, M-Prednisol®, MTC, MTX, Mustargen®, Mustine, Mutamycin®, Myleran®, Mylocel™, Mylotarg®, Navelbine®, Nelarabine, Neosar®, Neulasta™, Neumega®, Neupogen®, Nexavar®, Nilandron®, Nilotinib, Nilutamide, Nipent®, Nitrogen Mustard, Novaldex®, Novantrone®, Nplate, Octreotide, Octreotide acetate, Ofatumumab, Oncospar®, Oncovin®, Ontak®, Onxal™, Oprelvekin, Orapred®, Orasone®, Oxaliplatin, Paclitaxel, Paclitaxel Protein-bound, Pamidronate, Panitumumab, Panretin®, Paraplatin®, Pazopanib, Pediapred®, PEG Interferon, Pegaspargase, Pegfilgrastim, PEG-INTRON™, PEG-L-asparaginase, PEMETREXED, Pentostatin, Phenylalanine Mustard, Platinol®, Platinol-AQ®, Prednisolone, Prednisone, Prelone®, Procarbazine, PROCRIT®, Proleukin®, Prolifeprospan 20 with Carmustine Implant, Purinethol®, Raloxifene, Revlimid®, Rheumatrex®, Rituxan®, Rituximab, Roferon-A® (Interferon Alfa-2a), Romiplostim, Rubex®, Rubidomycin hydrochloride, Sandostatin®, Sandostatin LAR®, Sargramostim, Solu-Cortef®, Solu-Medrol®, Sorafenib, SPRYCEL™, STI-571, Streptozocin, SU11248, Sunitinib, Sutent®, Tamoxifen, Tarceva®, Targretin®, Tasigna®, Taxol®, Taxotere®, Temodar®, Temozolomide, Temsirolimus, Teniposide, TESPA, Thalidomide, Thalomid®, TheraCys®, Thioguanine, Thioguanine Tabloid®, Thiophosphoamide, Thioplex®, Thiotepa, TICE®, Toposar®, Topotecan, Toremifene, Torisel®, Tositumomab, Trastuzumab, Treanda®, Tretinoin, Trexall™, Trisenox®, TSPA, TYKERB®, VCR, Vectibix™, Velban®, Velcade®, VePesid®, Vesanoid®, Viadur™, Vidaza®, Vinblastine, Vinblastine Sulfate, Vincasar Pfs®, Vincristine, Vinorelbine, Vinorelbine tartrate, VLB, VM-26, Vorinostat, Votrient, VP-16, Vumon®, Xeloda®, Zanosar®, Zevalin™, Zinecard®, Zoladex®, Zoledronic acid, Zolinza, Zometa®, or combinations of any of the above.

In certain embodiments, a provided compound or composition may be administered together with a biguanide selected from metformin, phenformin, or buformin, to a patient in need thereof. In certain embodiments, the patient administered a combination of a provided compound and a biguanide is suffering from a cancer, obesity, a liver disease, diabetes or two or more of the above.

In some embodiments, a provided compound or composition may be administered together alone or with one or more additional therapeutic agents for the treatment of acne vulgaris. In some embodiments, the one or more additional therapeutic agents for the treatment of acne vulgaris are selected from topical anti-acne agents (e.g. retinoids, topical antibiotics, benzoyl peroxides), or systemic anti-acne agents (e.g. hormonal therapies, oral antibiotics, isotretinoin). In some embodiments, the hormonal therapy is an oral contraceptive or an androgen blocker. In some embodiments, the oral antibiotic is doxycycline, minocycline, tetracycline, or erythromycin.

In some embodiments, a provided compound or composition may be administered together alone or with one or more additional therapeutic agents for the treatment of seborrhea. In some embodiments, a provided compound or composition may be administered together alone or with one or more additional therapeutic agents for the treatment of seborrheic dermatitis. In some embodiments, a provided compound or composition may be administered together alone or with one or more additional therapeutic agents for the treatment of seborrheic keratosis.

In certain embodiments, a combination of two or more therapeutic agents may be administered together with a provided compound. In certain embodiments, a combination of 3 or more therapeutic agents may be administered with a provided compound.

Other examples of agents the compounds of this invention may also be combined with include, without limitation:

vitamins and nutritional supplements, cancer vaccines, treatments for neutropenia (e.g. G-CSF, filgrastim, lenograstim), treatments for thrombocytopenia (e.g. blood transfusion, erythropoietin), PI3 kinase (PI3K) inhibitors, MEK inhibitors, AMPK activators, PCSK9 inhibitors, SREBP site 1 protease inhibitors, HMG CoA-reductase inhibitors, antiemetics (e.g. 5-HT$_3$ receptor antagonists, dopamine antagonists, NK1 receptor antagonists, histamine receptor antagonists, cannabinoids, benzodiazepines, or anticholinergics), treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In certain embodiments, a provided compound, or a pharmaceutically acceptable composition thereof, are administered in combination with antisense agents, a monoclonal or polyclonal antibody or a siRNA therapeutic.

In some embodiments, the present invention provides a method of treating, stabilizing or lessening the severity or progression of a non-alcoholic fatty liver disease (NAFLD), comprising administering to a patient in need thereof a provided compound, or a pharmaceutically acceptable composition thereof, in combination with one or more additional therapeutic agents. In certain embodiments, the one or more additional therapeutic agents are independently selected from the group consisting of angiotensin II receptor antagonists, angiotensin converting enzyme (ACE) inhibitors, caspase inhibitors, cathepsin B inhibitors, CCR2 chemokine antagonists, CCR5 chemokine antagonists, chloride channel stimulators, cholesterol solubilizers, diacylglycerol O-acyltransferase 1 (DGAT1) inhibitors, dipeptidyl peptidase IV (DPPIV) inhibitors, farnesoid X receptor (FXR) agonists, FXR/TGR5 dual agonists, galectin-3 inhibitors, glucagon-like peptide 1 (GLP1) agonists, glutathione precursors, hepatitis C virus NS3 protease inhibitors, HMG CoA reductase inhibitors, 11β-hydroxysteroid dehydrogenase (11β-HSD1) inhibitors, IL-1β antagonists, IL-6 antagonists, IL-10 agonists, IL-17 antagonists, ileal sodium bile acid cotransporter inhibitors, leptin analogs, 5-lipoxygenase inhibitors, LPL gene stimulators, lysyl oxidase homolog 2 (LOXL2) inhibitors, PDE3 inhibitors, PDE4 inhibitors, phospholipase C (PLC) inhibitors, PPARα agonists, PPARγ agonists, PPARδ agonists, Rho associated protein kinase 2 (ROCK2) inhibitors, sodium glucose transporter-2 (SGLT2) inhibitors, stearoyl CoA desaturase-1 inhibitors, thyroid hormone receptor β agonists, tumor necrosis factor α (TNFα) ligand inhibitors, transglutaminase inhibitors, transglutaminase inhibitor precursors, PTP1b inhibitors, and ASK1 inhibitors.

In some embodiments, a provided compound, or a pharmaceutically acceptable composition thereof, is administered in combination with one or more additional therapeutic agents, wherein at least one of the additional therapeutic agents is an angiotensin II receptor antagonist.

In some embodiments, a provided compound, or a pharmaceutically acceptable composition thereof, is administered in combination with one or more additional therapeutic agents, wherein at least one of the additional therapeutic agents is an angiotensin converting enzyme (ACE) inhibitor. In some embodiments, the ACE inhibitor is enalapril.

In some embodiments, a provided compound, or a pharmaceutically acceptable composition thereof, is administered in combination with one or more additional therapeutic agents, wherein at least one of the additional therapeutic agents is a caspase inhibitor. In some embodiments the caspase inhibitor is emricasan.

In some embodiments, a provided compound, or a pharmaceutically acceptable composition thereof, is administered in combination with one or more additional therapeutic agents, wherein at least one of the additional therapeutic agents is a cathepsin B inhibitor. In some embodiments the cathepsin B inhibitor is a mixed cathepsin B/hepatitis C virus NS3 protease inhibitor. In some embodiments, the mixed cathepsin B/hepatitis C virus NS3 protease inhibitor is VBY-376.

In some embodiments, a provided compound, or a pharmaceutically acceptable composition thereof, is administered in combination with one or more additional therapeutic agents, wherein at least one of the additional therapeutic agents is a CCR2 chemokine antagonist. In some embodiments, the additional therapeutic agent is a mixed CCR2/CCR5 chemokine antagonist. In some embodiments, the mixed CCR2/CCR5 chemokine antagonist is cenicriviroc.

In some embodiments, a provided compound, or a pharmaceutically acceptable composition thereof, is administered in combination with one or more additional therapeutic agents, wherein at least one of the additional therapeutic agents is a CCR5 chemokine antagonist.

In some embodiments, a provided compound, or a pharmaceutically acceptable composition thereof, is administered in combination with one or more additional therapeutic agents, wherein at least one of the additional therapeutic agents is a chloride channel stimulator. In some embodiments, the chloride channel stimulator is cobiprostone.

In some embodiments, a provided compound, or a pharmaceutically acceptable composition thereof, is administered in combination with one or more additional therapeutic agents, wherein at least one of the additional therapeutic agents is a cholesterol solubilizer.

In some embodiments, a provided compound, or a pharmaceutically acceptable composition thereof, is administered in combination with one or more additional therapeutic agents, wherein at least one of the additional therapeutic agents is a diacylglycerol O-acyltransferase 1 (DGAT1) inhibitor. In some embodiments, the DGAT1 inhibitor is LCQ908.

In some embodiments, a provided compound, or a pharmaceutically acceptable composition thereof, is administered in combination with one or more additional therapeutic agents, wherein at least one of the additional therapeutic agents is a dipeptidyl peptidase IV (DPPIV) inhibitor. In some embodiments, the DPPIV inhibitor is linagliptin.

In some embodiments, a provided compound, or a pharmaceutically acceptable composition thereof, is administered in combination with one or more additional therapeutic agents, wherein at least one of the additional therapeutic agents is a farnesoid X receptor (FXR) agonist. In some embodiments, the FXR agonist is INT-747 (obeticholic acid). In some embodiments, the FXR agonist is PX-102.

In some embodiments, a provided compound, or a pharmaceutically acceptable composition thereof, is administered in combination with one or more additional therapeutic agents, wherein at least one of the additional therapeutic agents is an FXR/TGR5 dual agonist. In some embodiments, the FXR/TGR5 dual agonist is INT-767.

In some embodiments, a provided compound, or a pharmaceutically acceptable composition thereof, is administered in combination with one or more additional therapeutic agents, wherein at least one of the additional therapeutic agents is a galectin-3 inhibitor. In some embodiments, the galectin-3 inhibitor is GR-MD-02.

In some embodiments, a provided compound, or a pharmaceutically acceptable composition thereof, is administered in combination with one or more additional therapeutic agents, wherein at least one of the additional therapeutic agents is a glucagon-like peptide 1 (GLP1) agonist. In some embodiments, the GLP1 agonist is liraglutide. In some embodiments, the GLP1 agonist is exenatide.

In some embodiments, a provided compound, or a pharmaceutically acceptable composition thereof, is administered in combination with one or more additional therapeutic agents, wherein at least one of the additional therapeutic agents is a glutathione precursor.

In some embodiments, a provided compound, or a pharmaceutically acceptable composition thereof, is administered in combination with one or more additional therapeutic agents, wherein at least one of the additional therapeutic agents is a hepatitis C virus NS3 protease inhibitor. In some embodiments the heptatitis C virus NS3 protease inhibitor is a mixed cathepsin B/hepatitis C virus NS3 protease inhibitor. In some embodiments, the mixed cathepsin B/hepatitis C virus NS3 protease inhibitor is VBY-376.

In some embodiments, a provided compound, or a pharmaceutically acceptable composition thereof, is administered in combination with one or more additional therapeutic agents, wherein at least one of the additional therapeutic agents is an HMG CoA reductase inhibitor. In some embodiments, the HMG-CoA reductase inhibitor is a statin. In some embodiments, the HMG-CoA reductase inhibitor is atorvastatin.

In some embodiments, a provided compound, or a pharmaceutically acceptable composition thereof, is administered in combination with one or more additional therapeutic agents, wherein at least one of the additional therapeutic agents is an 11β-hydroxysteroid dehydrogenase (11β-HSD1) inhibitor. In some embodiments, the 11β-HSD1 inhibitor is RO5093151.

In some embodiments, a provided compound, or a pharmaceutically acceptable composition thereof, is administered in combination with one or more additional therapeutic agents, wherein at least one of the additional therapeutic agents is an IL-1β antagonist.

In some embodiments, a provided compound, or a pharmaceutically acceptable composition thereof, is administered in combination with one or more additional therapeutic agents, wherein at least one of the additional therapeutic agents is an IL-6 antagonist. In some embodiments, the IL-6 antagonist is a mixed IL-6/IL-1β/TNFα ligand inhibitor. In some embodiments, the mixed IL-6/IL-1β/TNFα ligand inhibitor is BLX-1002.

In some embodiments, a provided compound, or a pharmaceutically acceptable composition thereof, is administered in combination with one or more additional therapeutic agents, wherein at least one of the additional therapeutic agents is an IL-10 agonist. In some embodiments, the IL-10 agonist is peg-ilodecakin.

In some embodiments, a provided compound, or a pharmaceutically acceptable composition thereof, is administered in combination with one or more additional therapeutic agents, wherein at least one of the additional therapeutic agents is an IL-17 antagonist. In some embodiments, the IL-17 antagonist is KD-025.

In some embodiments, a provided compound, or a pharmaceutically acceptable composition thereof, is administered in combination with one or more additional therapeutic agents, wherein at least one of the additional therapeutic agents is an ileal sodium bile acid cotransporter inhibitor. In some embodiments, the ileal sodium bile acid cotransporter inhibitor is SHP-626.

In some embodiments, a provided compound, or a pharmaceutically acceptable composition thereof, is administered in combination with one or more additional therapeutic agents, wherein at least one of the additional therapeutic agents is a leptin analog. In some embodiments the leptin analog is metreleptin.

In some embodiments, a provided compound, or a pharmaceutically acceptable composition thereof, is administered in combination with one or more additional therapeutic agents, wherein at least one of the additional therapeutic agents is a 5-lipoxygenase inhibitor. In some embodiments, the 5-lipoxygenase inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, a provided compound, or a pharmaceutically acceptable composition thereof, is administered in combination with one or more additional therapeutic agents, wherein at least one of the additional therapeutic agents is a LPL gene stimulator. In some embodiments the LPL gene stimulator is alipogene tiparvovec.

In some embodiments, a provided compound, or a pharmaceutically acceptable composition thereof, is administered in combination with one or more additional therapeutic agents, wherein at least one of the additional therapeutic agents is a lysyl oxidase homolog 2 (LOXL2) inhibitor. In some embodiments, the LOXL2 inhibitor is an anti-LOXL2 antibody. In some embodiments, the anti-LOXL2 antibody is GS-6624.

In some embodiments, a provided compound, or a pharmaceutically acceptable composition thereof, is administered in combination with one or more additional therapeutic agents, wherein at least one of the additional therapeutic agents is a PDE3 inhibitor. In some embodiments, the PDE3 inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, a provided compound, or a pharmaceutically acceptable composition thereof, is administered in combination with one or more additional therapeutic agents, wherein at least one of the additional therapeutic agents is a PDE4 inhibitor. In some embodiments, the PDE4 inhibitor is ASP-9831. In some embodiments, the PDE4 inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, a provided compound, or a pharmaceutically acceptable composition thereof, is administered in combination with one or more additional therapeutic agents, wherein at least one of the additional therapeutic agents is a phospholipase C (PLC) inhibitor. In some embodiments, the PLC inhibitor is a mixed 5-lipoxygenase/PDE3/PDE4/PLC inhibitor. In some embodiments, the mixed 5-lipoxygenase/PDE3/PDE4/PLC inhibitor is tipelukast.

In some embodiments, a provided compound, or a pharmaceutically acceptable composition thereof, is administered in combination with one or more additional therapeutic agents, wherein at least one of the additional therapeutic agents is a PPARα agonist. In some embodiments the PPARα agonist is a mixed PPARα/δ agonist. In some embodiments, the mixed PPARα/δ agonist is GFT505.

In some embodiments, a provided compound, or a pharmaceutically acceptable composition thereof, is administered in combination with one or more additional therapeutic agents, wherein at least one of the additional therapeutic agents is a PPARγ agonist. In some embodiments, the PPARγ agonist is pioglitazone.

In some embodiments, a provided compound, or a pharmaceutically acceptable composition thereof, is administered in combination with one or more additional therapeutic agents, wherein at least one of the additional therapeutic agents is a PPARδ agonist.

In some embodiments, a provided compound, or a pharmaceutically acceptable composition thereof, is administered in combination with one or more additional therapeutic agents, wherein at least one of the additional therapeutic agents is a Rho associated protein kinase 2 (ROCK2) inhibitor. In some embodiments the ROCK2 inhibitor is KD-025.

In some embodiments, a provided compound, or a pharmaceutically acceptable composition thereof, is administered in combination with one or more additional therapeutic agents, wherein at least one of the additional therapeutic agents is a sodium glucose transporter-2 (SGLT2) inhibitor. In some embodiments, the SGLT2 inhibitor is remogliflozin etabonate.

In some embodiments, a provided compound, or a pharmaceutically acceptable composition thereof, is administered in combination with one or more additional therapeutic agents, wherein at least one of the additional therapeutic agents is a stearoyl CoA desaturase-1 inhibitor. In some embodiments, the stearoyl CoA desaturase-1 inhibitor is aramchol. In some embodiments, the stearoyl CoA desaturase-1 inhibitor is CVT-12805.

In some embodiments, a provided compound, or a pharmaceutically acceptable composition thereof, is administered in combination with one or more additional therapeutic agents, wherein at least one of the additional therapeutic agents is a thyroid hormone receptor β agonist. In some embodiments the thyroid hormone receptor β agonist is MGL-3196.

In some embodiments, a provided compound, or a pharmaceutically acceptable composition thereof, is administered in combination with one or more additional therapeutic agents, wherein at least one of the additional therapeutic agents is a tumor necrosis factor α (TNFα) ligand inhibitor.

In some embodiments, a provided compound, or a pharmaceutically acceptable composition thereof, is administered in combination with one or more additional therapeutic agents, wherein at least one of the additional therapeutic agents is a transglutaminase inhibitor. In some embodiments, the transglutaminase inhibitor precursor is mercaptamine.

In some embodiments, a provided compound, or a pharmaceutically acceptable composition thereof, is administered in combination with one or more additional therapeutic agents, wherein at least one of the additional therapeutic agents is a transglutaminase inhibitor precursor.

In some embodiments, a provided compound, or a pharmaceutically acceptable composition thereof, is administered in combination with one or more additional therapeutic agents, wherein at least one of the additional therapeutic agents is a PTP1b inhibitor. In some embodiments, the PTP1b inhibitor is A119505, A220435, A321842, CPT633, ISIS-404173, JTT-551, MX-7014, MX-7091, MX-7102, NNC-521246, OTX-001, OTX-002, or TTP814.

In some embodiments, a provided compound, or a pharmaceutically acceptable composition thereof, is administered in combination with one or more additional therapeutic agents, wherein at least one of the additional therapeutic agents is an ASK1 inhibitor. In some embodiments, the ASK1 inhibitor is GS-4977 (also known as selonsertib).

In some embodiments, the one or more additional therapeutic agents are independently selected from acetylsalicylic acid, alipogene tiparvovec, aramchol, atorvastatin, BLX-1002, cenicriviroc, cobiprostone, colesevelam, emricasan, enalapril, GFT-505, GR-MD-02, hydrochlorothiazide, icosapent ethyl ester (ethyl eicosapentaenoic acid), IMM-124E, KD-025, linagliptin, liraglutide, mercaptamine, MGL-3196, obeticholic acid, olesoxime, peg-ilodecakin, pioglitazone, PX-102, remogliflozin etabonate, SHP-626, solithromycin, tipelukast, TRX-318, ursodeoxycholic acid, and VBY-376.

In some embodiments, one of the one or more additional therapeutic agents is acetylsalicylic acid. In some embodiments, one of the one or more additional therapeutic agents is alipogene tiparvovec. In some embodiments, one of the one or more additional therapeutic agents is aramchol. In some embodiments, one of the one or more additional therapeutic agents is atorvastatin. In some embodiments, one of the one or more additional therapeutic agents is BLX-1002. In some embodiments, one of the one or more additional therapeutic agents is cenicriviroc. In some embodiments, one of the one or more additional therapeutic agents is cobiprostone. In some embodiments, one of the one or more additional therapeutic agents is colesevelam. In some embodiments, one of the one or more additional therapeutic agents is emricasan. In some embodiments, one of the one or more additional therapeutic agents is enalapril. In some embodiments, one of the one or more additional therapeutic agents is GFT-505. In some embodiments, one of the one or more additional therapeutic agents is GR-MD-02. In some embodiments, one of the one or more additional therapeutic agents is hydrochlorothiazide. In some embodiments, one of the one or more additional therapeutic agents is icosapent ethyl ester (ethyl eicosapentaenoic acid). In some embodiments, one of the one or more additional therapeutic agents is IMM-124E. In some embodiments, one of the one or more additional therapeutic agents is KD-025. In some embodiments, one of the one or more additional therapeutic agents is linagliptin. In some embodiments, one of the one or more additional therapeutic agents is liraglutide. In some embodiments, one of the one or more additional therapeutic agents is mercaptamine. In some embodiments, one of the one or more additional therapeutic agents is MGL-3196. In some embodiments, one of the one or more additional therapeutic agents is obeticholic acid. In some embodiments, one of the one or more additional therapeutic agents is olesoxime. In some embodiments, one of the one or more additional therapeutic agents is pegilodecakin. In some embodiments, one of the one or more additional therapeutic agents is pioglitazone. In some embodiments, one of the one or more additional therapeutic agents is PX-102. In some embodiments, one of the one or more additional therapeutic agents is remogliflozin etabonate. In some embodiments, one of the one or more additional therapeutic agents is SHP-626. In some embodiments, one of the one or more additional therapeutic agents is solithromycin. In some embodiments, one of the one or more additional therapeutic agents is tipelukast. In some embodiments, one of the one or more additional therapeutic agents is TRX-318. In some embodiments, one of the one or more additional therapeutic agents is ursodeoxycholic acid. In some embodiments, one of the one or more additional therapeutic agents is and VBY-376.

In some embodiments, at least one of the one or more additional therapeutic agents is an anti-diabetic agent. In some embodiments, the anti-diabetic agent is an adenosine $A_1$ receptor agonist (e.g. adenosine, CCPA, CVT-3619, GR-190718), an adenosine $A_2$ receptor antagonist (istradefylline, SCH-58261), an aldose reductase inhibitor, an α-amylase inhibitor (e.g. tendamistat, treastatin, AL-3688), an α-glucosidase inhibitor (e.g. acarbose, camiglibose, diposine, emiglitate, miglitol, pradimicin-Q, sarbostatin, voglibose), an amylin analog (e.g. AC164209 and pramlintide), an AMPK activator, a β3-adrenergic agonist (e.g. amibegron, AZ-40140, CL-316,243, KRP-204, L-742,791, L-796,568, LY-368,842, LY-377,604, mirabegron, Ro 40-2148, solabegron, SWR-0342SA), a β-ketoacyl-acyl carrier protein synthase inhibitor, a biguanide (e.g. metformin, buformin, phenformin), a carnitine palmitoyl transferase inhibitor, a DGAT-2 inhibitor, a DPP-4 inhibitor (e.g. alogliptin, anagliptin, dutogliptin, gemigliptin, linagliptin, omarigliptin, saxagliptin, sitagliptin, teneligliptin, trelagliptin, and vildagliptin), an ERN1 inhibitor, a fatty acid oxidation inhibitor, a fatty acid synthase (FAS) inhibitor, an FGF21 derivative, a fructose 1,6-diphosphatase inhibitor, a GLP1 agonist (e.g. albiglutide, dulaglutide, exenatide, liraglutide, lixisenatide, taspoglutide), a glucagon receptor modulator, a mixed glucagon receptor/GLP-1 agonist (e.g. MAR-701, ZP2929), a glucokinase inhibitor (e.g. TTP-399, TTP-355, TTP-547, AZD1656, ARRY403, MK-0599, TAK-329, AZD5658, and GKM-001), a glycogen phosphorylase inhibitor (e.g. GSK1362885), a GSK-3 inhibitor, a GPR119 agonist (e.g. MBX-2982, GSK1292263, APD597, PSN821), a GPBAR1 (TGR5) agonist (e.g. INT-777, XL-475), a GPR39 modulator, a GPR40 agonist (e.g. TAK-875), a GPR41 modulator, a GPR43 modulator, a GPR81 modulator, a GPR120 agonist, an HSL inhibitor, an IκB inhibitor, an IL-I-beta modulator, insulin or an insulin analog (including, but not limited to, oral, inhaled or injectable formulations thereof), insulin-like growth factor (IGF-1) or an analog thereof, an insulin secretagogue, a JNK inhibitor (e.g. CC-359), a kappa opioid receptor modulator, LY3084077, a Kv1.3 inhibitor (e.g. ChTX, clofazmine, WIN-173173), a MAP4K4 inhibitor, an MCi or MC4 agonist (e.g. afamelanotide, BMS-470539, bremelanotide, Melanotan II, PF-00446687, PL-6983, setmelanotide, and THIQ), a meglitinide (e.g. repaglinide, nateglinide, mitiglinide), a mineralocorticoid receptor inhibitor, a monoacylglycerol O-acyltransferase inhibitor, an NF-κB inhibitor, a nicotinic acid receptor (HM74A) activator, a PDE-10 inhibitor, a PDHK2 inhibitor, a PDHK4 inhibitor, a PKC (including PKC-alpha, PKC-beta, and PKC-gamma) inhibitor, a PPARα/γ dual agonist, a PTP1b inhibitor (e.g. trodusquemine), a retinol binding protein 4 inhibitor, a serine palmitoyl transferase inhibitor, an SGLT1 inhibitor (e.g. GSK1614235), a SIRT-1 inhibitor (e.g. resveratrol, GSK2245840, GSK184072), a somatostatin receptor inhibitor, a sulfonylurea (e.g. acetohexamide, chlorpropamide, diabinese, glibenclamide, glipizide, glyburide, blimipiride, gliclazide, glipentide, gliquidone, glisolamide, tolazamide, tolbutamide), a thiazolidinedione (e.g. ciglitazone, darglitazone, englitazone, lobeglitazone, MSDC-0602, netoglitazone, pioglitazone, rivoglitazone, rosiglitazone, and troglitazone), a TORC2 inhibitor, a urotensin II receptor agonist, a vasopressin agonist (e.g. DDAVP, WAY-141608), or a VPAC2 receptor agonist.

In some embodiments, at least one of the one or more additional therapeutic agents is an anti-antiobesity agent. In some embodiments, the anti-obesity agent is an apoB-MTP inhibitor (e.g. dirlotapide, JTT130, SLX4090, usistapide), a β3-adrenergic agonist (e.g. amibegron, AZ-40140, CL-316, 243, KRP-204, L-742,791, L-796,568, LY-368,842, LY-377, 604, mirabegron, Ro 40-2148, solabegron, SWR-0342SA), a bombesin receptor agonist, a BRS3 modulator, a CB1 receptor antagonist or inverse agonist, a CCKA agonist, ciliary neurotrophic factor (CNTF) or analog thereof (e.g. axokine, NT-501), Contrave™ (buproprion/naltrexone), a dopamine receptor agonist (e.g. bromocriptine), an 11β-hydroxysteroid dehydrogenase (11β-HSD1) inhibitor, Empatic™ (pramlintide/metreleptin), a 5-HT$_{2C}$ agonist (e.g. lorcaserin), a galanin antagonist, a ghrelin agonist or antagonist, a GLP1 agonist (e.g. albiglutide, dulaglutide, exenatide, liraglutide, lixisenatide, taspoglutide), a mixed glucagon receptor/GLP-1 agonist (e.g. MAR-701, ZP2929), an H3 antagonist or inverse agonist, a human agouti-related protein (AGRP) inhibitor, leptin or an analog thereof (e.g. metreleptin), a lipase inhibitor (e.g. tetrahydrolipstatin), an MCi or MC4 agonist (e.g. afamelanotide, BMS-470539, bremelanotide, Melanotan II, PF-00446687, PL-6983, setmelanotide, and THIQ), a melanocyte-stimulating hormone or analog thereof, a MetAp2 inhibitor (e.g. ZGN-433), a monoamine reuptake inhibitor (e.g. buproprion, sibutramine, phentermine, tesofensine), a neuromedin U receptor agonist, an NPY antagonist (e.g. velneperit), an opioid receptor antagonist (e.g. naltrexone), an orexin receptor antagonist (e.g. almorexant, lemborexant, SB-334,867, SB-408,124, SB-649,868, suvorexant), oxyntomodulin or an analog thereof, PYY or an analog thereof (e.g. PYY$_{1-36}$, PYY$_{3-36}$), Qsymia™ (phentermine/topiramate), an RXR-alpha modulator, a stearoyl-CoA desaturase (SCD-1) inhibitor, or a sympathomimetic agent.

In some embodiments, at least one of the one or more additional therapeutic agents is a lipid lowering agent. In some embodiments, the lipid lowering agent is an acyl coenzyme A cholesterol acyl transferase (ACAT) inhibitor, a bile acid reabsorption inhibitor, a cholesterol ester transfer protein (CETP) inhibitor, a 5-LOX inhibitor (e.g. BAY X 1005), a FLAP inhibitor (e.g. AM-679), an HMG CoA synthase inhibitor, a lipoprotein synthesis inhibitor, a low-density lipoprotein receptor inducer, an LXR receptor modulator, a microsomal triglyceride transport inhibitor, niacin, a platelet aggregation inhibitor, a renin-angiotensin system inhibitor, a squalene epoxidase inhibitor, a squalene synthetase inhibitor, or a triglyceride synthesis inhibitor.

In some embodiments, at least one of the one or more additional therapeutic agents is an agent for treating a metabolic disorder. In some embodiments, the agent for treating a metabolic disorder is an ABC transporter activator, ACT-434964 (Actelion), an ANG-5 inhibitor, an angiotensin II antagonist (e.g. MC4262), CCX-872, DUR-928 (Durect), ESP41091, F-652 (Generon), an FGF21 agonist (e.g. BMS-986036), fomepizole (Raptor), an FXR agonist, FXR/TGR5 dual agonist (e.g. INT-767), a ghrelin antagonist (e.g. TZP-301), a glucosylceramide synthase inhibitor, a GPR17 modulator, a GPR119 agonist, IG-MD-014 (Indigene), IMM-124E (Immuron), a lysosome pathway modulator (e.g. CAT5000), a melanin-concentrating hormone receptor 1 antagonist (e.g. KI-1361-17), an MCL1 inhibitor (e.g. CMPX-1023), an mTORC1 inhibitor, an NaCT (e.g. SLC13A5) inhibitor, a NHE3 inhibitor (e.g. RDX-011, tenapanor), NP003 (Neuraltus), PBI-4050 (ProMetic), a proteostasis regulator (e.g. PTI-130, PTI-428, PTI-C1811), PS248288 (Pharmacopeia/Merck), PX-102 (Phenex), RG7410. RG7652, a ROCK inhibitor, SBC-104 (Synageva BioPharma), SPX-100 (Spherix), a stearoyl CoA desaturase inhibitor (e.g. CVT-12805), TRC150094 (Torrent), or ZYH7 (Zydus Cadila).

In some embodiments, at least one of the one or more additional therapeutic agents is an agent for treating steatosis. In some embodiments, the agent for treating steatosis is an adiponectin analog (e.g. PX 811013), aramchol (Galmed), an ASK1 inhibitor (e.g. GS-4977, GS-4997), AZD4076 (AstraZeneca), a bile acid sequestrant (e.g. obeticholic acid), BL-1060 (Galmed), BMS986171 (Bristol-Myers Squibb), a CCR5/CCR2 antagonist (e.g. cenicriviroc), cannabidiol, CER-209 (Cerenis), a cysteamine analog (e.g. RP-103, RP-104), DS102 (DS Biopharma), EGS21 (Enzo), elafibranor (Genfit), emricasan (Idun), ethyl eicosapentaenoic acid (Mochida), an FXR agonist, a GPBAR1 agonist (e.g. RDX009), GR-MD-02 (Galectin Therapeutics), leucine/sildenafil/metformin (NuSirt), LCQ908 (Novartis), LJN452 (Novartis), a LOXL2 inhibitor (e.g. simtuzumab), MAT-8800 (Matinas), MB-10866 (Metabasis), an miR-103/107 inhibitor (e.g. RG-125), MK-4074 (Merck & Co.), nalmefene (TaiwanJ), nivocasan (Gilead), NGM-282 (NGM Biopharmaceuticals), an omega-3 carboxylic acid or mixture of the same (e.g. Epanova™), PX-102 (Phenex), PX-104 (Phenex), remogliflozin etabonate (Kissei), saroglitazar (Zydus-Cadila), SAR-548304 (sanofi-aventis), tipelukast (Kyorin), ursodeoxycholic acid, VK2809 (Viking), or XL335 (Exelixis).

In some embodiments, at least one of the one or more additional therapeutic agents is an agent for treating inflammation. In some embodiments, the agent for treating inflammation reduces the differentiation or activation of $T_h17$ cells. In some embodiments, the agent for treating inflammation is a caspase inhibitor (e.g. emricasan), a TGF-β inhibitor, an IL-1β inhibitor, an IL-6 inhibitor, an IL-17 inhibitor, an IL-17a inhibitor, an IL-17F inhibitor, an IL-21 inhibitor, an IL-23 inhibitor (e.g. guselkumab), IMM-124E, a $ROR\gamma_t$ inhibitor (e.g. JTE-151) a RORα inhibitor, solithromycin (Cempra), or a vascular adhesion protein-1 inhibitor (e.g. PXS-4728A).

In some embodiments, at least one of the one or more additional therapeutic agents is an agent for treating fibrosis. In some embodiments, the agent for treating fibrosis is cenicriviroc (Tobira/Takeda), CNX-014/023/024/025 (Connexios), an endothelin antagonist (e.g. A192621, ambrisentan, atracentan, bosentan, BQ-123, BQ-788, macitentan, sitaxentan, tezosentan, zibotentan), etanercept, evitar (Ade-Therapeutics), a fibroblast growth factor inhibitor, a galectin-3 inhibitor, imatinib, IVA337 (Inventiva), N-acetylcysteine, nintedanib, pirfenidone, RG6069 (Roche), SP20102 (Sarfez), tipelukast (Kyorin), or XOMA 089 (Xoma).

In some embodiments, the non-alcoholic fatty liver disease is steatosis. In some embodiments, the non-alcoholic fatty liver disease is non-alcoholic steatohepatitis (NASH). In some embodiments, the non-alcoholic fatty liver disease is liver fibrosis caused by NASH. In some embodiments, the non-alcoholic fatty liver disease is liver cirrhosis caused by NASH. In some embodiments, the non-alcoholic fatty liver disease is hepatocellular carcinoma (HCC) caused by NASH.

Those additional agents may be administered separately from a provided compound or composition thereof, as part of a multiple dosage regimen. Alternatively, those agents may be part of a single dosage form, mixed together with a provided compound in a single composition. If administered as part of a multiple dosage regime, the two active agents may be submitted simultaneously, sequentially or within a period of time from one another, normally within five hours from one another.

As used herein, the term "combination," "combined," "in conjunction" and related terms refers to the simultaneous or sequential administration of therapeutic agents in accordance with this invention. For example, a provided compound may be administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle.

The amount of both, a provided compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of a provided compound can be administered.

In those compositions which comprise an additional therapeutic agent, that additional therapeutic agent and a provided compound may act synergistically. Therefore, the amount of additional therapeutic agent in such compositions will be less than that required in a monotherapy utilizing only that therapeutic agent. In such compositions a dosage of between 0.01-100 µg/kg body weight/day of the additional therapeutic agent can be administered.

The amount of additional therapeutic agent present in a composition comprising a provided compound will be no more than the amount that would normally be administered in a composition comprising that therapeutic agent as the only active agent. Preferably the amount of additional therapeutic agent in a provided composition will range from about 50% to 100% of the amount normally present in a composition comprising that agent as the only therapeutically active agent.

EXEMPLIFICATION

As depicted in the Examples below, in certain exemplary embodiments, compounds and solid forms are prepared according to the preceding general procedures. It will be appreciated that, although the general methods depict the synthesis of certain compounds of the present invention, the following methods, and other methods known to one of ordinary skill in the art, can be applied to all compounds and subclasses and species of each of these compounds, as described herein.

Experimental Procedures

As used herein, "V"=volumes, "v/w"=volume/weight ratio, "v/v"=volume/volume ratio, and "w/w"=weight/weight ratio.

Example 1. Production of Amorphous Compound 1

1 gram of Compound 1, prepared according to the method described in US 2013/0123231 A1, was completely dissolved in 10 mL dichloromethane. The dichloromethane solution was evaporated rapidly under vacuum at 40° C., resulting in amorphous Compound 1 having the XRPD pattern depicted in FIG. 18.

Example 2. Production of Form I of Compound 1

50 milligrams of amorphous Compound 1, prepared according to the method of Example 1, was slurried in acetone and subjected to temperature cycling from 40° C. to 25° C., in 4 h cycles for 72 h. Solid Form I of Compound 1 was collected by filtration. Form I was determined to be an neat polymorph of Compound 1. Form I was determined to have poor aqueous solubility at pH 5.5 and below (<10 µg/mL), with a log D value of 1.06 at pH 7.4.

The DSC curve of Form I of Compound 1 (FIG. 3A and FIG. 3B) indicates an endothermic transition with onset at about 189-193° C. attributed to a melt. The TGA curve of Form I of Compound 1 shows no significant weight loss up at about 150° C., indicating an unsolvated phase. The moisture sorption curve of Form I of Compound 1 also indicates that Form I is slightly hygroscopic showing around a 0.45% weight gain at about 95% RH. An XRPD analysis of the sample after the DVS experiment shows that the material had not changed forms.

Single crystals of Form I were obtained from an attempted salt formation experiment. 0.5 mL Methyl ethyl ketone (MEK) was added to 40.5 milligrams Compound 1 to form a suspension. In a separate vial, 10.2 milligrams of L-proline was dissolved in 0.1 mL H$_2$O and the solution was added to the Compound 1 suspension. The sample was slurried at about 60° C. for about 5 days and formed a golden yellow solution. The solution was crash cooled to about 2-8° C. and remained at about 2-8° C. for about 4 days producing a golden yellow solution with white oil. The sample was placed at room temperature and after about 14 days, solids were observed in solution.

A suitable single crystal was selected and analyzed by single-crystal X-ray diffractometry. A colorless plate having approximate dimensions of 0.19×0.13×0.06 mm$^3$, was mounted on a nylon loop in random orientation. Preliminary examination and data collection were performed on a Rigaku SuperNova diffractometer, equipped with a copper anode microfocus sealed X-ray tube (Cu Kα λ=1.54184 Å) and a Dectris Pilatus3 R 200K hybrid pixel array detector. Cell constants and an orientation matrix for data collection were obtained from least-squares refinement using the setting angles of 15725 reflections in the range 3.5010°<θ<77.2150°. The space group was determined by the program CRYSALISPRO to be C2221 (international tables no. 20). The data were collected to a maximum diffraction angle (2θ) of 155.284° at room temperature.

It was found that the crystal system of Form I is orthorhombic and the space group is C2221. The cell parameters and calculated volume are: a=14.77743(18) Å, b=14.62619(16) Å, c=51.7778(8) Å, α=90°, β=90°, γ=90°, V=11191.1(3) Å3. The molecular weight is 569.62 g mol$^{-1}$ with Z=16, resulting in a calculated density of 1.352 g cm$^{-3}$. Standard uncertainty for this data is written in crystallographic parenthesis notation, e.g. 0.123(4) is equivalent to 0.123±0.004. The quality of the structure obtained is high, as indicated by the fit residual, R, of 0.0446 (4.46%). R-factors in the range 2-6% are quoted to be the most reliably determined structures.

It is contemplated that Form I is the most stable form of Compound 1.

Example 3. Production of Form II of Compound 1

Figure 37:
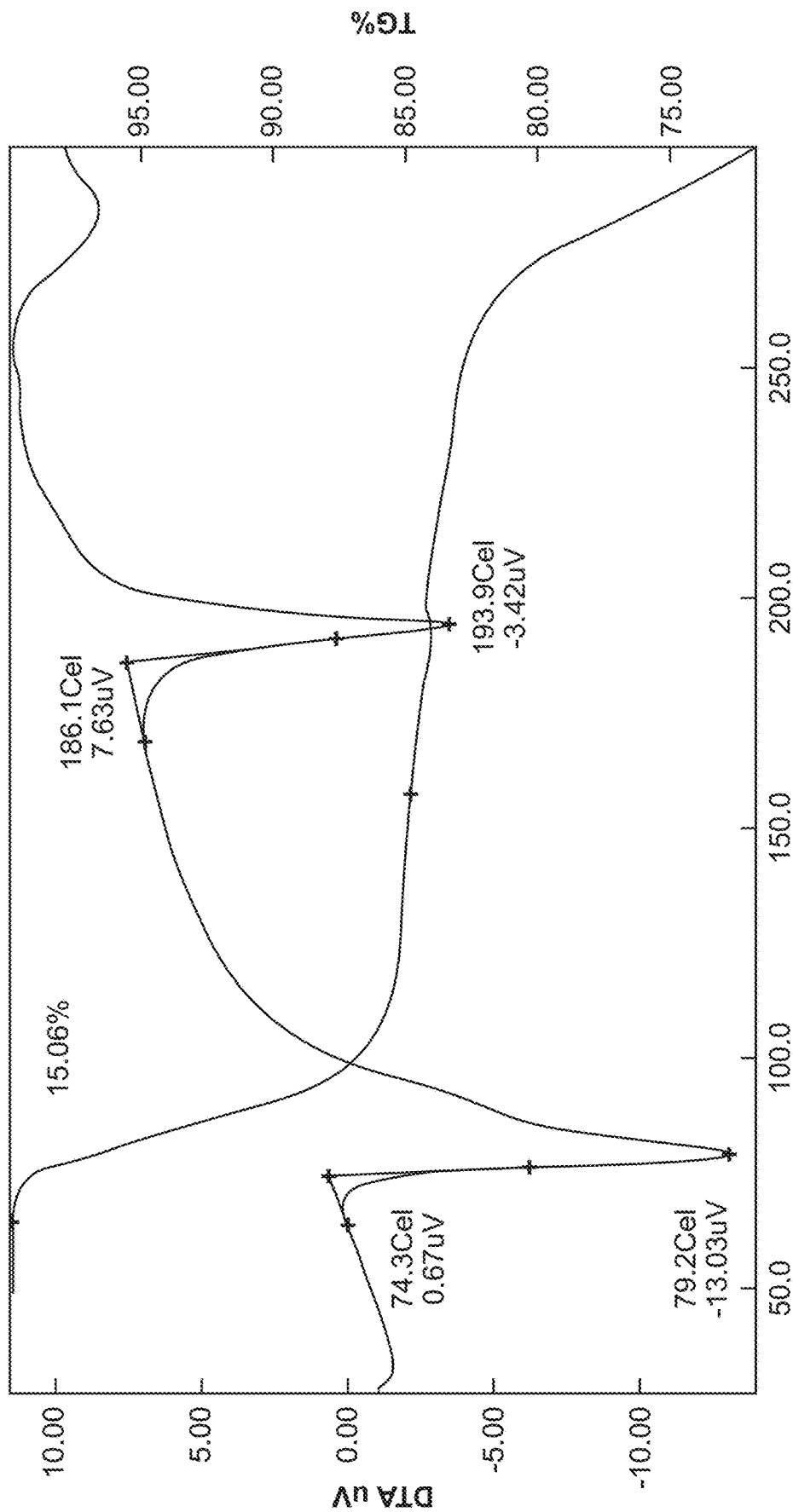
FIG. 37 depicts the differential scanning calorimeter (DSC) curve of Form II of Compound 1.

100 milligrams of amorphous Compound 1, prepared according to the method of Example 1, was slurried in dimethylformamide (DMF) and subjected to temperature cycling from 40° C. to 25° C., in 4 h cycles for 72 h. Solid Form II of Compound 1 was collected by filtration. The DSC curve shows the first endotherm around 74° C. and a second endotherm was observed above 180° C. (FIG. 37).

Example 4. Production of Form III of Compound 1

Figure 38:
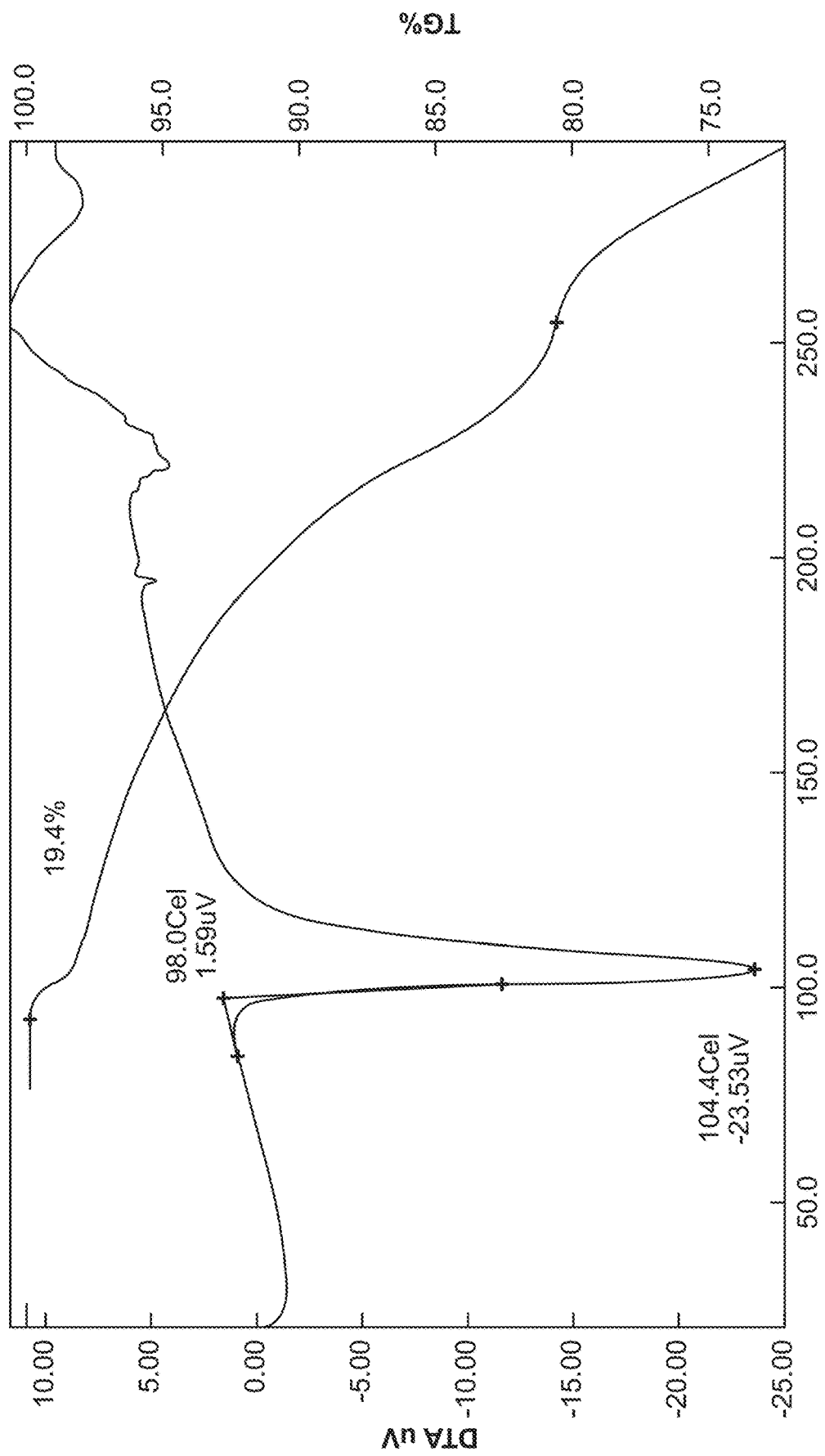
FIG. 38 depicts the differential scanning calorimeter (DSC) curve of Form III of Compound 1.

100 milligrams of amorphous Compound 1, prepared according to the method of Example 1, was slurried in dimethylsulfoxide (DMSO) and subjected to temperature cycling from 40° C. to 25° C., in 4 h cycles for 72 h. Solid Form III of Compound 1 was collected by filtration. Thermogravimetric analysis of Form III showed a large steady weight loss, suggesting that Form III may be a DMSO solvate of Compound 1. No additional thermal events were observed above the solvent loss (FIG. 38).

Example 5. Production of Form IV of Compound 1

500 milligrams of amorphous Compound 1, prepared according to the method of Example 1, was slurried in methanol and subjected to temperature cycling from 40° C. to 25° C., in 4 h cycles for 48 hours. Solid Form IV of Compound 1 was collected by filtration. DSC curve of Form IV comprises an endothermic transition with onset at 85° C., about 190° C., and about 202° C. and exotherm at 146° C.

Thermogravimetric analysis indicated a weight loss of 4.2% or 4.7% and corresponding endotherm between 82-92° C., indicating that Form IV is a methanol solvate of Compound 1. Upon further heating the sample to 120° C., XRPD analysis confirmed that the sample had converted to Form I.

Example 6. Production of Form V of Compound 1

Figure 39:
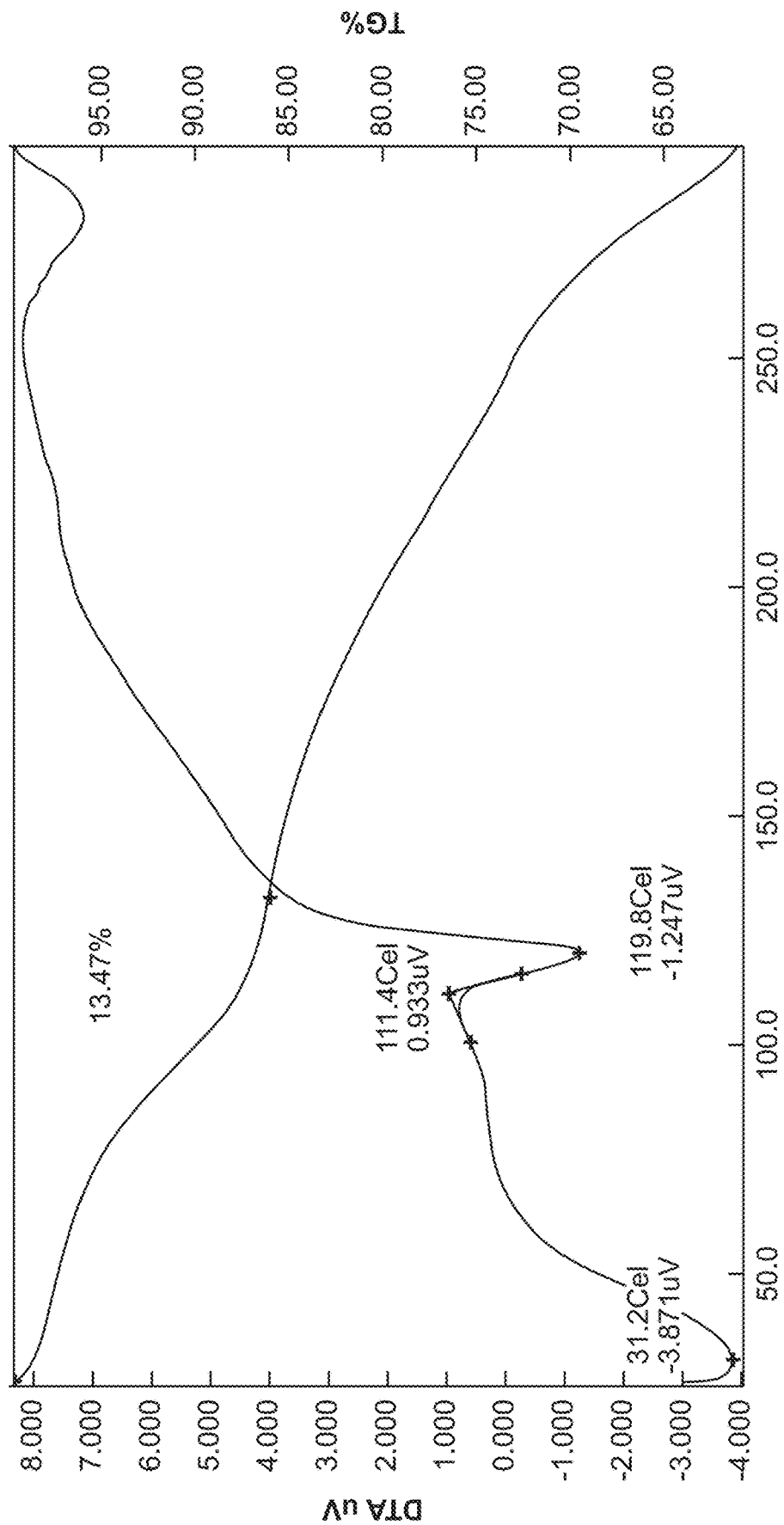
FIG. 39 depicts the differential scanning calorimeter (DSC) curve of Form V of Compound 1.

100 milligrams of amorphous Compound 1, prepared according to the method of Example 1, was slurried in N-methyl-2-pyrrolidone (NMP) and subjected to temperature cycling from 40° C. to 25° C., in 4 h cycles for 72 h. Solid Form V of Compound 1 was collected by filtration. Thermogravimetric analysis of Form V showed a large steady weight loss of 13.5%, suggesting that Form V may be a NMP solvate of Compound 1. No additional thermal events were observed above the solvent loss (FIG. 39).

Example 7. Production of Form VI of Compound 1

100 milligrams of amorphous Compound 1, prepared according to the method of Example 1, was dissolved in toluene and either crash cooled at −18° C. or the toluene was evaporated. In both cases, solid Form VI of Compound 1 was collected by filtration. XRPD analysis indicated a distinct toluene solvate form of Compound 1.

Example 8. Production of Form VII of Compound 1

Figure 40:
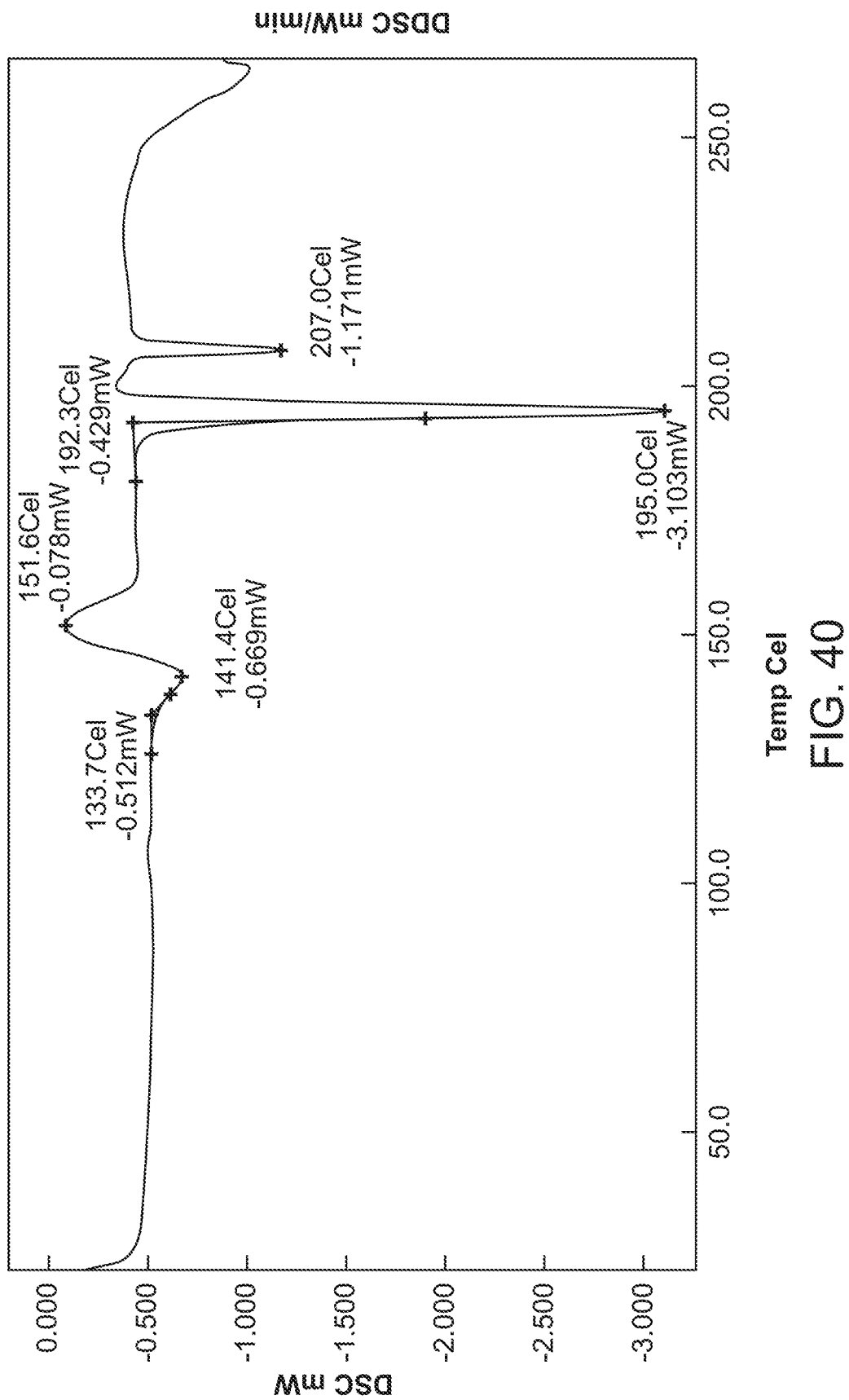
FIG. 40 depicts the differential scanning calorimeter (DSC) curve of Form VII of Compound 1.

100 milligrams of Form IV of Compound 1, prepared according to the method of Example 5, was heated to 80° C. in an oven. Form VII was confirmed to be a desolvated form of Form IV, produced by drying the methanol solvate Form IV. XRPD analysis showed that while Form VII had a similar diffraction pattern to that of Form I, there were a number of distinct peaks between the two forms which confirmed them to be distinct crystal forms. Differential scanning calorimetry (DSC) results (FIG. 40) were consistent with thermogravimetric analysis. Onset of the first endothermic event was observed at 133.7° C. (peak at 141.4° C.), with the peak of the exotherm at 151.6° C. The main, sharp endotherm was observed with an onset at 192.3° C. (peak at 195.0° C.). A smaller endotherm with a peak at 207.0° C. was likely to indicate formation of a higher melting crystalline form. Dynamic vapor sorption (DVS) analysis of Form VII indicated the material was moderately hygroscopic (>4% water uptake at 90% RH), and post DVS analysis showed no change in form. The uptake between 40 and 70% RH could potentially be indicative of hydrate formation (tentatively assigned the name Form IX). Karl-Fischer analysis showed a water content of 0.503%, consistent with observations of ambient humidity measured during DVS analysis. NMR and IR data confirmed the structural integrity of Compound 1 present. Aqueous solubility of Form VII was determined to be 0.109 mg/mL. XRPD analysis confirmed that prolonged exposure to water resulted in the conversion of Form VII to Form I. However, Form VII was determined to be chemically and physically stable following 7 days of storage at 40° C. and 75% RH. No change in form was observed, and the purity was determined to be 99.85%.

Example 9. Production of Form VIII of Compound 1

100 milligrams of anhydrous Form VII of Compound 1 was heated to 195° C. Consistent with the DSC analysis of Form VII, XRPD analysis of the resulting solid showed that Form VIII of Compound 1 was produced. The NMR spectrum was found to be consistent with that of Compound 1, and HPLC analysis of Form VIII indicated a purity of 99.4%. Form VIII was also prepared by running 50 grams of anhydrous Form I of Compound 1 through a Leistriz twin screw extruder utilizing multiple heat zones of about 170 to about 193° C. and a screw speed of 30 rpms.

DSC analysis of Form VIII showed the same sharp peak with onset at 204.7° C. (peak at 208.1° C.), corresponding to the melting point of Form VIII. Further DSC analysis of Form I indicate that cooling a melted sample of Form I, followed by a second heating event resulted in an endotherm with onset at 204.7° C. (peak at 208.1° C.), indicating that Form VIII is directly produced from Form I upon heating in that manner.

Figure 16:
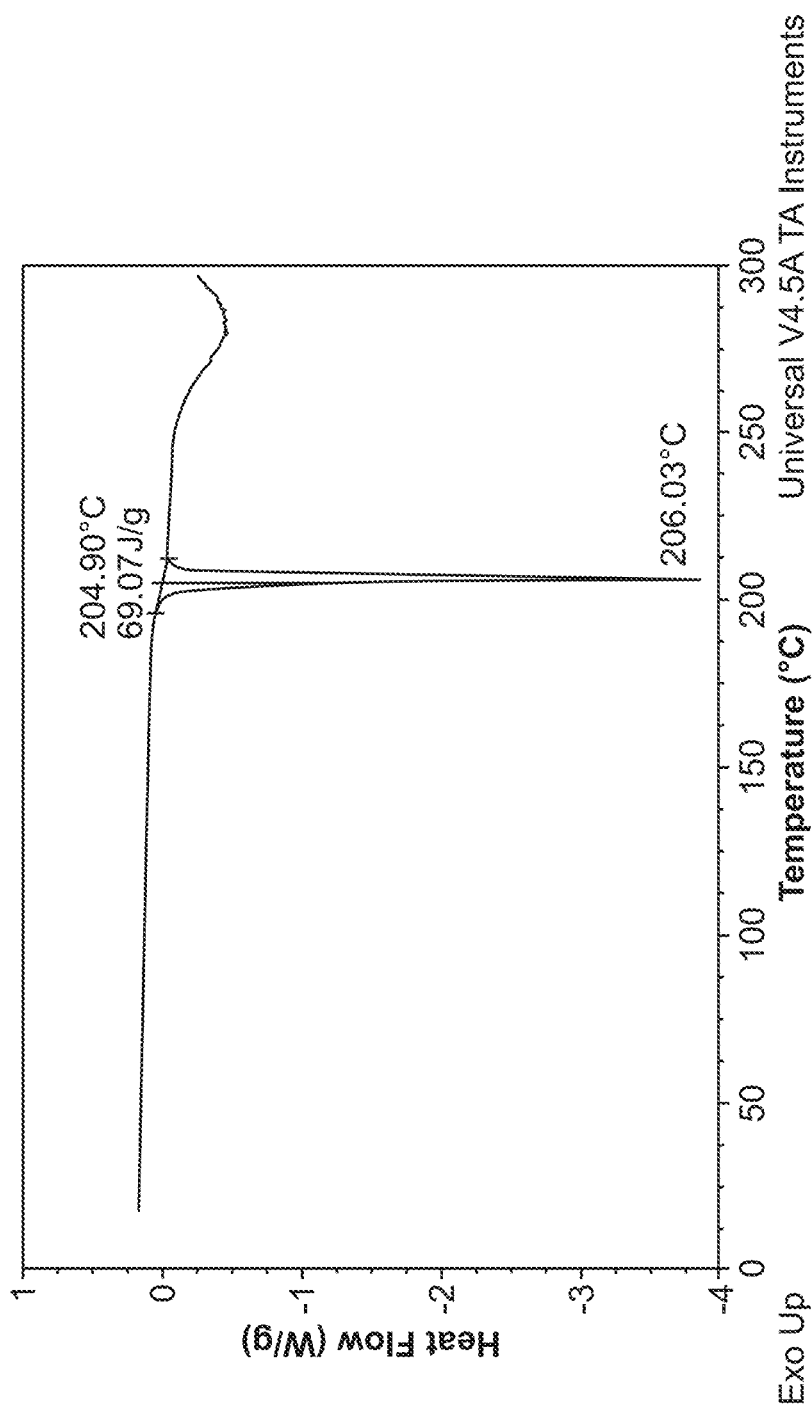
FIG. 16 depicts the differential scanning calorimeter (DSC) curve of Form VIII of Compound 1.

The DSC curve shown in FIG. 16 shows that Form VIII comprises an endotherm with onset at about 205° C.

Example 10. Competitive Slurrying of Form I and Form VII

Competitive slurrying of Form I and Form VII in acetone, acetonitrile:water (10%), ethanol, and ethyl acetate, at both ambient temperature and 60° C., resulted in conversion to Form I, as confirmed by XRPD and DSC.

Example 11. Competitive Slurrying of Form I and Form VIII

Competitive slurrying of Form I and Form VIII in acetone, acetonitrile:water (10%), ethanol, and ethyl acetate, at both ambient temperature and 60° C., resulted in conversion to Form I, as confirmed by XRPD and DSC.

Example 12. Competitive Slurrying of Form I and Form VIII

Competitive slurrying of Form I and Form VIII in a 1:1 ratio in a solution of 6:4 ethanol:water at room temperature for about two weeks resulted in conversion to Form I as confirmed by XRPD.

The results of the competitive slurrying analysis indicated that Form I is the more thermodynamically stable form between 22-60° C. Form VIII could be potentially the more stable form at high temperatures.

Example 13. Production of Compound 1 Sodium Form I

Figure 19:
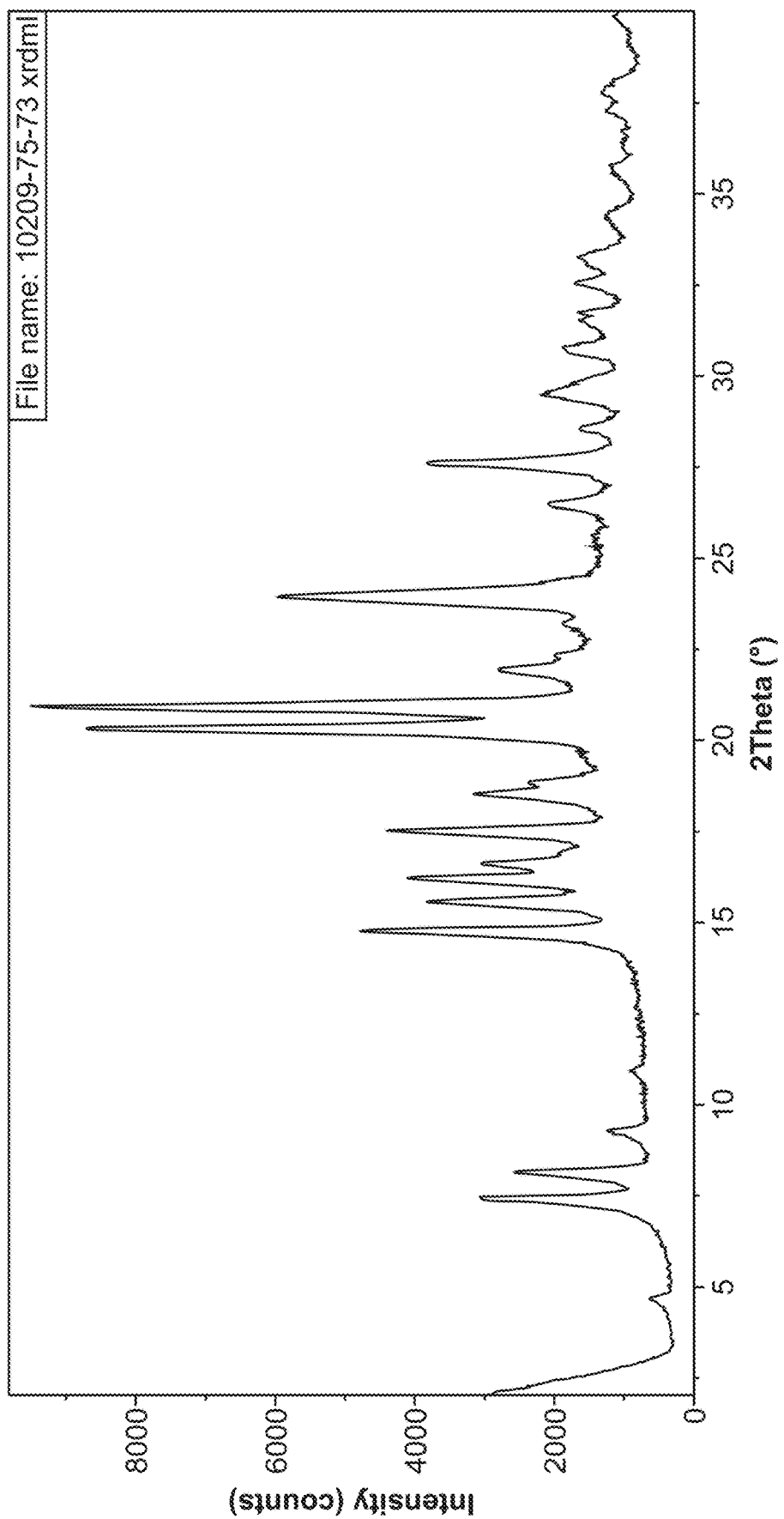
FIG. 19 depicts the X-Ray powder diffraction pattern of Compound 1 Sodium Form I.
Figure 20:
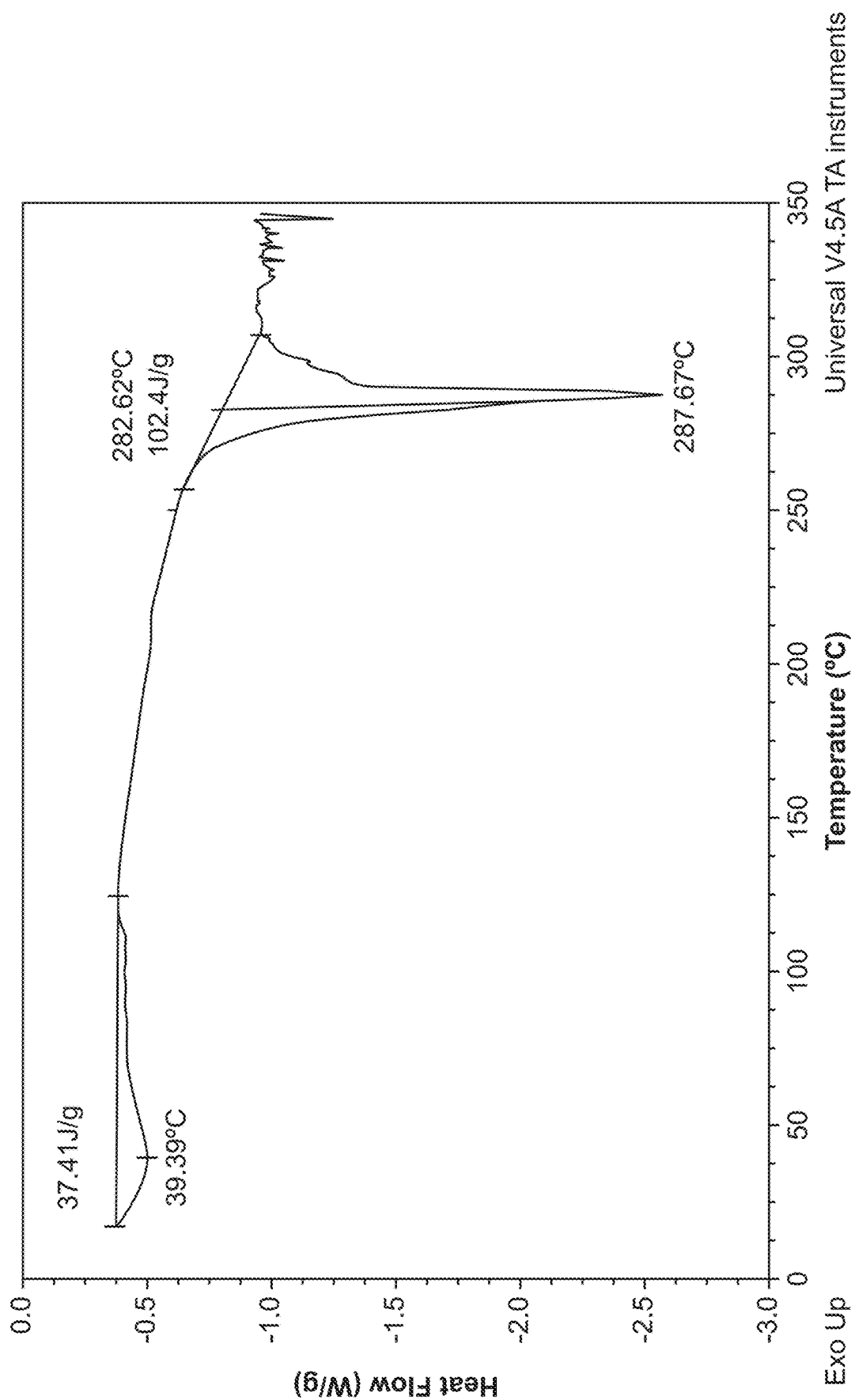
FIG. 20 depicts the differential scanning calorimeter (DSC) curve of Compound 1 Sodium Form I.

Sodium Form I (hydrate) was prepared as follows. 3.48 g of anhydrous Form I of Compound 1 was placed in a beaker with 0.27 g of NaOH and 40 mL of water. The sample was heated and stirred until solution became clear. Next, the solution was filtered into a vial and placed in a vacuum centrifuge. The resulting solids were slurried in ethyl acetate and then washed with acetone, filtered, and dried. The XRPD pattern of Compound 1 Sodium Form I is shown in FIG. 19. The DSC curve is shown in FIG. 20 and indicates multiple endothermic transitions with onset at 37° C. and 283° C. The TGA curve is shown in FIG. 21 and displays a weight loss (4.1% RT to 175° C.) that was identified as water based on TGA-Mass Spectrometry (TGA-MS). Weight loss above 250° C. is attributed to decomposition. The dynamic vapor sorption curve indicates that the form absorbs about 32 weight % of water up to 95% RH (relative humidity) at 25° C. The material was found to have deliquesced post experiment.

Example 14. Production of Compound 1 Sodium Form II

Figure 22:
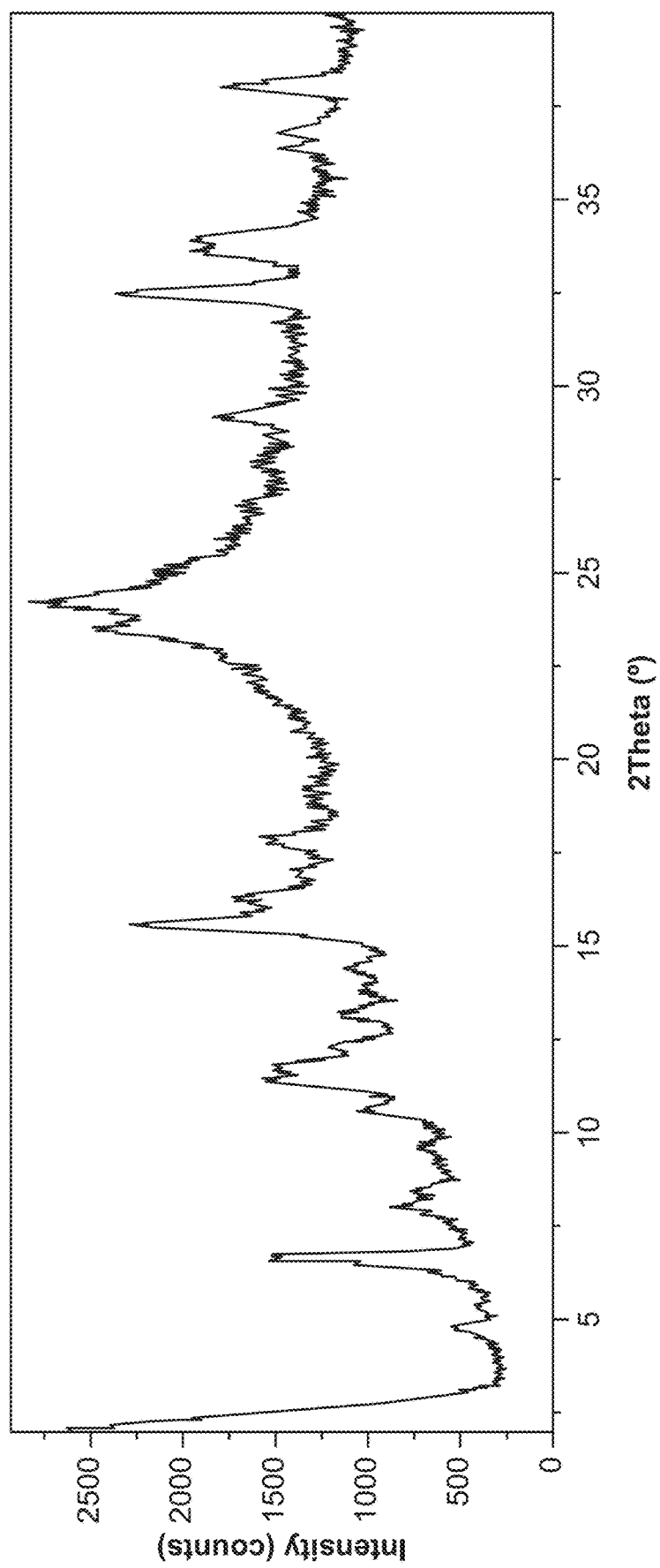
FIG. 22 depicts the X-Ray powder diffraction pattern of Compound 1 Sodium Form II.
Figure 23:
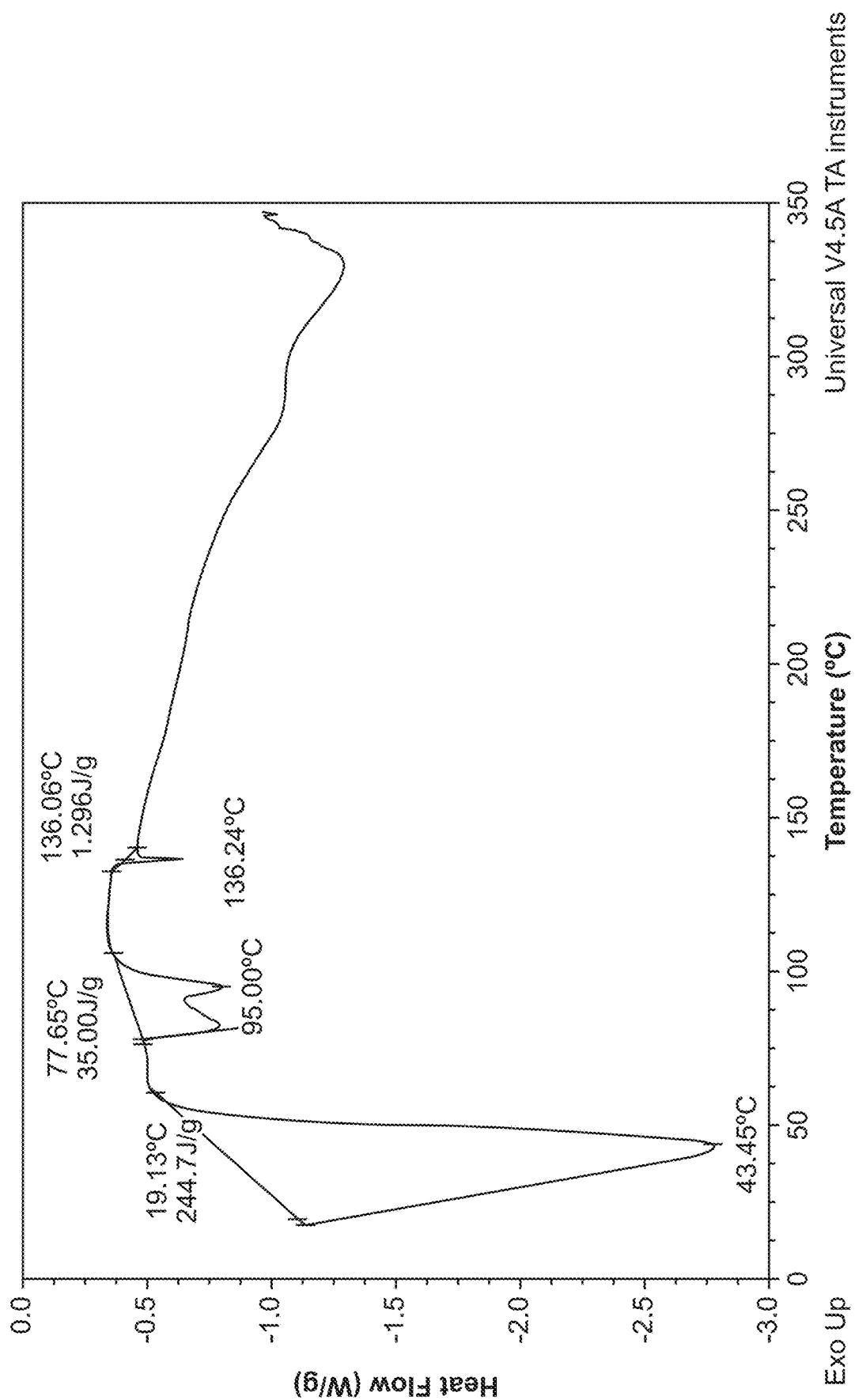
FIG. 23 depicts the differential scanning calorimeter (DSC) curve of Compound 1 Sodium Form II.

Compound 1 Sodium Form II (variable hydrate) was prepared as follows. 4.0 g of anhydrous Form I of Compound 1 was placed in a beaker with 0.4 g of NaOH and about 40 mL of water. The sample was heated and stirred until solution became clear. Next, the solution was filtered into a vial and placed in a vacuum centrifuge. The resulting solids from vacuum centrifuge were washed with 10% water in acetonitrile, and then the solids were dried and then slurried in ethyl acetate. The sample were sonicated for about 1 hour and then left to sit at room temperature. The solids were slurried in acetone and a portion was filtered to yield solids. The XRPD pattern of Compound 1 Sodium Form II is shown in FIG. 22. The DSC curve is shown in FIG. 23 and indicates multiple endothermic transitions with onset at about 19, about 78 and about 136° C. The TGA curve is shown in FIG. 24 and displays a weight loss (about 24% RT to about 150° C.) indicating a solvate that was identified as water based on TGA-MS. A second sample of Compound 1 Sodium Form II was prepared when 1092 mg of Form I of Compound 1 was placed in a vial with 76 mg of NaOH and 10 mL of water. Sample sonicated but solids till persisted. Another 45 mg of NaOH as added with an additional 10 mL and the solution became clear. Sample was then centrifuge evaporated over the weekend to yield dry solids. These solids were then slurried in EtOAc for approximately 10 days. The resulting solids had the same XRPD pattern as Compound 1 Sodium Form II and was found to only have about 10.4% weight loss up to about 175° C. This may indicate that this form can have anywhere from about 4-10 moles of water. Weight loss above about 250° C. is attributed to decomposition. The dynamic vapor sorption curve indicates that the form absorbs about 35 weight % of water up to about 95% RH at about 25° C. The material was found to have deliquesced post experiment.

Example 15. Production of Compound 1 Calcium Form I

Figure 25:
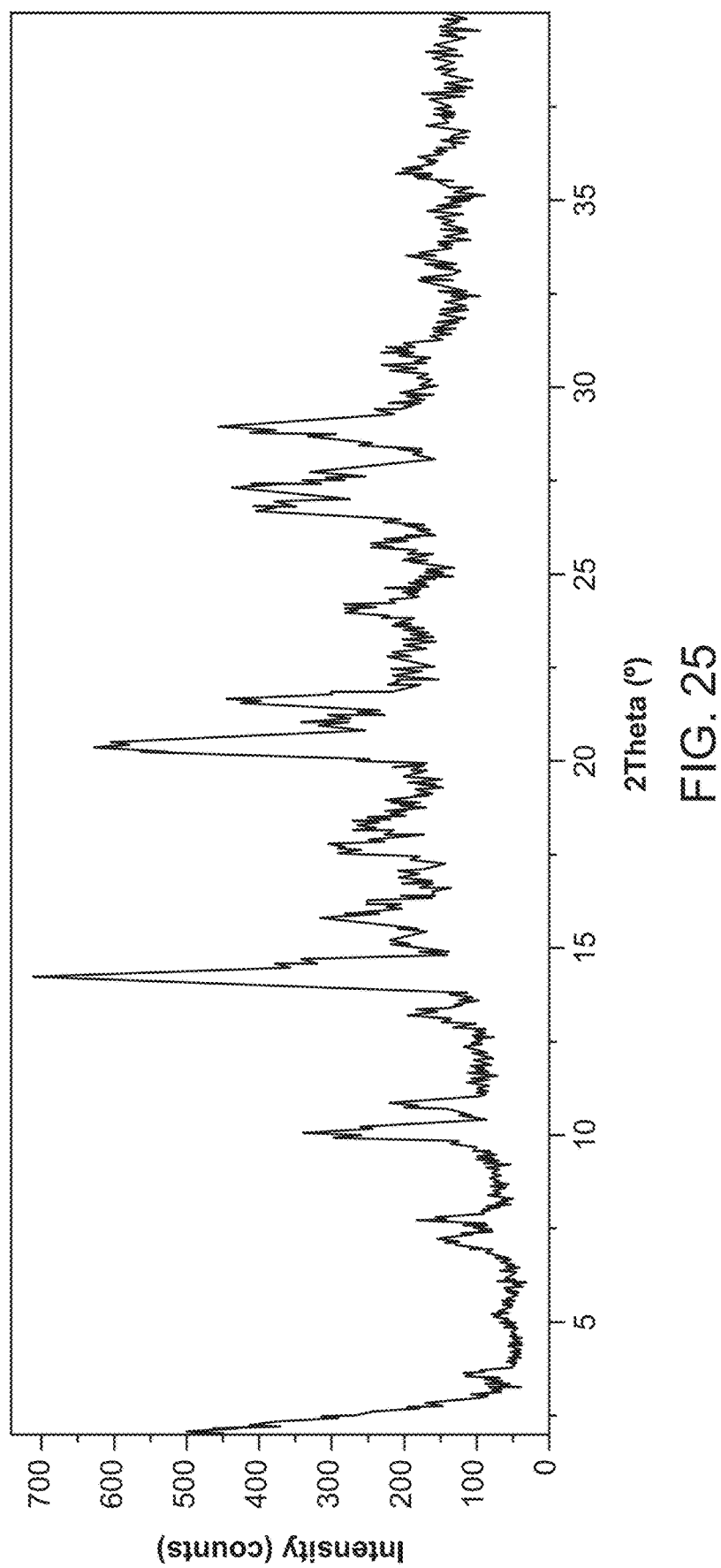
FIG. 25 depicts the X-Ray powder diffraction pattern of Compound 1 Calcium Form I.
Figure 26:
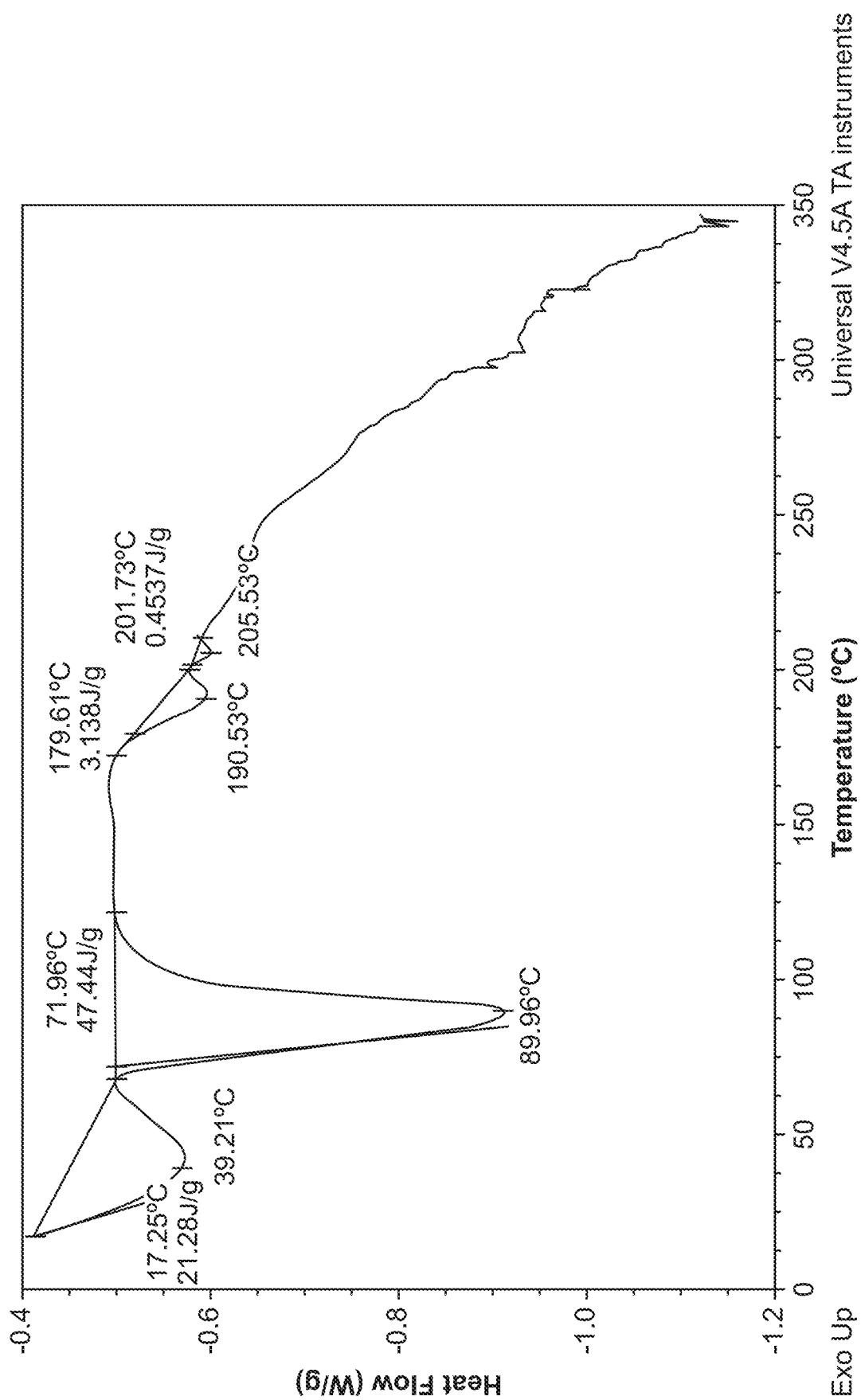
FIG. 26 depicts the differential scanning calorimeter (DSC) curve of Compound 1 Calcium Form I.

Compound 1 Calcium Form I (hydrate) was prepared as follows. 4.47 g of anhydrous Form I of Compound 1 was placed in a beaker with 0.4 g of KOH and about 25 mL of water. The sample was heated and stirred until solution became clear. Next, 0.5 g of calcium chloride was added and the sample was cooled to room temperature and left to stir for a few hours. The sample was then filtered and slurried in about 20% water in acetonitrile to yield a hazy solution. The sample was sonicated for about one hour to yield a slurry. The sample was then filtered and dried in a nitrogen box at 5 psi. The XRPD pattern of Compound 1 Calcium Form I is shown in FIG. 25. The DSC curve is shown in FIG. 26 and indicates multiple endothermic transitions with onset at about 17, about 72, about 180 and about 202° C. The TGA curve is shown in FIG. 27 and displays a weight loss (about 6.0% RT to about 200° C.) that was identified as water based on TGA-MS. Weight loss above about 250° C. is attributed to decomposition. The dynamic vapor sorption curve indicates that the form absorbs about 9 weight % of water up to about 95% RH at about 25° C. XRPD analysis of the sample after the DVS experiment shows that the material had not changed form.

Example 16. Production of Compound 1 Magnesium Form I

Figure 28:
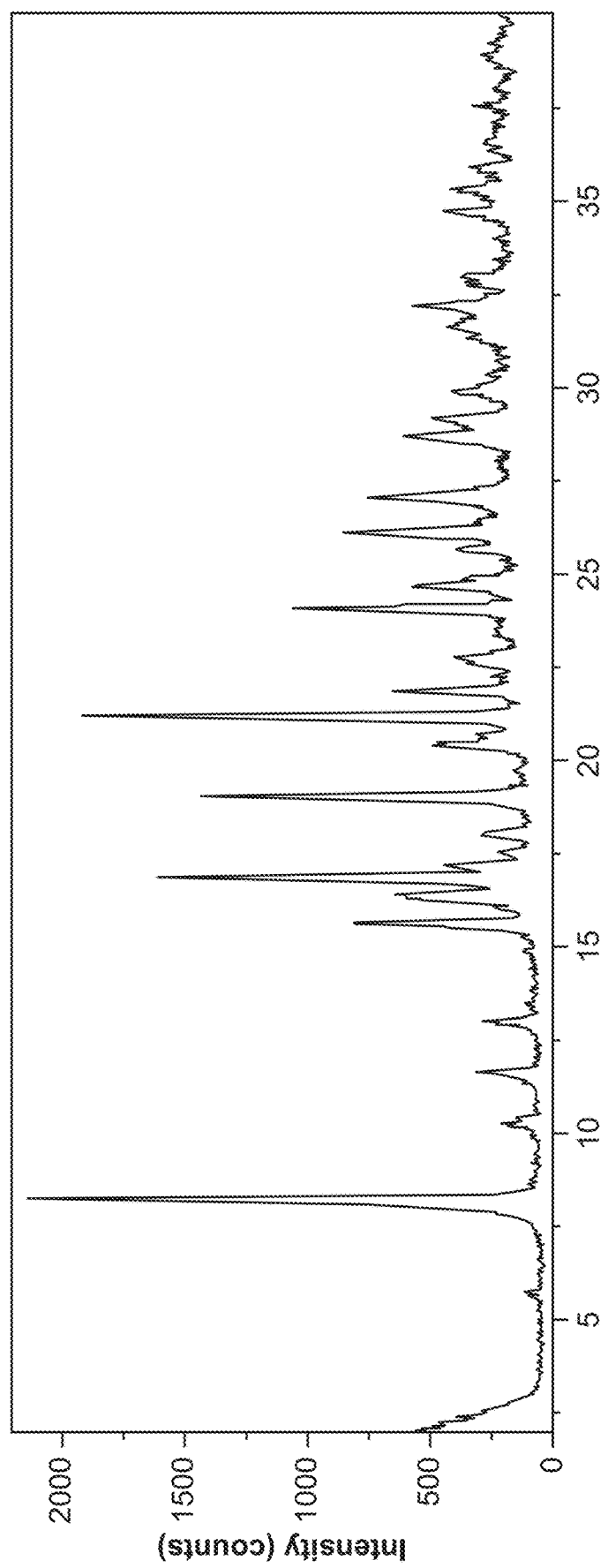
FIG. 28 depicts the X-Ray powder diffraction pattern of Compound 1 Magnesium Form I.
Figure 29:
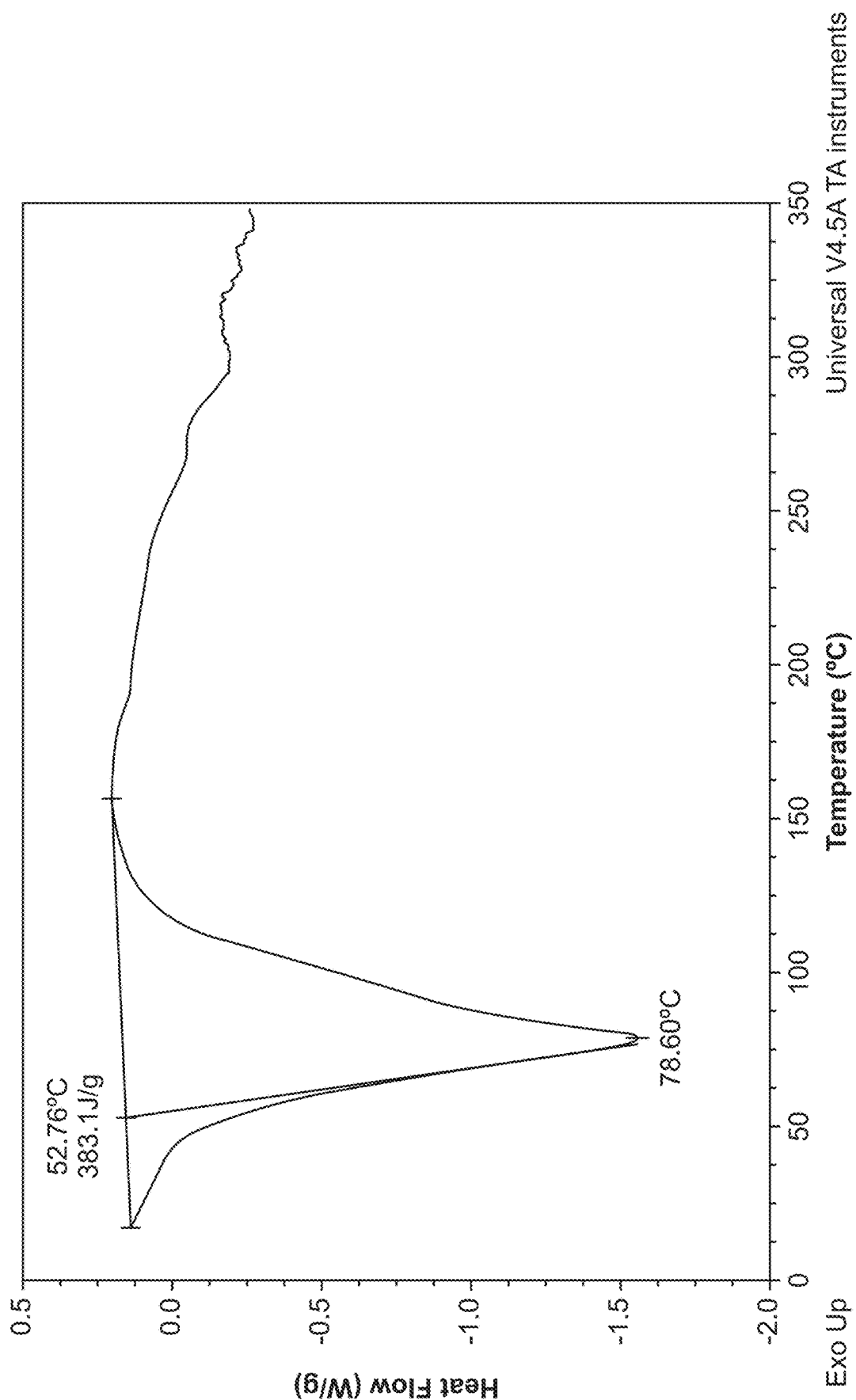
FIG. 29 depicts the differential scanning calorimeter (DSC) curve of Compound 1 Magnesium Form I.

Compound 1 Magnesium Form I (hydrate) was prepared as follows. 987.6 milligrams of anhydrous Form I of Compound 1 was placed in a vial with 156 milligrams of KOH and about 10 mL of water. The sample was sonicated and heated until the solution became clear. Next, 130 milligrams of magnesium acetate tetrahydrate was added, and the sample was left to stir at room temperature for about 3 days then isolated. The XRPD pattern of Compound 1 Magnesium Form I is shown in FIG. 28. The DSC curve is shown in FIG. 29 and indicates a single endotherm with onset at about 53° C. The TGA curve is shown in FIG. 30 and displays a weight loss (about 13.8% RT to about 150° C.) that was identified as water based on TGA-MS. Weight loss above about 250° C. is attributed to decomposition. The dynamic vapor sorption curve indicates that the form absorbs about 8 weight % of water up to about 95% RH at about 25° C. XRPD analysis of the sample after the DVS experiment shows that the material had not changed form.

Example 17. Production of Compound 1 Diethanolamine Form I

Figure 31:
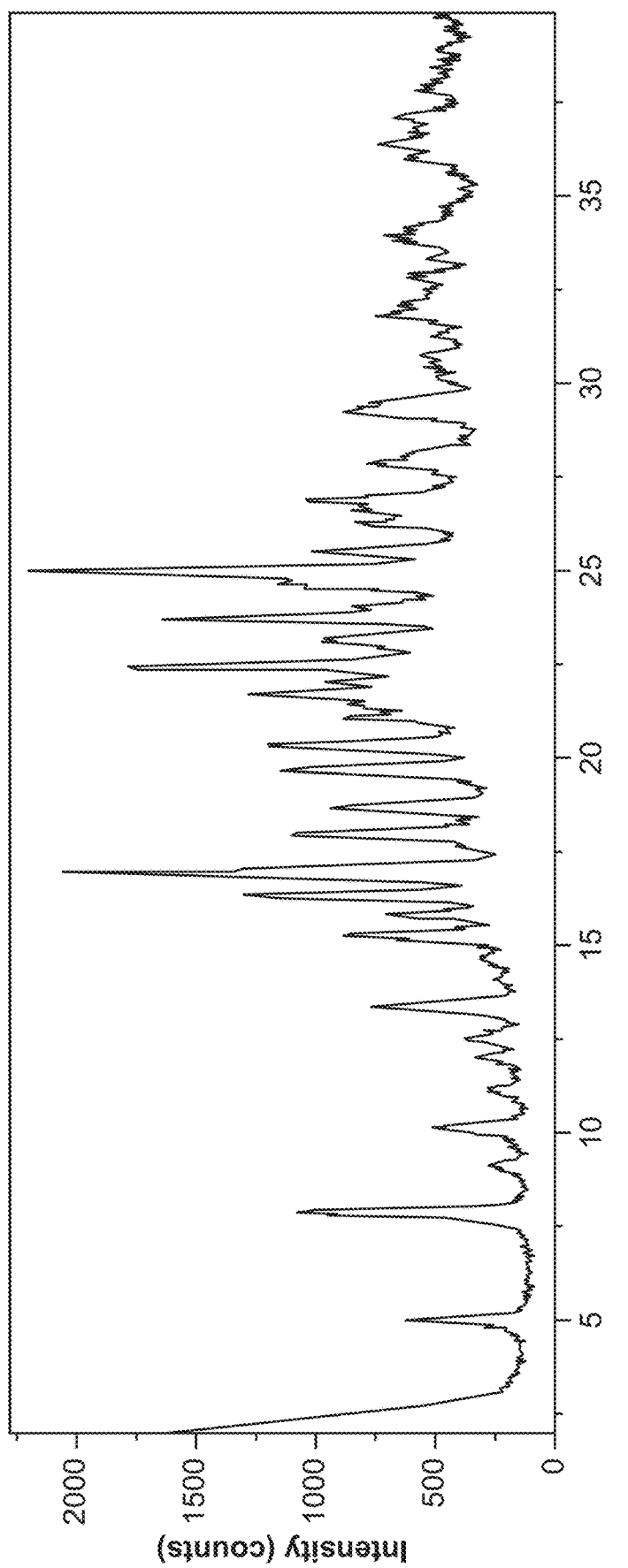
FIG. 31 depicts the X-Ray powder diffraction pattern of Compound 1 Diethanolamine Form I.
Figure 32:
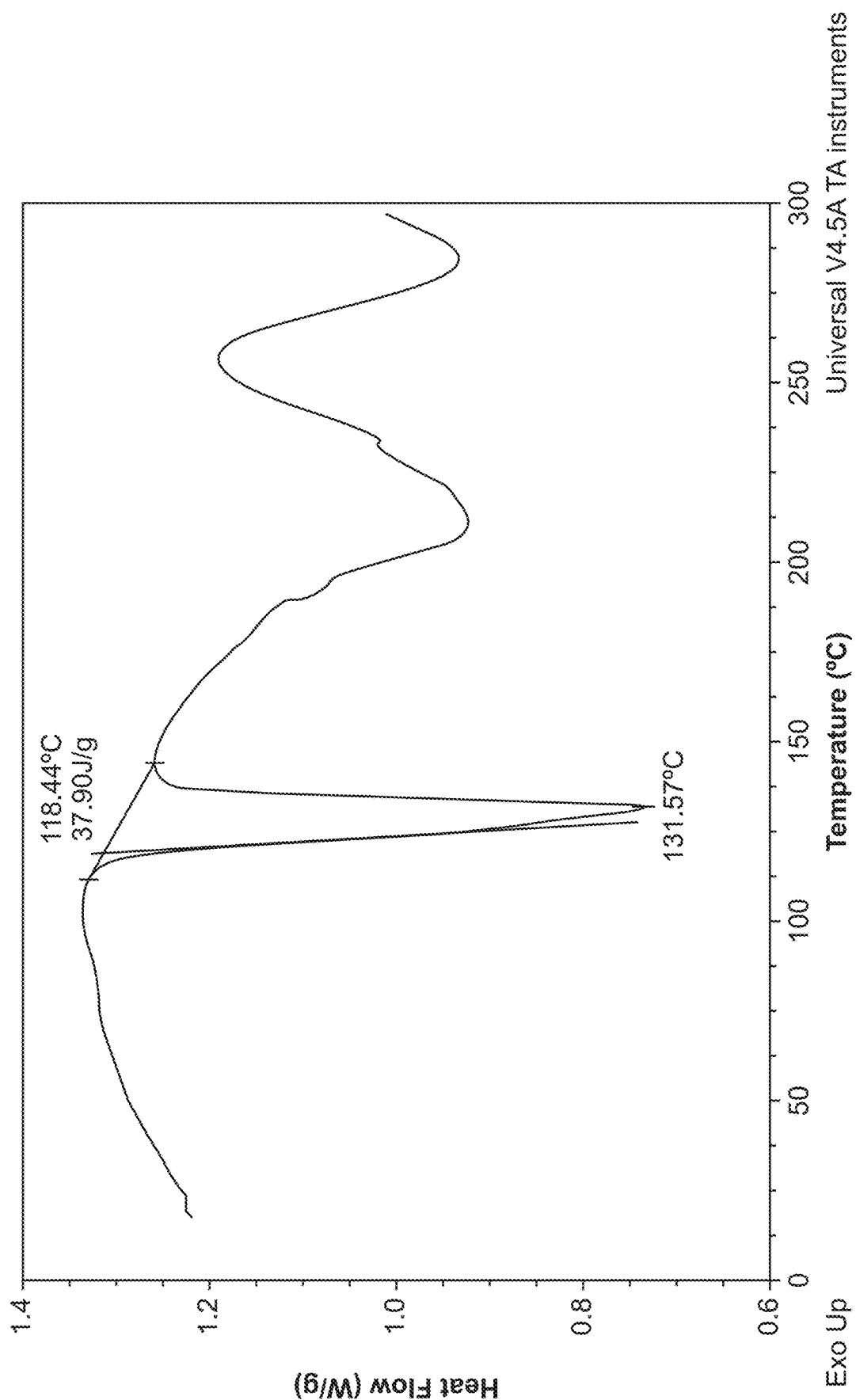
FIG. 32 depicts the differential scanning calorimeter (DSC) curve of Compound 1 Diethanolamine Form I.

Compound 1 Diethanolamine Form I (hydrate) was prepared as follows. 106.9 milligrams of anhydrous Form I of Compound 1 was dissolved in about 3 mL of acetone. 20 µL of diethanolamine was added, and the sample was sonicated for about 2 hours. An additional about 40 µL of diethanolamine was then added, and the sample further slurried at room temperature and then isolated. The XRPD pattern of Compound 1 Diethanolamine Form I is shown in FIG. 31. The DSC curve is shown in FIG. 32 and indicates an endothermic transition with onset at about 118° C. The TGA curve is shown in FIG. 33 and displays a weight loss (about 2.7% RT to about 150° C.) that was identified as water based on TGA-MS. Weight loss above about 250° C. is attributed to decomposition. The dynamic vapor sorption curve indicates that the form absorbs about 14 wt. % of water up to about 95% RH at about 25° C. XRPD analysis of the sample after the DVS experiment shows that the material had not changed form.

Example 18. Production of Compound 1 Piperazine Form I

Figure 34:
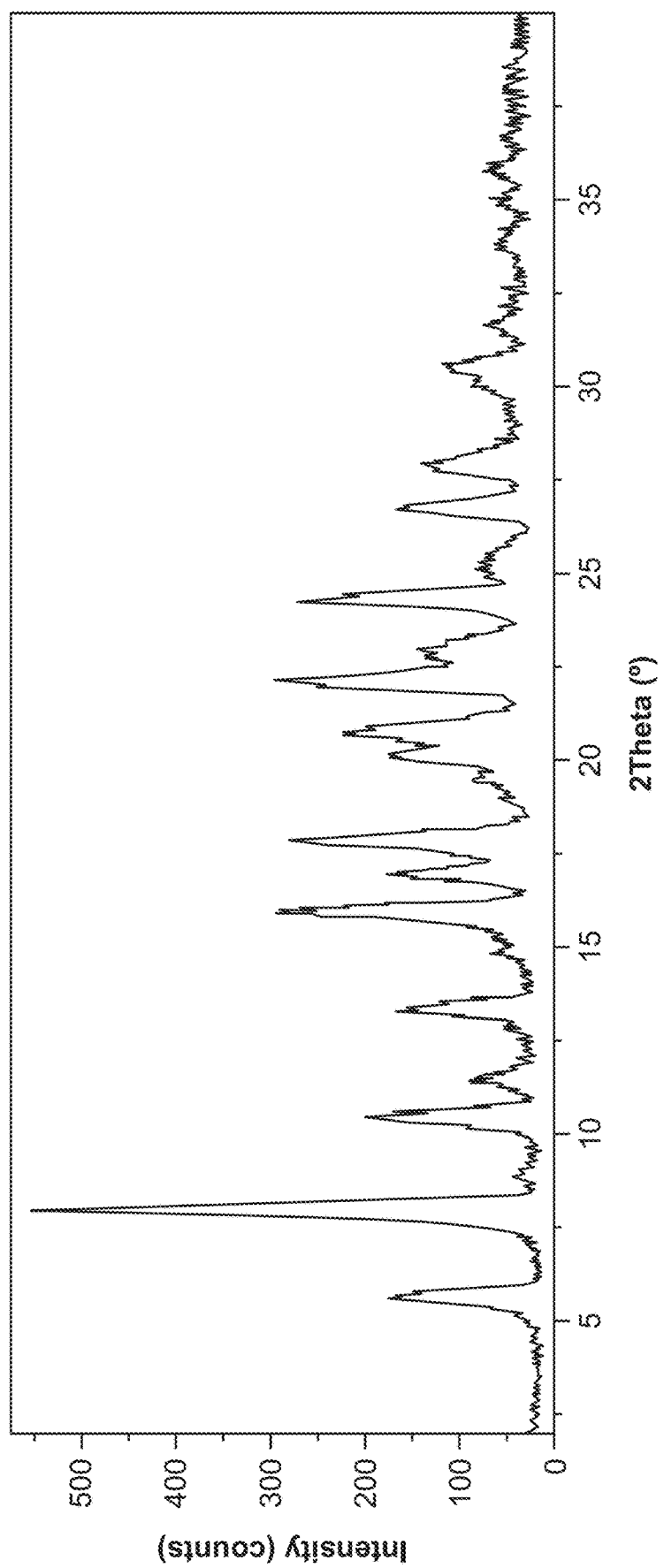
FIG. 34 depicts the X-Ray powder diffraction pattern of Compound 1 Piperazine Form I.
Figure 35:
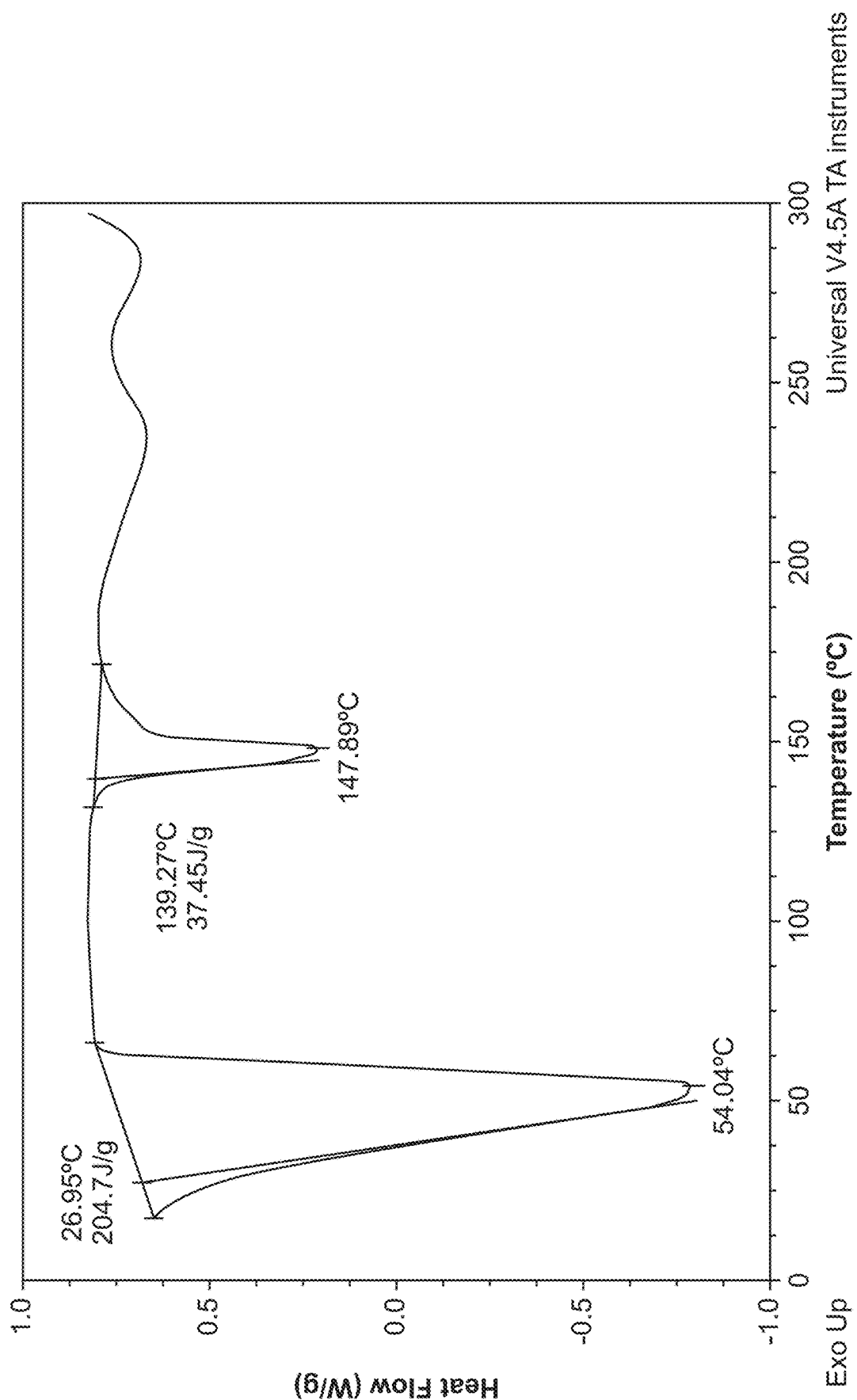
FIG. 35 depicts the differential scanning calorimeter (DSC) curve of Compound 1 Piperazine Form I.

Compound 1 Piperazine Form I (hydrate) was obtained as follows: anhydrous Form I of Compound 1 was placed in a centrifuge tube and one molar ratio of a piperazine was also added. Next, 30 µl of MeOH was added to the powders, and the sample was sonicated for about 30 minutes. The sample tube was then opened and allowed to dry in a nitrogen box. The XRPD pattern of Compound 1 Piperazine Form I is shown in FIG. 34. The DSC curve is shown in FIG. 35 and indicates multiple endothermic transitions with onset at about 27 and about 139° C. The TGA curve is shown in FIG. 36 and displays a weight loss (about 7.3% RT to about 100° C.) that was identified as water based on TGA-MS. Weight loss above about 250° C. is attributed to decomposition. The dynamic vapor sorption curve indicates that the form absorbs about 1.5 wt. % of water up to about 95% RH at about 25° C. XRPD analysis of the sample after the DVS experiment shows that the material had not changed form.

Example 19. X-Ray Powder Diffraction (XRPD) Analytical Method A

XRPD analysis of amorphous and Forms II, III, IV, V, VI, VII, and VIII of Compound 1 was carried out on a Siemens D5000 diffractometer, scanning the samples between 3 and 30 degrees 2θ. Material was gently compressed on a glass disc inserted into a sample holder. The sample was then loaded into the diffractometer running in reflection mode, and the analysis was conducted using the following experimental conditions.

| | |
|---|---|
| Raw Data Origin | Siemens-binary V2 (.RAW) |
| Start Position (°2θ) | 3.0000 |
| End Position (°2θ) | 30.0000 |
| Step Size (°2θ) | 0.0200 |
| Scan Step Time (seconds) | 1 |
| Scan Type | Continuous |
| Slit Types | Fixed |
| Divergence Slit Size (mm) | 2.0000 |
| Receiving Slit Size (mm) | 2.0000 |
| Detector Slit Size (mm) | 0.2000 |
| Measurement Temperature (° C.) | 20.00 |
| Anode Material | Cu |
| K-Alpha1 (Å) | 1.54060 |
| K-Alpha2 (Å) | 1.54443 |
| K-Beta (Å) | 1.39225 |

-continued

| | |
|---|---|
| K-A2/K-A1 Ratio | 0.50000 (nominal) |
| Generator Settings | 40 mA, 40 kV |
| Focussing Circle Diameter (mm) | 401.00 |
| Diffracted Beam Monochromator | Graphite |
| Spinning | No |

Example 20. X-Ray Powder Diffraction (XRPD) Analytical Method B

XRPD analysis of Form I of Compound 1 was carried out on a PANalytical Cubix Pro diffractometer. The sample was placed into the sample holder, such that the sample of Compound 1 was level with the zero height for the instrument. The following parameters were used to acquire the XRPD pattern of Form I of Compound 1.

| | |
|---|---|
| Start Position (°2θ) | 3.0100 |
| End Position (°2θ) | 45.0100 |
| Input Step Size (°2θ) | 0.03 |
| Actual Step Size (°2θ) | 0.02 |
| Time Per Step (seconds) | 10.1600 |
| Active Length (°2θ) | 2.54 |
| Scan Mode | Continuous |
| Voltage (kV) | 45 |
| Current (mA) | 40 |
| Anode | Cu |
| ASS Primary Slit | Fixed 1° |
| Divergence Slit (Prog.) | Automatic - 5 mm |
| Soller Slits (RS) | 0.02 radian |
| Scatter Slit (PASS) | Automatic - 5 mm |
| Spinner | 2 |

Example 21. X-Ray Powder Diffraction (XRPD) Analytical Method C

X-ray powder diffraction (XRPD) analysis of Compound 1 Sodium Form I, Compound 1 Sodium Form II, Compound 1 Calcium Form I, Compound 1 Magnesium Form I, Compound 1 Diethanolamine Form I, or Compound 1 Piperazine Form I was conducted on a diffractometer (PANalytical XPERT-PRO, PANalytical B. V., Almelo, Netherlands) using copper radiation (Cu Kα, λ=1.541874). Samples were spread evenly on a zero background sample plate. The generator was operated at a voltage of 45 kV and amperage of 40 mA. Slits were Soller 0.02 rad, antiscatter 1.0°, and divergence. Scans were performed from 2 to 40° 2θ with a 0.0167 step size. Data analysis was performed using X'Pert Data Viewer V1.2d (PANalytical B. V., Almelo, Netherlands).

Example 22. Thermogravimetric/Differential Thermal Analysis (TG/DTA)

For each analysis as discussed in Examples 3 to 6 and 8, 5 milligrams of material was weighed into an open aluminum pan and loaded into a simultaneous TG/DT analyzer and held at room temperature. The sample was then heated at a rate of 10° C./min from 25° C. to 300° C. during which time the change in sample weight was recorded along with any differential thermal events (DTA). Nitrogen was used as the purge gas, at a flow rate of 100 cm$^3$/min.

For Examples 2, 5, 7, 9, and 13 to 18, TGA was used to evaluate sample weight loss as a function of temperature by loading 1-10 milligrams of material onto a an aluminum weigh pan (TA Instruments, New Castle, Del.) and heated the sample to 350° C. or above at a rate of 10° C./min. The sample and reference pans were under a 60 mL/min and 40 mL/min nitrogen purge, respectively. Data analysis was completed using Universal Analysis 2000 Version 4.7A (TA Instruments, New Castle, Del.).

Example 23. Differential Scanning Calorimetry (DSC)

For each analysis as discussed in Examples 8 to 11, 5 milligrams of material was weighed into an aluminum DSC pan and sealed non-hermetically with a pierced aluminum lid. The sample pan was then loaded into a Seiko DSC6200 (equipped with a cooler), and cooled to and held at 25° C. Once a stable heat-flow response was obtained, the sample and reference were heated to approximately 280° C. (or degradation temperature observed by TG/DTA) at a scan rate of 10° C./min, and the resulting heat flow response was recorded.

For Examples 2, 5, 7, 9, and 13 to 18, DSC was run by loading 1-5 milligrams of material into a crimped Tzero standard aluminum pan and heating the sample at 10° C./min from 20 to 300° C. or above. The sample and reference pans were under a 50 mL/min nitrogen purge. Data analysis was completed using Universal Analysis 2000 Version 4.7A (TA Instruments, New Castle, Del.).

Example 24. Karl-Fischer Coulometric Titration (KF)

Prior to analyzing a compound sample, a blank sample containing methanol only was analyzed using a Mettler Toledo C30 Compact Titrator, to determine the blank water content. Approximately 10-15 milligrams of solid material was accurately weighed into a vial. The material was then dissolved in methanol and the amount added was recorded. The resultant was then manually introduced into the titration cell of the instrument. The water content was calculated as a percentage and the value recorded.

Example 25. Infrared Spectroscope (IR)

Infrared spectroscopy was carried out on a Bruker ALPHA P spectrometer. Sufficient material was placed onto the center of the plate of the spectrometer and the spectra were obtained using the following parameters.

| | |
|---|---|
| Resolution (cm$^{-1}$) | 4 |
| Background Scan Time (scans) | 16 |
| Sample Scan Time (scans) | 16 |
| Data Collection Range (cm$^{-1}$) | 4000-400 |
| Result Spectrum | Transmittance |
| Software | OPUS v.6 |

Example 26. Dynamic Vapor Sorption (DVS)

For DVS analysis as discussed in Example 8, approximately 10 milligrams of sample was placed into a mesh vapor sorption balance pan and loaded into a DVS-1 dynamic vapor sorption balance (Surface Measurement Systems). The sample was subjected to a ramping profile from 0-90% relative humidity (RH) at 10% increments, maintaining the sample at each step until a stable weight had been achieved (99.5% step completion). After completion of the sorption cycle, the sample was dried using the reverse procedure, lowering the RH to 0%. The weight change during the sorption/desorption cycles was plotted.

For Examples 2, 5, 7, 9, and 13 to 18, hygroscopicity was studied using dynamic vapor sorption (DVS, TA Q5000 SA, TA Instruments, New Castle, Del. or DVS, DVS Intrinsic, Surface Measurement Systems, London, UK). A sample (2-20 mg) was placed in an aluminum DVS pan and loaded on the sample side of the twin pan balance. The water sorption and desorption were studied as a function of relative humidity (RH) at 25° C. In 10% RH increments, the relative humidity was increased from 5% RH to 95% RH and then decreased back to 5%. Each relative humidity increment had an equilibration time of 180 minutes, unless weight change % was less than 0.002% in 30 minutes. Data analysis was performed using Universal Analysis 2000 Version 4.7A (TA Instruments, New Castle, Del.) for TA DVS runs and Microsoft Excel for SMS DVS runs.

Example 27. High Performance Liquid Chromatography-Ultraviolet Detection (HPLC-UV)

Purity and concentration analyses were carried out using the following method:

| Instrument | Agilent 1100 | |
|---|---|---|
| Column | Waters XBridge C18 3.5μ 150 × 3 mm | |
| Column Temperature (° C.) | 40 | |
| Autosampler Temperature (° C.) | 20 | |
| UV Wavelength (nm) | 315 | |
| Injection Volume (μL) | 5 | |
| Flow Rate (mL/min) | 0.8 | |
| Mobile Phase A | 0.05% TFA in water | |
| Mobile Phase B | 0.05 TFA in acetonitrile | |
| Gradient Program | Time (min) | Solvent B (%) |
| | 0.0 | 25 |
| | 25.0 | 75 |
| | 30.0 | 95 |
| | 35.0 | 95 |
| | 35.1 | 25 |
| | 40.0 | 25 |

Example 28. pKa Measurements pKa analysis was performed using a UV-metric method. The sample was titrated in a triple titration (pH 12.1 to pH 2) at concentrations of 32 to 20 μM under methanol-water co-solvent conditions (the methanol concentration varied from 53-30% (v/v). The pKa was determined using the spectroscopic data by a Yasuda-Shedlovsky extrapolation of the results from each titration.

Example 29. Log P and Log D Determination

Log P analysis was performed using a potentiometric (pH-metric) method. The sample was titrated in various ratios of octanol/water in two titrations covering the pH range from 1.9 to 12.0 at concentrations of 1.0 to 0.6 mM. The shift of the aqueous pKa in the presence of octanol was used to determine log P of the neutral and anionic species. From this information a lipophilicity profile was constructed, such that that log D at a given pH could be determined.

Example 30. Pharmaceutical Composition

A pharmaceutical composition comprising Form I of Compound 1 was prepared that contains the following ingredients.

| Ingredient | Quality Standard | Capsule Strength | | |
|---|---|---|---|---|
| | | 10 mg | 50 mg | 200 mg |
| Compound 1 (Form I) | In-house | 17.00 g | 110.0 g | 640.0 g |
| Gelucire ® 50/13 (stearoyl macrogol-32 glycerides; surfactant) | USP/NF, Ph. Eur. | 153.00 g | 198.0 g | 288.0 g |
| Fast Flo ® 316 (lactose monohydrate; filler) | NF | 556.75 g | 632.5 g | 440.0 g |
| Ac-Di-Sol ® SD-711 (croscarmellose sodium, disintegrant) | NF, Ph. Eur., JP | 38.25 g | 49.5 g | 72.0 g |
| Theoretical Batch Size (g) | | 765.00 g | 990.0 g | 1440.0 g |
| Theoretical Batch Size (# capsules) | | 1700 | 2200 | 3200 |

The pharmaceutical composition was prepared as follows.

Example 31. Micronization

Crystalline Compound 1 (Form I) was continuously fed into a 2 inch vertical loop jet mill. The compressed air supply was high purity nitrogen, with an inlet pressure of at least 110 p.s.i. The pusher nozzle and grinder nozzle pressures were both maintained at 80 p.s.i. throughout the milling process. The feed rate was controlled by a vibratory feeder, at an equipment set point of 3. Approximately 800 grams of material was generated over the course of approximately 5 hours in this manner. This material was then collected in a single container and mixed prior to incorporation into the hot melt granulations at 10 milligrams, 50 milligrams, and 200 milligrams dosage strengths.

Example 32. Hot Melt High Shear Granulation, Milling, and Blending

The granulations were prepared in a jacketed 4 L bowl on a Vector GMX Lab-Micro High Shear granulator. The bowl was jacketed with water at 60° C. Approximately half of the lactose monohydrate, croscarmellose sodium, and the micronized Compound 1 drug substance were added to the bowl. The remaining lactose was then used to dry wash the Compound 1 drug substance transfer container prior to addition to the bowl. The dry, solid components were then mixed until the blend reaches 55° C. Once this temperature is reached, the Gelucire 50/13 melted, and the granulation continued mixing until the product temperature drop occurred as the Gelucire 50/13 melts. The granulation continued mixing until the product temperature recovered to 55° C. to ensure complete melting and mixing of the Gelucire 50/13. This granulated product was then allowed to cool to room temperature. The cooled granulation was milled using a Quadro Comil 197S equipped with a 1905 μm screen and a round impeller.

Example 33. Capsule Preparation

The powder prepared in Example 22 was encapsulated using a Profill apparatus into size 0 white opaque gelating capsules, which were then dedusted. The final capsule drug product had a fill weight of 450 mg, of which 90 milligrams was Gelucire 50/13, 22.5 milligrams was croscarmellose sodium, and the remaining weight was comprised of lactose monohydrate and micronized Compound 1 drug substance. The amount of each of lactose monohydrate and Compound 1 was dependent on the dosage strength, with their combined weight equal to 337.5 to achieve a total 450 milligrams fill weight. A 100% weight sort was carried out, and the final product was packaged in white opaque HDPE bottles, which were then induction sealed.

Example 34. Synthesis of Intermediate (R)-G-1-a

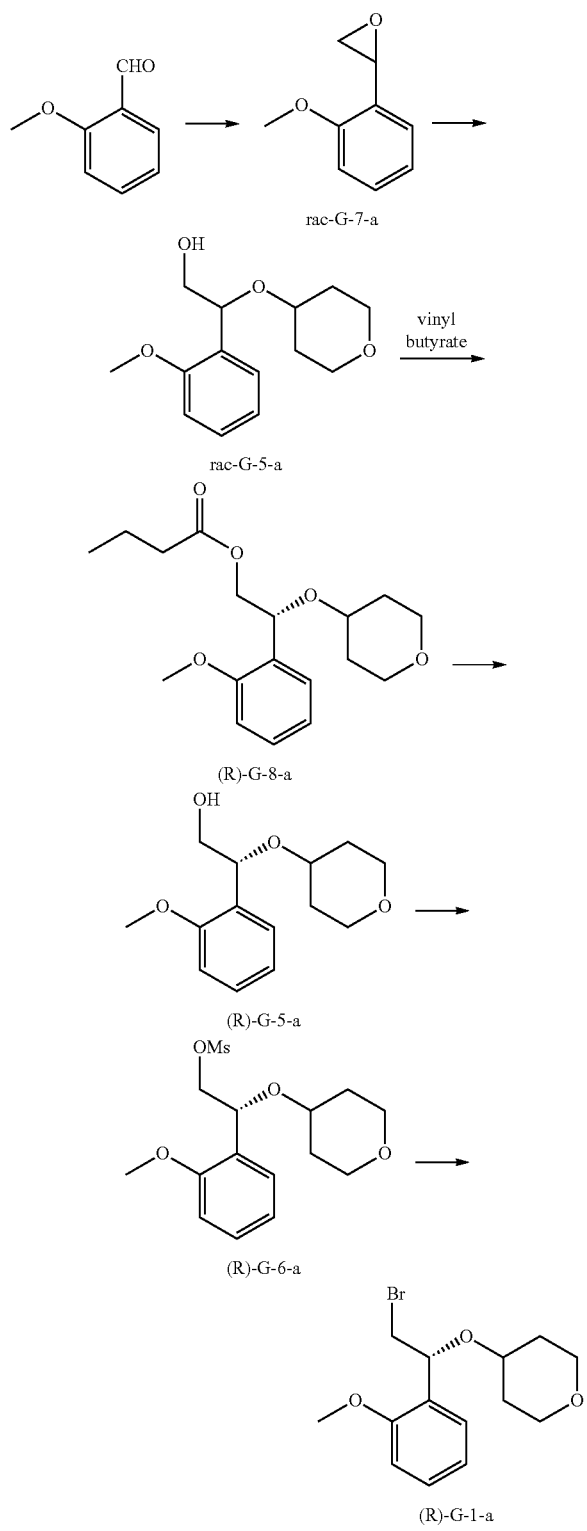

Step 1. Synthesis of rac-G-7-a

A 1000 L reactor was charged with 330 kg DMSO, and potassium t-butoxide (30 kg, 1.22 eq) were added at 10-25° C. Trimethylsulfoxonium iodide (58 kg, 1.2 eq) was added in several portions at 18-25° C., and the mixture was stirred in that temperature range for two hours. 2-Methoxybenzaldehyde (30.15 kg, 1.0 eq) was added in several portions while maintaining the reactor temperature between 18-25° C. The mixture was stirred at a temperature between 18-25° C. until 2-methoxybenzaldehyde was determined to be present at less than 0.5% by HPLC (typically 1-2 hours), whereupon 300 kg water was added to quench the reaction, maintaining the temperature below 25° C. The reaction mixture was extracted with heptane (3 portions of 204 kg), and the heptane extracts were combined, washed with water (3 portions of 300 kg), then brine (300 kg). The organic layer was concentrated under vacuum at 40-45° C., affording rac-G-7-a (18.55 kg, 56% isolated yield, HPLC purity 96.6% at 220 nm, 94% wt. by NMR) as an oil, which was used in the next step without any further purification.

Alternative Step 1: Synthesis of rac-G-7-a

To 2-methoxybenzaldehyde (1 eq) was added trimethylsulfonium methyl sulfate (1.08 eq), followed by dichloromethane (about 75.5 mL), and the resulting mixture was agitated. To the mixture was added ca. 50 wt % aqueous NaOH portion wise and stirred for about 2.5 hours at a temperature range of about 28° C. to about 22° C. Additional water was added, and the mixture cooled to a temperature of about 17° C. Dichloromethane was added to the mixture and stirred. The mixture was separated, and the organic layer was concentrated under vacuum, to provide rac-G-7-a. $^1$H NMR (400 MHz, CDCl$_3$): δ 7.28-7.25 (m, 1H), 7.15 (d, J=7.5 Hz, 1H), 6.94 (t, J=7.5 Hz, 1H), 6.88 (d, J=8.2 Hz, 1H), 4.21 (t, J=2.9 Hz, 1H), 3.87 (s, 3H), 3.14 (t, J=4.9 Hz, 1H), 2.71 (dd, J=5.6, 2.4 Hz, 1H).

Step 2. Synthesis of rac-G-5-a

Tetrahydro-2H-pyran-4-ol (16.3 kg, 4.0 eq) was charged into a 50 L reactor, followed by FeCl$_3$ (225 g, 0.035 eq). Intermediate rac-G-7-a (6.0 kg, 1.0 eq) was added dropwise, maintaining the temperature between −10 to 10° C. The reaction was stirred at between 0-10° C. until the starting epoxide was shown to be present at less than 0.5% by HPLC (typically 0.5-1 hours). Once the reaction was judged to be complete, the reaction mixture was diluted with toluene (240 L), and the toluene solution was extracted with water (3 portions of 24 kg), then brine (12 kg). The organic layer was concentrated under vacuum between 40-45° C., affording rac-G-5-a (19.64 kg, 47% yield) as an oil.

Alternative Step 2: Synthesis of rac-G-5-a

Toluene is charged to a reactor, followed by tetrahydro-2H-pyran-4-ol (4 eq), BF$_3$-Et$_2$O (0.005 v/w). Intermediate rac-G-7-a (1.0 eq) is added dropwise, maintaining the temperature between 0 to 10° C. The reaction is stirred for about an hour at a temperature between 0 to 10° C. The solution is combined with toluene (about 8 v/w) at about 15 to 25° C. and washed with water about three times. The water layers are combined, washed with MTBE, and the MTBE layers are washed with water about two times. The organic layers are then combined and concentrated under vacuum. To the resulting residue, THF is added, and the mixture is concentrated under vacuum, affording rac-G-5-a as an stock solution.

Step 3. Synthesis of (R)-G-5-a

A 50 L glass reactor was charged with toluene (5.0 v/w), followed by rac-G-5-a (6.2 kg, 1.0 eq) in one portion. The solution was warmed to 40° C. until the mixture became a clear solution, then cooled to 25° C. Vinyl butyrate (0.5 eq) was added in one portion to the above solution, and the mixture was stirred for 0.5 hours at a temperature between 25-30° C. until a clear solution was obtained. CAL-B lipase (1.5% w/w) was added in one portion to the reactor and the mixture was stirred at 22-26° C. until the reaction was deemed complete when IPC showed the ratio of (S)-G-5-a/(R)-G-5-a was 96:3.5 and the e.e. of (R)-G-8-a was 97.9% (typically 4 hours). The CAL-B was filtered out, and the filter cake washed with THF (11.6 L). The filtrate was combined with that of another batch of the same scale, and the combined filtrates were concentrated under vacuum at 35-40° C. until 13 L of residue remained. Petroleum ether (5.0 v/w) was added, and the mixture stirred for 30 minutes. The precipitated (S)-G-5-a was filtered, and the filter cake washed with petroleum ether (2.0 v/w). The filtrate was concentrated under vacuum at a temperature between 40-45° C., resulting in a crude oil. Toluene (3.0 v/w) was added to a 50 L glass reactor, followed by the oil from the previous step. Succinic anhydride (0.25 eq.) and dimethylaminopyridine (DMAP, 0.02 eq.) were added, and the mixture was heated to between 70-80° C. and stirred for two hours, sampling periodically until the amount of (S)-G-5-a remaining was no more than 0.5% by HPLC. The mixture was then cooled to between 10-20° C. and washed with saturated aqueous sodium bicarbonate (two portions of 1.0 v/w). HPLC analysis of the organic layer showed that the amount of (S)-G-5-a present was less than 0.1%. The organic solvent was concentrated to give an oil (9.9 kg, 53.6% yield, 89% purity, 97% e.e.) which was used in the next step without further purification. To a 100 L reactor was added methanol (40 L), followed by the oil from the previous step, followed by water (30 kg, 3.0 w/w). Sodium hydroxide (1.23 kg) in several portions while maintaining the temperature between 10-25° C. The reaction was stirred at that temperature until HPLC analysis indicated that the butyrate ester was completely consumed. The pH was adjusted to 7 with 3N aqueous HCl, and the mixture was concentrated at vacuum between 40-45° C. until 30 volumes remained. The mixture was filtered and the filter cake was collected to give crude (R)-G-5-a (9.0 kg, 96% purity, 96.8% e.e.). Ethyl acetate (4.3 L) and petroleum ether (26 L) were charged into a reactor, followed by the crude product from the previous step. The mixture was stirred for 1 hour at a temperature between 10-25° C., then filtered. The collected solids were dried in a vacuum oven at between 40-45° C., yielding pure (R)-G-5-a (5.2 kg, 70% yield for this step, 99% purity, 96% e.e.) as an off-white solid.

Alternate Step 3: Alternate Synthesis of (R)-G-5-a

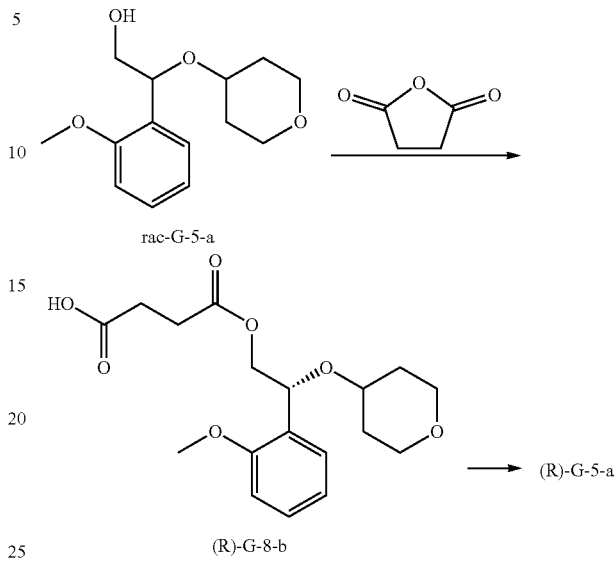

A 50 L glass reactor was charged with THF (29 L), followed by rac-G-5-a (5.8 kg, 1.0 eq) in one portion. Succinic anhydride (2.3 kg, 1.0 eq) was added in one portion to the above solution, and the mixture was stirred for 0.5 hours at a temperature between 25-30° C. until a clear solution was obtained. CAL-B lipase (406 g, 7% w/w) was added in one portion to the reactor and the mixture was stirred at 25-30° C. until the reaction was deemed complete (when the ratio of G-5-a to (R)-G-8-b was shown to be 51:49 by IPC (typically 24 hours). The CAL-B was filtered out, and the filter cake washed with THF (11.6 L). The filtrates were combined and concentrated under vacuum at 35-40° C. The resulting residue was diluted with ethyl acetate (58 L) at 15-25° C., and the ethyl acetate was washed with saturated sodium bicarbonate (four portions of 23 L) at 15-25° C. A sample from the ethyl acetate layer was analyzed by HPLC, which indicated that the ratio of (R)-G-8-b to G-5-a was no more than 1:99. The aqueous layers were combined and washed with ethyl acetate (three portions of 29 L). A sample from the aqueous layer was analyzed by HPLC, which indicated that the ratio of (R)-G-8-b to G-5-a was greater than 99.5:0.5. To the aqueous layer was added sodium hydroxide (5.8 kg) in several portions at a temperature between 15-25° C. The reaction was stirred at that temperature for 0.5-1 hours, until HPLC analysis indicated that the ratio of (R)-G-8-b to (R)-G-5-a was no greater than 1:99. The reaction mixture was filtered, and the filter cake was washed with water (5.8 L). The filter cake was dried at 40-45° C. to constant weight, yielding 2.4 kg of crude (R)-G-5-a with 96% purity and 98.9% e.e. Crude material from multiple batches was purified by recrystallization as follows. Into a 100 L reactor containing ethyl acetate (72 L, 6 volumes), was charged crude (R)-G-5-a (12 kg), and the mixture was warmed to 30-35° C. and stirred for 1 hour. The solution was filtered to remove undissolved solids, and the filtrate was concentrated under vacuum at 40-45° C. until approximately two volumes of solvent remained. To this solution was added heptanes (120 L, 10 volumes), and the mixture was heated to reflux to obtain a clear solution. The solution was cooled to a temperature between 15-20° C.

gradually over eight hours, and stirred for 12 hours at that temperature. The resulting solids were collected by filtration, and the filter cake was washed with a solution of ethyl acetate/heptanes (1:5, 12 L) once. The cake was collected and dried at 40-45° C. to constant weight, providing 10.2 kg of (R)-G-5-a (99.2% purity by HPLC, 99.8% e.e.) as an off-white solid.

Synthesis of (R)-G-5-a was also carried out similar to the method described above with Novozyme 435 in place of CAL-B lipase.

Step 4. Synthesis of (R)-G-6-a

Into a 100 L glass reactor under nitrogen, was charged dichloromethane (58 L) followed by (R)-G-5-a (5794 g, 1.0 eq.), and triethylamine (4.8 L), and the reaction mixture was cooled to between 0-10° C. Methanesulfonyl chloride (3160 g) was charged over 35 minutes, maintaining the reaction temperature no higher than 25° C. Then the mixture was stirred at between 20-30° C. for 18 hours, whereupon the amount of (R)-G-5-a remaining was determined to be no more than 1%. Purified water (58 L) was added, and the mixture was transferred to a 200 L glass reactor and stirred for at least one hour. The phases were separated and the organic layer was transferred to a 100 L reactor and washed with 2 N HCl (29 L), then 10% aqueous sodium bicarbonate (29 L), and the organic layer was concentrated under vacuum at 70° C. to a volume of 29 L. Isopropanol (58 L) was added and the mixture was concentrated under vacuum at 70° C. to a volume of 29 L. Isopropanol (58 L) was again added, and the mixture was concentrated to a final volume of 28 L. Purified water (29 L) was added, and the mixture was heated to between 50-60° C. with stirring until complete dissolution was observed. The mixture was then cooled to between 0-10° C. and stirred for at least 14 hours. The resulting solids were collected by filtration, washed with purified water (12 L), and dried in a vacuum oven at 25° C. for at least 12 hours. The isolated intermediate (R)-G-6-a (6962 g) was used without further purification in the next step.

Alternative Step 4. Synthesis of (R)-G-6-a

2-Methyltetrahydrofuran (1300 mL) was charged to a reactor containing (R)-G-5-a (200 g, 1.0 equiv.), followed by trimethylamine (120 g, 1.5 equiv.). The contents were cooled to 5° C. (2 to 8° C.) and methanesulfonyl chloride (109 g, 1.2 equivalents) was charged while maintaining the reaction contents at no more than about 25° C. 2-Methyltetrahydrofuran (120 mL) was used to rinse forward the methanesulfonyl chloride and the reaction was warmed to about 22° C. and stirred until the reaction was complete. Water (1600 mL) was then slowly added such that the internal temperature was less than about 40° C. and the solution was agitated for about 30 minutes. Agitation was stopped and the solution was allowed to settle. The bottom aqueous layer was removed and the organic layer was washed with an aqueous HCl solution (about 160 g concentrated HCl in 664 g water) at about 22° C. Agitation was again stopped and the solution was allowed to settle. The bottom aqueous layer was removed and the organic layer was then washed with an aqueous sodium bicarbonate solution (about 72 g NaHCO$_3$ in 776 g water) at about 22° C. Agitation was again stopped and the solution was allowed to settle. The bottom aqueous layer was removed and the organic layer was then washed with water (800 mL, about 4.0 v/w (R)-G-5-a). Agitation was again stopped and the solution was allowed to settle. The bottom aqueous layer was removed. The organic layers were distilled under vacuum to about 3V pot volume. 2-Propanol (1200 mL, about 6.0 v/w (R)-G-5-a) was added and the reaction was distilled to about 6V pot volume twice. Water (1000 mL, about 5.0 v/w (R)-G-5-a) was then added and the solution warmed to between about 55° C. to about 65° C. The solution was then cooled to about 22° C. (19 to 25° C.) and (R)-G-6-a seeds (made according to this method or from a previous alternate route such as described herein) (0.6 g, about 0.003 w/w (R)-G-6-a) were added and the solution was cooled to about 5° C. and filtered. The filter cake was washed with water (about 400 mL, 2.0 v/w (R)-G-6-a) and dried to afford (R)-G-6-a. $^1$H NMR (400 MHz, CDCl$_3$): δ 7.48 (d, J=7.6 Hz, 1H), 7.33 (t, J=8.0 Hz, 1H), 7.02 (t, J=7.6 Hz, 1H), 6.91 (d, J=8.0 Hz, 1H), 5.21 (d, J=8.0 Hz, 1H), 4.34 (d, J=10.8 Hz, 1H), 4.19 (dd, J=8.0, 10.8 Hz), 4.01 (m, 1H), 3.90 (m, 1H), 3.87 (s, 3H), 3.55 (m, 1H), 3.40 (dq, J=9.8, 2.2 Hz, 2H), 3.04 (s, 3H), 2.02 (m, 1H), 1.82 (m, 1H), 1.66 (m, 2H).

Step 5. Synthesis of (R)-G-1-a

Into a 100 L reactor under nitrogen was charged N-methylpyrrolidinone (NMP, 14 L), and the reactor was cooled to 0-10° C. Lithium bromide (9189 g) was added in three portions over one hour to the reactor allowing the temperature to return to between 0-10° C. after each addition. The mixture was heated to between 55-65° C. (R)-G-6-a (6962 g) was combined with in NMP (14 L) in a 72 L reactor and stirred at 30-40° C. until completely dissolved. This solution was transferred to the 100 L reactor containing the lithium bromide solution, and the mixture was stirred at 50-60° C. for 18 hours, taking samples for analysis by HPLC every hour, until the amount of (R)-G-6-a remaining was no more than 1%. The contents of the 100 L reactor were cooled to 15-25° C. and transferred to a 200 L glass reactor together with purified water (70 L) and ethyl acetate (70 L), and the mixture was stirred for at least 15 minutes, then the phases were separated. The aqueous phase was extracted with ethyl acetate (35 L) with stirring for at least 15 minutes. The combined organic phases were washed with two portions of brine (35 L each) and two portions of purified water (35 L each), then concentrated to dryness under vacuum at 40-50° C., affording (R)-G-1-a (6691 g, 92% yield) as an oil.

Alternative Synthesis of (R)-G-1-a

1-Methyl-2-pyrolidinone (NMP) (148 g, about 2.4 v/w was charged to a reactor, agitated, and adjusted to about 5° C. Lithium bromide (26.4 g, about 0.44 w/w (R)-G-6-a, 1.67 equiv.) was then added batch-wise to the reactor and agitated for about 30 minutes. Once the temperature reached about 5° C., the next charge of lithium bromide (26.4 g, about 0.44 w/w (R)-G-6-a, 1.67 equiv.) was performed. Once the reaction cooled back down to about 5° C., a third and final charge of lithium bromide (26.4 g, about 0.44 w/w (R)-G-6-a, 1.67 equiv.) was performed. Additional NMP (37.1 g, about 0.6 v/w (R)-G-6-a) was added and the temperature was adjusted to about 55° C. In a separate reactor was charged (R)-G-6-a (60.0 g, about 1.0 equivalent) followed by NMP (80.3 g, about 2.3 v/w (R)-G-6-a), which was then heated to about 30° C. to about 38° C. with agitation until all solids were dissolved. The NMP solution of (R)-G-6-a was charged to the about 55° C. NMP lithium bromide slurry. The (R)-G-6-a solution was rinsed forward with NMP (43.3 g, about 0.7 v/w (R)-G-6-a) and then stirred at about 55° C. Once complete, the pot temperature was adjusted to about 22° C., and water (300.1 g, about 5 v/w (R)-G-6-a) was charged slowly to quench the reaction such that the pot temperature remains no more than about 30° C. Ethyl acetate (271.0 g, about 5 v/w (R)-G-6-a) was charged and the solution was agitated. The layers were allowed to separate and the aqueous layer was removed and set aside. To this aqueous layer was charged ethyl acetate (271.1 g, about 5 v/w (R)-G-6-a) and the solution was agitated. The layers were then allowed to separate, and the aqueous layer was disposed of. The ethyl acetate organic layers were combined and brine was added [(water, 291.0 g, 4 about.85 v/w (R)-G-6-a), (sodium chloride, 29.1 g, about 0.485 w/w (R)-G-6-a)], the temperature was adjusted to about 22° C., and the mixture agitated. The layers were then separated. The organic layer was washed with water (300.0 g, about 5 v/w (R)-G-6-a) and the mixture agitated. The water layer was discarded, and another final water (300.0 g, about 5 v/w (R)-G-6-a) wash was performed. The organic layer was distilled to about 3V (pot volume) with max jacket temperature at about 45° C. Once at about 3V, acetonitrile (ACN) (376.0 g, about 8 v/w (R)-G-6-a) was charged to the reactor and contents distilled down to about 3 V (pot volume) with max jacket temperature at about 45° C. NMP (185.0 g, about 5.5 v/w (R)-G-6-a) was then added, and the contents distilled to about 3.3 V (pot volume) with max jacket temperature at about 90° C. Once distillation was complete, a NMP stock solution of (R)-G-1-a was achieved.

Example 35. Synthesis of Compound 1—Route A

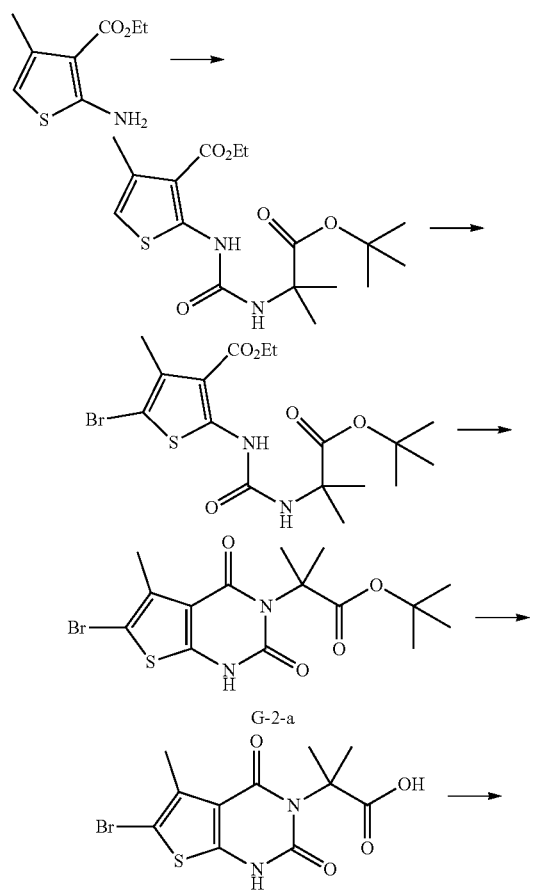

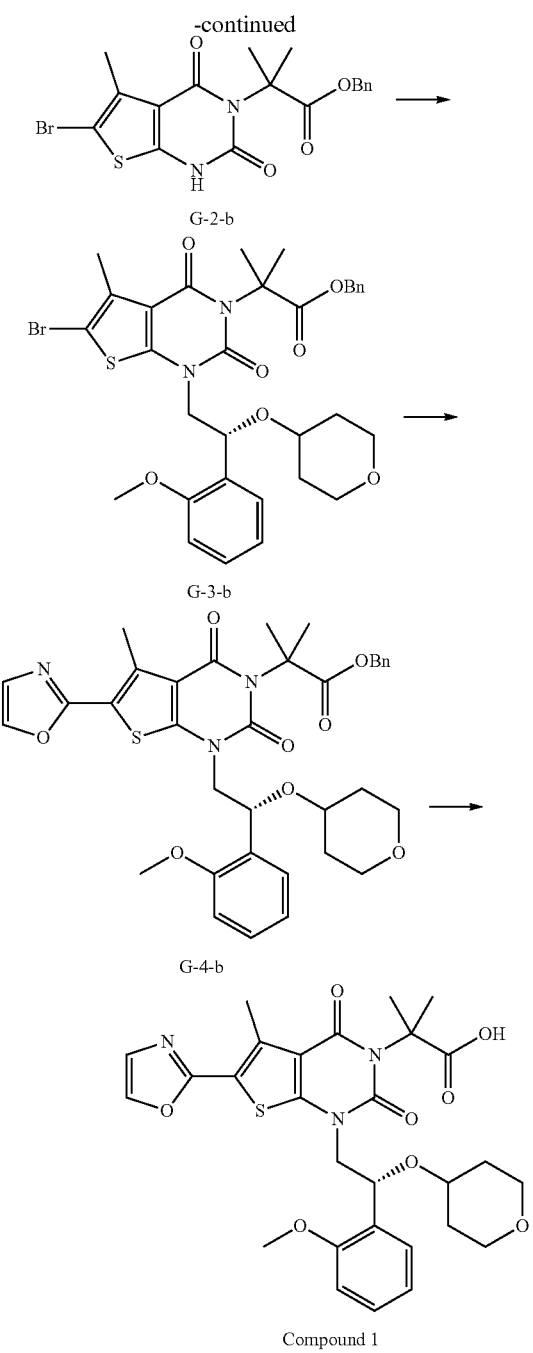

Step 1. Synthesis of Ethyl 4-methyl-2-[3-(1-methyl-1-tert-butoxycarbonylethyl)ureido]-3-thenoate Into a 300 L reactor under nitrogen was added dichloromethane (136.47 L), followed by ethyl 2-amino-4-methylthiophene-3-carboxylate (12.91 kg, 1.0 eq) at 15-25° C. Carbonyldiimidazole (12.66 kg, 1.1 eq) was added, while maintaining the temperature between 15-25° C. The mixture was stirred at that temperature, taking samples and quenching with methanol and analyzing by IPC until the starting material was determined to be present at 2.0% or less (typically 12 hours). Once this criterion was met, trimethylamine (7.80 kg, 1.1 eq) was added dropwise at a temperature below 25° C. tert-Butyl 2-amino-2-methylpropionate hydrochloride (14.98 kg, 1.1 eq) was added in portions, maintaining the temperature below 25° C. The reaction was stirred for 5 hours at a temperature between 15-25° C., taking samples, quenching with methanol and analyzing with IPC until the intermediate isocyanate was determined to be present at 3.0% or less. Once this criterion was met, purified water (52.52 L) was charged into the reactor, and the mixture was stirred for 30 minutes, then allowed to stand for 15 minutes. The phases were allowed to separate and the organic layer was collected and washed with water (two portions of 52.50 L). The organic layer was concentrated under vacuum at a temperature below 40° C. until no more than four volumes of solvent remained. MTBE (39.27 L, 3 volumes) was charged into the reactor, and the mixture was again concentrated under vacuum at a temperature below 40° C. until no more than four volumes of solvent remained. Again, MTBE (39.27 L, 3 volumes) was charged into the reactor, and the mixture was again concentrated under vacuum at a temperature below 40° C. until no more than four volumes of solvent remained. Petroleum ether (40.00 L, 3 volumes) was charged into the reactor, and the mixture was stirred for five hours between 15-25° C. The mixture was centrifuged, filtered, and the resulting cake was washed with petroleum ether (13.11 L, 1 volume), then dried in a vacuum oven at 35-45° C. for six hours, resulting in 23.38 kg of the desired product (90.5% yield, 98.0% yield) as an off-white solid.

In some embodiments, heptanes is used in place of petroleum ether.

Step 2. Synthesis of Ethyl 5-bromo-4-methyl-2-[3-(1-methyl-1-tert-butoxycarbonylethyl)ureido]-3-thenoate Into a 500 L reactor under nitrogen was charged DMF (279.47 L) followed by ethyl 4-methyl-2-[3-(1-methyl-1-tert-butoxycarbonylethyl)ureido]-3-thenoate (23.38 kg, 1.0 eq.). The mixture was cooled to −10 to 0° C., and N-bromosuccinimide (11.22 kg, 1.0 eq.) was added batchwise, maintaining the temperature below 0° C. The mixture was stirred at that temperature for one hour, sampling and assaying by IPC each half an hour until no more than 2.0% of the starting material remained. Once the reaction was deemed complete according to this criterion, the mixture was poured into purified water (1000 L, 42 volumes) slowly, and stirred for two hours. The mixture was centrifuged, filtered, and the collected solids were washed with water (48.00 L, 2 volumes), then dried for 12 hours at 35-45° C. in a vacuum oven. The product (26.20 kg, 92.39% yield, 98.8% purity) was isolated as an off-white solid, and had a water content less than 0.07% by Karl Fischer titration.

In some embodiments, about 15 volumes of purified water can be used in place of 42 volumes.

Step 3. Synthesis of tert-Butyl 2-(2-bromo-3-methyl-4,6-dioxo-1-thia-5,7-diaza-5,7-dihydroinden-5-yl)-2-methylpropionate (G-2-a)

Into a 1000 L reactor under nitrogen was charged 1,4-dioxane (393 L, 30 volumes, 0.03% water by Karl Fischer), followed by ethyl 5-bromo-4-methyl-2-[3-(1-methyl-1-tert-butoxycarbonylethyl)ureido]-3-thenoate (13.09 kg, 1.0 eq.). Potassium tert-butoxide (16.27 kg, 5.0 eq.) was added in batches. The mixture was heated to between 40-50° C., and stirred at that temperature for approximately 1 hour, sampling and assaying by HPLC every 30 minutes until the content of the starting material was determined to be no more than 2.0%. Once the reaction was determined to be complete, the mixture was cooled to between 20-30° C., and then poured into a solution of ammonium chloride (327.50 kg) in water (1310.00 kg, 100 volumes) that had been cooled to between 0-10° C. The quenched mixture was stirred for two hours at a temperature between 0-10° C., whereupon the precipitate was collected by centrifugation and filtration. The resulting solid was washed with water (52.00 L, 4 volumes), then dried in a vacuum oven held at 35-45° C. for 12 hours whereupon Karl Fischer analysis indicated that the water content was less than 1.0%. The solid material was collected, amounting to 8.89 kg of the product (75.68% yield, 97.1% purity) as an off-white solid.

Alternative Process to G-2-a

To ethyl 5-bromo-4-methyl-2-[3-(1-methyl-1-tert-butoxycarbonylethyl)ureido]-3-thenoate (0.65 kg, 1.0 eq.) was charged 1,4-dioxane (20.3 kg, 30 v/w). The resulting slurry is then analyzed by KF and water is added such that KF is between about 0.1% and about 0.4%. Potassium tert-butoxide (0.85 kg, 5.0 eq.) was then added and 1,4-dioxane (0.52 kg, 0.8 w/w) was added to wash down the hopper. The mixture was heated to about 47° C. until deemed complete, and then cooled to between about 10° C. and about 20° C., at which point acetic acid (0.44 kg, 5 eq.) is slowly added such that the temperature remains within this range. Water (1.95 kg, 3 v/wt) is added and the aqueous layer cut. While keeping the pot temperature at below about 40° C., the reaction is then concentrated to about 11V, then water (12.8 kg, 19.7 w/w) is added at 35° C. over 3 hours. The isolation mixture is cooled to 15° C. over 2 hours and after a further stirring (>1 hr) the quenched mixture was filtered. The resulting cake was washed with 1,4-Dioxane/demineralized water (1/2 (w/w) (2.62 w/w)), followed by washing with demineralized water (0.5 w/w). The wet product is dried under vacuum at 35° C.-45° C.

Step 4. Synthesis of 2-(2-Bromo-3-methyl-4,6-dioxo-1-thia-5,7-diaza-5,7-dihydroinden-5-yl)-2-methylpropionic acid Into a 300 L reactor under nitrogen was charged dichloromethane (176.70 L, 10 volumes), followed by intermediate G-2-a (17.74 kg, 1.0 eq.). Trifluoroacetic acid (32.4 L, 2 volumes) was added dropwise at a temperature between 15-25° C., and the reaction was stirred at this temperature for three hours, sampling periodically for analysis by IPC until the amount of starting material remaining was no more than 2.0%. The mixture was then cooled to between 0-10° C., and water (182.41 L, 10 volumes) was added dropwise, maintaining the temperature between 0-10° C. The reaction mixture was stirred for two hours at this temperature, and then the solid formed was collected by centrifugation and filtration. The solid was washed with dichloromethane (2.3 volumes), and water (5 volumes), then dried in a vacuum oven held at 35-45° C. for 12 hours, whereupon Karl Fischer analysis indicated that the water content was less than 0.5%. The solid material was collected, amounting to 13.2 kg of the product (86.7% yield, 98.1% purity) as an off-white solid.

Step 5. Synthesis of Benzyl 2-(2-bromo-3-methyl-4,6-dioxo-1-thia-5,7-diaza-5,7-dihydroinden-5-yl)-2-methylpropionate (G-2-b)

Into a 300 L reactor under nitrogen was charged dichloromethane (116.7 L, 10 volumes), followed by 2-(2-Bromo- 3-methyl-4,6-dioxo-1-thia-5,7-diaza-5,7-dihydroinden-5-yl)-2-methylpropionic acid (11.50 kg, 1.0 eq.). Carbonyldiimidazole (CDI, 6.51 kg, 1.2 eq.) was added batchwise to the reactor, maintaining the temperature of the mixture below 25° C. The reaction mixture was stirred for three hours at a temperature between 20-30° C., sampling hourly, quenching with methanol, for analysis by IPC until the amount of starting material remaining was determined to be no more than 3.0%. Benzyl alcohol (4.64 kg, 1.3 eq.) was then charged slowly into the reactor, keeping the temperature below 25° C. The mixture was stirred for two hours at this temperature, sampling hourly, quenching with methanol, for analysis by IPC until the amount of the intermediate was no more than 2.0%. Water (3 volumes) was added to the mixture, which was stirred for 30 minutes, whereupon the phases were allowed to separate, and the organic phase was collected, washed first with 1% HCl (3 volumes), then 2% sodium bicarbonate (3 volumes), and finally water (3 volumes). The organic phase was concentrated under vacuum at a temperature below 50° C. until the remaining residue was not more than 4 volumes. MTBE (4 volumes) was added to the reactor, and the mixture was again concentrated under vacuum below 50° C. until the remaining residue was not more than 4 volumes. MTBE (4 volumes) was again added to the reactor and the mixture concentrated under vacuum until the remaining residue was not more than 4 volumes. One volume of MTBE was added to the reactor, and the mixture was stirred for over five hours at a temperature between 5-15° C. The solid formed was centrifuged and collected by filtration. Into a 300 L reactor was charged purified water (86.25 L, 7.5 volumes) and acetonitrile (28.75 L, 2.5 volumes), followed by the solid isolated in the previous step. The mixture was stirred for 2-3 hours at a temperature between 15-25° C., then centrifuged, and the resulting solid collected by filtration. The solid was dried in a vacuum oven for 12 hours at a temperature between 35-45° C. The crude product (9.83 kg, 67.8% yield, 97.7% purity) was isolated as an off-white solid. This product, plus that produced in a separate run (1.55 kg) were purified together by stirring for 16 hours in a mixture of acetonitrile (20 L), and purified water (60 L) in a 200 L drum at 25° C. The solids were centrifuged, collected by filtration, and dried in a vacuum oven at 35-45° C. for 12 hours. The total overall yield of G-2-b was 11.18 kg (67.2% yield, 98.9% purity) as an off-white solid.

Step 6. Synthesis of Benzyl 2-{7-[(R)-2-(o-methoxyphenyl)-2-(tetrahydro-2H-pyran-4-yloxy) ethyl]-2-bromo-3-methyl-4,6-dioxo-1-thia-5,7-diaza-5,7-dihydroinden-5-yl}-2-methylpropionate (G-3-b)

Cesium carbonate (3369 g) was dried in a vacuum oven for 60 hours at 50-60° C. Into a 100 L glass reactor under nitrogen was added the dried cesium carbonate (3340 g) in one portion, along with 9.2 L of NMP. Into a 72 L glass reactor was charged NMP (15 L), (R)-G-1-a (3179 g), and G-2-b (3054 g), and the mixture was stirred until complete dissolution was observed. The solution in the 72 L reactor was transferred to the 100 L reactor, using additional NMP (6.1 L) to rinse the residual contents of the 72 L reactor into the 100 L reactor. The mixture in the 100 L reactor was then heated to 100° C., and stirred at that temperature for at least 60 hours, after which the amount of G-2-b remaining was 10.6% by HPLC. The temperature was decreased to between 45-55° C. and purified water (23 L) was added, and the entire mixture transferred to a 200 L glass reactor. Additional purified water (10 L), and methyl tert-butyl ether (MTBE, 31 L) were added, and the mixture was stirred for 15 minutes. The phases were separated, and the organic phase was washed with purified water (31 L). The aqueous phase was returned to the reactor, and washed with MTBE (31 L), and stirred for 15 minutes. The combined organic layers were washed with brine (two portions of 15 L) and transferred to a 100 L reactor. The organic mixture was concentrated under vacuum at 70° C. to a volume of 15 L. Ethanol (31 L) was added and the mixture was concentrated under vacuum at 70° C. to a volume of 21 L, and the ethanol addition and concentration was repeated one more times. The mixture was heated to between 70-80° C. and stirred until complete dissolution was observed. The temperature was decreased to between 45-55° C. over four hours, and held at that temperature for five hours. The temperature was then decreased to between 15-25° C. over at least three hours, and held at that temperature for three hours. The solids formed were vacuum filtered, and rinsed with ethanol (6.1 L). The resulting solids were dried in a vacuum oven at between 35-45° C. for 28 hours, affording G-3-b (2993 g, 64% yield).

Step 7. Synthesis of G-4-b

Into a 72 L glass reactor under nitrogen with stirring were charged THF (37 L) and oxazole (918 g), and the temperature was decreased to between −80 and −60° C. 2.5 Molar n-butyllithium in hexanes (3.98 kg, stored at room temperature) was added to the reactor, maintaining the temperature of the reaction below −60° C. The mixture was stirred at this temperature for 90 minutes. Zinc (II) chloride (5059 g) was added in eight portions, maintaining the temperature of the mixture below −60° C., and the mixture was stirred at that temperature for one hour before warming to 10-20° C. by removing the cooling bath. The contents of the 72 L reactor were transferred to a 100 L glass reactor under nitrogen, using THF (4145 mL) to rinse the residue from the 72 L reactor into the 100 L reactor. The mixture was stirred, and the temperature was adjusted to between 10-20° C. Intermediate G-4-b (4192 g, 1.0 eq.) was added to the reactor followed by Pd(PPh$_3$)$_4$ (357 g), and the temperature was adjusted to between 55-65° C., and the mixture was stirred at that temperature for 12 hours, whereupon the amount of G-4-b remaining was determined by HPLC to be no more than 0.07%. The temperature was decreased to between 15-25° C., and the mixture was transferred to a 200 L reactor together with methyl tert-butyl ether (MTBE, 41 L) and purified water (21 L). The mixture was stirred for 18 minutes, and the phases were separated. The organic phase was stirred with MTBE (41 L) and saturated ammonium chloride (41 L), the phases separated, and the organic phase washed again with saturated ammonium chloride (21 L), followed by 2N HCl (21 L), and twice with purified water (21 L each). The organic layer was transferred to a 100 L reactor and concentrated under vacuum at 70° C. to a volume of 41 L. The mixture was cooled to between 15-25° C., and transferred to a 75 L reactor and treated with activated charcoal (Darco G 60, 829 g), and stirred for at least 15 hours. The mixture was filtered through diatomaceous earth (Celite, 2520 g) slurried in MTBE (13 L), rinsing the reactor with MTBE (21 L). The filtrate was concentrated under vacuum at 70° C. to a volume of 29 L, then twice diluted with ethanol (41 L), and concentrated to a volume of 29 L. The temperature was increased to 79° C. whereupon complete dissolution was observed. The temperature was then lowered to between 45-55° C. over five hours, and held at that temperature for nine hours. The temperature was lowered to between 15-25° C. over at least 3 hours, and the solid formed was collected by filtration, using two portions of ethanol (4150 mL each) to rinse the contents of the reactor into the filter and wash the filter cake. The collected solids were dried in a vacuum oven at 45° C. for 18 hours, affording crude G-4-b (3463 g). The crude product was charged to a 100 L reactor containing ethanol (28 L), and purified water (7 L), and the mixture was heated to 70° C. with stirring, whereupon complete dissolution was observed. The mixture was cooled to 45° C. over 4.5 hours and held at that temperature for six hours. The mixture was then cooled to 20° C. over five hours, and held at that temperature for three hours, and the solids formed were collected by filtration, washing the contents of the reactor into the filter with ethanol (2770 mL) and purified water (693 mL). The purified solid was dried in a vacuum oven at 45° C. for 20 hours, resulting in purified G-4-b (4116 g, 75% yield).

Step 8. Synthesis of Compound 1 from G-4-b

Into a 20 L autoclave were charged THF (15 L) and G-4-b (1503 g, 1.0 eq.). 10% palladium on carbon (76 g, dry basis) was added, and the autoclave was purged three times, backfilling with 15 p.s.i. nitrogen each time, then purged five times, backfilling with 19 p.s.i. hydrogen gas each time. The mixture was stirred under 19 p.s.i. hydrogen for seven hours, and the autoclave was purged and backfilled with nitrogen. The mixture was filtered through diatomaceous earth (Celite, 1247 g) slurried in THF (6 L), and the autoclave was rinsed into the filter with an additional 3.8 L of THF. A second batch was processed in the same manner using 1538 g of G-4-b, and the filtrates from both batches were combined and transferred to a 100 L glass reactor. Si-Thiol (Silicycle, 757 g) was added to the reactor, and the temperature was adjusted to between 35-45° C. and stirred at that temperature for 15 hours. The temperature was then adjusted to between 15-25° C. and the mixture was filtered through diatomaceous earth (Celite, 1091 g), slurried in 8 L of THF. The reactor was washed into the filter with additional THF (15 L). The combined filtrates were concentrated to dryness under vacuum at a temperature between 35-40° C. MTBE (30 L) was added to dissolve the residue, followed by purified water (30 L), and the mixture was adjusted to pH 13 with 2N aqueous sodium hydroxide (2.8 L), and stirred for 15 minutes. The layers were separated and the aqueous phase was adjusted to pH 1 with 2N HCl (3.5 L). The aqueous mixture was extracted with two portions of dichloromethane (30 L each) and the combined organic extracts were washed with purified water (3.8 L). The organic layer was concentrated under vacuum at between 35-40° C., providing crude Compound 1 (3614 g). The crude product was combined with acetonitrile (18 L) and heated to 75-85° C. with stirring until complete dissolution was observed. Purified water (18 L) was added, and the mixture was again heated to 75-85° C. The temperature was then decreased to 15-25° C. over one hour. The solids formed with collected by filtration and the filter cake washed with acetonitrile (3614 g) and purified water (3614 g). The collected solids were dried in a vacuum oven at 35° C. for 21 hours, affording Compound 1 of intermediate purity (2220 g). This material was suspended in ethanol (15.5 L) and purified water (6.7 L), and heated with stirring to 76° C. until complete dissolution was observed. The temperature was decreased to 50° C. over four hours, and held at that temperature for an additional three hours. The temperature was decreased to 20° C. over three hours, then held at that temperature for an additional six hours. The solids formed were collected by filtration, and the filter cake was washed with ethanol (2664 mL) and purified water (1.8 L). The solids were dried in a vacuum oven at 45° C. for 26 hours, affording 1895 g (71% yield) of pure Compound 1.

Example 36. Synthesis of Compound 1—Route B

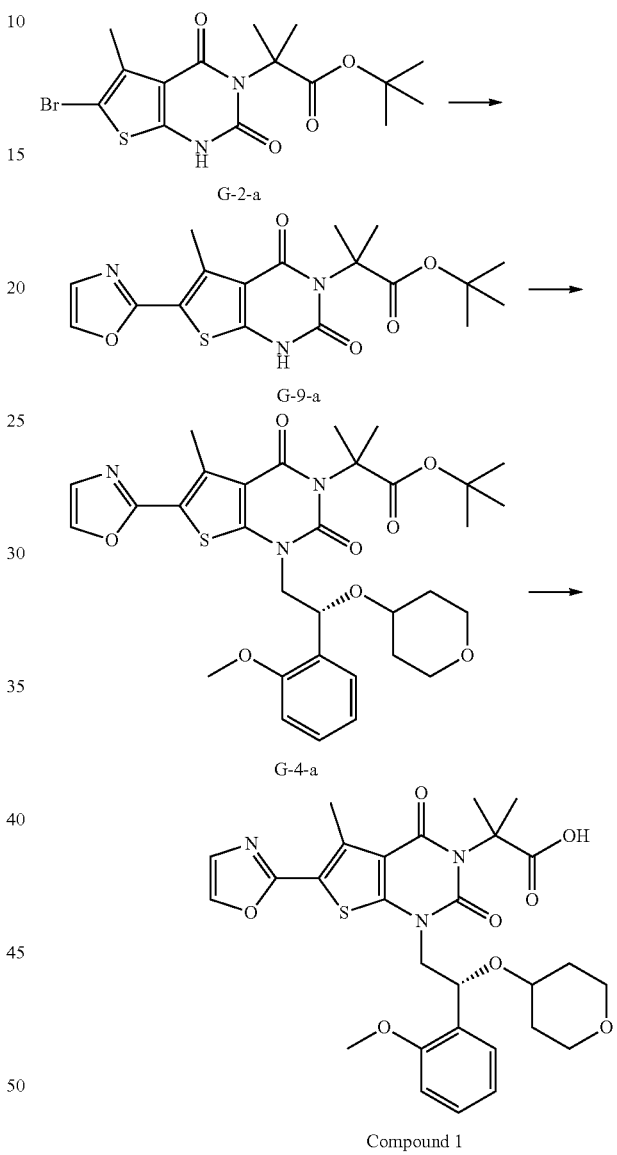

Step 1. Synthesis of tert-Butyl 2-methyl-2-[3-methyl-2-(1,3-oxazol-2-yl)-4,6-dioxo-1-thia-5,7-diaza-5,7-dihydroinden-5-yl]propionate (G-9-a)

Into a glass reactor under nitrogen were charged THF (10 volumes, 0.01% water by Karl Fischer), and oxazole (380.6 g, 4.0 eq., 0.05% water by Karl Fischer). The mixture was cooled to between −70 and −80° C., and n-butyllithium (2.5 M in hexanes, 2.65 L, 4.8 eq.) was added such that the temperature was maintained between −70 and −80° C., and the mixture was stirred for an additional hour at that temperature. Zinc (II) chloride (1500 g, 8.0 eq.) was added in batches, such that the temperature was maintained between −70 and −80° C. The mixture was then warmed to between 15-25° C., and the mixture was stirred for an additional two hours at that temperature. Pd(PPh$_3$)$_4$ (79.5 g, 0.05 eq.) and G-2-a (556.5 g, 1.0 eq.) were added, and the mixture was heated to 60° C. and stirred for 27 hours at that temperature. Once it was determined that less than 5.0% of G-2-a remained by HPLC, the reaction was cooled to between 30-40° C. and filtered. The filter cake was washed with THF (two volumes), and the combined filtrates were combined and concentrated under vacuum. Saturated aqueous ammonium chloride (10 volumes), and methanol (10 volumes) were added to the residue, and this mixture was stirred for one hour, then filtered. The filter cake was slurried with methanol (5 volumes), and purified water (1 volume), and stirred for 2 hours. The solids were collected by filtration, and dried in a vacuum oven at 35-45° C. to constant weight. The dried solids were slurried in 1N HCl (15-20 volumes) for 24 hours, and the solids were again collected by filtration and the filter cake washed with purified water until the pH of the filtrate reached pH 7. The collected solids were dried in a vacuum oven at 35-45° C. to constant weight. The dried solids were slurried in acetonitrile (8 volumes) at 80° C. for 30 minutes, then the mixture was cooled to between 20-30° C. and stirred for 3 hours. The resulting solids were collected by filtration and washed with acetonitrile (2 volumes), then dried in a vacuum oven at 35-45° C. to constant weight affording pure G-9-a.

Alternative Synthesis 2 of G-9-a

To a reactor was combined THF (482 mL, 6.9 v/w G-2-a) and oxazole (36.08 g, 0.51 w/w G-2-a, 3 equiv.). The contents were cooled to about −20° C. and 2M isopropylmagnesium chloride in THF (304.8 g, 4.4 w/w G-2-a, 3.6 equiv.) was charged dropwise maintaining the reaction contents at not more than about −10° C. Once the addition was complete the reactor was cooled once more to about −15° C. and THF (35.1 g, 0.5 w/w G-2-a) was used to rinse the Grignard solution forward. The solution was cooled to about −20° C. and zinc chloride (141.8 g, 2 w/w G-2-a, 6 equiv.) was charged portionwise while maintaining the reaction contents at not more than about −10° C. Once the addition was complete the reaction contents were warmed to about 22° C. over about one hour. To the reaction was charged G-2-a (70.0 g) and THF (35.4 g, 0.5 w/w G-2-a) was used to rinse the material into the reactor. The contents of the reactor were adjusted to about 60° C. and a slurry of palladium tetrakistriphenyphosphine (10.05 g, 0.14 w/w G-2-a, 0.05 equiv.) in THF (142 mL, 2 v/w G-2-a) was charged. The slurry was rinsed forward with THF (39.4 mL, 0.5 v/w G-2-a) and the contents increased to about 65° C. for about 6 hours. The contents of the reactor were adjusted to about 20° C. and a solution of acetic acid (38.8 g, 0.55 w/w G-2-a, 3.7 equiv.) in 2-methyltetrahydrofuran (662 mL, 9.5 v/w G-2-a) was charged over not less than about three hours. The reaction contents were then concentrated under vacuum to about 14V before being filtered. The reactor was charged with water (525 mL, 7.5 v/w G-2-a) which was then transferred to the filter and used to slurry the filter cake. The slurry was filtered and the resulting cake was washed successively with water to remove salts. The solids were then removed from the filter and combined with acetonitrile (1046 mL, 15 v/w G-2-a) in a reactor. The reactor contents were heated to reflux for about 2 hours then cooled to about 0° C. over about four hours and held at about 0° C. The slurry was filtered. The filter cake was washed with two portions of acetonitrile (2×143 mL, 2 v/w G-2-a) and then dried to afford G-9-a. $^1$H NMR (400 MHz, CDCl$_3$): δ 12.31 (s, 1H), 8.20 (s, 1H), 7.36 (s, 1H), 2.73 (s, 3H), 1.64 (s, 6H), 1.37 (s, 9H).

In some embodiments, the process above can be carried out wherein the palladium catalyst can be added as a dry solid directly to the reaction mixture.

Alternative Synthesis 3 of G-9-a

To a reactor was combined THF (395 mL, 7.9 v/w G-2-a) and oxazole (25.6 g, 0.51 w/w G-2-a, 3 equiv.). The contents were cooled to about −20° C. and 2M isopropylmagnesium chloride in THF (191.4 g, 3.9 w/w G-2-a, 3.2 equiv.) was charged dropwise maintaining the reaction contents at not more than about −10° C. Once the addition was complete the reactor was cooled once more to about −15° C. and a pre-made solution of zinc chloride (102.0 g, 2 w/w G-2-a, 6 equiv.) in 2-methyltetrahydrofuran (349 mL, 7 v/w) was charged maintaining the reaction contents at not more than about −10° C. Once the addition was complete, THF (22.07 g, 0.45 w/w G-2-a) was charged and the reaction contents were warmed to about 22° C. over about one hour. To the reaction was charged G-2-a (50.05 g) and THF (22.1 g, 0.45 w/w G-2-a) was used to rinse the material into the reactor. The contents of the reactor were adjusted to about 45° C. and palladium tetrakistriphenyphosphine (10.05 g, 0.14 w/w G-2-a, 0.05 equiv.) was charged. The reactor contents were heated to about 65° C. for about 6 hours. The contents of the reactor were adjusted to about 20° C. and the reaction mixture was filtered, rinsing forward twice with THF (2×113 mL, 2.26 v/w G-2-a). To the filtrate in a reactor was charged acetic acid (27.6 g, 0.55 w/w G-2-a, 3.7 equiv) over not less than about three hours. The contents were aged about 8 hours at 22° C. before concentrating to about 6 volumes. The reactor was charged with methanol (249 mL, 5 v/w G-2-a) over not less than about three hours. The reactor contents were then aged for about 12 hours at 20° C. before cooling to about −15° C. over about six hours and held at about −15° C. The slurry was filtered. The filter cake was washed with two portions of methanol (2×101 mL, 2 v/w G-2-a), one portion of acetonitrile (100 mL, 2 v/w G-2-a), and then dried to afford G-9-a. $^1$H NMR (400 MHz, CDCl$_3$): δ 12.31 (s, 1H), 8.20 (s, 1H), 7.36 (s, 1H), 2.73 (s, 3H), 1.64 (s, 6H), 1.37 (s, 9H).

Alternative Synthesis 4 of G-9-a

To a reactor was charged THF (80.5 mL, 8 v/w G-2-a), oxazole (5.18 g, 0.51 w/w G-2-a, 3 equiv.) and lithium chloride (3.80 g, 0.38 w/w G-2-a, 3.6 equiv). The contents were cooled to about −20° C. and 2M isopropylmagnesium chloride in THF (43.1 g, 4.31 w/w G-2-a, 3.6 equiv.) was charged dropwise maintaining the reaction contents at not more than about −10° C. Once the addition was complete, the reactor was cooled once more to about −20° C. and 1.9 mol/L zinc chloride (78 mL, 7.8 w/w G-2-a, 6 equiv.) was charged maintaining the reaction contents at not more than about −10° C. Once the addition was complete, the reaction contents were warmed to about 22° C. over about 30 minutes and aged for about 45 minutes. To the reaction was charged G-2-a (9.94 g) and the contents of the reactor were adjusted to about 45° C. Tetrakis(triphenylphosphine)palladium(0) (1.39 g, 0.14 w/w G-2-a, 0.05 equiv.) and THF (9.67 mL, 1 v/w G-2-a) were then charged. The contents were adjusted to about 65° C. for about 12 hours. The contents of the reactor were adjusted to about 20° C. and a solution of acetic acid (5.52 g, 0.55 w/w G-2-a, 3.7 equiv.) in 2-methyltetrahydrofuran (17.5 mL, 1.7 v/w G-2-a) was charged over not less than about three hours and aged. The reaction contents were then concentrated under vacuum to about 14V. The slurry was warmed to about 45° C. for about 1 hour, cooled to about 20° C. over about 2 hours, aged at about 20° C. and cooled to about 0° C. over about 4 hours and aged. The slurry was filtered at about 0° C. and the filter cake returned to the reactor. Water (149.92 mL, 15 v/w G-2-a) was then charged and the slurry was agitated for about 1 hour at about 20° C. before filtration. The filter cake was washed twice with water before drying at about 40° C. under vacuum. The dry solids were charged to a reactor with acetonitrile (149 mL, 15 v/w G-2-a) and heated to reflux (about 77 to 80° C.) for about 2 hours, then cooled to 0° C. over about 4 hours and aged about 1 hour before filtration. The filter cake was washed twice with acetonitrile before drying at about 40° C. under vacuum to yield G-9-a. $^1$H NMR (400 MHz, DMSO-$d_6$): δ 12.31 (s, 1H), 8.20 (s, 1H), 7.36 (s, 1H), 2.73 (s, 3H), 1.64 (s, 6H), 1.37 (s, 9H).

Alternative Synthesis 5 of G-9-a

Oxazole (1.76 g, 0.51 w/w G-2-a, 2 equiv.) and THF (12.5 mL, 2.5 v/w G-2-a) were charged to a reactor and the contents cooled to about 0° C. TMPZnCl·LiCl (33 mL, 6.6 v/w G-2-a, 2.4 equiv.) was charged such that the internal temperature was about <5° C. In a separate reactor, G-2-a (5.03 g) and THF (40.0 mL, 8 v/w G-2-a) were charged to a reactor and cooled to about 0° C. TMPZnCl·LiCl (16 mL, 3.2 v/w G-2-a, 1.2 equiv.) was charged such that the internal temperature was about <5° C. The solutions were aged at about 0° C. for about 1 hour before warming to about 20° C. and aging at that temperature. The solution of G-2-a was transferred to the oxazole solution. $ZnCl_2$ (6.80 g, 1.36 w/w G-2-a, 4 equiv.) was charged to the reaction mixture and the contents adjusted to reflux (about 65 to 70° C.). t-BuXPhos Pd G3 precatalyst (0.40 g, 0.08 w/w G-2-a, 0.04 equiv.) was then added as a slurry in THF (10.0 mL, 2 mL/g). The reaction mixture was stirred at reflux for about 60 minutes. The reaction mixture was cooled to about 20° C. and distilled to about 10V pot volume under vacuum. The concentrated reaction mixture was slowly quenched into an aqueous HCl solution (125 mL, 1N HCl, 25 v/w G-2-a) and agitated for about 17 hours. The slurry was filtered and the cake neutralized by washing three times with water (about 50 mL each wash, 5 v/w G-2-a). The filter cake was dried at about 40° C. under vacuum. The dry solids were charged to a reactor with acetonitrile (75.0 mL, 15 v/w G-2-a) and heated to reflux (about 77 to 80° C.) for about 90 minutes, then cooled to about 20° C. over about 4 hours and aged about 17 hours before filtration. The filter cake was washed twice with acetonitrile (about 10 mL each wash, 2 v/w G-2-a) before drying at about 40° C. under vacuum to yield G-9-a. $^1$H NMR (400 MHz, DMSO-$d_6$): δ 12.31 (s, 1H), 8.20 (s, 1H), 7.36 (s, 1H), 2.73 (s, 3H), 1.64 (s, 6H), 1.37 (s, 9H).

Alternative Synthesis 6 of G-9-a

Oxazole (3.38 g, 0.51 w/w G-2-a, 3 equiv.) was charged to a reactor containing THF (40.0 mL, 6 v/w G-2-a) and the contents were cooled to about −15° C. A freshly prepared solution of TMPMgCl·LiCl (68 mL, 10.5 w/w G-2-a, 0.85 mol/L, 3.6 equiv.) was charged such that the internal temperature was less than about −10° C. The temperature was adjusted to about −20° C., and a freshly prepared solution of $ZnCl_2$ in 2-methyltetrahydrofuran (51 mL, 7.8 v/w G-2-a, 1.9 mol/L, 6.0 equiv.) was charged such that the internal temperature was less than about −10° C. The reaction mixture was warmed to about 20° C. over about 30 minutes and aged. G-2-a (6.47 g) was charged and the reaction mixture warmed to about 45° C. Tetrakis(triphenylphosphine)-palladium (0) (0.92 g, 0.14 w/w G-2-a, 0.05 equiv) was then charged and rinsed forward with THF (6.3 mL, 1 v/w G-2-a). The temperature was adjusted to about 65° C. and stirred for about 20 hours. The temperature was then adjusted to about 20° C. and a freshly prepared solution of acetic acid (3.56 g, 0.55 w/w G-2-a, 3.7 equiv.) in 2-methyltetrahydrofuran (11.0 mL, 1.7 v/w G-2-a) was added over about 3 hours. The slurry was aged an additional about 4 hours before distilling to about 14V pot volume under vacuum. The slurry was warmed to about 45° C. for about 1 hour, cooled to about 20° C. over about 2 hours, aged at about 20° C. for about 6 hours and cooled to about 0° C. over about 4 hours and aged for about 8 hours. The slurry was filtered at about 0° C. and the filter cake returned to the reactor. Water (97.52 g, 15 v/w G-2-a) was then charged and the slurry was agitated for about 4 hours at about 20° C. before filtration. The filter cake was washed twice with water (about 13 mL each wash, 2 v/w G-2-a) before drying to yield G-9-a. $^1$H NMR (400 MHz, DMSO-$d_6$): δ 12.31 (s, 1H), 8.20 (s, 1H), 7.36 (s, 1H), 2.73 (s, 3H), 1.64 (s, 6H), 1.37 (s, 9H).

Step 2. Synthesis of tert-Butyl 2-{7-[(R)-2-(o-methoxyphenyl)-2-(tetrahydro-2H-pyran-4-yloxy) ethyl]-3-methyl-2-(1,3-oxazol-2-yl)-4,6-dioxo-1-thia-5,7-diaza-5,7-dihydroinden-5-yl}-2-methylpropionate (G-4-a)

Into a glass reactor under nitrogen were charged G-9-a (150.0 g, 1.0 eq.) and NMP (3 volumes), followed by G-1-a (1.10 eq.) and potassium carbonate (1.05 eq.). The mixture was heated to 130° C. and stirred at that temperature for 16 hours. Once it was determined that less than 4.6% of G-9-a remained by HPLC, the reaction was cooled to between 25-35° C., and purified water was added (20 volumes) and stirred for 2 hours. The solids formed were collected by filtration, and the filter cake was washed with purified water (5 volumes), then dried under vacuum at room temperature. The crude product was slurried in methanol (8 volumes) and the mixture was heated to reflux, then cooled to between 15-25° C. The solids formed were collected by filtration, affording purified G-4-a (170.7 g, 71.2% yield) as an off-white solid. Alternative Synthesis of G-4-a The stock solution of (R)-G-6-a stock solution (as prepared according to Alternative Synthesis of (R)-G-1-a discussed above) (89.34 g solution, 21.67% (R)-G-1-a wt %, 1.2 equiv.) was charged to a reactor containing G-9-a (20.00 g, 1.0 equiv.), followed by a NMP rinse forward (3.0 g, 0.15 v/w G-9-a) and addition of potassium carbonate (7.4 g, 0.37 w/w G-9-a, 1.05 equiv.). The contents were heated to about 115° C. and stirred for a minimum of about 22 hours until the reaction was deemed complete. The contents were cooled to about 30° C., and then slowly added into drinking water (200.0 g, 10 v/w G-9-a). Dichloromethane (211.6 g, 8 v/w G-9-a) was then added, and the solution was agitated for about 30 minutes at about 22° C. Agitation was stopped and the solution was allowed to settle. The bottom organic layer was collected and the top aqueous layer was extracted with dichloromethane (211.6 g, 8 v/w G-9-a) at about 22° C. for about 30 minutes. Agitation was again stopped and the solution was allowed to settle. The top aqueous layer was removed and the bottom organic layer was combined with another organic layer. The combined organic layers were distilled under vacuum to between about 3V and about 4V pot volume. Methanol (130.0 g, 8 v/w G-9-a) was added and the solution was distilled down to between about 3V and about 4V pot volume. Methanol (79.6 g, 5 v/w G-9-a) was added and the slurry was heated to reflux (about 63 to 69° C.) for about 2 hours. The slurry was then cooled to about 0° C. and filtered. The filter cake was washed with methanol (31.60 g, 2 v/w G-9-a) at about 0° C. and dried to afford G-4-a. $^1$H NMR (400 MHz, CDCl$_3$): δ 7.70 (d, J=0.4 Hz, 1H), 7.58 (dd, J=1.6 Hz, J=7.6 Hz, 1H), 7.29 (td, J=1.6 Hz, J=8.0 Hz, 1H), 7.21 (d, J=0.8 Hz, 1H), 7.03 (t, J=7.2 Hz, 1H), 6.86 (d, J=8.0 Hz, 1H), 5.39 (dd, J=4.4 Hz, J=8.8 Hz, 1H), 4.18-4.15 (m, 1H), 3.99 (br, 1H), 3.86 (s, 3H), 3.78-3.73 (m, 1H), 3.70-3.65 (m, 1H), 3.46-3.40 (m, 1H), 3.36-3.30 (m, 2H), 2.86 (s, 3H), 1.80 (s, 3H), 1.76 (s, 3H), 1.76-1.71 (m, 2H), 1.59-1.51 (m, 1H), 1.46 (s, 9H) 1.46-1.37 (m, 1H).

Step 3. Synthesis of Compound 1

Into a glass reactor under nitrogen were charged 9 M aq. H$_2$SO$_4$ (5 volumes) and isopropyl alcohol (5 volumes), and the mixture was cooled to between 5-10° C. G-4-a (150.0 g, 1.0 eq.) was added such that the temperature of the mixture was maintained between 5-10° C., and the reaction was stirred at that temperature for 20 hours. Once it was determined that no more than 0.3% of starting G-4-a remained by HPLC, the mixture was poured into purified water (20 volumes) dropwise and stirred for one hour. The solids formed were collected by filtration, and the filter cake was washed with purified water (5 volumes). The cake was resuspended in purified water (10 volumes) and the pH was adjusted to 8-9 with aqueous sodium hydroxide (20% w/w). The aqueous solution was extracted with ethyl acetate (three portions of 5 volumes), and the aqueous layer was acidified to pH 4-5 with 4 M HCl. The aqueous solution was extracted with ethyl acetate (three portions of 10 volumes), and the combined organic extracts were filtered, and concentrated under vacuum to dryness. The residue was dissolved in ethanol/water (7:3, 10 volumes) at between 70-80° C., and the resulting solution was cooled to 50° C. over 4 hours and held at that temperature overnight. The solution was then cooled to 20° C. over 3 hours, and held at that temperature for at least three hours. The resulting solids were collected by filtration, and the filter cake was washed with ethanol/water (7:3, 2 volumes), then dried under vacuum to constant weight, affording purified Compound 1 (110.0 g, 80.5% yield, >99% purity by HPLC, NMR).

Alternative Synthesis of Compound 1

A sulfuric acid solution was prepared by addition of concentrated sulfuric acid (47 g, 4.7 w/w G-4-a) to water (12 g, 1.2 v/w G-4-a) followed by a water (15 g, 1.5 v/w G-4-a) rinse forward. 2-Propanol (37 g, 4.7 v/w G-4-a) was slowly charged to a reactor containing sulfuric acid solution at about 9° C. while maintaining the reaction contents at no more than about 40° C., and the solution was cooled to about 5° C. G-4-a (10 g, 1.0 eq.) was charged to the solution, followed by a 2-propanol rinse forward (2 g, 0.25 v/w G-4-a). The contents were cooled to about 7° C. and stirred for a minimum of about 21 hours. The contents were slowly added into water, and the slurry was agitated for about 30 minutes. The slurry was filtered, and the filter cake was washed and dried under vacuum for about 4 hours. The crude wet cake was charged back to the reactor, followed by additions of ethyl acetate (40 g, 4.4 v/w G-4-a) and water (100 g, 10 v/w G-4-a). The slurry was adjusted to pH at about 8-9 with an about 20 wt % sodium hydroxide solution at about 22° C., and then agitated for about 30 minutes at about 22° C. The solution was allowed to settle. The top organic layer was collected and the bottom aqueous layer was washed with ethyl acetate (40 g, 4.4 v/w G-4-a) at about 22° C. for about 30 minutes. The solution was allowed to settle, and the top organic layer was removed. 2-Methyltetrahydrofuran (86 g, 10 v/w G-4-a) was then added, was adjusted to pH at about 4-5 with an about 4 N HCl solution at about 22° C. The solution was agitated for about 30 minutes at about 22° C. and then allowed to settle. The bottom aqueous layer was extracted with 2-methyltetrahydrofuran (52 g, 6 v/w G-4-a) at about 22° C. for about 30 minutes. After the solution was allowed to settle, the bottom aqueous layer was removed. The organic layers were combined and distilled under vacuum (jacket at about <45° C.) to about 4V pot volume. Ethanol (55.4 g, 7 v/w G-4-a) was added and the reaction as distilled (repeated twice). Ethanol was again added (23.7 g, 3 v/w G-4-a), followed by water (30 g, 3 v/w G-4-a). The reaction was heated to about 75° C. and then cooled over about 4 hours to about 50° C., then to about 0° C. over about 5 hours. The reaction is then aged and filtered, and the cake is washed with a precooled mixture of ethanol (9.5 g, 1.2 v/w G-4-a) and water (6 g, 0.6 v/w G-4-a). The resulting filter cake was washed with dried to afford Compound 1. $^1$H NMR (400 MHz, CDCl$_3$): δ 7.70 (s, 1H), 7.57 (dd, J=1.6 Hz, J=7.6 Hz, 1H), 7.29 (td, J=1.6 Hz, J=8.0 Hz, 1H), 7.23 (d, J=0.4 Hz, 1H), 7.02 (t, J=7.6 Hz, 1H), 6.86 (d, J=8.4 Hz, 1H), 5.39 (dd, J=5.6 Hz, J=8.0 Hz, 1H), 4.17-4.14 (m, 1H), 4.04 (br, 1H), 3.86 (s, 3H), 3.78-3.67 (m, 2H), 3.46-3.40 (m, 1H), 3.37-3.32 (m, 2H), 2.85 (s, 3H), 1.87 (s, 3H), 1.83 (s, 3H), 1.75-1.72 (m, 2H), 1.59-1.51 (m, 1H), 1.48-1.39 (m, 1H).

Example 37. Enzymatic Resolution Screen

A variety of lipase enzymes were assayed for their effectiveness in the kinetic resolution of racemic alcohols of formula rac-G-5, according to the following procedure. Test substrate rac-G-5-a was dissolved in either toluene or MTBE together with 1 equivalent of acyl donor (vinyl acetate). 5-10 milligrams of the lipase to be tested was added, and the mixture was stirred for 3-10 hours while being sampled periodically for analysis by chiral HPLC. Table 10 below reports the results of the enzymatic resolution screen. ND means "not determined".

TABLE 10

| | Results of enzymatic resolution screen | | | | | |
|---|---|---|---|---|---|---|
| | % Substrate remaining | % Product formed | Selectivity (% AUC, 220 nm) | | | |
| Enzyme | (28 h) | (acetate; 28 h) | R-acetate | S-acetate | R-alcohol | S-alcohol |
| Lipase OF | 59.9 | 40.1 | 16.55 | 21.43 | 26.27 | 32.75 |
| Acylase (Amano) | >95% | <5% | ND | ND | ND | ND |

TABLE 10-continued

Results of enzymatic resolution screen

| Enzyme | % Substrate remaining (28 h) | % Product formed (acetate; 28 h) | Selectivity (% AUC, 220 nm) | | | |
|---|---|---|---|---|---|---|
| | | | R-acetate | S-acetate | R-alcohol | S-alcohol |
| Lipase PS30 | >95% | <5% | ND | ND | ND | ND |
| CAL-B | 21.4 | 78.6 | 48.87 | 30.25 | 0 | 20.26 |
| Lipase PPL | >95% | <5% | ND | ND | ND | ND |
| CAL-A | 40.4 | 59.6 | 37.92 | 13.96 | 4.13 | 28.85 |
| Lipase Mucor Meihei | 58.9 | 41.1 | 9.74 | 30.51 | 40.92 | 18.18 |

Example 38. Enzymatic Resolution Substrate Screen

The enzymatic resolution and hydrolysis of Example 37 was also performed on a wide range of alcohol substrates of formula rac-G-5 to demonstrate the scope of the transformation. Table 11 below reports the results of the substrate screen.

TABLE 11

Results of substrate screen

| Alcohol structures following acyl group hydrolysis | % e.e. of alcohol |
|---|---|
| 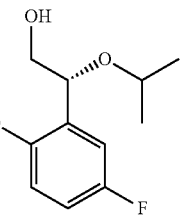 | 95-100 |
| 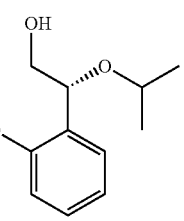 | 95-100 |
| 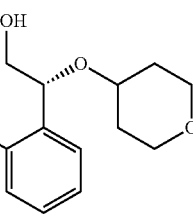 | 95-100 |
| 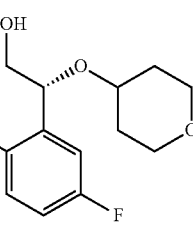 | 95-100 |

TABLE 11-continued

Results of substrate screen

| Alcohol structures following acyl group hydrolysis | % e.e. of alcohol |
|---|---|
| | 95-100 |
| | 95-100 |
| | 95-100 |
| | 95-100 |
| | 95-100 |

TABLE 11-continued
Results of substrate screen
| Alcohol structures following acyl group hydrolysis | % e.e. of alcohol |
|---|---|
| 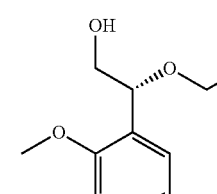 | 95-100 |
| 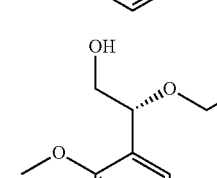 | 95-100 |
| 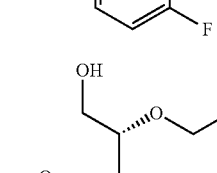 | 95-100 |
| 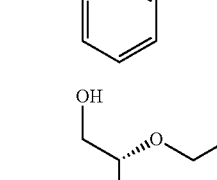 | 95-100 |
| 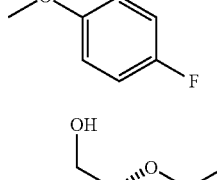 | 95-100 |
| 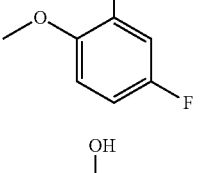 | 95-100 |
| 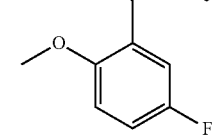 | 95-100 |
| 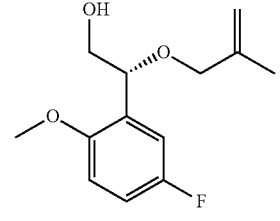 [SMILES: C=C(C)CO[C@@H](CO)c1cc(F)ccc1OC] | 95-100 |
| 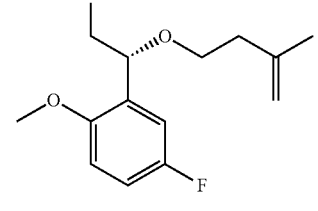 | 95-100 |
| 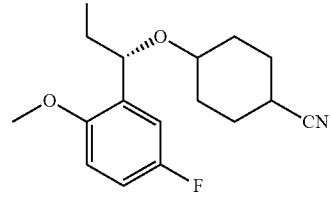 | 95-100 |
| 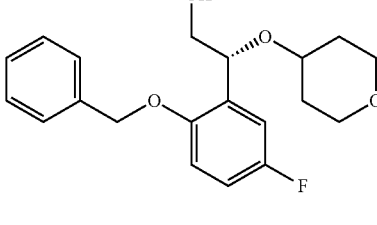 | 95-100 |
| 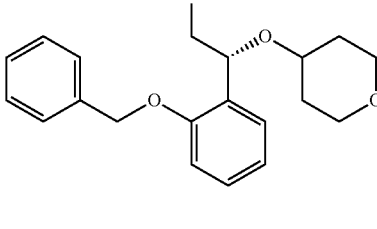 | 95-100 |
| 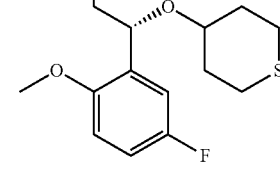 | 95-100 |

TABLE 11-continued
Results of substrate screen
| Alcohol structures following acyl group hydrolysis | % e.e. of alcohol |
|---|---|
| 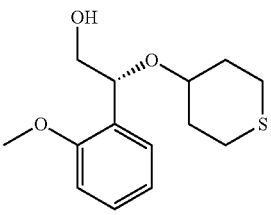 [SMILES: COc1ccccc1[C@H](CO)OC1CCSCC1] | 95-100 |
| 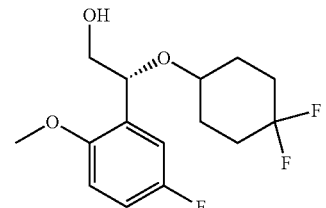 | 95-100 |
| 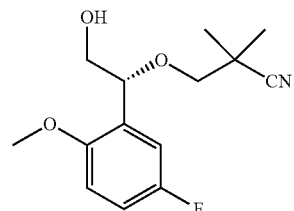 | 95-100 |
| 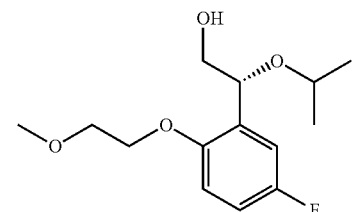 | 95-100 |
| 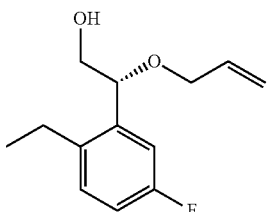 | 95-100 |
| 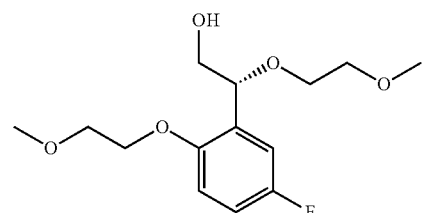 | 95-100 |
| 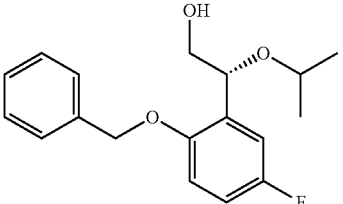 | 95-100 |
| 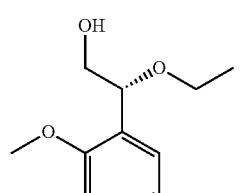 | 95-100 |
| 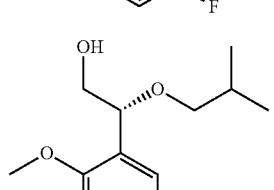 | 95-100 |
| 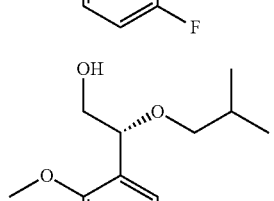 | 95-100 |
| 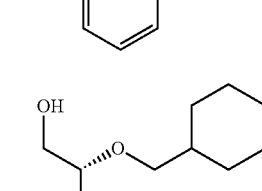 | 95-100 |
| 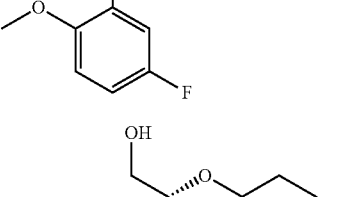 | 95-100 |
| 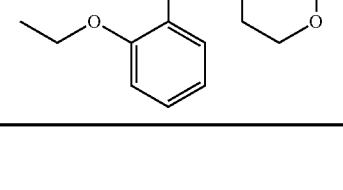 | 95-100 |
| 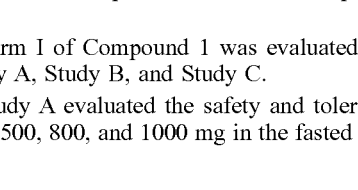 | 95-100 |
|  | 95-100 |
Example 39. Studies of Compound 1
Form I of Compound 1 was evaluated in three studies: Study A, Study B, and Study C.
Study A evaluated the safety and tolerability of 30, 80, 200, 500, 800, and 1000 mg in the fasted state and 200 mg following a high fat meal (fed state) to cohorts of 8 healthy subjects (6 active and 2 placebo control per group).

Study B (five (5) cohorts of 8 subjects (6 active and 2 placebo)) evaluated 50 mg twice daily (BID) (100 mg daily), 100 mg once daily (QD) (100 mg daily), 100 mg BID (200 mg daily), 200 mg QD (200 mg daily), or 150 mg QD (150 mg daily), or matching placebo. Subjects received multiple oral doses of Compound 1 or placebo for 9 consecutive days, with a single oral dose of Compound 1 or placebo on the morning of Day 10. Doses were administered approximately 30 minutes after meals.

Study C evaluated the effects on fractional de novo lipogenesis (DNL) of a single oral dose of 20, 50, or 200 mg Compound 1 compared to placebo (3 cohorts of 10 subjects). DNL was assessed by measuring appearance of de novo synthesis of palmitate in very-low density lipoproteins (VLDL) in response to oral fructose (30 minute intervals over 10 hours) using [$^{13}C$]acetate and mass isotopomer distribution analysis (MIDA). The two dosing periods were separated by a minimum of 5 days for washout of the [$^{13}C$]acetate and study medication.

Study A

Table 12 summarizes PK parameters (mean) under fasted conditions of Study A. The reported factors may vary up to about 2%.

The comparisons of plasma Compound 1 $AUC_t$ and $AUC_\infty$ following 200 mg Compound 1 under fed versus fasted conditions resulted in 90% confidence intervals with lower bounds outside the 80% to 125% reference interval, the geometric mean ratios (GMRs) demonstrated that overall plasma Compound 1 exposure was only approximately 9% to 14% lower under fed compared to fasted conditions, which may not be a clinically relevant difference. The comparison of plasma Compound 1 $C_{max}$ following 200 mg Compound 1 under fed versus fasted conditions indicated maximum plasma Compound 1 exposure was approximately 68% lower under fed compared to fasted conditions. The plasma Compound 1 concentration versus time profiles demonstrated a delay in the first quantifiable concentration and a prolonged absorption/distribution phase observed under fed compared to fasted conditions. However, the mean $t_{1/2}$, CL/F, and Vz/F values and median $t_{max}$ values were comparable following 200 mg Compound administered under fed and fasted conditions.

TABLE 12

Mean (SD) Pharmacokinetic Parameters after a Single Dose of Oral Compound 1 to Healthy Volunteers

| PK Parameters | 30 mg (n = 6) | 80 mg (n = 6) | 200 mg (n = 6) | 500 mg (n = 6) | 800 mg (n = 6) | 1000 mg (n = 6) |
|---|---|---|---|---|---|---|
| $t_{1/2}$ | 4.5 ± 1.6 | 7 ± 2.8 | 12 ± 1.4 | 10.2 ± 2.1 | 8.2 ± 3.3 | 9.5 ± 2.6 |
| $t_{max}$ (hr)[a] | 1.3 (0.23, 2.0) | 1.8 (1.5, 2.0) | 1.9 (1.0, 4.0) | 1.9 (1.0, 3.0) | 2.1 (1.0, 3.0) | 2.4 (1.0, 4.0) |
| $C_{max}$ (ng/mL) | 80 ± 66 | 101 ± 48 | 416 ± 22 | 1112 ± 1149 | 2571 ± 1875 | 8375 ± 3207 |
| $AUC_{0-12}$ (h * ng/ml) | $NC^b$ | 395 ± 198 | 1005 ± 545 | 1244 ± 547 | $NC^b$ | $NC^b$ |
| $AUC_{0-t}$ (h * ng/ml) | 176 ± 104 | 363 ± 215 | 1209 ± 536 | 2931 ± 2438 | 6424 ± 3184 | 17419 ± 8403 |
| $AUC_{\infty*}$ (h * ng/ml) | 179 ± 115 | 402 ± 225 | 1254 ± 616 | 2963 ± 2458 | 6464 ± 3186 | 17509 ± 8413 |
| % Metabolite/ Parent Ratio | 8.0% | 6.6% | 8.4% | 5.9% | 9.7% | 5.6% |

[a]Mean (Min, Max)
[b]NC - Not calculated

Study B

Table 13 summarizes PK parameters of Study B after 10 days. The reported factors may vary up to about 2%.

Maximal exposure ($C_{max}$) of Compound 1 generally increased from Day 1 to Day 10 and overall exposure ($AUC_t$) increased approximately 1.5-3.0 fold on Day 10 compared to Day 1. Mean $t_{1/2}$ was within a 2-fold range independent of dose or regimen on each study day, and exhibited a trend for longer mean half-life on Day 10 versus Day 1 except at the highest dose (200 mg QD).

TABLE 13

Pharmacokinetic Parameters after Multiple Dose of Compound 1

| | 50 mg BID (n = 6) | | 100 mg QD (n = 6) | | 100 mg BID (n = 6) | | 150 mg QD (n = 6) | | 200 mg QD (n = 6) | |
|---|---|---|---|---|---|---|---|---|---|---|
| PK Parameter | Day 1 | Day 10 | Day 1 | Day 10 | Day 1 | Day 10 | Day 1 | Day 10 | Day 1 | Day 10 |
| $t_{1/2}$ | 3.5 ± 1.6 | 10.3 ± 6.7 | 4.3 ± 0.7 | 7.9 ± 4.5 | $5.6^a$ | 6.8 ± 1.6 | 3.9 ± 1.1 | 6.6 ± 2.8 | 5.9 ± 3.6 | 5.9 ± 1 |
| $t_{max}$ (hr)[bc] | 2.4 (1.5, 3) | 4.5 (2, 8) | 3.3, (1, 6) | 4.5 (2, 12) | 5.2 (3, 8) | 5.2 (2, 6) | 3.3 (1, 3) | 6.5 (1, 12) | 4.7 (2, 6) | 3.7 (1.5, 6) |
| $C_{max}$ (ng/ml)[d] | 41 ± 14 | 49 ± 15 | 65 ± 32 | 54 ± 22 | 61.6 ± 15 | 121 ± 56 | 94 ± 40 | 111 ± 52 | 152 ± 68 | 198 ± 87 |
| $AUC_{0-12}$ (h * ng/mL) | 143 ± 29 | $ND^e$ | 234 ± 86 | 285 ± 115 | 345 ± 78 | $ND^e$ | 489 ± 218 | 637 ± 246 | 707 ± 191 | 1224 ± 362 |

TABLE 13-continued

Pharmacokinetic Parameters after Multiple Dose of Compound 1

| PK Parameter | 50 mg BID (n = 6) | | 100 mg QD (n = 6) | | 100 mg BID (n = 6) | | 150 mg QD (n = 6) | | 200 mg QD (n = 6) | |
|---|---|---|---|---|---|---|---|---|---|---|
| | Day 1 | Day 10 | Day 1 | Day 10 | Day 1 | Day 10 | Day 1 | Day 10 | Day 1 | Day 10 |
| $AUC_{0-t}$ (h * ng/ml) | 143 ± 29 | 403 ± 104 | 268 ± 96 | 400 ± 181 | 345 ± 77 | 1122 ± 362 | 572 ± 247 | 933 ± 424 | 868 ± 220 | 2051 ± 819 |
| $AUC_{\infty*}$ (h * ng/mL) | 178 ± 41 | $ND^e$ | 278 ± 110 | $ND^e$ | $671^a$ | $ND^e$ | 587 ± 254 | $ND^e$ | 979 ± 286 | $ND^e$ |
| % Metabolite/ Parent Ratio | 6.4% | 7.2% | 4.2% | 7.3% | 6.3% | 5.0% | 8.3% | 6.2% | 6.4% | 5.2% |

[a] Value available for one subject, therefore no STD calculated
[b] Tmax D10-steady state
[c] Mean (Min, Max)
[d] Cmax D10 - steady state
[e] ND - Not done Study C In Study C, mean Compound 1 plasma PK parameters are summarized as follows: at a dose of 20 mg, $t_{max}$ $(hr)^a$=1.8 (1,3), $C_{max}$ (ng/mL)=15.5±11.5, $AUC_t$ (hr*mg/mL)=40.0±16.0, % Metabolite/Parent Ratio=4.3%; at a dose of 50 mg, $t_{max}$ $(hr)^a$=1.30 (0.99, 2), $C_{max}$ (ng/mL)= 36.5±17.0, $AUC_t$ (hr*mg/mL)=98.8±41.3, % Metabolite/Parent Ratio=11%; at a dose of 200 mg, $t_{max}$ $(hr)^a$=2.0 (1.3), $C_{max}$ (ng/mL)=222±196, $AUC_t$ (hr*mg/mL)=518.±295, % Metabolite/Parent Ratio=5.0%. $^a$ indicates Mean (Min, Max). The reported factors may vary up to about 2%.

Example 40. Studies of Compound 1 in Subjects with Normal and Impaired Hepatic Function This study evaluates Form I of Compound 1 in subjects with normal and impaired hepatic function and to evaluate the safety and tolerability of Compound 1 single-dose administration in subjects with normal and impaired hepatic function.

The cohorts are as follows: Cohort 1 (Mild Hepatic Impairment) includes approximately 20 subjects (10 per group (mildly impaired and matched controls) for 8 evaluable per group); Cohort 2 (Moderate Hepatic Impairment) includes approximately 20 subjects (10 per group (moderately impaired and matched controls) for 8 evaluable per group); and Cohort 3 (Severe Hepatic Impairment) includes approximately 20 subjects (10 per group (severely impaired and matched controls) for 8 evaluable per group)

Eligible subjects include male and non-pregnant/non-lactating female subjects, ages 18-70 years inclusive with mildly impaired, moderately impaired, severely impaired, and normal hepatic function. Subjects will be current non-smokers (no use of tobacco, nicotine-containing or THC containing products within the last 14 days). Each subject in the control group will be matched for age (±10 years), gender, race, and body mass index (±15% 18≤BMI≤36 kg/m₂) with a subject in the hepatic impairment group. A subject with normal hepatic function may serve as a matched control across cohorts but may only serve as a matched control to one hepatic impaired subject within a cohort. Cohorts 1 and 2 may be dosed in parallel, with dosing for Cohort 3 (severe hepatic impairment) proceeding after review of safety and preliminary PK data (if available) from hepatically impaired subjects in the previous cohorts. Based on the cumulative review of safety and PK data from Cohorts 1 and 2, Cohort 3 may or may not be initiated at the discretion of the investigator and Sponsor. Dosing in subjects with normal hepatic function will begin after a matched subject with hepatic impairment has completed all Day 1 PK assessments (e.g., 96 hours postdose).

Eligible subjects may exhibit varying degrees of hepatic impairment and matched healthy controls. Those subjects with hepatic impairment will be categorized based upon the CPT classification system for hepatic impairment as recommended by the United States FDA and international guidance documents (U.S. Department of Health and Human Services Food and Drug Administration Center for Drug Evaluation and Research (CDER); Center for Biologics Evaluation and Research (CBER) 2003). Within the Child-Pugh-Turcotte (CPT) system, subjects will be assigned to Class A, B, or C (CPT Class A, B, or C) based on a cumulative score evaluating the presence and severity of hyperbilirubinemia, hypoalbuminemia, prolongation of INR for coagulation time, ascites, and hepatic encephalopathy. Classification of hepatic impairment will be assigned as follows: (1) Mild: Class A, CPT score of 5-6; (2) Moderate: Class B, CPT score of 7-9; and (3) Severe: Class C, CPT score of 10-15.

Also, subjects with hepatic impairment and healthy matched controls may be enrolled. The control group may consist of matched healthy subjects with normal hepatic function.

Inclusion Criteria

Additional inclusion criteria may be used, for example:
Aside from hepatic insufficiency, the subject must, in the opinion of the investigator, be sufficiently healthy for study participation based upon medical history, physical examination, vital signs, and screening laboratory evaluations
May have diagnosis of chronic (>6 months), stable hepatic impairment with no clinically significant changes within 3 months (or 90 days) prior to study drug administration (Day 1)
May meet all of the following laboratory parameters at Screening:
  alanine aminotransferase (previously serum glutamic pyruvic transaminase (ALT) value≤10×upper limit of normal (ULN)
  aspartate aminotransferase (AST) value≤10×ULN
  Absolute neutrophil count≥1,000/mm³
  Platelets≥25,000/mm³
  Hemoglobin≥8 g/dL
  α-fetoprotein≤50 ng/mL
Subjects with mild hepatic impairment must have a score on the Child Pugh Turcotte scale of 5-6 at Screening. If a subject's score changes during the course of the study, the score at Screening will be used for classification Subjects with moderate hepatic impairment must have a score on the Child Pugh Turcotte scale of 7-9 at Screening. If a subject's score changes during the course of the study, the score at Screening will be used for classification Subjects with severe hepatic impairment must have a score on the Child Pugh Turcotte scale of 10-15 at Screening. If a subject's score changes during the course of the study, the score at Screening will be used for classification.

Subjects with hepatic impairment with comorbid diseases not associated with hepatic impairment requiring medication(s) must be taking the medication(s) without a change in dose for at least 4 weeks (or 5 half-lives, whichever is longer) prior to Screening. Any change in the dosage during this timeframe should be reviewed and approved by the Sponsor.

Dosing and Administration

On Day 1 subjects will receive a single oral dose of 20 mg Compound 1 (2×10 mg capsule) orally. Dosing in subjects with normal hepatic function will begin after a matched subject with hepatic impairment has completed all Day 1 PK assessments (e.g., 96 hours postdose). Cohorts 1 and 2 may be dosed in parallel, with dosing for Cohort 3 (severe hepatic impairment) proceeding after review of safety and preliminary PK data (if available) from hepatic impaired subjects in the previous cohorts. Based on the cumulative review of safety and PK data from Cohorts 1 and 2, Cohort 3 may or may not be initiated at the discretion of the investigator and Sponsor. Pharmacokinetic Assessments and other Assessments (as discussed above) may be performed.

Example 41. Studies Compound 1 in Subjects with NASH

This study evaluates the safety, tolerability, and efficacy of Form I of Compound 1 in subjects with NASH. To be eligible to participate, subjects may have hepatic steatosis and increased liver stiffness as assessed by Magnetic Resonance Imaging—Protein Density Fat Fraction (MRI-PDFF) and Magnetic Resonance Elastography (MRE), respectively, or a historical liver biopsy consistent with NASH and noncirrhotic fibrosis. Any subject with history of decompensated liver disease, including ascites, hepatic encephalopathy or variceal bleeding may be ineligible.

Subjects meeting the study's entry criteria will be randomly assigned in a 2:2:1 ratio to 1 of 3 different treatment groups, A, B, and C as discussed below. Randomization may be stratified by the presence or absence of diabetes mellitus as determined by medical history, use of medication for indication of diabetes mellitus, or based on Screening lab values if previously undiagnosed (i.e., hemoglobin A1c≥6.5% OR fasting plasma glucose≥126 mg/dL). Study drugs will be administered for a total of 12 weeks from the Baseline/Day 1 visit.

5 milligrams of Compound 1 or placebo, or 10 milligrams of Compound 1 or placebo, may be administered with or without food once daily. Study drug dosing and administration may occur as follows based on treatment group randomization:

Treatment Group A: Compound 1 5 mg administered orally once daily;

Treatment Group B: Compound 1 20 mg administered orally once daily;

Treatment Group C: Placebo administered orally once daily.

Subjects may be evaluated during the studies at weeks 0, 1, 2, 3, 4, 5, 6, 7, 8, 9, 10, 11, 12, 13, 14, 15, 16, 17, 18, 19, 20, 21, 22, 23, or 24 weeks by the following:

QoL Questionnaires (Short Form (36) Health Survey (SF-36), World Productivity and Activity Impairment (WPAI), and Chronic Liver Disease questionnaire (CLDQ)). Note: It is recommended that QoL questionnaires be completed prior to any study procedures being performed and prior to the subject seeing a health care provider.

Symptom driven physical examination

Record vital signs, waist circumference, and body weight

Obtain blood samples for Chemistry, Hematology, Coagulation Panel, Lipid Profile, Hemoglobin A1c, Biomarkers, or Genomic testing (only if the subject consented to participate in the optional genomic research)

Conduct standard 12-Lead ECG

Perform FibroScan® (if available)

Collect urine samples for urine pregnancy test for females of child bearing potential only or biomarkers Collect stool sample for Biomarkers (see Study Reference Binder for instructions)

Dispense study drugs, and provide subject with instruction on appropriate dosing and administration; subject will take the Baseline/Day 1 dose of study drugs on-site Collect MRE data Collect MRI-PDFF data Record all concomitant medications that the subject has taken since the previous visit Record any serious adverse events and all adverse events occurring since the Screening visit.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of the formula:

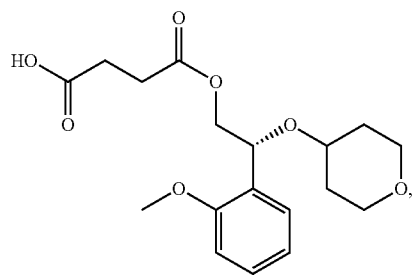 [SMILES: COc1ccccc1[C@H](COC(=O)CCC(=O)O)OC1CCOCC1]

or a salt thereof.

* * * * *